US 7,723,368 B2

May 25, 2010

(12) United States Patent
Malamas et al.

(10) Patent No.: US 7,723,368 B2
(45) Date of Patent: May 25, 2010

(54) AMINO-5-[4-(DIFLUOROMETHOXY) PHENYL]-5-PHENYLIMIDAZOLONE COMPOUNDS FOR THE INHIBITION OF BETA-SECRETASE

(75) Inventors: Michael Sotirios Malamas, Jamison, PA (US); Albert Jean Robichaud, Ringoes, NJ (US); Alexander Michael Porte, Pennington, NJ (US); Koi Michele Morris, Plainsboro, NJ (US); William R. Solvibile, East Windsor, NJ (US); Ji-In Kim, Princeton, NJ (US); Schuyler Adam Antane, Princeton Junction, NJ (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 12/053,086

(22) Filed: Mar. 21, 2008

(65) Prior Publication Data

US 2009/0048320 A1 Feb. 19, 2009

Related U.S. Application Data

(60) Provisional application No. 60/896,707, filed on Mar. 23, 2007.

(51) Int. Cl.
*A61K 31/4166* (2006.01)
*A61K 31/4168* (2006.01)
*C07D 233/30* (2006.01)

(52) U.S. Cl. .................................... 514/386; 548/321.5
(58) Field of Classification Search .............. 548/321.5; 514/386
See application file for complete search history.

(56) References Cited

U.S. PATENT DOCUMENTS

| | | | |
|---|---|---|---|
| 4,140,793 | A | 2/1979 | Ward |
| 4,225,613 | A | 9/1980 | Ward |
| 6,054,457 | A | 4/2000 | Setoi et al. |
| 6,399,824 | B1 | 6/2002 | Hofmeister et al. |
| 6,656,957 | B1 | 12/2003 | Allgeier et al. |
| 6,689,804 | B2 | 2/2004 | Wu et al. |
| 6,974,829 | B2 | 12/2005 | Tung et al. |
| 7,285,682 | B2 | 10/2007 | Hu |
| 2005/0282825 | A1 | 12/2005 | Malamas et al. |
| 2005/0282826 | A1 | 12/2005 | Malamas et al. |
| 2006/0111370 | A1 | 5/2006 | Zhu et al. |
| 2006/0160828 | A1 | 7/2006 | Malamas et al. |
| 2006/0173049 | A1 | 8/2006 | Malamas et al. |
| 2006/0183790 | A1 | 8/2006 | Cole et al. |
| 2006/0183792 | A1 | 8/2006 | Fobare et al. |
| 2007/0004730 | A1 | 1/2007 | Zhou |
| 2007/0004786 | A1 | 1/2007 | Malamas et al. |
| 2007/0027199 | A1 | 2/2007 | Malamas et al. |
| 2007/0072925 | A1 | 3/2007 | Malamas et al. |
| 2007/0191431 | A1 | 8/2007 | Zhou |
| 2007/0203116 | A1 | 8/2007 | Quagliato et al. |
| 2008/0051390 | A1 | 2/2008 | Malamas et al. |
| 2008/0076801 | A1 | 3/2008 | Yin et al. |

FOREIGN PATENT DOCUMENTS

| | | |
|---|---|---|
| EP | 0861831 A1 | 9/1998 |
| GB | 2013192 A | 8/1979 |
| WO | WO 97/45417 A1 | 12/1997 |
| WO | WO 98/45267 | 10/1998 |
| WO | WO 01/87829 A1 | 11/2001 |
| WO | WO 03/053938 A1 | 7/2003 |
| WO | WO 03/064396 A1 | 8/2003 |
| WO | WO 03/094854 A2 | 11/2003 |
| WO | WO 2004/058727 A1 | 7/2004 |
| WO | WO 2005/005412 A1 | 1/2005 |
| WO | WO 2005/058311 A1 | 6/2005 |
| WO | WO 2006/009653 A1 | 1/2006 |
| WO | WO 2006/065277 A2 | 6/2006 |
| WO | WO 2007/005404 A1 * | 1/2007 |
| WO | WO 2007/005404 A1 | 1/2007 |
| WO | WO 2007/016012 A2 | 2/2007 |

OTHER PUBLICATIONS

Abbott et al., Molecular Medicine Today, 1996, vol. 2, p. 106-113.
Allimony et al., "Synthesis and antimicrobial activity of some nitrogen heterobicyclic systems: Part I", Indian Journal of Chemistry, 1999, vol. 38B, pp. 445-451.
Fact Sheet Alzheimer's Association, 2006.
Lefrance-Jullien et al., "Design and charaterization of a new cell-permeant inhibitor of the beta-secretase BACE1", British Journal of Pharmacology, 2005, vol. 145, pp. 228-235.
Lyketsos et al., "Position statement of the American Association for Geriatric Psychiatry regarding principles of care for patients with dementia resulting from Alzheimer's Disease", 2006, vol. 14, pp. 561-573.
Alzheimer's Disease, retrieved from internet on Jun. 27, 2007, http://www.mayoclinic.com/health/alzheimers-disease/DA00161/DSECTION-3.
National Institute of Neurological Discorders and Stroke, "Alzheimer's Disease Information Page", retrieved from internet on Jun. 27, 2007, http://www.ninds.nih.gov/disorders/alzheimersdisease/alzheimersdisease.htm.
Selkoe, "Alzheimer's Disease: Genes, Proteins, and Therapy", Physiological Reviews, 2001, vol. 81(2), pp. 741-766.
Su et al. "Drug delivery across the blood-brain barrier: why is it difficult? How to measure and improve it?", Expert Opinion on Drug Delivery, Abstract, 2006, vol. 3, pp. 419-425.
Tao et al., "Synthesis of Conformationally constrained spirohydantoins with a Dibenzo[a,d]heptadiene ring", Synthesis 2000, No. 10, pp. 1449-1453.
Vandana et al., "Transferring coupled liposomes as drug delivery carriers for brain trageting of 5-florouracil", Journal of Drug Targeting, Abstract, 2005, vol. 13 pp. 245-250.

(Continued)

*Primary Examiner*—Kamal A Saeed
*Assistant Examiner*—Janet L Coppins
(74) *Attorney, Agent, or Firm*—Ram W. Sabnis

(57) ABSTRACT

The present invention provides compounds and methods for the use thereof to inhibit β-secretase (BACE) and treat β-amyloid deposits and neurofibrillary tangles.

27 Claims, No Drawings

OTHER PUBLICATIONS

Varghese et al., "Human beta-secretase (BACE) and BACE Inhibitors", J. Med. Chem. 2003, vol. 46(22), pp. 4625-4630.

Xiao et al., "An improved procedure for the synthesis of 4,4-disubstituted-3-oxo-1,2,5-thiadiazolidine 1,1-dioxides", J. Heterocyclic Chem., 2000, vol. 37, pp. 773-777.

Yamada et al., "Hydantoin derivatives, I. Actions on central nervous system of 5,5-diarylhydantoins and 5,5-diarylhydantion-2-imines", Abstract, Oyo Yakuri, 1975, vol. 9(6), pp. 841-847.

* cited by examiner

AMINO-5-[4-(DIFLUOROMETHOXY) PHENYL]-5-PHENYLIMIDAZOLONE COMPOUNDS FOR THE INHIBITION OF BETA-SECRETASE

CROSS-REFERENCE TO RELATED APPLICATIONS

This application claims the benefit under 35 U.S.C. §119 (e) to co-pending U.S. Provisional Application Ser. No. 60/896,707, filed Mar. 23, 2007, which is hereby incorporated by reference in its entirety.

FIELD OF THE INVENTION

The present invention relates to amino-5-[4-(difluoromethoxy)phenyl]-5-phenylimidazolone compounds, which are inhibitors of β-secretase, compositions and kits containing these derivatives, and methods of their preparation and use for the prevention and treatment of diseases or disorders associated with β-Amyloid deposits and neurofibrillary tangles, including Alzheimer's disease, Trisomy 21 (Down's Syndrome), Hereditary Cerebral Hemorrhage with Amyloidosis of the Dutch-type (HCHWA-D), and other neurodegenerative disorders.

BACKGROUND

β-Amyloid deposits and neurofibrillary tangles are two major pathologic characterizations associated with Alzheimer's disease (AD). Clinically, AD is characterized by the of loss of memory, cognition, reasoning, judgment, and orientation. Also affected, as the disease progresses, are motor, sensory, and linguistic abilities until global impairment of multiple cognitive functions occurs. These cognitive losses take place gradually, but typically lead to severe impairment and eventual death in 4-12 years.

Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other neurodegenerative disorders including dementia-inducing disorders (Varghese, J., et al, Journal of Medicinal Chemistry, 2003, 46, 4625-4630).

β-amyloid deposits are predominately an aggregate of Aβ peptide, which in turn is a product of the proteolysis of amyloid precursor protein (APP). More specifically, Aβ peptide results from the cleavage of APP at the C-terminus by one or more γ-secretases, and at the N-terminus by β-secretase enzyme (BACE), also known as aspartyl protease, as part of the β-amyloidogenic pathway.

BACE activity is correlated directly to the generation of Aβ peptide from APP (Sinha, et al, Nature, 1999, 402, 537-540), and studies increasingly indicate that the inhibition of BACE inhibits the production of Aβ peptide (Roberds, S. L., et al, Human Molecular Genetics, 2001, 10, 1317-1324).

Therefore, it is an object of this invention to provide methods, compositions and compounds which are inhibitors of β-secretase and are useful as therapeutic agents in the treatment, prevention or amelioration of a disease or disorder characterized by elevated β-amyloid deposits or β-amyloid levels in a patient.

It is a feature of this invention that the compounds provided may also be useful to further study and elucidate the β-secretase enzyme.

These and other objects and features of the invention will become more apparent by the detailed description set forth hereinbelow.

SUMMARY OF THE INVENTION

In one aspect, the present invention provides a compound of formula I

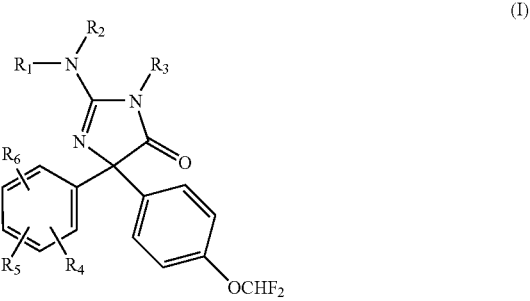

(I)

wherein $R_1$ and $R_2$ are each independently H or an alkyl, cycloalkyl, cycloheteroalkyl, aryl or heteroaryl group each optionally substituted or $R_1$ and $R_2$ may be taken together with the atom to which they are attached form an optionally substituted 5- to 7-membered ring optionally interrupted by an additional heteroatom selected from O, N or S;

$R_3$ is H or an alkyl, cycloalkyl, cycloheteroalkyl, aryl or heteroaryl group each optionally substituted;

$R_4$, $R_5$ and $R_6$ are each independently H, halogen, $NO_2$, CN, $COR_7$, $NR_{10}CO_2R_{11}$, $NR_{15}COR_{16}$, $OR_{14}$, $NR_{12}R_{13}$, $SO_nR_{17}$ or an alkyl, haloalkyl, alkenyl, haloalkenyl, alkynyl, cycloalkyl or cycloheteroalkyl group each optionally substituted or when attached to adjacent carbon atoms $R_4$ and $R_5$ may be taken together with the atoms to which they are attached to form an optionally substituted 5- to 7-membered ring optionally containing one or two heteroatoms selected from O, N or S;

$R_7$ and $R_{17}$ are each independently H, $NR_8R_9$ or an alkyl, haloalkyl, alkoxyalkyl, alkenyl, alkynyl, cycloalkyl or aryl group each optionally substituted;

$R_8$ and $R_9$ are each independently H or an alkyl, alkenyl, alkynyl or cycloalkyl group each optionally substituted or $R_8$ and $R_9$ may be taken together with the atom to which they are attached to form an optionally substituted 5- to 7-membered ring optionally containing an additional heteroatom selected from O, N or S;

$R_{11}$, $R_{14}$ and $R_{16}$ are each independently H or an alkyl, haloalkyl, alkoxyalkyl, alkenyl, alkynyl, cycloalkyl, heteroaryl or an aryl group each optionally substituted;

$R_{10}$ and $R_{15}$ are each independently H or an optionally substituted alkyl group; and $R_{12}$ and $R_{13}$ are each independently H or an alkyl, alkenyl, aryl or cycloalkyl group each optionally substituted or $R_{12}$ and $R_{13}$ may be taken together with the atom to which they are attached to form an optionally substituted 5- to 7-membered ring optionally containing an additional heteroatom selected from O, N or S; or a tautomer thereof, a stereoisomer thereof or a pharmaceutically acceptable salt thereof.

In a more particular embodiment, the compound is one of Examples 2-141.

The present invention also relates to the use of any of these compounds for the treatment of β-amyloid deposits and neurofibrillary tangles. The compounds are particularly useful in treating Alzheimer's disease, cognitive impairment, Down's Syndrome, HCHWA-D, cognitive decline, senile dementia, cerebral amyloid angiopathy, degenerative dementia, or other neurodegenerative disorders.

DETAILED DESCRIPTION OF THE INVENTION

Alzheimer's disease (AD) is a major degenerative disease of the brain which presents clinically by progressive loss of memory, cognition, reasoning, judgment and emotional stability and gradually leads to profound mental deterioration and death. The exact cause of AD is unknown, but increasing evidence indicates that amyloid beta peptide (A-beta) plays a central role in the pathogenesis of the disease. (D. B. Schenk; R. E. Rydel et al, Journal of Medicinal Chemistry, 1995, 21, 4141 and D. J. Selkoe, Physiology Review, 2001, 81, 741). Patients with AD exhibit characteristic neuropathological markers such as neuritic plaques (and in β-amyloid angiopathy, deposits in cerebral blood vessels) as well as neurofibrillary tangles detected in the brain at autopsy. A-beta is a major component of neuritic plaques in AD brains. In addition, β-amyloid deposits and vascular β-amyloid angiopathy also characterize individuals with Downs Syndrome, Hereditary Cerebral Hemorrhage with Amyloidosis of the Dutch type and other neurodegenerative and dementia-inducing disorders. Overexpression of the amyloid precursor protein (APP), altered cleavage of APP to A-beta or a decrease in the clearance of A-beta from a patient's brain may increase the levels of soluble or fibrullar forms of A-beta in the brain. The β-site APP cleaving enzyme, BACE1, also called memapsin-2 or Asp-2, was identified in 1999 (R. Vassar, B. D. Bennett, et al, Nature, 1999, 402, 537). BACE1 is a membrane-bound aspartic protease with all the known functional properties and characteristics of β-secretase. Low molecular weight, non-peptide, non-substrate-related inhibitors of BACE1 or β-secretase are earnestly sought both as an aid in the study of the β-secretase enzyme and as potential therapeutic agents.

Surprisingly, it has now been found that the compounds of the invention demonstrate inhibition of β-secretase and the selective inhibition of BACE1. Advantageously, said compounds may be used as effective therapeutic agents for the treatment, prevention or amelioration of a disease or disorder characterized by elevated β-amyloid deposits or β-amyloid levels in a patient.

Accordingly, in one aspect, the present invention provides a compound of formula I

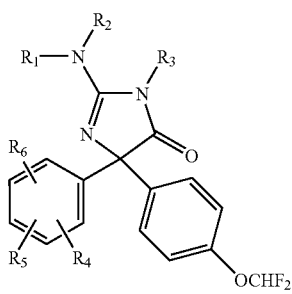

(I)

wherein $R_1$ and $R_2$ are each independently H or an alkyl, cycloalkyl, cycloheteroalkyl, aryl or heteroaryl group each optionally substituted or $R_1$ and $R_2$ may be taken together with the atom to which they are attached form an optionally substituted 5- to 7-membered ring optionally interrupted by an additional heteroatom selected from O, N or S;

$R_3$ is H or an alkyl, cycloalkyl, cycloheteroalkyl, aryl or heteroaryl group each optionally substituted;

$R_4$, $R_5$ and $R_6$ are each independently H, halogen, $NO_2$, CN, $COR_7$, $NR_{10}CO_2R_{11}$, $NR_{15}COR_{16}$, $OR_{14}$, $NR_{12}R_{13}$, $SO_nR_{17}$ or an alkyl, haloalkyl, alkenyl, haloalkenyl, alkynyl, cycloalkyl or cycloheteroalkyl group each optionally substituted or when attached to adjacent carbon atoms $R_4$ and $R_5$ may be taken together with the atoms to which they are attached to form an optionally substituted 5- to 7-membered ring optionally containing one or two heteroatoms selected from O, N or S;

$R_7$ and $R_{17}$ are each independently H, $NR_8R_9$ or an alkyl, haloalkyl, alkoxyalkyl, alkenyl, alkynyl, cycloalkyl or aryl group each optionally substituted;

$R_8$ and $R_9$ are each independently H or an alkyl, alkenyl, alkynyl or cycloalkyl group each optionally substituted or $R_8$ and $R_9$ may be taken together with the atom to which they are attached to form an optionally substituted 5- to 7-membered ring optionally containing an additional heteroatom selected from O, N or S;

$R_{11}$, $R_{14}$ and $R_{16}$ are each independently H or an alkyl, haloalkyl, alkoxyalkyl, alkenyl, alkynyl, cycloalkyl, heteroaryl or an aryl group each optionally substituted;

$R_{10}$ and $R_{15}$ are each independently H or an optionally substituted alkyl group; and $R_{12}$ and $R_{13}$ are each independently H or an alkyl, alkenyl, aryl or cycloalkyl group each optionally substituted or $R_{12}$ and $R_{13}$ may be taken together with the atom to which they are attached to form an optionally substituted 5- to 7-membered ring optionally containing an additional heteroatom selected from O, N or S; or a tautomer thereof, a stereoisomer thereof or a pharmaceutically acceptable salt thereof.

In another aspect of the invention, the compound is as described in formula I, II, IIA, IIB, III, IV, IVA, V, VI, VII, VIII, IXA or IXB, provided that the compound is not any one of the following compounds:

2-amino-5-[4-(difluoromethoxy)phenyl]-3-methyl-5-phenyl-3,5-dihydro-4H-imidazol-4-one;
(5S)-2-Amino-5-[4-(difluoromethoxy)phenyl]-3-methyl-5-phenyl-3,5-dihydro-4H-imidazol-4-one;
(5R)-2-Amino-5-[4-(difluoromethoxy)-phenyl]-3-methyl-5-phenyl-3,5-dihydro-4H-imidazol-4-one;
(5R)-2-amino-5-(3-bromophenyl)-5-[4-(difluoromethoxy)phenyl]-3-methyl-3,5-dihydro-4H-imidazol-4-one;
2-amino-5-(3-bromophenyl)-5-[4-(difluoromethoxy)phenyl]-3-methyl-3,5-dihydro-4H-imidazol-4-one;
(5R)-2-Amino-5-(3-bromo-4-fluorophenyl)-5-[4-(difluoromethoxy)phenyl]-3-methyl-3,5-dihydro-4H-imidazol-4-one;
2-Amino-5-(3-bromo-4-fluorophenyl)-5-[4-(difluoromethoxy)phenyl]-3-methyl-3,5-dihydro-4H-imidazol-4-one;
2-Amino-5-[4-(difluoromethoxy)phenyl]-3-methyl-5-(3-propylphenyl)-3,5-dihydro-4H-imidazol-4-one;
(5R)-2-Amino-5-[4-(difluoromethoxy)phenyl]-3-methyl-5-(3-propylphenyl)-3,5-dihydro-4H-imidazol-4-one;
(5S)-2-Amino-5-[4-(difluoromethoxy)phenyl]-3-methyl-5-(3-propylphenyl)-3,5-dihydro-4H-imidazol-4-one;
(5R)-2-amino-5-(3-butylphenyl)-5-[4-(difluoromethoxy)phenyl]-3-methyl-3,5-dihydro-4H-imidazol-4-one;
(5S)-2-amino-5-(3-butylphenyl)-5-[4-(difluoromethoxy)phenyl]-3-methyl-3,5-dihydro-4H-imidazol-4-one;
2-amino-5-(3-butylphenyl)-5-[4-(difluoromethoxy)phenyl]-3-methyl-3,5-dihydro-4H-imidazol-4-one;
2-Amino-5-[4-(difluoromethoxy)phenyl]-3-methyl-5-(3-pentylphenyl)-3,5-dihydro-4H-imidazol-4-one;
2-Amino-5-[4-(difluoromethoxy)phenyl]-3-methyl-5-[3-(2-methylbutyl)phenyl]-3,5-dihydro-4H-imidazol-4-one;

2-Amino-5-(3-but-3-en-1-ylphenyl)-5-[4-(difluoromethoxy)phenyl]-3-methyl-3,5-dihydro-4H-imidazol-4-one;

2-Amino-5-[3-(cyclopropylmethyl)phenyl]-5-[4-(difluoromethoxy)phenyl]-3-methyl-3,5-dihydro-4H-imidazol-4-one;

3-(3-{2-Amino-4-[4-(difluoromethoxy)phenyl]-1-methyl-5-oxo-4,5-dihydro-1H-imidazol-4-yl}phenyl)propanenitrile;

(5R)-2-Amino-5-[4-(difluoromethoxy)phenyl]-3-methyl-5-(3-pent-4-en-1-ylphenyl)-3,5-dihydro-4H-imidazol-4-one;

(5S)-2-Amino-5-[4-(difluoromethoxy)phenyl]-3-methyl-5-(3-pent-4-en-1-ylphenyl)-3,5-dihydro-4H-imidazol-4-one;

2-Amino-5-[4-(difluoromethoxy)phenyl]-3-methyl-5-(3-pent-4-en-1-ylphenyl)-3,5-dihydro-4H-imidazol-4-one;

N-(3-{(4R)-2-Amino-4-[4-(difluoromethoxy)phenyl]-1-methyl-5-oxo-4,5-dihydro-1H-imidazol-4-yl}phenyl)-2-methoxyacetamide;

N-(3-{(4S)-2-Amino-4-[4-(difluoromethoxy)phenyl]-1-methyl-5-oxo-4,5-dihydro-1H-imidazol-4-yl}phenyl)-2-methoxyacetamide;

N-(3-{2-Amino-4-[4-(difluoromethoxy)phenyl]-1-methyl-5-oxo-4,5-dihydro-1H-imidazol-4-yl}phenyl)-2-methoxyacetamide;

2-Amino-5-[4-(difluoromethoxy)phenyl]-3-methyl-5-[3-(4,4,4-trifluorobutyl)phenyl]-3,5-dihydro-4H-imidazol-4-one;

5-(3-{2-Amino-4-[4-(difluoromethoxy)phenyl]-1-methyl-5-oxo-4,5-dihydro-1H-imidazol-4-yl}phenyl)pentanenitrile;

4-(3-{2-amino-4-[4-(difluoromethoxy)phenyl]-1-methyl-5-oxo-4,5-dihydro-1H-imidazol-4-yl}phenyl)butanenitrile;

2-Amino-5-[3-(1,4-difluorobutyl)phenyl]-5-[4-(difluoromethoxy)-phenyl]-3-methyl-3,5-dihydro-4H-imidazol-4-one;

2-Amino-5-[4-(difluoromethoxy)phenyl]-5-[3-(3-fluorobut-3-en-1-yl)phenyl]-3-methyl-3,5-dihydro-4H-imidazol-4-one;

2-Amino-5-[3-(4,4-difluorobut-3-en-1-yl)phenyl]-5-[4-(difluoromethoxy)phenyl]-3-methyl-3,5-dihydro-4H-imidazol-4-one 2-Amino-5-[3-(4,4-difluorobutyl)phenyl]-5-[4-(difluoromethoxy)-phenyl]-3-methyl-3,5-dihydro-4H-imidazol-4-one 2-Amino-5-[4-(difluoromethoxy)phenyl]-5-[3-(4-hydroxy-but-1-yn-1-yl)phenyl]-3-methyl-3,5-dihydro-4H-imidazol-4-one;

2-Amino-5-[4-(difluoromethoxy)phenyl]-5-[3-(4-hydroxybutyl)-phenyl]-3-methyl-3,5-dihydro-4H-imidazol-4-one;

2-Amino-5-[4-(difluoromethoxy)phenyl]-5-[3-(3-methoxyprop-1-yn-1-yl)-phenyl]-3-methyl-3,5-dihydro-4H-imidazol-4-one;

2-Amino-5-[4-(difluoromethoxy)phenyl]-5-{3-[(1Z)-3-methoxyprop-1-en-1-yl]phenyl}-3-methyl-3,5-dihydro-4H-imidazol-4-one;

2-Amino-5-[4-(difluoromethoxy)phenyl]-5-[3-(3-methoxypropyl)phenyl]-3-methyl-3,5-dihydro-4H-imidazol-4-one;

2-Amino-5-[4-(difluoromethoxy)phenyl]-5-[3-(5-fluoropentyl)-phenyl]-3-methyl-3,5-dihydro-4H-imidazol-4-one;

2-Amino-5-[4-(difluoromethoxy)phenyl]-5-[3-(4-fluorobutyl)-phenyl]-3-methyl-3,5-dihydro-4H-imidazol-4-one;

2-Amino-5-[4-(difluoromethoxy)phenyl]-5-[3-(6-fluorohexyl)-phenyl]-3-methyl-3,5-dihydro-4H-imidazol-4-one;

3-{2-Amino-4-[4-(difluoromethoxy)phenyl]-1-methyl-5-oxo-4,5-dihydro-1H-imidazol-4-yl}-N-propylbenzamide;

2-Amino-5-[4-(difluoromethoxy)phenyl]-5-{3-[(2-fluoroethoxy)-methyl]phenyl}-3-methyl-3,5-dihydro-4H-imidazol-4-one;

2-amino-5-[4-(difluoromethoxy)phenyl]-3-methyl-5-{3-[(2,2,2-trifluoroethoxy)methyl]phenyl}-3,5-dihydro-4H-imidazol-4-one;

2-amino-5-[4-(difluoromethoxy)phenyl]-3-methyl-5-{3-[(2,2,3,3-tetrafluoropropoxy)methyl]phenyl}-3,5-dihydro-4H-imidazol-4-one;

2-Amino-5-[4-(difluoromethoxy)phenyl]-5-{3-[(1E)-6-methoxy-hex-1-en-1-yl]-phenyl}-3-methyl-3,5-dihydro-4H-imidazol-4-one;

2-Amino-5-[4-(difluoromethoxy)phenyl]-5-{3-[(1E)-5-hydroxy-pent-1-en-1-yl]-phenyl}-3-methyl-3,5-dihydro-4H-imidazol-4-one;

2-Amino-5-[4-(difluoromethoxy)phenyl]-5-{3-[2-(methoxymethyl)-cyclopropyl]phenyl}-3-methyl-3,5-dihydro-4H-imidazol-4-one;

2-Amino-5-[4-(difluoromethoxy)phenyl]-5-{3-[2-(2-methoxyethyl)-cyclopropyl]phenyl}-3-methyl-3,5-dihydro-4H-imidazol-4-one;

5-(3-Acetylphenyl)-2-amino-5-[4-(difluoromethoxy)phenyl]-3-methyl-3,5-dihydro-4H-imidazol-4-one;

2-Amino-5-[4-(difluoromethoxy)phenyl]-5-[3-(3-hydroxy-hex-4-yn-1-yl)phenyl]-3-methyl-3,5-dihydro-4H-imidazol-4-one 2-Amino-5-[4-(difluoromethoxy)phenyl]-5-[3-(3-fluoroprop-1-yn-1-yl)phenyl]-3-methyl-3,5-dihydro-4H-imidazol-4-one;

2-Amino-5-[4-(difluoromethoxy)phenyl]-5-[3-(3hydroxyphenyl)-3-methyl-3,5-dihydro-4H-imidazol-4-one;

2-Amino-5-[4-(difluoromethoxy)phenyl]-5-[3-(3-fluoropropox-1-yl)phenyl]-3-methyl-3,5-dihydro-4H-imidazol-4-one;

2-Amino-5-[4-(difluoromethoxy)phenyl]-5-(4-fluoro-3-hydroxy-phenyl)-3-methyl-3,5-dihydro-4H-imidazol-4-one;

(5R)-2-Amino-5-[4-(difluoromethoxy)phenyl]-5-[4-fluoro-3-(3-fluoropropox-1-yl)phenyl]-3-methyl-3,5-dihydro-4H-imidazol-4-one;

(5S)-2-Amino-5-[4-(difluoromethoxy)phenyl]-5-[4-fluoro-3-(3-fluoropropox-1-yl)phenyl]-3-methyl-3,5-dihydro-4H-imidazol-4-one;

(5R)-2-Amino-5-[3-(2,2-difluoroethoxy)-4-fluorophenyl]-5-[4-(difluoromethoxy)phenyl]-3-methyl-3,5-dihydro-4H-imidazol-4-one;

(5S)-2-Amino-5-[3-(2,2-difluoroethoxy)-4-fluorophenyl]-5-[4-(difluoromethoxy)-phenyl]-3-methyl-3,5-dihydro-4H-imidazol-4-one;

2-Amino-5-{3-[(4,4-difluorobut-3-en-1-yl)oxy]phenyl}-5-[4-(difluoromethoxy)phenyl]-3-methyl-3,5-dihydro-4H-imidazol-4-one 2-Amino-5-{3-[(4,4-difluorobut-3-en-1-yl)oxy]-4-fluorophenyl}-5-[4-(difluoromethoxy)phenyl]-3-methyl-3,5-dihydro-4H-imidazol-4-one 2-Amino-5-[4-(difluoromethoxy)phenyl]-5-(4-fluoro-3-pent-4-en-1-yl)-3-methyl-3,5-dihydro-4H-imidazol-4-one 2-Amino-5-(3-but-3-en-1-yl-4-fluorophenyl)-5-[4-(difluoromethoxy)phenyl]-3-methyl-3,5-dihydro-4H-imidazol-4-one;

2-Amino-5-[4-(difluoromethoxy)phenyl]-5-[3-(1-hydroxybut-2-yn-1-yl)phenyl]-3-methyl-3,5-dihydro-4H-imidazol-4-one;

2-Amino-5-[4-(difluoromethoxy)phenyl]-5-[3-(1,4-dihydroxybut-2-yn-1-yl)phenyl]-3-methyl-3,5-dihydro-4H-imidazol-4-one;
2-Amino-5-[4-(difluoromethoxy)phenyl]-5-[3-(2,2-dimethyl-3-oxocyclobutyl)phenyl]-3-methyl-3,5-dihydro-4H-imidazol-4-one;
2-Amino-5-[4-(difluoromethoxy)phenyl]-3-methyl-5-[3-(3-oxocyclobutyl)phenyl]-3,5-dihydro-4H-imidazol-4-one;
2-Amino-5-[4-(difluoromethoxy)phenyl]-5-[3-(3-hydroxycyclobutyl)phenyl]-3-methyl-3,5-dihydro-4H-imidazol-4-one;
ethyl[3-(3-{2-Amino-4-[4-(difluoromethoxy)phenyl]-1-methyl-5-oxo-4,5-dihydro-1H-imidazol-4-yl}phenyl)cyclobutylidene]acetate;
methyl[3-(3-{2-Amino-4-[4-(difluoromethoxy)phenyl]-1-methyl-5-oxo-4,5-dihydro-1H-imidazol-4-yl}phenyl)cyclobutylidene]acetate;
methyl[3-(3-{2-Amino-4-[4-(difluoromethoxy)phenyl]-1-methyl-5-oxo-4,5-dihydro-1H-imidazol-4-yl}phenyl)cyclobutyl]acetate;
2-Amino-5-[3-(difluoromethoxy)phenyl]-5-[4-(difluoromethoxy)-phenyl]-3-methyl-3,5-dihydro-4H-imidazol-4-one
(5S)-2-Amino-5-[3-(difluoromethoxy)phenyl]-5-[4-(difluoro-methoxy)phenyl]-3-methyl-3,5-dihydro-4H-imidazol-4-one;
(5R)-2-Amino-5-[3-(difluoromethoxy)phenyl]-5-[4-(difluoromethoxy)phenyl]-3-methyl-3,5-dihydro-4H-imidazol-4-one;
2-Amino-5-[4-(difluoromethoxy)phenyl]-5-{3-[(1R)-1-fluoropent-4-en-1-yl]phenyl}-3-methyl-3,5-dihydro-4H-imidazol-4-one;
2-Amino-5-[4-(difluoromethoxy)phenyl]-5-{3-[(1R)-1-fluorobut-3-en-1-yl]phenyl}-3-methyl-3,5-dihydro-4H-imidazol-4-one;
N-(3-{2-Amino-4-[4-(difluoromethoxy)phenyl]-1-methyl-5-oxo-4,5-dihydro-1H-imidazol-4-yl}phenyl)ethanesulfonamide;
2-Amino-5-[4-(difluoromethoxy)phenyl]-5-[3-(5-hydroxypent-1-yn-1-yl)phenyl]-3-methyl-3,5-dihydro-4H-imidazol-4-one;
2-Amino-5-{3-[(E)-2-cyclopropylvinyl]phenyl}-5-[4-(difluoromethoxy)phenyl]-3-methyl-3,5-dihydro-4H-imidazol-4-one;
and provided that the compound is not as shown in any one of the following tables (A-H):

A

| R |
|---|
| CH₂CH₂CF₃ |
| CH₃ |
| CH₂CH₂CH₂CH₃ |
| CH₂—▷ |

A

| R |
|---|
| CH₂CH₃ |
| CH₂CH₂CH₃ |
| CH(CH₂F)CH₂F |

B

| R | R5 |
|---|---|
| CH₂CH₂OCH₃ | H |
| OCH₃ | H |
| CH₂OCH₃ | H |
| CH₂OH | H |
| CH₂F | H |
| CH₂CH₂F | H |
| CH₂F | F |
| CHF₂ | H |

C

| R4 |
|---|
| CH₂CH₂F |
| COCH₂CH₂CH₂CH₂F |
| COCH₂CH₂CH₂F |

D

| R | R5 |
|---|---|
| CH₂-cyclopropyl | H |
| CH₂CH₂CH₂CF₃ | H |
| CH₂CHF₂ | H |
| CH₂CH₂CH₂CH₂F | H |
| CH₂CH₂CH₂OC₆H₅ | H |
| CH₂CH₂CH₂CN | H |
| CH₂CH₂CHF₂ | F |
| H₂C—≡—CH₃ | F |
| CH₂CH₂CH₂CH₂F | F |
| CH₂CHF₂ | F |
| CH₂CH₂CH=CH₂ | H |
| CH₂CH₂CH=CH₂ | F |
| CH₂CH₂CH₂CH=CH₂ | H |
| (R)-CH₂(CH₃)CH₂CH=CH₂ | H |
| (S)-CH₂(CH₃)CH₂CH=CH₂ | H |
| CH₂=CHCH₂(CH₃)CH₂ | H |
| CH₃C(=CH₂)CH₂CH₂ | H |
| CH₂=CHCH₂ | H |

E

| R |
|---|
| 3,4-difluorophenyl |
| 3-methoxyphenyl |
| 3-chlorophenyl |
| n-propyl |
| 3-cyanophenyl |
| 3-(trifluoromethoxy)phenyl |
| 3-pyridyl |
| 4-cyanophenyl |
| 2-thienyl |
| benzyl |
| 3,5-difluorophenyl |

F

| Chiral | R | R' |
|---|---|---|
| — | CH₂OCH₃ | H |
| — | CH₂OCH₃ | CH₃ |
| 4-R | CH₂OCH₃ | H |
| 4-S | CH₂OCH₃ | H |

G

| Chiral | R | R5 |
|---|---|---|
| — | CH₂CH₂CH₂F | H |
| — | CH₂CH₂CH₂Cl | H |
| — | CH₂CH₂CH₃ | H |
| — | CH₂CH₂OH | H |
| — | CH₂CH₂CH₂CH₂OH | H |
| — | CH₂CH₂CH₂CH₂F | H |
| — | CH₂CH₂Cl | H |
| 5-R | CH₂CH₃ | H |
| 5-S | CH₂CH₃ | H |
| 5-S | CH₂CH₂CH₂OH | H |
| 5-R | CH₂CH₂CH₂CH₂OH | H |
| 5-S | CH₂CH₂CH₂CH₂OH | H |
| 5-R | CH₂CH₂OH | H |
| 5-S | CH₂CH₂OH | H |
| 5-S | CH₂CH₂CH₂F | H |
| 5-R | CH₂CH₂CH₂F | H |
| 5-S | CH₂CH₂CH₂OH | F |
| 5-R | CH₂CH₂CH₂OH | F |
| 5-S | CH₂CH₂CH₂F | F |
| 5-R | CH₂CH₂CH₂F | F |
| — | CH₂CH₂OCH₃ | H |
| — | CH₂OCH₃ | H |
| 5-S | CH₂CH₂OCH₃ | H |
| 5-R | CH₂CH₂OCH₃ | H |
| — | CH₂CH₂F | H |
| — | CH₂CH(CH₃)₂ | H |
| — | CH(OH)CH₂CH₃ | H |
| — | CH₂CH(OH)CH₃ | H |
| — | CH(CH₃)₂ | H |
| — | CH₂CH₃ | H |
| — | CH₂CH₂CH₂CH₃ | H |
| — | cyclopropyl | H |
| — | cyclohexyl | H |
| — | cyclopentylmethyl | H |
| — | cyclohexylmethyl | H |
| 5-S | CH₂OCH₃ | H |
| 5-R | CH₂OCH₃ | H |

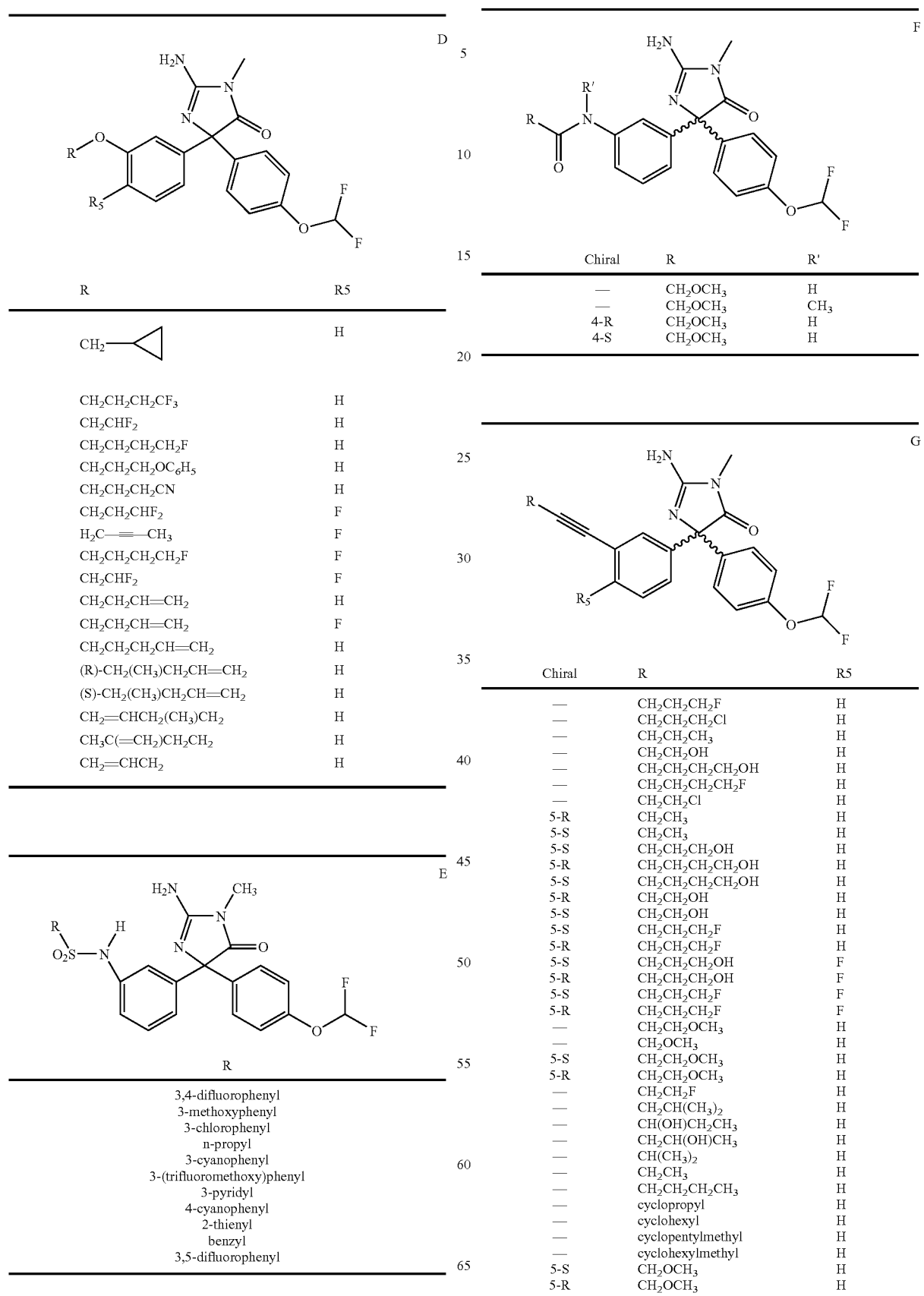

-continued

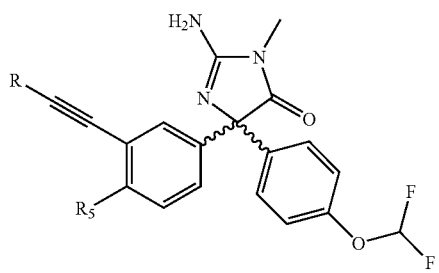

G

| Chiral | R | R5 |
|---|---|---|
| — | CH₂OCH₃ | F |
| — | CH₂CH₂OCH₃ | F |
| — | CH₂OH | H |
| — | (S)-CH(OH)CH₃ | H |
| — | (R)-CH(OH)CH₃ | H |
| — | CH(OH)CH(CH₃)₂ | H |
| — | 1-hydroxycyclopentyl | H |
| — | 1-hydroxycyclohexyl | H |
| — | C(OH)(CH₃)₂ | H |
| — | C(OH)(CH₃)CH₂CH₃ | H |
| — | H | H |
| — | (S)-CH(OH)C₆H₅ | H |
| 5-S | CH₂CH₂OCH₃ | H |
| 5-R | CH₂CH₂OCH₃ | H |
| 5-S | CH₂OCH₃ | H |
| 5-R | CH₂OCH₃ | H |
| — | CH₃ | F |
| — | CH₃ | H |
| 5-R | (S)-CH(OH)CH₃ | H |
| 5-S | (S)-CH(OH)CH₃ | H |
| 5-R | CH₃ | H |
| 5-S | CH₃ | H |
| 5-R | CH₂CH₂CH₂OH | H | or

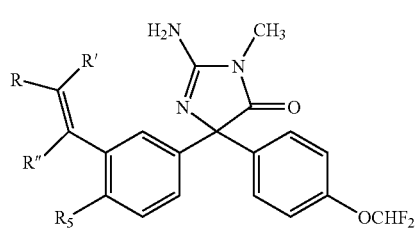

H

| R | R' | R" | R5 |
|---|---|---|---|
| CH₃ | H | H | H |
| CH₃ | H | H | F |
| H | H | H | H |
| CH₃ | CH₃ | H | F |
| H | H | CH₃ | H |
| CH₂CH₂CH₃ | H | H | H |
| CH₂CH₂CH₂CH₃ | H | H | H |
| CH₂CH₂CH₂Cl | H | H | H |
| C₆H₅ | H | H | H |
| 2,4-difluorophenyl | H | H | H |
| CH₂CH₂CH₂CH₂CH₃ | H | H | H |
| H | H | C₆H₅ | H |
| CH₂CH₂CH₂CH₃ | H | H | H. |

In another aspect, the present invention provides a compound of formula II

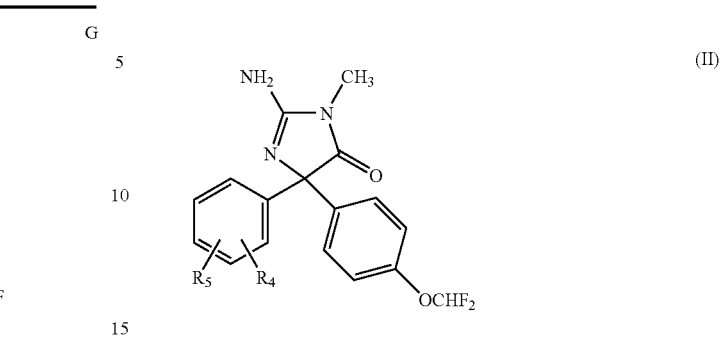

wherein $R_4$ and $R_5$ are as defined above for formula I, with the proviso that only one of $R_4$ and $R_5$ can be hydrogen; or a tautomer thereof, a stereoisomer thereof or a pharmaceutically acceptable salt thereof.

In certain embodiments the compound of formula II is a compound of formula IIA

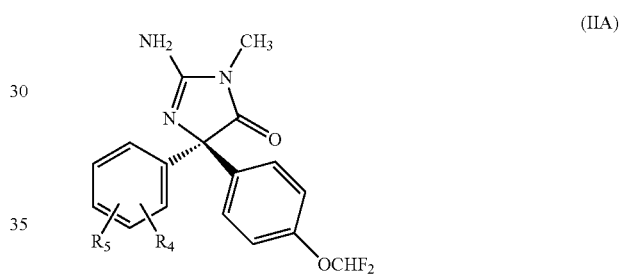

wherein $R_4$ and $R_5$ are as defined above for formula I, with the proviso that only one of $R_4$ and $R_5$ can be hydrogen; or a tautomer thereof or a pharmaceutically acceptable salt thereof.

In other embodiments the compound of formula II is a compound of formula IIB

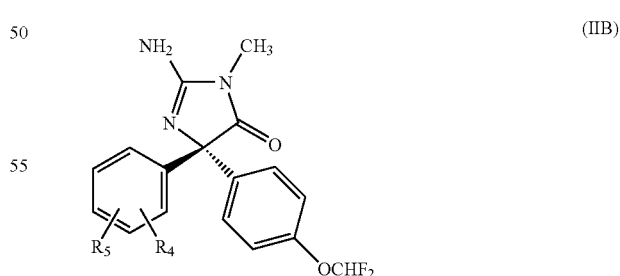

wherein $R_4$ and $R_5$ are as defined above for formula I, with the proviso that only one of $R_4$ and $R_5$ can be hydrogen; or a tautomer thereof or a pharmaceutically acceptable salt thereof.

In yet another aspect, the present invention provides a compound of formula III

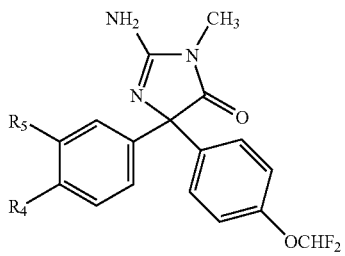

(III)

wherein
R$_4$ and R$_5$ are as defined above for formula I, with the proviso that only one of R$_4$ and R$_5$ can be hydrogen; or
a tautomer thereof, a stereoisomer thereof or a pharmaceutically acceptable salt thereof.

In certain embodiments the compound of formula III is a compound of formula IIIA

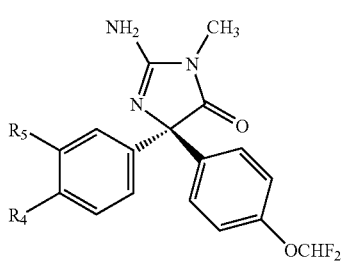

(IIIA)

wherein
R$_4$ and R$_5$ are as defined above for formula I, with the proviso that only one of R$_4$ and R$_5$ can be hydrogen; or
a tautomer thereof or a pharmaceutically acceptable salt thereof.

In other embodiments the compound of formula III is a compound of formula IIIB

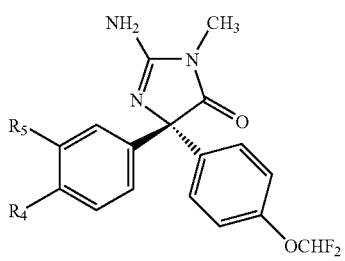

(IIIB)

wherein
R$_4$ and R$_5$ are as defined above for formula I, with the proviso that only one of R$_4$ and R$_5$ can be hydrogen; or
a tautomer thereof or a pharmaceutically acceptable salt thereof.

In a further aspect, the present invention provides compounds of formula I, II, IIA, IIB, III, IIIA and/or IIIB, tautomers thereof and pharmaceutically acceptable salts thereof wherein:

(1) R$_4$ is H or fluorine and R$_5$ is OR$_{18}$ where R$_{18}$ is an alkyl, haloalkyl, alkenyl or haloalkenyl group each optionally substituted;

(2) R$_4$ is H and R$_5$ is OR$_{18}$ where R$_{18}$ is an alkyl group substituted with a cycloalkyl group;

(3) R$_4$ is H and R$_5$ is OR$_{18}$ where R$_{18}$ is an alkyl group substituted with a cyclopropyl group;

(4) R$_4$ is H and R$_5$ is OR$_{18}$ where R$_{18}$ is an optionally substituted alkenyl group;

(5) R$_4$ is H and R$_5$ is OR$_{18}$ where R$_{18}$ is an optionally substituted haloalkyl group;

(6) R$_4$ is fluorine and R$_5$ is OR$_{18}$ where R$_{18}$ is an optionally substituted haloalkyl group;

(7) R$_4$ is H and R$_5$ is OR$_{18}$ where R$_{18}$ is an optionally substituted haloalkenyl group;

(8) R$_4$ is H and R$_5$ is NHR$_{19}$ where R$_{19}$ is H or an alkyl, cycloalkyl, alkenyl or aryl group each optionally substituted;

(9) R$_4$ is H and R$_5$ is NHR$_{19}$ where R$_{19}$ is an alkyl group substituted with a heteroaryl group;

(10) R$_4$ is H and R$_5$ is NHCOR$_{20}$ where R$_{20}$ is an alkyl, haloalkyl, cycloalkyl, alkoxyalkyl, alkenyl, aryl or heteroaryl group each optionally substituted;

(11) R$_4$ is H and R$_5$ is NHCOR$_{20}$ where R$_{20}$ is an optionally substituted alkyl group;

(12) R$_4$ is H and R$_5$ is NHCOR$_{20}$ where R$_{20}$ is an optionally substituted haloalkyl group;

(13) R$_4$ is H and R$_5$ is NHCOR$_{20}$ where R$_{20}$ is an optionally substituted cycloalkyl group;

(14) R$_4$ is H and R$_5$ is NHCOR$_{20}$ where R$_{20}$ is an optionally substituted heteroaryl group;

(15) R$_4$ is H and R$_5$ is NHCOR$_{20}$ where R$_{20}$ is an optionally substituted heteroaryl group containing one O heteroatom;

(16) R$_4$ is H and R$_5$ is NHCOR$_{20}$ where R$_{20}$ is an optionally substituted heteroaryl group containing one S heteroatom;

(17) R$_4$ is H and R$_5$ is NHCOR$_{20}$ where R$_{20}$ is a heteroaryl group fused to an aryl group;

(18) R$_4$ is H and R$_5$ is CH$_2$NR$_{21}$R$_{22}$ where R$_{21}$ and R$_{22}$ are independently H or an optionally substituted alkyl group or R$_{21}$ and R$_{22}$ may be taken together with the N atom to which they are attached to form an optionally substituted 5-membered ring;

(19) R$_4$ is H or fluorine and R$_5$ is an alkenyl or haloalkenyl group each optionally substituted;

(20) R$_4$ is fluorine and R$_5$ is an optionally substituted alkenyl group;

(21) R$_4$ is H and R$_5$ is an optionally substituted haloalkenyl group;

(22) R$_4$ is H and R$_5$ is a haloalkenyl group substituted with a cycloalkyl group;

(23) R$_4$ is H and R$_5$ is a haloalkenyl group substituted with a cyclopropyl group;

(24) R$_4$ is H and R$_5$ is a haloalkenyl group substituted with a cyclopropyl group where the haloalkenyl group contains one fluorine atom;

(25) $R_4$ is H and $R_5$ is an optionally substituted group of formula IV

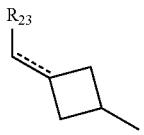

(IV)

where the dashed line denotes an optional double bond and $R_{23}$ is a haloalkyl or alkoxyalkyl group each optionally substituted or $CO_2R_{24}$ where $R_{24}$ is an alkyl group;

(26) $R_4$ is H and $R_5$ is an optionally substituted group of formula IVA

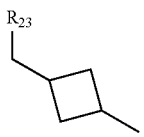

(IVA)

where $R_{23}$ is a haloalkyl group;

(27) $R_4$ is H and $R_5$ is an optionally substituted group of formula V

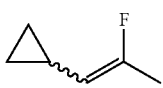

(V)

where the double bond can be in a cis or trans configuration;

(28) $R_4$ and $R_5$ are attached to adjacent carbon atoms and are taken together with the atoms to which they are attached to form an optionally substituted 5- to 7-membered ring containing one O heteroatom;

(29) $R_4$ and $R_5$ are attached to adjacent carbon atoms and are taken together with the atoms to which they are attached to form an optionally substituted 5-membered ring containing one O heteroatom;

(30) $R_4$ is H and $R_5$ is an optionally substituted cycloalkyl group;

(31) $R_4$ is $OR_{25}$ where $R_{25}$ is an optionally substituted haloalkyl group and $R_5$ is H;

(32) $R_4$ is H or fluorine and $R_5$ is an alkyl, haloalkyl, alkoxyalkyl, alkenyl, haloalkenyl or alkynyl group each optionally substituted;

(33) $R_4$ is H or fluorine and $R_5$ is an optionally substituted group of formula VI

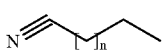

(VI)

where n is an integer of 1-4;

(34) $R_4$ is H or fluorine and $R_5$ is a group of formula VII

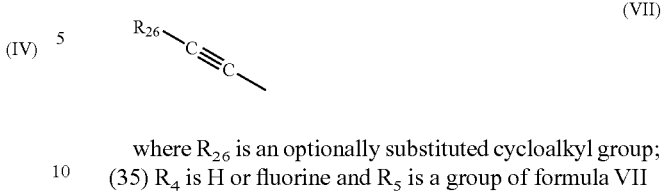

(VII)

where $R_{26}$ is an optionally substituted cycloalkyl group;

(35) $R_4$ is H or fluorine and $R_5$ is a group of formula VII

(VII)

where $R_{26}$ is an optionally substituted cyclopropyl group;

(36) $R_4$ is H or fluorine and $R_5$ is a group of formula VIII

(VIII)

where $R_{27}$ is an alkyl, haloalkyl or alkoxyalkyl group each optionally substituted;

(37) $R_4$ is H or fluorine and $R_5$ is a group of formula VIII

(VIII)

where $R_{27}$ is an optionally substituted alkyl group;

(38) $R_4$ is H or fluorine and $R_5$ is a group of formula VIII

(VIII)

where $R_{27}$ is an optionally substituted haloalkyl group;

(39) $R_4$ is H or fluorine and $R_5$ is a group of formula VIII

(VIII)

where $R_{27}$ is an optionally substituted alkoxyalkyl group; or

(40) $R_4$ is an optionally substituted alkoxyalkyl group and $R_5$ is CN.

In one embodiment, the aforementioned compounds are of the formula IIA. In another embodiment, the aforementioned compounds are of the formula IIIA. In one embodiment, the aforementioned compounds are of the formula IIB. In another embodiment, the aforementioned compounds are of the formula IIIB.

In another aspect, the present invention provides compounds of formula IXA, IXB or a mixture thereof

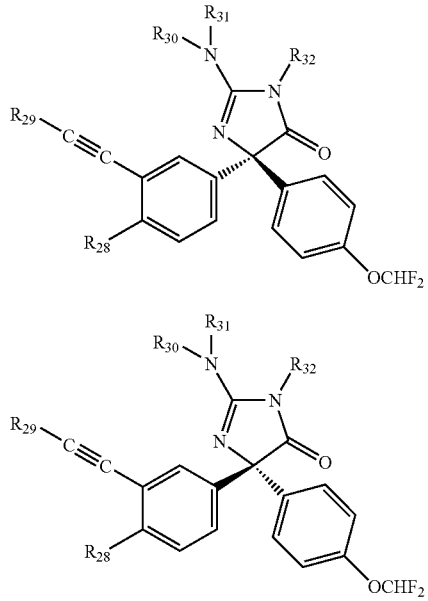

wherein $R_{28}$ is H or halogen;

$R_{29}$ is an alkyl, haloalkyl, alkoxyalkyl or cycloalkyl group each optionally substituted;

$R_{30}$ and $R_{31}$ are each independently H or an alkyl, cycloalkyl, cycloheteroalkyl, aryl or heteroaryl group each optionally substituted or $R_{30}$ and $R_{31}$ may be taken together with the atom to which they are attached form an optionally substituted 5- to 7-membered ring optionally interrupted by an additional heteroatom selected from O, N or S; and $R_{32}$ is H or an alkyl, cycloalkyl, cycloheteroalkyl, aryl or heteroaryl group each optionally substituted.

In another aspect of the invention, the compound is selected from the group consisting of:

(E)-2-amino-5-[3-(2-cyclopropyl-1-fluorovinyl)phenyl]-5-[4-(difluoromethoxy)phenyl]-3-methyl-3,5-dihydro-4H-imidazol-4-one;

(Z)-2-amino-5-[3-(2-cyclopropyl-1-fluorovinyl)phenyl]-5-[4-(difluoromethoxy)phenyl]-3-methyl-3,5-dihydro-4H-imidazol-4-one;

2-amino-5-[4-(difluoromethoxy)phenyl]-5-(4-fluoro-3-prop-1-en-1-ylphenyl)-3-methyl-3,5-dihydro-4H-imidazol-4-one;

2-amino-5-[4-(difluoromethoxy)phenyl]-5-(3-ethylphenyl)-3-methyl-3,5-dihydro-4H-imidazol-4-one;

(E)-2-amino-4-(4-(difluoromethoxy)phenyl)-4-(3-(4-methoxybut-2-en-2-yl)phenyl)-1-methyl-1H-imidazol-5(4H)-one;

2-amino-4-(3-cyclopropylphenyl)-4-(4-(difluoromethoxy)phenyl)-1-methyl-1H-imidazol-5(4H)-one;

2-amino-5-[4-(difluoromethoxy)phenyl]-5-(3-{[(2-furylmethyl)-amino]methyl}phenyl)-3-methyl-3,5-dihydro-4H-imidazol-4-one;

2-amino-5-[4-(difluoromethoxy)phenyl]-3-methyl-5-{3-[(propylamino)-methyl]phenyl}-3,5-dihydro-4H-imidazol-4-one;

2-amino-5-[4-(difluoromethoxy)phenyl]-5-{3-[(ethylamino)methyl]phenyl}-3-methyl-3,5-dihydro-4H-imidazol-4-one;

2-amino-5-[4-(difluoromethoxy)phenyl]-5-{3-[(dimethylamino)-methyl]phenyl}-3-methyl-3,5-dihydro-4H-imidazol-4-one;

2-Amino-5-(4-difluoromethoxy-phenyl)-5-[3-(isopropylamino-methyl)-phenyl]-3-methyl-3,5-dihydro-imidazol-4-one;

methyl[3-(3-{2-amino-4-[4-(difluoromethoxy)phenyl]-1-methyl-5-oxo-4,5-dihydro-1H-imidazol-4-yl}phenyl)-1-methoxycyclobutyl]acetate;

methyl[3-(3-{2-amino-4-[4-(difluoromethoxy)phenyl]-1-methyl-5-oxo-4,5-dihydro-1H-imidazol-4-yl}phenyl)cyclobutylidene]acetate;

2-amino-5-[3-(5-chloropent-1-yn-1-yl)-4-fluorophenyl]-5-[4-(difluoromethoxy)phenyl]-3-methyl-3,5-dihydro-4H-imidazol-4-one;

2-amino-5-[4-(difluoromethoxy)phenyl]-5-[4-fluoro-3-(5-fluoropent-1-yn-1-yl)phenyl]-3-methyl-3,5-dihydro-4H-imidazol-4-one;

2-Amino-5-(4-difluoromethoxy-phenyl)-3-methyl-5-o-tolyl-3,5-dihydro-imidazol-4-one;

2-Amino-5-(4-difluoromethoxy-phenyl)-5-(4-fluoro-3-fluoromethyl-phenyl)-3-methyl-3,5-dihydro-imidazol-4-one;

5-[2-Amino-4-(4-difluoromethoxy-phenyl)-1-methyl-5-oxo-4,5-dihydro-1H-imidazol-4-yl]-2-methoxy-benzonitrile;

4-{5-[2-Amino-4-(4-difluoromethoxy-phenyl)-1-methyl-5-oxo-4,5-dihydro-1H-imidazol-4-yl]-2-fluoro-phenyl}-butyronitrile;

2-Amino-5-(4-difluoromethoxy-phenyl)-5-[4-fluoro-3-(1-fluoro-pent-4-enyl)-phenyl]-3-methyl-3,5-dihydro-imidazol-4-one;

2-Amino-5-(4-difluoromethoxy-phenyl)-5-[3-(1-fluoro-pent-4-enyl)-phenyl]-3-methyl-3,5-dihydro-imidazol-4-one;

5-(3-{(4S)-2-amino-4-[4-(difluoromethoxy)phenyl]-1-methyl-5-oxo-4,5-dihydro-1H-imidazol-4-yl}phenyl)pentanenitrile;

5-(3-{(4R)-2-amino-4-[4-(difluoromethoxy)phenyl]-1-methyl-5-oxo-4,5-dihydro-1H-imidazol-4-yl}phenyl)pentanenitrile;

(R)-2-amino-4-(4-(difluoromethoxy)phenyl)-1-methyl-4-(3-(pent-4-enyloxy)phenyl)-1H-imidazol-5(4H)-one;

(R)-2-amino-4-(4-(difluoromethoxy)phenyl)-1-methyl-4-(3-((R)-pent-4-en-2-yloxy)phenyl)-1H-imidazol-5(4H)-one;

(R)-2-amino-4-(4-(difluoromethoxy)phenyl)-1-methyl-4-(3-((S)-pent-4-en-2-yloxy)phenyl)-1H-imidazol-5(4H)-one;

(4R)-2-amino-4-(4-(difluoromethoxy)phenyl)-1-methyl-4-(3-(2-methylbut-3-enyloxy)phenyl)-1H-imidazol-5(4H)-one;

(R)-2-amino-4-(4-(difluoromethoxy)phenyl)-1-methyl-4-(3-(3-methylbut-3-enyloxy)phenyl)-1H-imidazol-5(4H)-one;

(R)-4-(3-(allyloxy)phenyl)-2-amino-4-(4-(difluoromethoxy)phenyl)-1-methyl-1H-imidazol-5(4H)-one;

2-amino-5-[3-(but-3-en-1-yloxy)phenyl]-5-[4-(difluoromethoxy)phenyl]-3-methyl-3,5-dihydro-4H-imidazol-4-one;

(5S)-2-Amino-5-[4-(difluoromethoxy)phenyl]-5-(4-fluoro-3-prop-1-yn-1-ylphenyl)-3-methyl-3,5-dihydro-4H-imidazol-4-one;

(5R)-2-Amino-5-[4-(difluoromethoxy)phenyl]-5-(4-fluoro-3-prop-1-yn-1-ylphenyl)-3-methyl-3,5-dihydro-4H-imidazol-4-one;

2-amino-5-[4-(difluoromethoxy)phenyl]-3-methyl-5-(3-prop-1-yn-1-ylphenyl)-3,5-dihydro-4H-imidazol-4-one;

(5S)-2-Amino-5-[3-(cyclopropylethynyl)phenyl]-5-[4-(difluoromethoxy)phenyl]-3-methyl-3,5-dihydro-4H-imidazol-4-one;

(5R)-2-Amino-5-[3-(cyclopropylethynyl)phenyl]-5-[4-(difluoromethoxy)-phenyl]-3-methyl-3,5-dihydro-4H-imidazol-4-one;

(5R)-2-Amino-5-[3-(cyclopropylethynyl)-4-fluorophenyl]-5-[4-(difluoromethoxy)phenyl]-3-methyl-3,5-dihydro-4H-imidazol-4-one;

(5S)-2-Amino-5-[3-(cyclopropylethynyl)-4-fluorophenyl]-5-[4-(difluoromethoxy)phenyl]-3-methyl-3,5-dihydro-4H-imidazol-4-one;

methyl[3-(3-{2-amino-4-[4(difluoromethoxy)phenyl]-1-methyl-5-oxo-4,5-dihydro-1H-imidazol-4-yl}phenyl)cyclobutylidene]acetate;

ethyl[3-(3-{2-amino-4-[4-(difluoromethoxy)phenyl]-1-methyl-5-oxo-4,5-dihydro1H-imidazol-4-yl}phenyl)cyclobutylidene]acetate;

methyl[3-(3-{2-amino-4[4-(difluoromethoxy)phenyl]-1-methyl-5-oxo-4,5-dihydro-1H-imidazol-4-yl}phenyl)cyclobutylidene]acetate;

methyl[3-(3-{2-amino-4-[4-(difluoromethoxy)phenyl]-1-methyl-5-oxo-4,5-dihydro1H-imidazol-4-yl}phenyl)-1-methoxycyclobutyl]acetate;

2-amino-5-[4-(difluoromethoxy)phenyl]-5-{3-[3-(2-hydroxyethylidene)cyclobutyl]phenyl}-3-methyl-3,5-dihydro-4H-imidazol-4-one;

2-amino-5-[4-(difluoromethoxy)phenyl]-5-[3-(1-fluorobut-3-en-1-yl)phenyl]-3-methyl-3,5-dihydro-4H-imidazol-4-one;

2-amino-5-[4-(difluoromethoxy)phenyl]-5-{3-[3-(2-fluoroethyl)cyclobutyl]phenyl}-3-methyl-3,5-dihydro-4H-imidazol-4-one;

2-amino-5-[4-(difluoromethoxy)phenyl]-5-{3-[3-(2-methoxyethyl)cyclobutyl]phenyl}-3-methyl-3,5-dihydro-4H-imidazol-4-one;

2-amino-5-(3-anilinophenyl)-5-[4-(difluoromethoxy)phenyl]-3-methyl-3,5-dihydro-4H-imidazol-4-one;

2-amino-5-[4-(difluoromethoxy)phenyl]-5-{3-[(isopropylamino)methyl]phenyl}-3-methyl-3,5-dihydro-4H-imidazol-4-one;

2-amino-5-[4-(difluoromethoxy)phenyl]-5-{3-[(dimethylamino)methyl]phenyl}-3-methyl-3,5-dihydro-4H-imidazol-4-one;

2-amino-5-[4-(difluoromethoxy)phenyl]-3-methyl-5-{3-[(ethylamino)methyl]phenyl}-3,5-dihydro-4H-imidazol-4-one;

2-amino-5-[4-(difluoromethoxy)phenyl]-3-methyl-5-{3-[(propylamino)methyl]phenyl}-3,5-dihydro-4H-imidazol-4-one;

2-amino-5-{3-[(butylamino)methyl]phenyl}-5-[4-(difluoromethoxy)phenyl]-3-methyl-3,5-dihydro-4H-imidazol-4-one;

2-amino-5-[4-(difluoromethoxy)phenyl]-3-methyl-5-[3-(pyrrolidin-1-ylmethyl)phenyl]-3,5-dihydro-4H-imidazol-4-one;

2-amino-5,5-bis[4-(difluoromethoxy)phenyl]-3-methyl-3,5-dihydro-4H-imidazol-4-one;

2-amino-5-[4-(difluoromethoxy)phenyl]-5-(3-{[(2-furylmethyl)amino]methyl}phenyl)-3-methyl-3,5-dihydro-4H-imidazol-4-one;

2-amino-5-(3-cyclopropylphenyl)-5-[4-(difluoromethoxy)phenyl]-3-methyl-3,5-dihydro-4H-imidazol-4-one;

2-amino-5-[4-(difluoromethoxy)phenyl]-5-{3-[(1E)-3-methoxy-1-methylprop-1-en-1-yl]phenyl}-3-methyl-3,5-dihydro-4H-imidazol-4-one;

2-amino-5-[4-(difluoromethoxy)phenyl]-5-{3-[(1E)-3-ethoxy-1-methylprop-1-en-1-yl]phenyl}-3-methyl-3,5-dihydro-4H-imidazol-4-one;

2-amino-5-[4-(difluoromethoxy)phenyl]-3-methyl-5-{3-[(1S)-1-methylbut-3-en-1-yl]phenyl}-3,5-dihydro-4H-imidazol-4-one;

2-amino-5-[4-(difluoromethoxy)phenyl]-5-[3-(3-methoxy-1-methylpropyl)phenyl]-3-methyl-3,5-dihydro-4H-imidazol-4-one;

2-amino-5-[4-(difluoromethoxy)phenyl]-5-[3-(3-ethoxy-1-methylpropyl)phenyl]-3-methyl-3,5-dihydro-4H-imidazol-4-one;

2-amino-5-[4-(difluoromethoxy)phenyl]-3-methyl-5-{3-[(1R)-1-methylbut-3-en-1-yl]phenyl}-3,5-dihydro-4H-imidazol-4-one;

2-amino-5-[4-(difluoromethoxy)phenyl]-3-methyl-5-(2-methyl-1-benzofuran-5-yl)-3,5-dihydro-4H-imidazol-4-one;

2-amino-5-[4-(difluoromethoxy)phenyl]-3-methyl-5-(2-methyl-1-benzofuran-5-yl)-3,5-dihydro-4H-imidazol-4-one;

2-amino-5-(3-aminophenyl)-5-[4-(difluoromethoxy)phenyl]-3-methyl-3,5-dihydro-4H-imidazol-4-one;

N-(3-{2-amino-4-[4-(difluoromethoxy)phenyl]-1-methyl-5-oxo-4,5-dihydro-1H-imidazol-4-yl}phenyl)acetamide;

N-(3-{2-amino-4-[4-(difluoromethoxy)phenyl]-1-methyl-5-oxo-4,5-dihydro-1H-imidazol-4-yl}phenyl)propanamide;

N-(3-{2-amino-4-[4-(difluoromethoxy)phenyl]-1-methyl-5-oxo-4,5-dihydro-1H-imidazol-4-yl}phenyl)butanamide;

N-(3-{2-amino-4-[4-(difluoromethoxy)phenyl]-1-methyl-5-oxo-4,5-dihydro-1H-imidazol-4-yl}phenyl)pentanamide;

N-(3-{2-amino-4-[4-(difluoromethoxy)phenyl]-1-methyl-5-oxo-4,5-dihydro-1H-imidazol-4-yl}phenyl)-3-chloropropanamide;

N-(3-{2-amino-4-[4-(difluoromethoxy)phenyl]-1-methyl-5-oxo-4,5-dihydro-1H-imidazol-4-yl}phenyl)-2,2,2-trifluoroacetamide;

N-(3-{2-amino-4-[4-(difluoromethoxy)phenyl]-1-methyl-5-oxo-4,5-dihydro-1H-imidazol-4-yl}phenyl)-3-methylbutanamide;

N-(3-{2-amino-4-[4-(difluoromethoxy)phenyl]-1-methyl-5-oxo-4,5-dihydro-1H-imidazol-4-yl}phenyl)-2-methylpropanamide;

N-(3-{2-amino-4-[4-(difluoromethoxy)phenyl]-1-methyl-5-oxo-4,5-dihydro-1H-imidazol-4-yl}phenyl)cyclopropanecarboxamide;

N-(3-{2-amino-4-[4-(difluoromethoxy)phenyl]-1-methyl-5-oxo-4,5-dihydro-1H-imidazol-4-yl}phenyl)cyclobutanecarboxamide;

(2E)-N-(3-{2-amino-4-[4-(difluoromethoxy)phenyl]-1-methyl-5-oxo-4,5-dihydro-1H-imidazol-4-yl}phenyl)but-2-enamide;

N-(3-(2-amino-4-(4-(difluoromethoxy)phenyl)-1-methyl-5-oxo-4,5-dihydro-1H-imidazol-4-yl)phenyl)-3-methylbut-2-enamide;

(2E)-N-(3-{2-amino-4-[4-(difluoromethoxy)phenyl]-1-methyl-5-oxo-4,5-dihydro-1H-imidazol-4-yl}phenyl)-3-phenylacrylamide;

N-(3-{2-amino-4-[4-(difluoromethoxy)phenyl]-1-methyl-5-oxo-4,5-dihydro-1H-imidazol-4-yl}phenyl)-2-furamide;

N-(3-{2-amino-4-[4-(difluoromethoxy)phenyl]-1-methyl-5-oxo-4,5-dihydro-1H-imidazol-4-yl}phenyl)-2-(benzyloxy)acetamide;

2-amino-5-[4-(difluoromethoxy)phenyl]-3-methyl-5-[3-(propylamino)phenyl]-3,5-dihydro-4H-imidazol-4-one;

2-amino-5-[3-(butylamino)phenyl]-5-[4-(difluoromethoxy)phenyl]-3-methyl-3,5-dihydro-4H-imidazol-4-one;

2-amino-5-[4-(difluoromethoxy)phenyl]-5-[3-(isobutylamino)phenyl]-3-methyl-3,5-dihydro-4H-imidazol-4-one;

2-amino-5-[4-(difluoromethoxy)phenyl]-5-[3-(isopropylamino)phenyl]-3-methyl-3,5-dihydro-4H-imidazol-4-one;

2-amino-5-[3-(cyclopentylamino)phenyl]-5-[4-(difluoromethoxy)phenyl]-3-methyl-3,5-dihydro-4H-imidazol-4-one;

2-amino-5-[3-(cyclohexylamino)phenyl]-5-[4-(difluoromethoxy)phenyl]-3-methyl-3,5-dihydro-4H-imidazol-4-one;

2-amino-5-{3-[(2E)-but-2-en-1-ylamino]phenyl}-5-[4-(difluoromethoxy)phenyl]-3-methyl-3,5-dihydro-4H-imidazol-4-one;

2-amino-5-[3-(cyclobutylamino)phenyl]-5-[4-(difluoromethoxy)phenyl]-3-methyl-3,5-dihydro-4H-imidazol-4-one;

2-amino-5-[4-(difluoromethoxy)phenyl]-5-{3-[(2-furylmethyl)amino]phenyl}-3-methyl-3,5-dihydro-4H-imidazol-4-one;

N-(3-{2-amino-4-[4-(difluoromethoxy)phenyl]-1-methyl-5-oxo-4,5-dihydro-1H-imidazol-4-yl}phenyl)benzamide;

N-(3-{2-amino-4-[4-(difluoromethoxy)phenyl]-1-methyl-5-oxo-4,5-dihydro-1H-imidazol-4-yl}phenyl)-2,2,2-trichloroacetamide;

N-(3-{2-amino-4-[4-(difluoromethoxy)phenyl]-1-methyl-5-oxo-4,5-dihydro-1H-imidazol-4-yl}phenyl)-1-phenyl-5-(trifluoromethyl)-1H-pyrazole-4-carboxamide;

N-(3-{2-amino-4-[4-(difluoromethoxy)phenyl]-1-methyl-5-oxo-4,5-dihydro-1H-imidazol-4-yl}phenyl)-1-(4-chlorophenyl)-5-(trifluoromethyl)-1H-pyrazole-4-carboxamide;

N-(3-{2-amino-4-[4-(difluoromethoxy)phenyl]-1-methyl-5-oxo-4,5-dihydro-1H-imidazol-4-yl}phenyl)-3-bromothiophene-2-carboxamide;

N-(3-{2-amino-4-[4-(difluoromethoxy)phenyl]-1-methyl-5-oxo-4,5-dihydro-1H-imidazol-4-yl}phenyl)-1-benzofuran-3-carboxamide;

N-(3-{2-amino-4-[4-(difluoromethoxy)phenyl]-1-methyl-5-oxo-4,5-dihydro-1H-imidazol-4-yl}phenyl)-2,3-dihydro-1-benzofuran-5-carboxamide;

N-(3-{2-amino-4-[4-(difluoromethoxy)phenyl]-1-methyl-5-oxo-4,5-dihydro-1H-imidazol-4-yl}phenyl)thiophene-2-carboxamide;

(5S)-2-amino-5-[4-(difluoromethoxy)phenyl]-3-methyl-5-[3-(3-methylbut-1-yn-1-yl)phenyl]-3,5-dihydro-4H-imidazol-4-one;

2-amino-5-[3-(cyclopropylethynyl)phenyl]-5-[4-(difluoromethoxy)phenyl]-3-methyl-3,5-dihydro-4H-imidazol-4-one;

(5S)-2-amino-5-[3-(cyclopropylethynyl)phenyl]-5-[4-(difluoromethoxy)phenyl]-3-methyl-3,5-dihydro-4H-imidazol-4-one;

(5R)-2-amino-5-[3-(cyclopropylethynyl)phenyl]-5-[4-(difluoromethoxy)phenyl]-3-methyl-3,5-dihydro-4H-imidazol-4-one;

2-amino-5-[3-(cyclopropylethynyl)-4-fluorophenyl]-5-[4-(difluoromethoxy)phenyl]-3-methyl-3,5-dihydro-4H-imidazol-4-one;

(5R)-2-amino-5-[3-(cyclopropylethynyl)-4-fluorophenyl]-5-[4-(difluoromethoxy)phenyl]-3-methyl-3,5-dihydro-4H-imidazol-4-one;

(5S)-2-amino-5-[3-(cyclopropylethynyl)-4-fluorophenyl]-5-[4-(difluoromethoxy)phenyl]-3-methyl-3,5-dihydro-4H-imidazol-4-one;

(5S)-2-amino-5-[3-(cyclopropylethynyl)-4-fluorophenyl]-5-[4-(difluoromethoxy)phenyl]-3-methyl-3,5-dihydro-4H-imidazol-4-one;

2-amino-5-[4-(difluoromethoxy)phenyl]-5-{4-fluoro-3-[(1E)-prop-1-en-1-yl]phenyl}-3-methyl-3,5-dihydro-4H-imidazol-4-one;

2-amino-5-[4-(difluoromethoxy)phenyl]-5-(4-fluoro-3-prop-1-yn-1-ylphenyl)-3-methyl-3,5-dihydro-4H-imidazol-4-one;

(5R)-2-amino-5-[4-(difluoromethoxy)phenyl]-5-(4-fluoro-3-prop-1-yn-1-ylphenyl)-3-methyl-3,5-dihydro-4H-imidazol-4-one;

(5S)-2-amino-5-[4-(difluoromethoxy)phenyl]-5-(4-fluoro-3-prop-1-yn-1-ylphenyl)-3-methyl-3,5-dihydro-4H-imidazol-4-one;

(5R)-2-amino-5-[4-(difluoromethoxy)phenyl]-5-{4-fluoro-3-[(1E)-prop-1-en-1-yl]phenyl}-3-methyl-3,5-dihydro-4H-imidazol-4-one;

(5S)-2-amino-5-[4-(difluoromethoxy)phenyl]-5-{4-fluoro-3-[(1E)-prop-1-en-1-yl]phenyl}-3-methyl-3,5-dihydro-4H-imidazol-4-one;

(5S)-2-amino-5-[4-(difluoromethoxy)phenyl]-5-{4-fluoro-3-[(1Z)-prop-1-en-1-yl]phenyl}-3-methyl-3,5-dihydro-4H-imidazol-4-one;

2-amino-5-[4-(difluoromethoxy)phenyl]-5-{4-fluoro-3-[prop-1-en-1-yl]phenyl}-3-methyl-3,5-dihydro-4H-imidazol-4-one;

2-amino-5-[4-(difluoromethoxy)phenyl]-5-{4-fluoro-3-[(1Z)-prop-1-en-1-yl]phenyl}-3-methyl-3,5-dihydro-4H-imidazol-4-one;

2-amino-5-[4-(difluoromethoxy)phenyl]-5-{4-fluoro-3-[(1E)-prop-1-en-1-yl]phenyl}-3-methyl-3,5-dihydro-4H-imidazol-4-one;

(5R)-2-amino-5-[4-(difluoromethoxy)phenyl]-5-{4-fluoro-3-[(1Z)-prop-1-en-1-yl]phenyl}-3-methyl-3,5-dihydro-4H-imidazol-4-one;

2-amino-5-{3-[(Z)-2-cyclopropyl-1-fluorovinyl]phenyl}-5-[4-(difluoromethoxy)phenyl]-3-methyl-3,5-dihydro-4H-imidazol-4-one;

2-amino-5-{3-[(E)-2-cyclopropyl-1-fluorovinyl]phenyl}-5-[4-(difluoromethoxy)phenyl]-3-methyl-3,5-dihydro-4H-imidazol-4-one;

5-(3-{(4S)-2-amino-4-[4-(difluoromethoxy)phenyl]-1-methyl-5-oxo-4,5-dihydro-1H-imidazol-4-yl}phenyl)pentanenitrile;

5-(3-{(4R)-2-amino-4-[4-(difluoromethoxy)phenyl]-1-methyl-5-oxo-4,5-dihydro-1H-imidazol-4-yl}phenyl)pentanenitrile;

2-amino-5-[4-(difluoromethoxy)phenyl]-5-[3-(1-fluoropent-4-en-1-yl)phenyl]-3-methyl-3,5-dihydro-4H-imidazol-4-one;

2-amino-5-[4-(difluoromethoxy)phenyl]-5-[4-fluoro-3-(1-fluoropent-4-en-1-yl)phenyl]-3-methyl-3,5-dihydro-4H-imidazol-4-one;

4-(5-{2-amino-4-[4-(difluoromethoxy)phenyl]-1-methyl-5-oxo-4,5-dihydro-1H-imidazol-4-yl}-2-fluorophenyl)butanenitrile;

2-amino-5-[4-(difluoromethoxy)phenyl]-5-(4-fluoro-3-methylphenyl)-3-methyl-3,5-dihydro-4H-imidazol-4-one;

5-{2-amino-4-[4-(difluoromethoxy)phenyl]-1-methyl-5-oxo-4,5-dihydro-1H-imidazol-4-yl}-2-methoxybenzonitrile;

2-amino-5-[4-(difluoromethoxy)phenyl]-5-[4-fluoro-3-(fluoromethyl)phenyl]-3-methyl-3,5-dihydro-4H-imidazol-4-one;
2-amino-5-[4-(difluoromethoxy)phenyl]-3-methyl-5-(2-methylphenyl)-3,5-dihydro-4H-imidazol-4-one;
2-amino-5-[4-(difluoromethoxy)phenyl]-5-[4-fluoro-3-(5-fluoropent-1-yn-1-yl)phenyl]-3-methyl-3,5-dihydro-4H-imidazol-4-one;
2-amino-5-[3-(5-chloropent-1-yn-1-yl)-4-fluorophenyl]-5-[4-(difluoromethoxy)phenyl]-3-methyl-3,5-dihydro-4H-imidazol-4-one;
2-amino-5-[4-(difluoromethoxy)phenyl]-3-methyl-5-(3-methylphenyl)-3,5-dihydro-4H-imidazol-4-one;
2-amino-5-[4-(difluoromethoxy)phenyl]-5-[3-(4-ethoxybut-1-yn-1-yl)phenyl]-3-methyl-3,5-dihydro-4H-imidazol-4-one;
2-amino-5-[4-(difluoromethoxy)phenyl]-5-[3-(3-hydroxypent-4-yn-1-yl)phenyl]-3-methyl-3,5-dihydro-4H-imidazol-4-one;
2-amino-5-[4-(difluoromethoxy)phenyl]-5-(3-hex-5-en-1-ylphenyl)-3-methyl-3,5-dihydro-4H-imidazol-4-one;
2-amino-5-[4-(difluoromethoxy)phenyl]-5-{3-[(1E)-4-fluoro-1-methylbut-1-en-1-yl]phenyl}-3-methyl-3,5-dihydro-4H-imidazol-4-one;
2-amino-5-[4-(difluoromethoxy)phenyl]-5-{3-[(1E)-3,3-difluoroprop-1-en-1-yl]phenyl}-3-methyl-3,5-dihydro-4H-imidazol-4-one;
2-amino-5-[4-(difluoromethoxy)phenyl]-5-{3-[(1E)-3-fluoroprop-1-en-1-yl]phenyl}-3-methyl-3,5-dihydro-4H-imidazol-4-one;
2-amino-5-[4-(difluoromethoxy)phenyl]-5-(3-hex-5-en-1-ylphenyl)-3-methyl-3,5-dihydro-4H-imidazol-4-one;
2-amino-5-[4-(difluoromethoxy)phenyl]-5-(3-hexylphenyl)-3-methyl-3,5-dihydro-4H-imidazol-4-one;
2-amino-5-[4-(difluoromethoxy)phenyl]-5-(3-ethylphenyl)-3-methyl-3,5-dihydro-4H-imidazol-4-one;
(5S)-2-amino-5-{3-[(4,4-difluorobut-3-en-1-yl)oxy]phenyl}-5-[4-(difluoromethoxy)phenyl]-3-methyl-3,5-dihydro-4H-imidazol-4-one;
(5S)-2-amino-5-{3-[(4,4-difluorobut-3-en-1-yl)oxy]-4-fluorophenyl}-5-[4-(difluoromethoxy)phenyl]-3-methyl-3,5-dihydro-4H-imidazol-4-one;
(5R)-2-amino-5-{3-[(4,4-difluorobut-3-en-1-yl)oxy]-4-fluorophenyl}-5-[4-(difluoromethoxy)phenyl]-3-methyl-3,5-dihydro-4H-imidazol-4-one;
(5R)-2-amino-5-[3-(cyclopropylmethoxy)phenyl]-5-[4-(difluoromethoxy)phenyl]-3-methyl-3,5-dihydro-4H-imidazol-4-one;
(5S)-2-amino-5-[3-(cyclopropylmethoxy)phenyl]-5-[4-(difluoromethoxy)phenyl]-3-methyl-3,5-dihydro-4H-imidazol-4-one;
(R,E)-2-amino-4-(4-(difluoromethoxy)phenyl)-4-(3-(6-methoxyhex-1-enyl)phenyl)-1-methyl-1H-imidazol-5(4H)-one;
(5S)-2-amino-5-[3-(2,2-difluoroethoxy)phenyl]-5-[4-(difluoromethoxy)phenyl]-3-methyl-3,5-dihydro-4H-imidazol-4-one;
(5R)-2-amino-5-[3-(2,2-difluoroethoxy)phenyl]-5-[4-(difluoromethoxy)phenyl]-3-methyl-3,5-dihydro-4H-imidazol-4-one;
(5S)-2-amino-5-[4-(difluoromethoxy)phenyl]-5-{3-[(1E)-4-methoxybut-1-en-1-yl]phenyl}-3-methyl-3,5-dihydro-4H-imidazol-4-one;
(5R)-2-amino-5-[4-(difluoromethoxy)phenyl]-5-{3-[(1E)-4-methoxybut-1-en-1-yl]phenyl}-3-methyl-3,5-dihydro-4H-imidazol-4-one;
(5S)-2-amino-5-[4-(difluoromethoxy)phenyl]-5-{3-[(1E)-3-methoxyprop-1-en-1-yl]phenyl}-3-methyl-3,5-dihydro-4H-imidazol-4-one;
(5R)-2-amino-5-[4-(difluoromethoxy)phenyl]-5-{3-[(1E)-3-methoxyprop-1-en-1-yl]phenyl}-3-methyl-3,5-dihydro-4H-imidazol-4-one;
(5R)-2-amino-5-[4-(difluoromethoxy)phenyl]-3-methyl-5-[3-(pent-4-en-1-yloxy)phenyl]-3,5-dihydro-4H-imidazol-4-one;
(5R)-2-amino-5-[4-(difluoromethoxy)phenyl]-3-methyl-5-(3-{[(1S)-1-methylbut-3-en-1-yl]oxy}phenyl)-3,5-dihydro-4H-imidazol-4-one;
(5R)-2-amino-5-[4-(difluoromethoxy)phenyl]-3-methyl-5-(3-{[(1R)-1-methylbut-3-en-1-yl]oxy}phenyl)-3,5-dihydro-4H-imidazol-4-one;
(5R)-2-amino-5-[4-(difluoromethoxy)phenyl]-3-methyl-5-[3-[(2-methylbut-3-en-1-yl)oxy]phenyl]-3,5-dihydro-4H-imidazol-4-one;
(5R)-2-amino-5-[4-(difluoromethoxy)phenyl]-3-methyl-5-[3-[(3-methylbut-3-en-1-yl)oxy]phenyl]-3,5-dihydro-4H-imidazol-4-one;
(5R)-5-[3-(allyloxy)phenyl]-2-amino-5-[4-(difluoromethoxy)phenyl]-3-methyl-3,5-dihydro-4H-imidazol-4-one;
2-amino-5-[4-(difluoromethoxy)phenyl]-5-(4-fluoro-3-isopropoxyphenyl)-3-methyl-3,5-dihydro-4H-imidazol-4-one;
2-amino-5-[4-(difluoromethoxy)phenyl]-5-[4-fluoro-3-(2-fluoroethoxy)phenyl]-3-methyl-3,5-dihydro-4H-imidazol-4-one;
2-amino-5-[4-(difluoromethoxy)phenyl]-5-[4-fluoro-3-(3-methylbut-1-yn-1-yl)phenyl]-3-methyl-3,5-dihydro-4H-imidazol-4-one;
(5R)-2-amino-5-[4-(difluoromethoxy)phenyl]-5-{3-[(1E)-5-methoxypent-1-en-1-yl]phenyl}-3-methyl-3,5-dihydro-4H-imidazol-4-one;
(5R)-2-amino-5-[4-(difluoromethoxy)phenyl]-5-{4-fluoro-3-[(1E)-4-fluorobut-1-en-1-yl]phenyl}-3-methyl-3,5-dihydro-4H-imidazol-4-one; and
(5S)-2-amino-5-[4-(difluoromethoxy)phenyl]-5-{4-fluoro-3-[(1E)-4-fluorobut-1-en-1-yl]phenyl}-3-methyl-3,5-dihydro-4H-imidazol-4-one; or
a tautomer thereof; or
a pharmaceutically acceptable salt thereof.

In another aspect of the invention, the compound is selected from the group consisting of:
2-amino-5-[4-(difluoromethoxy)phenyl]-5-(4-fluoro-3-morpholin-4-ylphenyl)-3-methyl-3,5-dihydro-4H-imidazol-4-one;
2-amino-5-(3-but-3-en-1-yn-1-yl-4-fluorophenyl)-5-[4-(difluoromethoxy)phenyl]-3-methyl-3,5-dihydro-4H-imidazol-4-one;
2-amino-5-[4-(difluoromethoxy)phenyl]-5-[3-(2-furylmethyl)phenyl]-3-methyl-3,5-dihydro-4H-imidazol-4-one;
2-amino-5-[4-(difluoromethoxy)phenyl]-5-[3-(3,3-difluoropropoxy)phenyl]-3-methyl-3,5-dihydro-4H-imidazol-4-one;
(5R)-2-amino-5-[4-(difluoromethoxy)phenyl]-5-[3-(3,3-difluoropropoxy)phenyl]-3-methyl-3,5-dihydro-4H-imidazol- (5S)-2-amino-5-[4-(difluoromethoxy)phenyl]-5-[3-(3,3-difluoropropoxy)phenyl]-3-methyl-3,5-dihydro-4H-imidazol-4-one;

2-amino-5-[4-(difluoromethoxy)phenyl]-5-[3-(3,3-difluoropropoxy)-4-fluorophenyl]-3-methyl-3,5-dihydro-4H-imidazol-4-one;

(5S)-2-amino-5-[4-(difluoromethoxy)phenyl]-5-[3-(3,3-difluoropropoxy)-4-fluorophenyl]-3-methyl-3,5-dihydro-4H-imidazol-4-one;

(5R)-2-amino-5-[4-(difluoromethoxy)phenyl]-5-[3-(3,3-difluoropropoxy)-4-fluorophenyl]-3-methyl-3,5-dihydro-4H-imidazol-4-one;

2-amino-5-[4-(difluoromethoxy)phenyl]-3-methyl-5-(3-methylphenyl)-3,5-dihydro-4H-imidazol-4-one;

2-amino-5-[4-(difluoromethoxy)phenyl]-5-[3-(4-ethoxybut-1-yn-1-yl)phenyl]-3-methyl-3,5-dihydro-4H-imidazol-4-one;

2-amino-5-[4-(difluoromethoxy)phenyl]-5-[3-(3-fluoroprop-1-yn-1-yl)phenyl]-3-methyl-3,5-dihydro-4H-imidazol-4-one;

2-amino-5-[4-(difluoromethoxy)phenyl]-5-[3-(4-fluorobut-1-yn-1-yl)phenyl]-3-methyl-3,5-dihydro-4H-imidazol-4-one;

2-amino-5-[4-(difluoromethoxy)phenyl]-5-[4-fluoro-3-(3-fluoroprop-1-yn-1-yl)phenyl]-3-methyl-3,5-dihydro-4H-imidazol-4-one;

(5R)-2-amino-5-[4-(difluoromethoxy)phenyl]-5-[3-(3-fluoroprop-1-yn-1-yl)phenyl]-3-methyl-3,5-dihydro-4H-imidazol-4-one;

(5S)-2-amino-5-[4-(difluoromethoxy)phenyl]-5-[3-(3-fluoroprop-1-yn-1-yl)phenyl]-3-methyl-3,5-dihydro-4H-imidazol-4-one;

2-amino-5-[4-(difluoromethoxy)phenyl]-5-[4-fluoro-3-(4-fluorobut-1-yn-1-yl)phenyl]-3-methyl-3,5-dihydro-4H-imidazol-4-one;

(5S)-2-amino-5-[4-(difluoromethoxy)phenyl]-5-[4-fluoro-3-(4-fluorobut-1-yn-1-yl)phenyl]-3-methyl-3,5-dihydro-4H-imidazol-4-one;

(5R)-2-amino-5-[4-(difluoromethoxy)phenyl]-5-[4-fluoro-3-(4-fluorobut-1-yn-1-yl)phenyl]-3-methyl-3,5-dihydro-4H-imidazol-4-one;

(5S)-2-amino-5-[4-(difluoromethoxy)phenyl]-5-[3-(4-fluorobut-1-yn-1-yl)phenyl]-3-methyl-3,5-dihydro-4H-imidazol-4-one;

(5R)-2-amino-5-[4-(difluoromethoxy)phenyl]-5-[3-(4-fluorobut-1-yn-1-yl)phenyl]-3-methyl-3,5-dihydro-4H-imidazol-4-one;

(5R)-2-amino-5-[4-(difluoromethoxy)phenyl]-5-[4-fluoro-3-(3-fluoroprop-1-yn-1-yl)phenyl]-3-methyl-3,5-dihydro-4H-imidazol-4-one; and (5S)-2-amino-5-[4-(difluoromethoxy)phenyl]-5-[4-fluoro-3-(3-fluoroprop-1-yn-1-yl)phenyl]-3-methyl-3,5-dihydro-4H-imidazol-4-one; or a tautomer thereof; or a pharmaceutically acceptable salt thereof.

In another aspect of the invention, the compound is as shown in one of the following tables (I or J):

X

| Chiral | R | R' |
|---|---|---|
| — | $CH_2CH_3$ | H |
| — | $CH_2CH_2CH_3$ | H |
| — | $CH_2CH_2CH_2CH_3$ | H |
| — | $CH_2CH_2Cl$ | H |
| — | $CF_3$ | H |
| — | $CH_2CH(CH_3)_2$ | H |
| — | $CH_2(CH_3)_2$ | H |
| — | cyclopropyl | H |
| — | cyclobutyl | H |
| — | $CH_3CH{=}CH$ | H |
| — | $(CH_3)_2C{=}CH$ | H |
| — | $PhCH{=}CH$ | H |
| — | Furan-2-yl | H |
| — | $PhCH_2OCH_2$ | H |
| — | Ph | H |
| — | $Cl_3C$ | H |
| — | 1-Ph-5-$CF_3$-pyrazole-4-yl | H |
| — | 1-(4-Cl-Ph)-5-$CF_3$-pyrazole-4-yl | H |
| — | 3-bromo-thiophen-2-yl | H |
| — | Benzofuran-3-yl | H |
| — | Benzofuran-5-yl | H |
| — | Thiophen-2-yl | H |

Y

| Chiral | R | R' |
|---|---|---|
| — | $CH_2CH_2CH_3$ | H |
| — | $CH_2CH_2CH_2CH_3$ | H |
| — | $(CH_3)_2CHCH_2$ | H |
| — | Isopropyl | H |
| — | Cyclopentyl | H |
| — | cyclohexyl | H |
| — | $CH_3CH{=}CH$ | H |
| — | cycobutyl | H |
| — | Furan-2-yl-$CH_2$ | H | or a tautomer thereof; or a pharmaceutically acceptable salt thereof.

In another aspect of the invention, the compound is selected from the group consisting of:

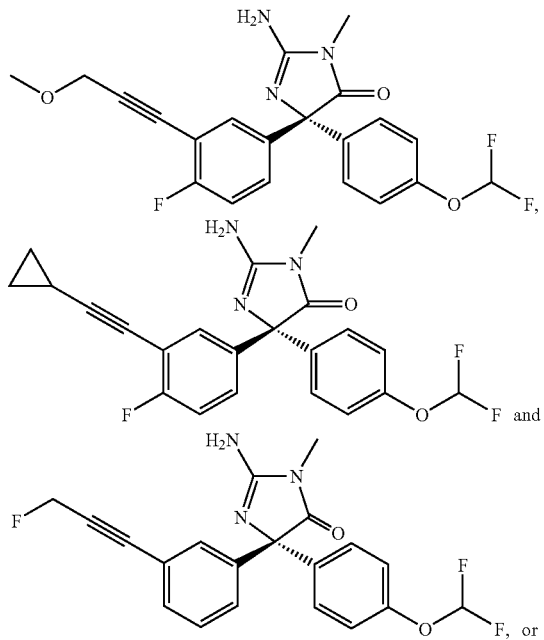

a tautomer thereof; or
a pharmaceutically acceptable salt thereof.

In one embodiment, compounds of formula IXA or IXB are provided wherein $R_{28}$ is halogen and $R_{29}$ is an optionally substituted cycloalkyl group. In one embodiment $R_{28}$ is fluorine. In certain embodiments, the cycloalkyl group is a monocyclic moiety of 3-10 carbon atoms. In certain embodiments, the cycloalkyl group is a monocyclic moiety of 3-5 carbon atoms. In one embodiment the cycloalkyl group is cyclopropyl. In certain embodiments, $R_{30}$, $R_{31}$ and $R_{32}$ are each independently H or an alkyl group. In one embodiment, $R_{30}$ and $R_{31}$ are both H and $R_{32}$ is an alkyl group, e.g., a methyl group. In one embodiment the compound is a compound of formula IXA. In one embodiment the compound is a compound of formula IXB. In one embodiment a composition is provided which includes a mixture of compounds of formula IXA and IXB, e.g., a racemic mixture.

In one embodiment, compounds of formula IXA or IXB are provided wherein $R_{28}$ is H and $R_{29}$ is an optionally substituted cycloalkyl group. In one embodiment $R_{28}$ is fluorine. In certain embodiments, the cycloalkyl group at $R_{29}$ is a monocyclic moiety of 3-10 carbon atoms. In certain embodiments, the cycloalkyl group at $R_{29}$ is a monocyclic moiety of 3-5 carbon atoms. In one embodiment the cycloalkyl group at $R_{29}$ is cyclopropyl. In certain embodiments, $R_{30}$, $R_{31}$ and $R_{32}$ are each independently H or an alkyl group. In one embodiment, $R_{30}$ and $R_{31}$ are both H and $R_{32}$ is an alkyl group, e.g., a methyl group. In one embodiment the compound is a compound of formula IXA. In one embodiment the compound is a compound of formula IXB.

In another embodiment of any of the formulas provided herein, $R_1$ and $R_2$ are H and $R_3$ is methyl.

In one embodiment, compounds of formula IXA or IXB are provided wherein $R_{28}$ is halogen and $R_{29}$ is an optionally substituted alkyl group. In one embodiment $R_{28}$ is fluorine. In certain embodiments, the alkyl group at $R_{29}$ is a straight chain monovalent saturated hydrocarbon moiety of 1-12 carbon atoms. In other embodiments, the alkyl group at $R_{29}$ is a branched chain monovalent saturated hydrocarbon moiety of 1-12 carbon atoms. For example, the alkyl group at $R_{29}$ may be a moiety of 1-5 carbon atoms or 1-3 carbon atoms. In certain embodiments the alkyl group at $R_{29}$ may be a methyl group. In certain embodiments, $R_{30}$, $R_{31}$ and $R_{32}$ are each independently H or an alkyl group. In one embodiment, $R_{30}$ and $R_{31}$ are both H and $R_{32}$ is an alkyl group, e.g., a methyl group. In one embodiment the compound is a compound of formula IXA. In one embodiment the compound is a compound of formula IXB.

It is understood that the claims encompass all possible stereoisomers and prodrugs. Moreover, unless stated otherwise, each alkyl, alkoxy, alkenyl, alkynyl, cycloalkyl, cycloheteroalkyl, aryl or heteroaryl group is contemplated as being optionally substituted.

An optionally substituted moiety may be substituted with one or more substituents. The substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, aryloxy, amino, alkylamino, dialkylamino, formyl, carbonyl, alkoxycarbonyl, carboxyl, alkanoyl, alkylthio, alkylsulfinyl, alkylsulfonyl, carbamoyl, alkylamido, phenyl, phenoxy, benzyl, benzyloxy, cycloalkyl or cycloheteroalkyl groups, preferably halogen atoms, lower alkyl or lower alkoxy groups, wherein 'lower' is from 1 to 4 carbon atoms. In one embodiment the substituent groups may be selected from halo, cyano, hydroxy, alkyl, alkenyl, alkynyl, alkoxy or cycloalkyl. Unless otherwise specified, typically, 0-4 substituents may be present. When any of the foregoing substituents represents or contains an alkyl substituent group, this may be linear or branched and may contain up to 12 carbon atoms, preferably up to 6 carbon atoms, more preferably up to 4 carbon atoms. Substituent groups that have one or more available hydrogen atoms can in turn optionally bear further independently selected substituents, to a maximum of three levels of substitutions. For example, the term "optionally substituted aryl" is intended to mean an aryl group that can optionally have up to four of its hydrogen atoms replaced with substituent groups as defined above (i.e., a first level of substitution), wherein each of the substituent groups attached to the aryl group can optionally have up to four of its hydrogen atoms replaced by substituent groups as defined above (i.e., a second level of substitution), and each of the substituent groups of the second level of substitution can optionally have up to four of its hydrogen atoms replaced by substituent groups as defined above (i.e., a third level of substitution).

As used herein, the term "alkyl" includes both straight chain and branched-chain (unless defined otherwise) monovalent saturated hydrocarbon moieties of 1-12 carbon atoms, preferably 1-6 carbon atoms ($C_1$-$C_6$ alkyl), more preferably 'lower' alkyl of 1-4 carbon atoms. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, and the like. Alkyl groups can be optionally substituted. Suitable alkyl substitutions include, but are not limited to, CN, OH, halogen, alkenyl, alkynyl, cycloalkyl, phenyl, carbamoyl, carbonyl, alkoxy or aryloxy.

As used herein the term "haloalkyl" designates a $C_nH_{2n+1}$ group having from one to $2n+1$ halogen atoms which may be the same or different. Examples of haloalkyl groups include $CF_3$, $CH_2Cl$, $C_2H_3BrCl$, $C_3H_5F_2$, or the like. Similarly, the term haloalkoxy designates an $OC_nH_{2n+1}$ group having from one to 2n+1 halogen atoms which may be the same or different. Preferably the haloalkyl groups are $C_1$-$C_6$ haloalkyl groups.

The term "alkoxyalkyl" as used herein, refers to an alkyl group as hereinbefore defined substituted with at least one $C_1$-$C_4$ alkoxy group or $C_1$-$C_6$ alkoxy group.

The term "alkenyl", as used herein, refers to either a straight chain or branched-chain hydrocarbon moiety containing at least one double bond and having from 2-12 carbon atoms, preferably 2-6 carbon atoms ($C_2$-$C_6$ alkenyl), more preferably 2-4 carbon atoms. Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkenyl moieties include, but are not limited to, chemical groups such as vinyl, 2-propenyl, isopropenyl, crotyl, 2-isopentenyl, butadienyl, 2-(butadienyl), 2,4-pentadienyl, 3-(1,4-pentadienyl), and higher homologs, isomers, or the like. Preferred alkenyl groups are $C_2$-$C_6$ alkenyl.

The term "haloalkenyl" as used herein, designates an alkenyl group as defined hereinabove substituted with one or more halogen atoms which may be the same or different.

The term "alkynyl", as used herein, refers to an alkyl group having one or more triple carbon-carbon bonds. Alkynyl groups preferably contain 2 to 6 carbon atoms ($C_2$-$C_6$ alkynyl). Examples of alkynyl groups include, but are not limited to, ethynyl, propynyl, butynyl, pentynyl, and the like. In some embodiments, alkynyl groups can be substituted with up to four substituent groups, as described hereinabove. Preferred alkynyl groups are $C_2$-$C_6$ alkynyl.

The term "cycloalkyl", as used herein, refers to a monocyclic, bicyclic, tricyclic, fused, bridged, or spiro saturated carbocyclic moiety of 3-10 carbon atoms ($C_3$-$C_{10}$ cycloalkyl). Any suitable ring position of the cycloalkyl moiety may be covalently linked to the defined chemical structure. Examples of cycloalkyl moieties include, but are not limited to, chemical groups such as cyclopropyl, cyclobutyl, cyclopentyl, cyclohexyl, cycloheptyl, norbornyl, adamantyl, spiro[4.5]decanyl, and homologs, isomers, or the like.

The term "cycloheteroalkyl" as used herein designates a 5- to 7-membered cycloalkyl ring system containing 1, 2 or 3 heteroatoms, which may be the same or different, selected from N, O or S, and optionally containing one double bond. Exemplary of the cycloheteroalkyl ring systems included in the term as designated herein are the following rings wherein $X_1$ is NR', O or S, and R' is H or an optional substituent as defined hereinabove.

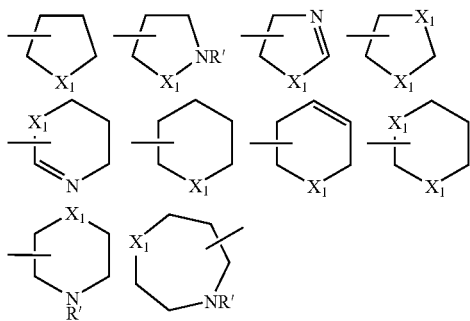

The term "aryl", as used herein, designates an aromatic carbocyclic moiety of up to 20 carbon atoms, e.g. 6-20 carbon atoms, which may be a single ring (monocyclic) or multiple rings (bicyclic, up to three rings) fused together or linked covalently. Examples of aryl moieties include, but are not limited to, chemical groups such as phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like. In some embodiments "aryl" groups can be substituted with from 1-5 substituents. Preferred aryl groups are $C_6$-$C_{10}$ aryl.

The term "heteroaryl" as used herein designates an aromatic heterocyclic ring system, e.g. having from 5-20 ring atoms, which may be a single ring (monocyclic) or multiple rings (bicyclic, up to three rings) fused together or linked covalently. Preferably, heteroaryl is a 5- to 6-membered ring. The rings may contain from one to four hetero atoms selected from nitrogen, oxygen, or sulfur, wherein the nitrogen or sulfur atom(s) are optionally oxidized, or the nitrogen atom(s) are optionally quaternized. Examples of heteroaryl moieties include, but are not limited to, heterocycles such as furan, thiophene, pyrrole, pyrazole, imidazole, oxazole, isoxazole, thiazole, isothiazole, 1H-tetrazole, 1,3,4-oxadiazole, 1H-1,2,4-triazole, 1,3,4-triazole, pyridine, pyrimidine, pyrazine, pyridazine, benzoxazole, benzisoxazole, benzothiazole, benzofuran, benzothiophene, thianthrene, benzimidazole, indole, indazole, quinoline, isoquinoline, quinazoline, quinoxaline, purine, pteridine, 9H-carbazole, α-carboline, or the like.

The term "halogen", as used herein, designates fluorine, chlorine, bromine, or iodine.

The compounds of the present invention may be converted to salts, in particular pharmaceutically acceptable salts using art recognized procedures. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethyl-propylamine, or a mono-, di-, or trihydroxy lower alkylamine, for example mono-, di- or triethanolamine. Internal salts may furthermore be formed. Salts which are unsuitable for pharmaceutical uses but which can be employed, for example, for the isolation or purification of free compounds or their pharmaceutically acceptable salts, are also included. The term "pharmaceutically acceptable salt", as used herein, refers to salts derived form organic and inorganic acids such as, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

Compounds of the invention may exist as one or more tautomers. One skilled in the art will recognize that the compounds the invention may also exist as the tautomer It as shown below for compounds of formula I.

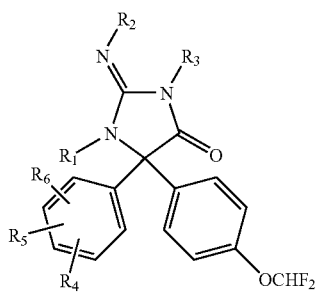

(It)

Tautomers often exist in equilibrium with each other. As these tautomers interconvert under environmental and physiological conditions, they provide the same useful biological effects. The present invention includes mixtures of such tautomers as well as the individual tautomers, for example the compounds of formulas I, It, IIAt, IIBt and the like.

The compounds of this invention may contain an asymmetric carbon atom and some of the compounds of this invention may contain one or more asymmetric centers and may thus give rise to optical isomers and diastereomers. While shown without respect to stereochemistry in certain formulas herein, the present invention includes such optical isomers and diastereomers; as well as the racemic and resolved, enantiomerically pure R and S stereoisomers; as well as other mixtures of the R and S stereoisomers and pharmaceutically acceptable salts thereof. Where a stereoisomer is preferred, it may in some embodiments be provided substantially free of the corresponding enantiomer. Thus, an enantiomer substantially free of the corresponding enantiomer refers to a compound that is isolated or separated via separation techniques or prepared free of the corresponding enantiomer. "Substantially free", as used herein, means that the compound is made up of a significantly greater proportion of one steriosomer, preferably less than about 50%, more preferably less than about 75%, and even more preferably less than about 90%.

Preferred compounds of formula I are those compounds wherein $R_1$ and $R_2$ are H. Another group of preferred compounds are those compounds of formula I wherein $R_3$ is $C_1$-$C_4$alkyl. Also preferred are those compounds of formula I wherein $R_4$, $R_5$ and $R_6$ are each independently H, halogen, $COR_7$, $OR_{14}$, or an alkyl, haloalkyl, alkoxy, haloalkoxy, alkynyl or cycloalkyl group each optionally substituted.

More preferred compounds of the invention are those compounds of formula I wherein $R_1$ and $R_2$ are H and $R_3$ is methyl. Another group of more preferred compounds of the invention are those compounds of formula I wherein $R_4$ is H, $COR_7$, $OR_{14}$ or an alkyl, haloalkyl, alkoxy, haloalkoxy, alkynyl or cycloalkyl group each group optionally substituted; and $R_5$ and $R_6$ are each independently H or halogen. In one embodiment $R_4$ is optionally substituted with one or more groups selected from alkenyl, alkynyl, halo, hydroxy, alkoxy or cycloalkyl. In another embodiment $R_4$ is at the 3-position of the phenyl ring.

A further group of more preferred compounds of the invention are those compounds of formula I wherein $R_1$ and $R_2$ are H; $R_3$ is methyl; $R_4$ is H, $COR_7$ or an alkyl, haloalkyl, alkoxy, haloalkoxy, alkynyl or cycloalkyl group each group optionally substituted; $R_5$ and $R_6$ are each independently H or halogen; and $R_4$ is at the 3-position of the phenyl ring.

Exemplary compounds described herein include:
(5-R)-2-Amino-5-[4-(difluoromethoxy)phenyl]-5-(4-fluoro-3-prop-1-yn-1-ylphenyl)-3-methyl-3,5-dihydro-4H-imidazol-4-one;
(5-S)-2-Amino-5-[4-(difluoromethoxy)phenyl]-5-(4-fluoro-3-prop-1-yn-1-ylphenyl)-3-methyl-3,5-dihydro-4H-imidazol-4-one;
(5S)-2-Amino-5-[3-(cyclopropylethynyl)phenyl]-5-[4-(difluoromethoxy)phenyl]-3-methyl-3,5-dihydro-4H-imidazol-4-one;
(5R)-2-Amino-5-[3-(cyclopropylethynyl)phenyl]-5-[4-(difluoromethoxy)phenyl]-3-methyl-3,5-dihydro-4H-imidazol-4-one;
2-Amino-5-[3-(cyclopropylethynyl)-4-fluorophenyl]-5-[4 (difluoromethoxy)phenyl]-3-methyl-3,5-dihydro-4H-imidazol-4-one;
(5R)-2-Amino-5-[3-(cyclopropylethynyl)-4-fluorophenyl]-5-[4 (difluoromethoxy)phenyl]-3-methyl-3,5-dihydro-4H-imidazol-4-one;
(5S)-2-Amino-5-[3-(cyclopropylethynyl)-4-fluorophenyl]-5-[4 (difluoromethoxy)phenyl]-3-methyl-3,5-dihydro-4H-imidazol-4-one;
(5S)-2-Amino-5-[4-(difluoromethoxy)phenyl]-3-methyl-5-phenyl-3,5-dihydro-4H-imidazol-4-one;
(5R)-2-Amino-5-[4-(difluoromethoxy)-phenyl]-3-methyl-5-phenyl-3,5-dihydro-4H-imidazol-4-one;
(5R)-2-amino-5-(3-bromophenyl)-5-[4-(difluoromethoxy) phenyl]-3-methyl-3,5-dihydro-4H-imidazol-4-one;
(5S)-2-amino-5-(3-bromophenyl)-5-[4-(difluoromethoxy) phenyl]-3-methyl-3,5-dihydro-4H-imidazol-4-one;
(5R)-2-Amino-5-(3-bromo-4-fluorophenyl)-5-[4-(difluoromethoxy)phenyl]-3-methyl-3,5-dihydro-4H-imidazol-4-one;
(5S)-2-Amino-5-(3-bromo-4-fluorophenyl)-5-[4-(difluoromethoxy)phenyl]-3-methyl-3,5-dihydro-4H-imidazol-4-one;
(5R)-2-Amino-5-[4-(difluoromethoxy)phenyl]-3-methyl-5-(3-propylphenyl)-3,5-dihydro-4H-imidazol-4-one;
(5S)-2-Amino-5-[4-(difluoromethoxy)phenyl]-3-methyl-5-(3-propylphenyl)-3,5-dihydro-4H-imidazol-4-one;
2-Amino-5-[4-(difluoromethoxy)phenyl]-5-[3-(3-fluoropropyl)phenyl]-3-methyl-3,5-dihydro-4H-imidazol-4-one;
2-Amino-5-[4-(difluoromethoxy)phenyl]-5-[3-(3,3-difluoropropyl)phenyl]-3-methyl-3,5-dihydro-4H-imidazol-4-one;
2-Amino-5-[4-(difluoromethoxy)phenyl]-5-[3-(4-fluorobutyl)phenyl]-3-methyl-3,5-dihydro-4H-imidazol-4-one;
2-Amino-5-[3-(4,4-difluorobutyl)phenyl]-5-[4-(difluoromethoxy)phenyl]-3-methyl-3,5-dihydro-4H-imidazol-4-one;
2-Amino-5-[4-(difluoromethoxy)phenyl]-5-[3-(2-fluoroethyl)phenyl]-3-methyl-3,5-dihydro-4H-imidazol-4-one;
2-Amino-5-[3-(2,2-difluoroethyl)phenyl]-5-[4-(difluoromethoxy)phenyl]-3-methyl-3,5-dihydro-4H-imidazol-4-one;
2-Amino-5-[4-(difluoromethoxy)phenyl]-3-methyl-5-[3-(2,2,2-trifluoroethyl)phenyl]-3,5-dihydro-4H-imidazol-4-one;
2-Amino-5-[4-(difluoromethoxy)phenyl]-3-methyl-5-[3-(3,3,3-trifluoropropyl)phenyl]-3,5-dihydro-4H-imidazol-4-one;
2-Amino-5-[4-(difluoromethoxy)phenyl]-3-methyl-5-[3-(4,4,4-trifluorobutyl)phenyl]-3,5-dihydro-4H-imidazol-4-one;
(5R)-2-amino-5-(3-butylphenyl)-5-[4-(difluoromethoxy) phenyl]-3-methyl-3,5-dihydro-4H-imidazol-4-one;

(5S)-2-amino-5-(3-butylphenyl)-5-[4-(difluoromethoxy)phenyl]-3-methyl-3,5-dihydro-4H-imidazol-4-one;
2-Amino-5-[4-(difluoromethoxy)phenyl]-3-methyl-5-(3-pentylphenyl)-3,5-dihydro-4H-imidazol-4-one;
2-Amino-5-[4-(difluoromethoxy)phenyl]-3-methyl-5-[3-(2-methylbutyl)phenyl]-3,5-dihydro-4H-imidazol-4-one;
2-Amino-5-(3-but-3-en-1-ylphenyl)-5-[4-(difluoromethoxy)phenyl]-3-methyl-3,5-dihydro-4H-imidazol-4-one;
2-Amino-5-[3-(cyclopropylmethyl)phenyl]-5-[4-(difluoromethoxy)phenyl]-3-methyl-3,5-dihydro-4H-imidazol-4-one;
3-(3-{2-Amino-4-[4-(difluoromethoxy)phenyl]-1-methyl-5-oxo-4,5-dihydro-1H-imidazol-4-yl}phenyl)propanenitrile;
(5R)-2-Amino-5-[4-(difluoromethoxy)phenyl]-3-methyl-5-(3-pent-4-en-1-ylphenyl)-3,5-dihydro-4H-imidazol-4-one;
(5S)-2-Amino-5-[4-(difluoromethoxy)phenyl]-3-methyl-5-(3-pent-4-en-1-ylphenyl)-3,5-dihydro-4H-imidazol-4-one;
N-(3-{(4R)-2-Amino-4-[4-(difluoromethoxy)phenyl]-1-methyl-5-oxo-4,5-dihydro-1H-imidazol-4-yl}phenyl)-2-methoxyacetamide;
N-(3-{(4S)-2-Amino-4-[4-(difluoromethoxy)phenyl]-1-methyl-5-oxo-4,5-dihydro-1H-imidazol-4-yl}phenyl)-2-methoxyacetamide;
(5S)-2-amino-5-[4-(difluoromethoxy)phenyl]-3-methyl-5-phenyl-3,5-dihydro-4H-imidazol-4-one;
2-amino-5-[4-(difluoromethoxy)phenyl]-5-[3-(4-hydroxybut-1-yn-1-yl)phenyl]-3-methyl-3,5-dihydro-4H-imidazol-4-one;
2-amino-5-[4-(difluoromethoxy)phenyl]-5-[3-(4-hydroxybutyl)phenyl]-3-methyl-3,5-dihydro-4H-imidazol-4-one;
2-amino-5-[4-(difluoromethoxy)phenyl]-5-[3-(5-fluoropentyl)phenyl]-3-methyl-3,5-dihydro-4H-imidazol-4-one;
2-amino-5-[4-(difluoromethoxy)phenyl]-5-[3-(4-fluorobutyl)phenyl]-3-methyl-3,5-dihydro-4H-imidazol-4-one;
2-amino-5-[4-(difluoromethoxy)phenyl]-5-[3-(6-fluorohexyl)phenyl]-3-methyl-3,5-dihydro-4H-imidazol-4-one;
2-amino-5-[4-(difluoromethoxy)phenyl]-5-[3-(4-methoxybutyl)phenyl]-3-methyl-3,5-dihydro-4H-imidazol-4-one;
2-amino-5-[4-(difluoromethoxy)phenyl]-5-{3-[(1Z)-3-methoxyprop-1-en-1-yl]phenyl}-3-methyl-3,5-dihydro-4H-imidazol-4-one;
2-amino-5-[4-(difluoromethoxy)phenyl]-5-[3-(3-methoxypropyl)phenyl]-3-methyl-3,5-dihydro-4H-imidazol-4-one;
2-amino-5-[3-(4,4-difluorobutyl)phenyl]-5-[4-(difluoromethoxy)phenyl]-3-methyl-3,5-dihydro-4H-imidazol-4-one;
3-{2-amino-4-[4-(difluoromethoxy)phenyl]-1-methyl-5-oxo-4,5-dihydro-1H-imidazol-4-yl}-N-propylbenzamide;
(1E)-3-chloroprop-1-enyl 2,5-dichlorophenyl sulfone;
2-amino-5-[4-(difluoromethoxy)phenyl]-5-{3-[(2-fluoroethoxy)methyl]phenyl}-3-methyl-3,5-dihydro-4H-imidazol-4-one;
2-amino-5-[4-(difluoromethoxy)phenyl]-3-methyl-5-{3-[(3,3,3-trifluoropropoxy)methyl]phenyl}-3,5-dihydro-4H-imidazol-4-one;
2-amino-5-[4-(difluoromethoxy)phenyl]-5-[3-(methoxymethyl)phenyl]-3-methyl-3,5-dihydro-4H-imidazol-4-one;
2-amino-5-[3-(butoxymethyl)phenyl]-5-[4-(difluoromethoxy)phenyl]-3-methyl-3,5-dihydro-4H-imidazol-4-one;
2-amino-5-{3-[(cyclopropylmethoxy)methyl]phenyl}-5-[4-(difluoromethoxy)phenyl]-3-methyl-3,5-dihydro-4H-imidazol-4-one;
2-amino-5-[4-(difluoromethoxy)phenyl]-5-[3-(ethoxymethyl)phenyl]-3-methyl-3,5-dihydro-4H-imidazol-4-one;
2-amino-5-[4-(difluoromethoxy)phenyl]-3-methyl-5-[3-(propoxymethyl)phenyl]-3,5-dihydro-4H-imidazol-4-one;
2-amino-5-[4-(difluoromethoxy)phenyl]-5-(3-{[2-fluoro-1-(fluoromethyl)ethoxy]methyl}phenyl)-3-methyl-3,5-dihydro-4H-imidazol-4-one;
2-amino-5-[4-(difluoromethoxy)phenyl]-3-methyl-5-{3-[(2,2,2-trifluoroethoxy)methyl]phenyl}-3,5-dihydro-4H-imidazol-4-one;
2-amino-5-[4-(difluoromethoxy)phenyl]-3-methyl-5-{3-[(2,2,3,3-tetrafluoropropoxy)methyl]phenyl}-3,5-dihydro-4H-imidazol-4-one;
4-[4-(difluoromethoxy)phenyl]-4-[3-(3-methoxyprop-1-yn-1-yl)phenyl]-1-methyl-4,5-dihydro-1H-imidazol-2-amine;
2-amino-5-[3-(1,4-difluorobutyl)phenyl]-5-[4-(difluoromethoxy)phenyl]-3-methyl-3,5-dihydro-4H-imidazol-4-one;
2-amino-5-[4-(difluoromethoxy)phenyl]-5-[3-(3-fluorobut-3-en-1-yl)phenyl]-3-methyl-3,5-dihydro-4H-imidazol-4-one;
2-amino-5-[3-(4,4-difluorobut-3-en-1-yl)phenyl]-5-[4-(difluoromethoxy)phenyl]-3-methyl-3,5-dihydro-4H-imidazol-4-one;
2-amino-5-[4-(difluoromethoxy)phenyl]-3-methyl-5-[3-(4,4,4-trifluorobutyl)phenyl]-3,5-dihydro-4H-imidazol-4-one;
5-(3-{2-amino-4-[4-(difluoromethoxy)phenyl]-1-methyl-5-oxo-4,5-dihydro-1H-imidazol-4-yl}phenyl)pentanenitrile;
4-(3-{2-amino-4-[4-(difluoromethoxy)phenyl]-1-methyl-5-oxo-4,5-dihydro-1H-imidazol-4-yl}phenyl)butanenitrile;
2-amino-5-{3-[(1E)-4,4-difluorobut-1-en-1-yl]phenyl}-5-[4-(difluoromethoxy)phenyl]-3-methyl-3,5-dihydro-4H-imidazol-4-one;
2-amino-5-[4-(difluoromethoxy)phenyl]-5-[3-(3-hydroxyhex-4-yn-1-yl)phenyl]-3-methyl-3,5-dihydro-4H-imidazol-4-one;
2-amino-5-[4-(difluoromethoxy)phenyl]-5-{3-[(1E)-6-methoxyhex-1-en-1-yl]phenyl}-3-methyl-3,5-dihydro-4H-imidazol-4-one;
2-amino-5-[4-(difluoromethoxy)phenyl]-5-{3-[(1E)-5-methoxypent-1-en-1-yl]phenyl}-3-methyl-3,5-dihydro-4H-imidazol-4-one;
2-amino-5-[4-(difluoromethoxy)phenyl]-5-{3-[2-(methoxymethyl)cyclopropyl]phenyl}-3-methyl-3,5-dihydro-4H-imidazol-4-one;
2-amino-5-[4-(difluoromethoxy)phenyl]-5-{3-[(1E)-5-hydroxypent-1-en-1-yl]phenyl}-3-methyl-3,5-dihydro-4H-imidazol-4-one;
2-amino-5-[4-(difluoromethoxy)phenyl]-5-{3-[(1E)-3-methoxyprop-1-en-1-yl]phenyl}-3-methyl-3,5-dihydro-4H-imidazol-4-one;
2-amino-5-[4-(difluoromethoxy)phenyl]-5-{3-[(1E)-4-methoxybut-1-en-1-yl]phenyl}-3-methyl-3,5-dihydro-4H-imidazol-4-one;
2-amino-5-[4-(difluoromethoxy)phenyl]-5-{3-[(1E)-4-hydroxybut-1-en-1-yl]phenyl}-3-methyl-3,5-dihydro-4H-imidazol-4-one;
2-amino-5-[4-(difluoromethoxy)phenyl]-5-{3-[2-(2-methoxyethyl)cyclopropyl]phenyl}-3-methyl-3,5-dihydro-4H-imidazol-4-one;

2-amino-5-[4-(difluoromethoxy)phenyl]-5-{3-[(1E)-4-fluorobut-1-en-1-yl]phenyl}-3-methyl-3,5-dihydro-4H-imidazol-4-one;

2-amino-5-[4-(difluoromethoxy)phenyl]-5-{3-[(1E)-5-fluoropent-1-en-1-yl]phenyl}-3-methyl-3,5-dihydro-4H-imidazol-4-one;

5-(3-acetylphenyl)-2-amino-5-[4-(difluoromethoxy)phenyl]-3-methyl-3,5-dihydro-4H-imidazol-4-one;

2-amino-5-[4-(difluoromethoxy)phenyl]-5-{4-fluoro-3-[(1E)-4-fluorobut-1-en-1-yl]phenyl}-3-methyl-3,5-dihydro-4H-imidazol-4-one;

2-amino-5-[4-(difluoromethoxy)phenyl]-5-[3-(3-fluoroprop-1-yn-1-yl)phenyl]-3-methyl-3,5-dihydro-4H-imidazol-4-one;

2-amino-5-[4-(difluoromethoxy)phenyl]-5-(3-hydroxyphenyl)-3-methyl-3,5-dihydro-4H-imidazol-4-one;

2-amino-5-[4-(difluoromethoxy)phenyl]-5-[3-(3-fluoropropoxy)phenyl]-3-methyl-3,5-dihydro-4H-imidazol-4-one;

2-amino-5-[3-(cyclopropylmethoxy)phenyl]-5-[4-(difluoromethoxy)phenyl]-3-methyl-3,5-dihydro-4H-imidazol-4-one;

2-amino-5-[4-(difluoromethoxy)phenyl]-3-methyl-5-[3-(4,4,4-trifluorobutoxy)phenyl]-3,5-dihydro-4H-imidazol-4-one;

2-amino-5-[3-(2,2-difluoroethoxy)phenyl]-5-[4-(difluoromethoxy)phenyl]-3-methyl-3,5-dihydro-4H-imidazol-4-one;

2-amino-5-[4-(difluoromethoxy)phenyl]-5-[3-(4-fluorobutoxy)phenyl]-3-methyl-3,5-dihydro-4H-imidazol-4-one;

2-amino-5-[4-(difluoromethoxy)phenyl]-3-methyl-5-[3-(3-phenoxypropoxy)phenyl]-3,5-dihydro-4H-imidazol-4-one;

4-(3-{2-amino-4-[4-(difluoromethoxy)phenyl]-1-methyl-5-oxo-4,5-dihydro-1H-imidazol-4-yl}phenoxy)butanenitrile;

2-amino-5-[4-(difluoromethoxy)phenyl]-5-[4-fluoro-3-(3-fluoropropoxy)phenyl]-3-methyl-3,5-dihydro-4H-imidazol-4-one;

2-amino-5-[3-(but-2-yn-1-yloxy)-4-fluorophenyl]-5-[4-(difluoromethoxy)phenyl]-3-methyl-3,5-dihydro-4H-imidazol-4-one;

2-amino-5-[4-(difluoromethoxy)phenyl]-5-[4-fluoro-3-(4-fluorobutoxy)phenyl]-3-methyl-3,5-dihydro-4H-imidazol-4-one;

2-amino-5-[3-(2,2-difluoroethoxy)-4-fluorophenyl]-5-[4-(difluoromethoxy)phenyl]-3-methyl-3,5-dihydro-4H-imidazol-4-one;

(5R)-2-amino-5-[4-(difluoromethoxy)phenyl]-5-[4-fluoro-3-(3-fluoropropoxy)phenyl]-3-methyl-3,5-dihydro-4H-imidazol-4-one;

(5S)-2-amino-5-[4-(difluoromethoxy)phenyl]-5-[4-fluoro-3-(3-fluoropropoxy)phenyl]-3-methyl-3,5-dihydro-4H-imidazol-4-one;

2-amino-5-{3-[(4,4-difluorobut-3-en-1-yl)oxy]phenyl}-5-[4-(difluoromethoxy)phenyl]-3-methyl-3,5-dihydro-4H-imidazol-4-one;

(5S)-2-amino-5-[3-(2,2-difluoroethoxy)-4-fluorophenyl]-5-[4-(difluoromethoxy)phenyl]-3-methyl-3,5-dihydro-4H-imidazol-4-one;

(5R)-2-amino-5-[3-(2,2-difluoromethoxy)-4-fluorophenyl]-5-[4-(difluoromethoxy)phenyl]-3-methyl-3,5-dihydro-4H-imidazol-4-one;

2-amino-5-[4-(difluoromethoxy)phenyl]-5-[3-(2-fluoroethyl)phenyl]-3-methyl-3,5-dihydro-4H-imidazol-one;

2-amino-5-[4-(difluoromethoxy)phenyl]-5-[3-(5-fluoropentanoyl)phenyl]-3-methyl-3,5-dihydro-4H-imidazol-4-one;

2-amino-5-[4-(difluoromethoxy)phenyl]-5-[3-(4-fluorobutanoyl)phenyl]-3-methyl-3,5-dihydro-4H-imidazol-4-one;

2-amino-5-[3-(but-3-en-1-yloxy)phenyl]-5-[4-(difluoromethoxy)phenyl]-3-methyl-3,5-dihydro-4H-imidazol-4-one;

2-amino-5-[3-(but-3-en-1-yloxy)-4-fluorophenyl]-5-[4-(difluoromethoxy)phenyl]-3-methyl-3,5-dihydro-4H-imidazol-4-one;

(5R)-2-amino-5-[3-(but-3-en-1-yloxy)phenyl]-5-[4-(difluoromethoxy)phenyl]-3-methyl-3,5-dihydro-4H-imidazol-4-one;

(5S)-2-amino-5-[3-(but-3-en-1-yloxy)phenyl]-5-[4-(difluoromethoxy)phenyl]-3-methyl-3,5-dihydro-4H-imidazol-4-one;

2-amino-5-{3-[(4,4-difluorobut-3-en-1-yl)oxy]-4-fluorophenyl}-5-[4-(difluoromethoxy)phenyl]-3-methyl-3,5-dihydro-4H-imidazol-4-one;

2-amino-5-[4-(difluoromethoxy)phenyl]-5-(4-fluoro-3-pent-4-en-1-ylphenyl)-3-methyl-3,5-dihydro-4H-imidazol-4-one;

2-amino-5-(3-but-3-en-1-yl-4-fluorophenyl)-5-[4-(difluoromethoxy)phenyl]-3-methyl-3,5-dihydro-4H-imidazol-4-one;

3-{2-amino-4-[4-(difluoromethoxy)phenyl]-1-methyl-5-oxo-4,5-dihydro-1H-imidazol-4-yl}benzaldehyde;

2-amino-5-[4-(difluoromethoxy)phenyl]-5-[3-(1-hydroxybut-2-yn-1-yl)phenyl]-3-methyl-3,5-dihydro-4H-imidazol-4-one;

2-amino-5-[4-(difluoromethoxy)phenyl]-5-[3-(1,4-dihydroxybut-2-yn-1-yl)phenyl]-3-methyl-3,5-dihydro-4H-imidazol-4-one;

(5R)-2-amino-5-[3-(difluoromethoxy)phenyl]-5-[4-(difluoromethoxy)phenyl]-3-methyl-3,5-dihydro-4H-imidazol-4-one;

2-amino-5-[4-(difluoromethoxy)phenyl]-5-[3-(2,2-dimethyl-3-oxocyclobutyl)phenyl]-3-methyl-3,5-dihydro-4H-imidazol-4-one;

2-amino-5-[4-(difluoromethoxy)phenyl]-3-methyl-5-[3-(3-oxocyclobutyl)phenyl]-3,5-dihydro-4H-imidazol-4-one;

2-amino-5-[4-(difluoromethoxy)phenyl]-5-[3-(3-hydroxycyclobutyl)phenyl]-3-methyl-3,5-dihydro-4H-imidazol-4-one;

methyl[3-(3-{2-amino-4-[4-(difluoromethoxy)phenyl]-1-methyl-5-oxo-4,5-dihydro-1H-imidazol-4-yl}phenyl)cyclobutyl]acetate;

methyl[3-(3-{2-amino-4-[4-(difluoromethoxy)phenyl]-1-methyl-5-oxo-4,5-dihydro-1H-imidazol-4-yl}phenyl)cyclobutylidene]acetate;

or a tautomer thereof, a stereoisomer thereof or a pharmaceutically acceptable salt thereof.

More exemplary compounds described herein include:

(5S)-2-amino-5-[4-(difluoromethoxy)phenyl]-3-methyl-5-phenyl-3,5-dihydro-4H-imidazol-4-one;

(5R)-2-amino-5-[4-(difluoromethoxy)phenyl]-3-methyl-5-(3-pent-4-en-1-ylphenyl)-3,5-dihydro-4H-imidazol-4-one;

(5R)-2-amino-5-[4-(difluoromethoxy)phenyl]-3-methyl-5-(3-prop-1-yn-1-ylphenyl)-3,5-dihydro-4H-imidazol-4-one;

(5R)-2-amino-5-[4-(difluoromethoxy)phenyl]-3-methyl-5-(3-pent-1-yn-1-ylphenyl)-3,5-dihydro-4H-imidazol-4-one;

- (5R)-2-amino-5-[4-(difluoromethoxy)phenyl]-3-methyl-5-[3-(3-methylbut-1-yn-1-yl)phenyl]-3,5-dihydro-4H-imidazol-4-one;
- (5R)-2-amino-5-[4-(difluoromethoxy)phenyl]-5-[3-(3-methoxyprop-1-yn-1-yl)phenyl]-3-methyl-3,5-dihydro-4H-imidazol-4-one;
- (5R)-2-amino-5-[4-(difluoromethoxy)phenyl]-5-[3-(4-methoxybut-1-yn-1-yl)phenyl]-3-methyl-3,5-dihydro-4H-imidazol-4-one;
- (5R)-2-amino-5-[4-(difluoromethoxy)phenyl]-5-[3-(5-fluoropent-1-yn-1-yl)phenyl]-3-methyl-3,5-dihydro-4H-imidazol-4-one;
- (5R)-2-amino-5-[4-(difluoromethoxy)phenyl]-5-{3-[(3S)-3-hydroxybut-1-yn-1-yl]phenyl}-3-methyl-3,5-dihydro-4H-imidazol-4-one;
- (5R)-2-amino-5-[4-(difluoromethoxy)phenyl]-5-[4-fluoro-3-(3-methoxyprop-1-yn-1-yl)phenyl]-3-methyl-3,5-dihydro-4H-imidazol-4-one;
- (5R)-2-amino-5-[4-(difluoromethoxy)phenyl]-5-[4-fluoro-3-(4-methoxybut-1-yn-1-yl)phenyl]-3-methyl-3,5-dihydro-4H-imidazol-4-one;
- (5R)-2-amino-5-[4-(difluoromethoxy)phenyl]-5-[4-fluoro-3-(3-fluoropropoxy)phenyl]-3-methyl-3,5-dihydro-4H-imidazol-4-one;
- (5R)-2-amino-5-[3-(2,2-difluoroethoxy)-4-fluorophenyl]-5-[4-(difluoromethoxy)phenyl]-3-methyl-3,5-dihydro-4H-imidazol-4-one;
- (5R)-2-amino-5-{3-[(4,4-difluorobur-3-en-1-yl)oxy]phenyl}-5-[4-(difluoromethoxy)phenyl]-3-methyl-3,5-dihydro-4H-imidazol-4-one;

or a tautomer thereof, a stereoisomer thereof or a pharmaceutically acceptable salt thereof.

Other exemplary compounds include those that are presented in Examples 2-141.

Compounds of formula I (and others described herein including compounds of formula II, IIA, IIB, III, IIIA, IIIB, IXA and IXB) may be prepared using conventional synthetic methods and, if required, standard separation or isolation techniques. For example, compounds of formula I may be prepared by reacting a diketone of formula X with an aminoguanidine derivative of formula XI in the presence of a base such as a metal carbonate to give the desired formula I compound. The reaction is shown below in flow diagram I.

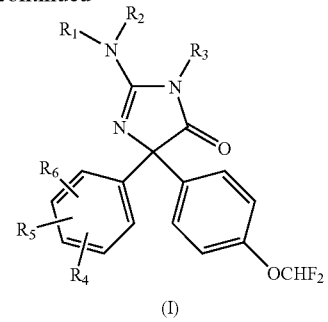

(I)

Diketone compounds of formula X may be prepared by reacting an alkyne of formula XII with an oxidizing agent such as Pd(II)Cl$_2$/DMSO, N-bromosuccinimide/DMSO, ozone, sodium periodate with ruthenium (IV) oxide hydrate, sulfur trioxide, KMnO$_4$, I$_2$/DMSO, or combinations thereof, preferable KMnO$_4$ and I$_2$/DMSO. The reaction is shown in flow diagram II.

FLOW DIAGRAM II

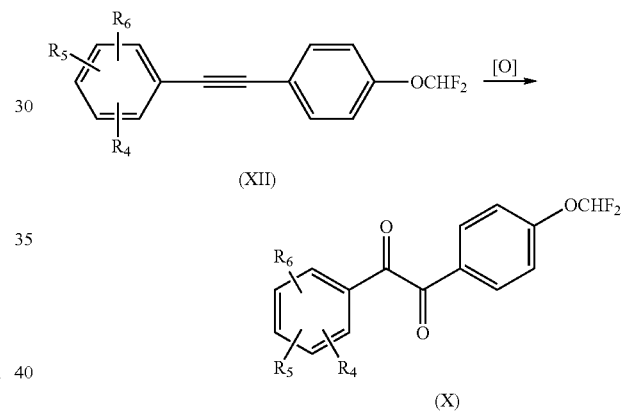

Alkyne compounds of formula XII may be prepared by reacting an ethynylbenzene compound of formula XIII with 4-(difluoromethoxy)-1-iodobenzene in the presence of a Pd catalyst, such as dichlorobis(triphenylphosphine)palladium (II), and CuI to give the desired phenylethynylbenzene compound of formula XII. The reaction is shown in flow diagram III.

FLOW DIAGRAM I

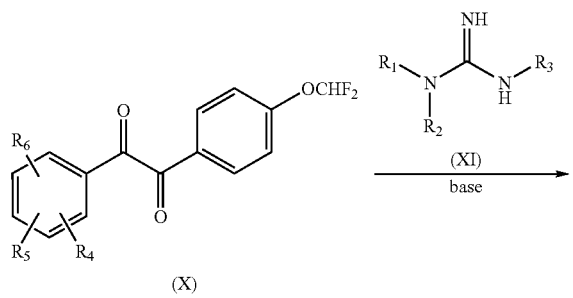

FLOW DIAGRAM III

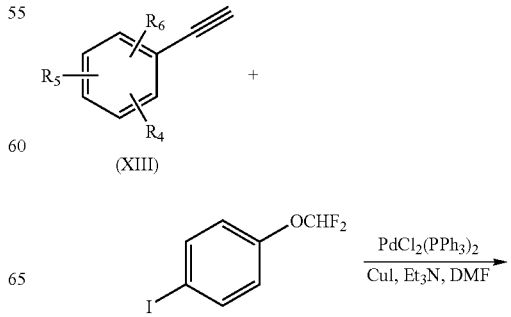

-continued

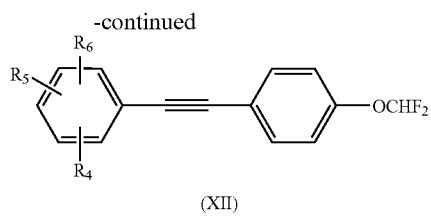

(XII)

Advantageously, the compounds of the present invention act as BACE inhibitors for the treatment of β-amyloid deposits and neurofibrillary tangles associated with such diseases as Alzheimer's disease, Trisomy 21 (Down's Syndrome), Hereditary Cerebral Hemorrhage with Amyloidosis of the Dutch-type (HCHWA-D), and other neurodegenerative disorders. Accordingly, the present invention provides methods for modulating BACE and treating, preventing, or ameliorating β-amyloid deposits and neurofibrillary tangles associated with diseases and disorders such as Alzheimer's disease, Trisomy 21 (Down's Syndrome), Hereditary Cerebral Hemorrhage with Amyloidosis of the Dutch-type (HCHWA-D), or other neurodegenerative disorders. Such methods include providing a patient suffering from or being susceptible to a disease or injury associated with excessive BACE activity an effective amount of a compound of the present invention (e.g., compounds of formula I, II, IIA, IIB, III, IIIA, IIIB, IXA and IXB). Also according to the present invention there is provided a method of treating Alzheimer's disease and related senile dementia's in humans or other mammals which comprises administering to a human or other mammal an effective amount of a compound of the present invention.

The present invention also provides a method for the treatment of a disorder related to or associated with excessive BACE activity in a patient in need thereof which comprises providing said patient a therapeutically effective amount of at least one compound of the present invention (e.g., compounds of formula I, II, IIA, IIB, III, IIIA, IIIB, IXA and IXB). Representative disorders include Alzheimer's disease, cognitive impairment, Down's Syndrome, HCHWA-D, cognitive decline, senile dementia, cerebral amyloid angiopathy, degenerative dementia, or other neurodegenerative disorders. Certain of these diseases are characterized by production of β-amyloid deposits or neurofibrillary tangles.

The present invention also provides a method for inhibiting the activity of BACE, comprising administering to a patient or contacting a receptor thereof with an effective amount of at least one compound of the present invention (e.g., compounds of formula I, II, IIA, IIB, III, IIIA, IIIB, IXA and IXB). Certain methods further comprise determining BACE activity, either before or after said contacting step.

The present invention also provides a method of ameliorating β-amyloid deposits or neurofibrillary tangles in a mammal which comprises providing said mammal an effective amount of at least one compound of the present invention (e.g., compounds of formula I, II, IIA, IIB, III, IIIA, IIIB, IXA and IXB).

Also provided are methods of ameliorating symptoms of Alzheimer's disease, cognitive impairment, Down's Syndrome, HCHWA-D, cognitive decline, senile dementia, cerebral amyloid angiopathy, degenerative dementia, or other neurodegenerative disorders in a mammal which comprises providing said mammal an effective amount of at least one compound of the present invention (e.g., compounds of formula I, II, IIA, IIB, III, IIIA, IIIB, IXA and IXB).

Further methods prevent Alzheimer's disease, cognitive impairment, Down's Syndrome, HCHWA-D, cognitive decline, senile dementia, cerebral amyloid angiopathy, degenerative dementia, or other neurodegenerative disorders in a mammal that is known to suffer from or suspected to be at risk of suffering from such diseases. These methods comprise providing said mammal an effective amount of at least one compound of the present invention (e.g., compounds of formula I, II, IIA, IIB, III, IIIA, IIIB, IXA and IXB).

As used in accordance with this invention, the term "providing," with respect to providing a compound or substance covered by this invention, means either directly administering such a compound or substance, or administering a prodrug, derivative, or analog which will form the effective amount of the compound or substance within the body. This invention also covers providing the compounds of this invention to treat the disease states disclosed herein that the compounds are useful for treating.

The term "patient", as used herein, refers to a mammal, preferably a human.

The terms "administer", "administering", or "administration", as used herein, refer to either directly administering a compound or composition to a patient, or administering a prodrug derivative or analog of the compound to the patient, which will form an equivalent amount of the active compound or substance within the patient's body.

The terms "effective amount", "therapeutically effective amount" and "effective dosage" as used herein, refer to the amount of a compound that, when administered to a patient, is effective to at least partially ameliorate (and, in preferred embodiments, cure) a condition from which the patient is suspected to suffer.

It is understood that the effective dosage of the active compounds of this invention may vary depending upon the particular compound utilized, the mode of administration, the condition, and severity thereof, of the condition being treated, as well as the various physical factors related to the individual being treated. For treating Alzheimer's disease and other related senile dementia's, generally, satisfactory results may be obtained when the compounds of this invention are administered to the individual in need at a daily dosage of from about 0.1 mg to about 1 mg per kilogram of body weight, preferably administered in divided doses two to six times per day, or in a sustained release form. For most large mammals, the total daily dosage is from about 3.5 mg to about 140 mg preferably from about 3.5 to about 5 mg. In the case of a 70 kg human adult, the total daily dose will generally be from about 7 mg to about 70 mg and may be adjusted to provide the optimal therapeutic result. This regimen may be adjusted to provide the optimal therapeutic response.

In one aspect, the present invention is directed to compositions comprising one or more compounds of the present invention (e.g., compounds of formula I, II, IIA, IIB, III, IIIA, IIIB, IXA and IXB) and one or more pharmaceutically acceptable carriers.

The present invention also comprises pharmaceutical compositions comprising compounds of the present invention (e.g., compounds of formula I, II, IIA, IIB, III, IIIA, IIIB, IXA and IXB) and a pharmaceutically acceptable carrier.

The term "carrier", as used herein, shall encompass carriers, excipients, and diluents. Examples of carriers are well known to those skilled in the art and are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), which is incorporated herein by reference in its entirety. Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or encapsulating materials. They are formulated in conventional manner, for example, in a manner similar to that used for known antihypertensive agents, diuretics and β-blocking agents. Oral formulations containing the active compounds of this invention may comprise any conventionally used oral forms, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. The powders and tablets preferably contain up to 99% of the active ingredient.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or fruit juice, containing appropriate solubilizers or emulsifiers as needed.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration may be in either liquid or solid form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. Such administrations may be carried out using the present compounds, or pharmaceutically acceptable salts thereof, in lotions, creams, foams, patches, suspensions, solutions, and suppositories (rectal and vaginal).

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. In therapeutic application, compounds of the present invention are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient.

In some cases it may be desirable to administer the compounds directly to the airways in the form of an aerosol. For administration by intranasal or intrabronchial inhalation, the compounds of this invention may be formulated into an aqueous or partially aqueous solution.

The compounds of this invention may be administered parenterally or intraperitoneally. Solutions or suspensions of these active compounds as a free base or pharmaceutically acceptable salt may be prepared in water suitably mixed with a surfactant such as hydroxyl-propylcellulose. Dispersions may also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of this invention can be administered transdermally through the use of a transdermal patch. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream, such as a semi-permeable membrane covering a reservoir containing the active ingredient with or without a carrier, or a matrix containing the active ingredient. Other occlusive devices are known in the literature.

The compounds of this invention may be administered rectally or vaginally in the form of a conventional suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

In certain embodiments, the present invention is directed to prodrugs. Various forms of prodrugs are known in the art, for example, as discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al. (ed.), "Design and Application of Prodrugs", Textbook of Drug Design and Development, Chapter 5, 113-191 (1991), Bundgaard, et al., Journal of Drug Deliver reviews, 8:1-38 (1992), Bundgaard, J. of Pharmaceutical Sciences, 77:285 et seq. (1988); and Higuchi and Stella (eds.) Prodrugs as Novel Drug Delivery Systems, American Chemical Society (1975), each of which is incorporated by reference in its entirety.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

For a more clear understanding, and in order to illustrate the invention more clearly, specific examples thereof are set forth hereinbelow. The following examples are merely illustrative and are not to be understood as limiting the scope and underlying principles of the invention in any way.

Unless otherwise stated, all parts are parts by weight. The terms TEA, DMSO and DMF designate triethyl amine, dimethyl sulfoxide and N,N-dimethylformamide, respectively. The terms EtOAc and THF designate ethyl acetate and tetrahydrofuran, respectively. The term NMR designates proton nuclear magnetic resonance and the term MS designates mass spectroscopy with (+) referring to the positive mode which generally gives a M+1 (or M+H) absorption where M=the molecular mass. All compounds are analyzed at least by MS and NMR.

In the chemical drawings, the term Ph represents phenyl.

Proton nuclear magnetic resonance spectra were obtained on a Bruker AVANCE 300 spectrometer at 300 MHz or VARIAN 400 spectrometer at 400 MHz. Spectra are given in ppm (δ) and coupling constants, J values, are reported in Hertz. Tetramethylsilane was used as an internal reference standard. Mass spectra were obtained on a Perkin Elmer Sciex 100.

Example 1

Preparation of (5S)-2-Amino-5-[4-(difluoromethoxy)phenyl]-3-methyl-5-phenyl-3,5-dihydro-4H-imidazol-4-one [A] and (5R)-2-Amino-5-[4-(difluoromethoxy)-phenyl]-3-methyl-5-phenyl-3,5-dihydro-4H-imidazol-4-one [B]

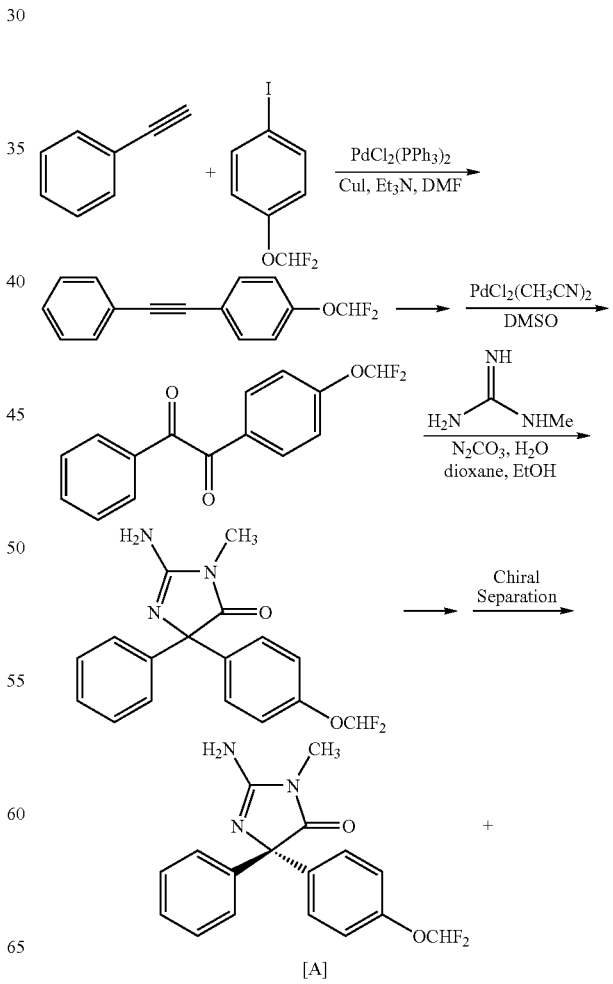

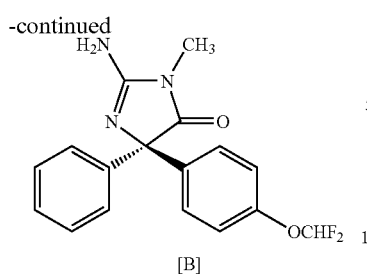

[B]

Step a) 1-(Difluoromethoxy)-4-(phenylethynyl)benzene

Into a mixture of ethynylbenzene (1.9 g, 18.5 mmol), 1-(difluoromethoxy)-4-iodobenzene (5 g, 18.5 mmol), N,N-dimethylformamide (35 mL), and triethylamine (12.8 mL, 92.6 mmol) was introduced anhydrous argon for 5 minutes. Then, copper(I) iodide (1.85 mmol, 351 mg) and dichlorobis(triphenylphosphine)palladium(II) (1.11, 0.71 g) were added into the mixture and the new mixture was stirred at 60° C. for 3 hours. The mixture cooled to room temperature, poured into water and extracted with ethyl ether. The organic extracts were dried over $MgSO_4$. Evaporation and purification on silica gel (ISCO) using hexanes/EtOAc (100/1) as the eluting solvent, gave 1-(difluoromethoxy)-4-(phenylethynyl)benzene as a clear oil (3.45 g, 76% yield). MS m/e M+244; $^1$H NMR (400 MHz, DMSO-$d_6$) δ 7.2 (d, J=8.78 Hz, 2H), 7.28-7.45 (m, 4H), 7.5-7.55 (m, 2H), 7.6 (d, J=7.78 Hz, 2H).

Step b) 1-[4-(Difluoromethoxy)phenyl]-2-phenylethane-1,2-dione

Into a mixture of 1-(difluoromethoxy)-4-(phenylethynyl)benzene (2.85 g, 11.68 mmol) and dimethylsulfoxide (40 mL) was introduced anhydrous argon gas for 5 minutes. Then, bis(acetonitrile)dichloropalladium(II) (1.16, 0.3 g) was added into the mixture and the new mixture was stirred at 145° C. for 20 hours. The mixture cooled to room temperature, poured into water and extracted with EtOAc. The organic extracts were dried over $MgSO_4$. Evaporation and purification on silica gel (ISCO) using hexanes/EtOAc (30/1) as the eluting solvent gave 1-[4-(difluoromethoxy)phenyl]-2-phenylethane-1,2-dione as a clear oil (2.92 g, 91% yield). MS m/e M$^+$ 276; $^1$H NMR (400 MHz, DMSO-$d_6$) δ 7.2 (d, J=8.78 Hz, 2H), 7.6 (m, 3H), 7.75 (t J=8.54 Hz, 1H), 7.88 (d, J=8.54 Hz, 2H), 7.98 (d, J=8.78 Hz, 2H).

Step c) 2-Amino-5-[4-(difluoromethoxy)phenyl]-3-methyl-5-phenyl-3,5-dihydro-4H-imidazol-4-one Into a mixture of 1-[4-(difluoromethoxy)phenyl]-2-phenylethane-1,2-dione (3.7 g, 13.4 mmol), dioxane (180 mL) and EtOH (240 mL) were added 1-methylguanidine hydrochloride (6.6 g, 60.3 mmol), and a solution of $Na_2CO_3$ (6.4 g, 60.3 mmol) in $H_2O$ (20 mL). The new mixture was stirred at 95° C. for 3 hours. Then, the volatiles were removed under vacuum and the residue was taken in water and extracted with EtOAc. The organic extracts were dried over $MgSO_4$. Evaporation and purification on silica gel (ISCO) using MeOH/EtOAc (1/20) as the eluting solvent gave 2-amino-5-[4-(difluoromethoxy)phenyl]-3-methyl-5-phenyl-3,5-dihydro-4H-imidazol-4-one as a white solid (3.65 g, 94% yield). MS m/e (M+H)$^+$ 332; $^1$H NMR (400 MHz, DMSO-$d_6$) δ 2.93 (s, 3H), 6.61 (brs, 2H), 7.1 (d, J=8.54 Hz, 2H), 7.15-7.31 (m, 4H), 7.38 (m, 2H), 7.42 (d, J=8.54 Hz, 2H).

Step d) (5S)-2-Amino-5-[4-(difluoromethoxy)phenyl]-3-methyl-5-phenyl-3,5-dihydro-4H-imidazol-4-one [A] and (5R)-2-Amino-5-[4-(difluoromethoxy)phenyl]-3-methyl-5-phenyl-3,5-dihydro-4H-imidazol-4-one [B]

A racemic mixture of 2-amino-5-[4-(difluoromethoxy)phenyl]-3-methyl-5-phenyl-3,5-dihydro-4H-imidazol-4-one was separated by chiral chromatography technique (Chiralcel OJ, 0.46×10 cm, using 15% ethanol in 85% hexane and diethylamine as the mobile phase) to produce the two enantiomers as white solids; [A] (5S)-2-amino-5-[4-(difluoromethoxy)phenyl]-3-methyl-5-phenyl-3,5-dihydro-4H-imidazol-4-one, MS m/e (M+H)$^+$ 332; $^1$H NMR (400 MHz, DMSO-$d_6$) 2.93 (s, 3H), 6.61 (brs, 2H), 7.1 (d, J=8.54 Hz, 2H), 7.15-7.31 (m, 4H), 7.38 (m, 2H), 7.42 (d, J=8.54 Hz, 2H); $[\alpha]_D^{25}$=+20 (c=1% in MeOH), and

[B] (5R)-2-amino-5-[4-(difluoromethoxy)phenyl]-3-methyl-5-phenyl-3,5-dihydro-4H-imidazol-4-one, MS m/e (M+H)$^+$ 332; $^1$H NMR (400 MHz, DMSO-$d_6$) δ 2.93 (s, 3H), 6.61 (brs, 2H), 7.1 (d, J=8.54 Hz, 2H), 7.15-7.31 (m, 4H), 7.38 (m, 2H), 7.42 (d, J=8.54 Hz, 2H); $[\alpha]_D^{25}$=−22 (c=1% in MeOH).

Example 2

Preparation of 2-Amino-5-[3-(cyclopropylethynyl)-4-fluorophenyl]-5-[4-(difluoromethoxy)phenyl]-3-methyl-3,5-dihydro-4H-imidazol-4-one

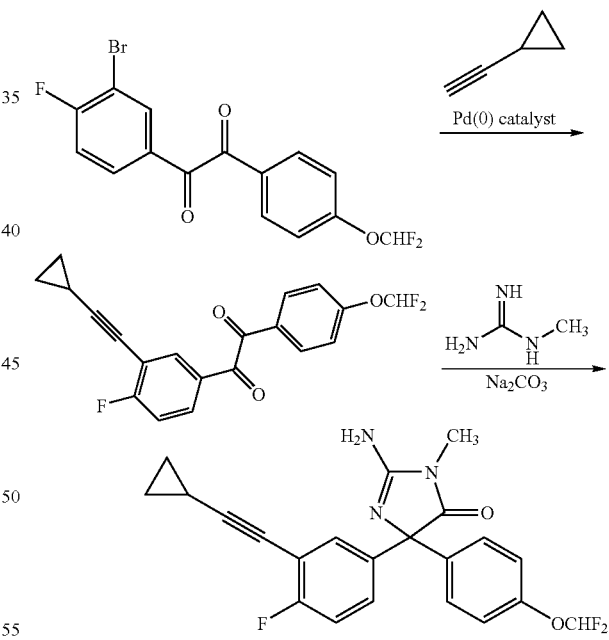

Step a) 1-[3-(cyclopropylethynyl)-4-fluorophenyl]-2-[4-(difluoromethoxy)-phenyl]ethane-1,2-dione A mixture of 1-(3-bromo-4-fluorophenyl)-2-[4-(difluoromethoxy)phenyl-]ethane-1,2-dione (2.1 g, 5.63 mmol), 2,6-dimethylpiperidine (10 mL), and ethynylcyclopropane (0.74 g, 11.27 mmol) was degassed with argon for 5 minutes. The reaction mixture was treated with tetrakis(triphenylphosphine) palladium (0) (327 mg, 0.28 mmol), stirred at 80° C. for 5 h, cooled to room temperature, poured into water and extracted with EtOAc. The extracts were combined, dried over MgSO$_4$, and concentrated in vacuo. Purification of the resultant residue by ICSO (hexane/EtOAc 5/1) gave 1-[3-(cyclopropylethynyl)-4-fluorophenyl]-2-[4-(difluoromethoxy)phenyl]ethane-1,2-dione as a yellow oil solid (1.37 g);

MS m/e (M)$^+$ 358.

Step b) 2-Amino-5-[3-(cyclopropylethynyl)-4-fluorophenyl]-5-[4-(difluoromethoxy)phenyl]-3-methyl-3,5-dihydro-4H-imidazol-4-one A mixture of 1-[3-(cyclopropylethynyl)-4-fluorophenyl]-2-[4-(difluoromethoxy)phenyl]ethane-1,2-dione (1.35 g, 3.97 mmol), ethanol (30 mL), 1-methylguanidine hydrochloride (0.65 g, 5.96 mmol), and Na$_2$CO$_3$ (0.63 g, 5.96 mmol) was stirred at 95° C. for 2 h, cooled to room temperature and concentrated under vacuum. The resultant residue was taken up in water and extracted with EtOAc. The extracts were combined, dried over MgSO$_4$ and concentrated in vacuo. Purification of this residue on silica gel (ISCO) using CH$_3$OH/EtOAc (1/20) as the eluting solvent gave the title product as a white solid (0.29 g), identified by NMR and mass spectral analyses. MS m/e (M+H)$^+$ 414

Example 3

Preparation of (5R)-2-Amino-5-[3-(cyclopropylethynyl)-4-fluorophenyl]-5-[4-(difluoromethoxy)phenyl]-3-methyl-3,5-dihydro-4H-imidazol-4-one (A) and (5S)-2-Amino-5-[3-(cyclopropylethynyl)-4-fluorophenyl]-5-[4-(difluoromethoxy)-phenyl]-3-methyl-3,5-dihydro-4H-imidazol-4-one (B)

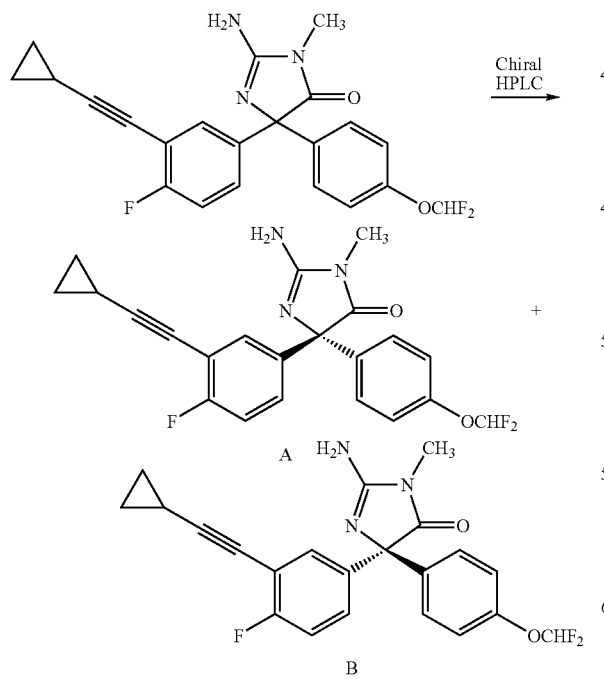

A racemic mixture of 2-amino-5-[3-(cyclopropylethynyl)-4-fluorophenyl]-5-[4-(difluoromethoxy)phenyl]-3-methyl-3,5-dihydro-4H-imidazol-4-one was separated by chiral chromatography technique (Chiralcel AD, 5×50 cm, using 10% (MeOH/EtOH-8/2)/DEA in hexane/DEA as the mobile phase) to produce the title products as white solids, identified by NMR and mass spectral analyses. [A] (5R)-enantiomer, MS m/e (M−H)$^-$ 412; [α]$_D$$^{25}$=6.2 (c=1% in MeOH) and [B] (5S)-enantiomer, MS m/e (M−H)$^-$ 412; [α]$_D$$^{25}$=−8.2 (c=1% in MeOH).

Example 4

Preparation of 2-Amino-5-[3-(cyclopropylethynyl)phenyl]-5-[4-(difluoromethoxy)phenyl]-3-methyl-3,5-dihydro-4H-imidazol-4-one

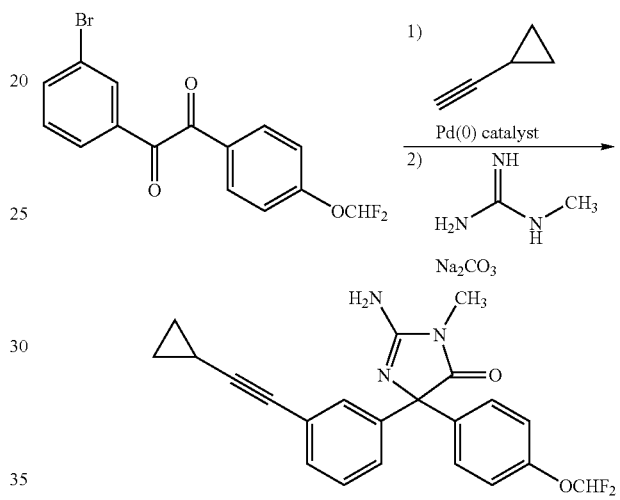

Using essentially the same procedure described in Example 2 and employing 1-(3-bromophenyl)-2-[4-(difluoromethoxy)phenyl]ethane-1,2-dione in step a, the title product was obtained as a white solid, identified by NMR and mass spectral analyses. MS m/e (M+H)$^+$ 396.

Example 5

Preparation of (5S)-2-Amino-5-[3-(cyclopropylethynyl)phenyl]-5-[4-(difluoromethoxy)phenyl]-3-methyl-3,5-dihydro-4H-imidazol-4-one (A) and (5R)-2-Amino-5-[3-(cyclopropylethynyl)phenyl]-5-[4-(difluoromethoxy)-phenyl]-3-methyl-3,5-dihydro-4H-imidazol-4-one (B)

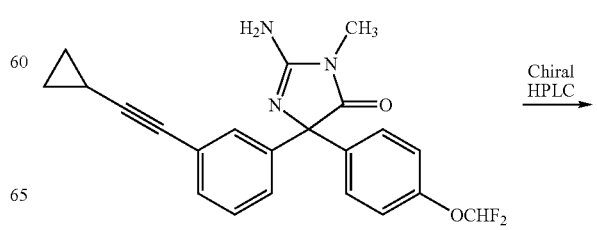

-continued

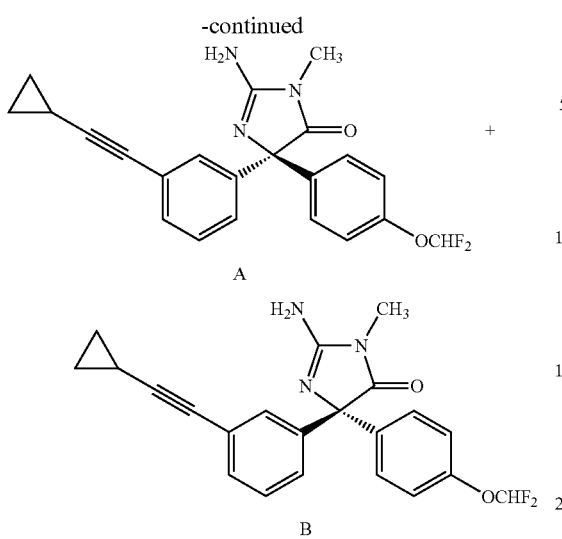

A

B

A racemic mixture of 2-amino-5-[3-(cyclopropylethynyl)phenyl]-5-[4-(difluoromethoxy)phenyl]-3-methyl-3,5-dihydro-4H-imidazol-4-one was separated by chiral chromatography technique (Chiralcel AD-H, 0.46×25 cm, using 10% CH$_3$OH/EtOH-8/2 with 0.1% DEA as the mobile phase to produce the title products as white solids; [A] (5S)-enantiomer, MS m/e (M−H)$^+$ 396; [α]$_D^{25}$=12.4 (c=1% in MeOH) and [B] (5R)-isomer, MS m/e (M−H)$^+$ 396; [α]$_D^{25}$=−13 (c=1% in MeOH).

Example 6

Preparation of 2-Amino-5-[4-(difluoromethoxy)phenyl]-3-methyl-5-(3-prop-1-yn-1-ylphenyl)-3,5-dihydro-4H-imidazol-4-one

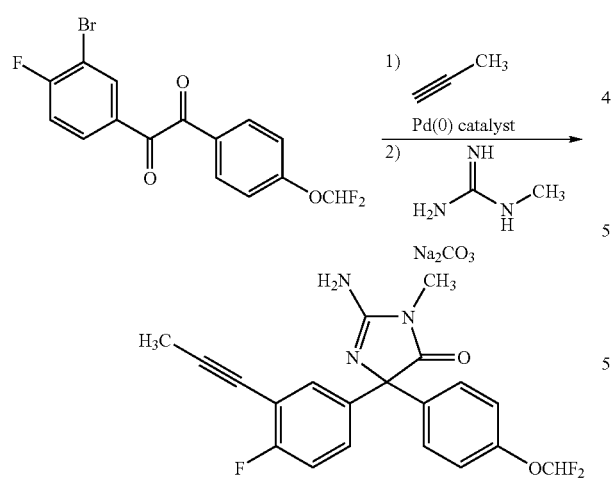

Using essentially the same procedure described in Example 2 and employing 1-(3-bromo-4-fluorophenyl)-2-[4-(difluoromethoxy)phenyl]ethane-1,2-dione and prop-1-yne in step a, the title product was obtained as a white solid, identified by NMR and mass spectral analyses. MS m/e (M+H)$^+$ 370.

Example 7

Preparation of (5S)-2-Amino-5-[4-(difluoromethoxy)phenyl]-5-(4-fluoro-3-prop-1-yn-1-ylphenyl)-3-methyl-3,5-dihydro-4H-imidazol-4-one (A) and (5R)-2-Amino-5-[4-(difluoromethoxy)phenyl]-5-(4-fluoro-3-prop-1-yn-1-ylphenyl)-3-methyl-3,5-dihydro-4H-imidazol-4-one (B)

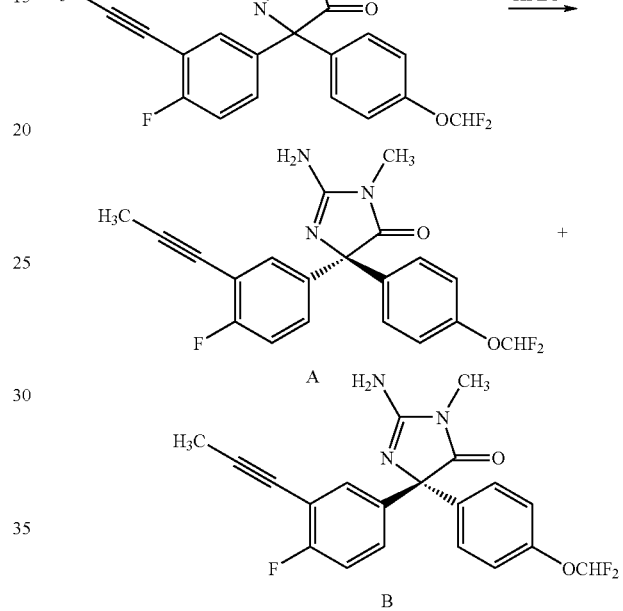

A racemic mixture of 2-amino-5-[4-(difluoromethoxy)phenyl]-5-(4-fluoro-3-prop-1-yn-1-ylphenyl)-3-methyl-3,5-dihydro-4H-imidazol-4-one was separated by chiral chromatography technique (Chiralcel AD 5×25 cm, using 13% EtOH in hexane and 0.1% DEA as the mobile phase to produce the title products as white solids; [A] (5S)-enantiomer, MS m/e (M−H)$^+$ 396; [α]$_D^{25}$=8.8 (c=1% in MeOH) and

[B] (5R)-enantiomer, MS m/e (M−H)$^+$ 396; [α]$_D^{25}$=−7 (c=1% in MeOH).

Example 8

Preparation of 2-amino-5-[3-(but-3-en-1-yloxy)phenyl]-5-[4-(difluoromethoxy)-phenyl]-3-methyl-3,5-dihydro-4H-imidazol-4-one

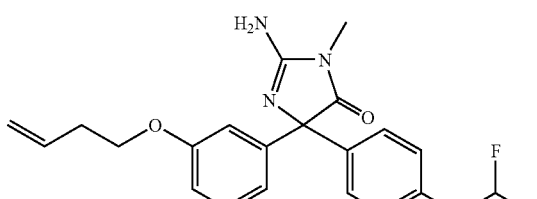

Step 1)
3-((4-(difluoromethoxy)phenyl)ethynyl)phenol

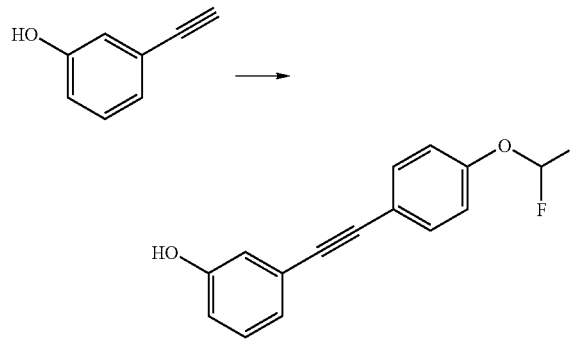

A mixture of 1-(difluoromethoxy)-4-iodobenzene (0.300 g, 1.11 mmol), 3-ethynylphenol (0.252 g, 1.39 mmol), bis(triphenylphosphino)palladium(II) chloride (0.039 g, 55 μmol), copper(I) iodide (0.006 g, 32 μmol) and triethylamine (0.62 g, 6.11 mmol) in DMF (4 mL) was stirred at RT for 3 h. The solvent is removed and the material is absorbed onto celite and purified by flash chromatography (silica, 5:95 ethyl acetate/hexanes) to afford 1-3-((4-(difluoromethoxy)phenyl) ethynyl)phenol (0.25 g, 86%) as an off white solid.

Step 2) 1-(4-(difluoromethoxy)phenyl)-2-(3-hydroxyphenyl)ethane-1,2-dione

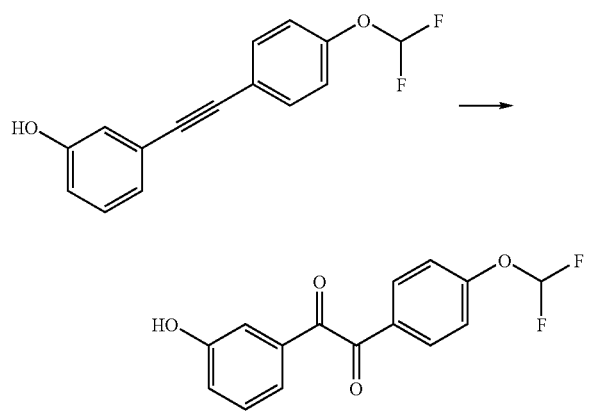

3-((4-(difluoromethoxy)phenyl)ethynyl)phenol (0.100 g, 0.38 mmol) is dissolved in acetone (2 mL) and added to a solution of NaHCO$_3$ (0.019 g, 0.23 mmol) and MgSO$_4$ (0.069 g, 0.53 mmol) in H$_2$O (2 mL). KMnO$_4$ (0.134 g, 0.85 mmol) is added in one portion and the solution is stirred for 2 h. EtOAc is added and the mixture is filtered through a pad of celite. The remaining solution is washed with H$_2$O, brine, dried and the solvent removed to yield 1-(4-(difluoromethoxy)phenyl)-2-(3-hydroxyphenyl)ethane-1,2-dione as a yellow solid (0.1 μg, 98%).

Step 3) 2-amino-4-(4-(difluoromethoxy)phenyl)-4-(3-hydroxyphenyl)-1-methyl-1H-imidazol-5(4H)-one

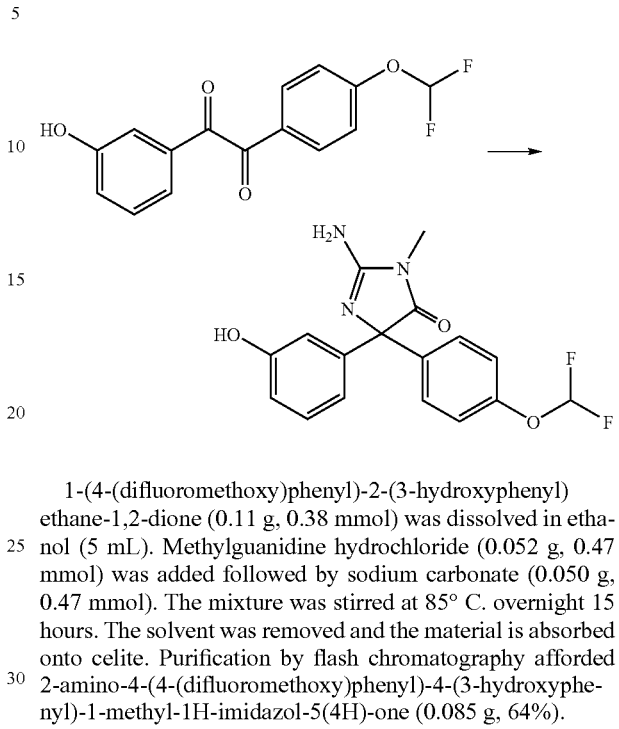

1-(4-(difluoromethoxy)phenyl)-2-(3-hydroxyphenyl) ethane-1,2-dione (0.11 g, 0.38 mmol) was dissolved in ethanol (5 mL). Methylguanidine hydrochloride (0.052 g, 0.47 mmol) was added followed by sodium carbonate (0.050 g, 0.47 mmol). The mixture was stirred at 85° C. overnight 15 hours. The solvent was removed and the material is absorbed onto celite. Purification by flash chromatography afforded 2-amino-4-(4-(difluoromethoxy)phenyl)-4-(3-hydroxyphenyl)-1-methyl-1H-imidazol-5(4H)-one (0.085 g, 64%).

Step 4) 2-amino-4-(3-(but-3-enyloxy)phenyl)-4-(4-(difluoromethoxy)phenyl)-1-methyl-1H-imidazol-5(4H)-one

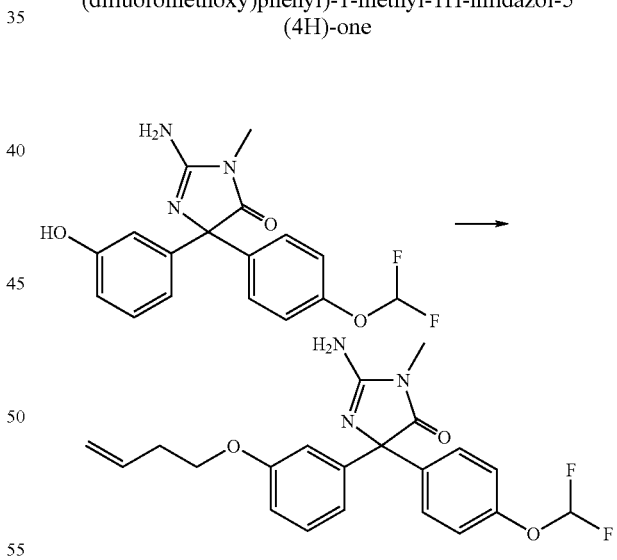

To a solution of 2-amino-4-(4-(difluoromethoxy)phenyl)-4-(3-hydroxyphenyl)-1-methyl-1H-imidazol-5(4H)-one (0.070 g, 0.20 mmol), but-3-en-1-ol (0.023 g, 0.32 mmol), and PS—PPh$_3$ (0.145 g, 0.32 mmol, 2.2 mmol/g) in THF (2 mL) is added diethylazodicarboxylate (0.058 g, 0.38 mmol) in THF (0.5 mL) dropwise. The mixture is stirred at 60° C. for 4 h. The solution is cooled to RT and the PPh$_3$ is filtered and washed with CH$_2$Cl$_2$ and MeOH. The solvent is removed, the remaining material is absorbed onto Celite and purified by Flash Chromatography (15:1 CH$_2$CL$_2$:MeOH) to yield 2-amino-4-(3-(but-3-enyloxy)phenyl)-4-(4-(difluoromethoxy)phenyl)-1-methyl-1H-imidazol-5(4H)-one (0.051 g, 73%) as an off white foam.

Example 9

Preparation of 2-amino-5-[3-(but-3-en-1-yloxy)-4-fluorophenyl]-5-[4-(difluoromethoxy)phenyl]-3-methyl-3,5-dihydro-4H-imidazol-4-one

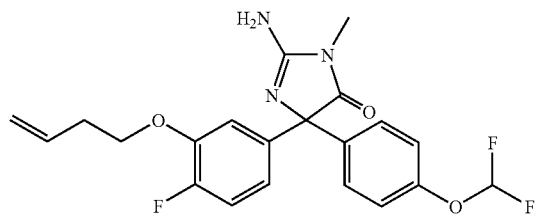

Step 1) 2-fluoro-5-((triisopropylsilyl)ethynyl)phenol

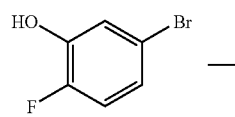

A solution of Ethynyl-triisopropyl-silane (1.13 g, 6.20 mmol), 5-bromo-2-fluorophenol (0.955 g, 4.98 mmol), bis(triphenylphosphino)palladium(II) chloride (0.105 g, 0.15 mmol), copper iodide (0.039 g, 0.205 mmol) and triethylamine (2.9 g, 28.7 mmol) in DMF (4.0 mL) is irradiated in the CEM explorer at 80° C. for 30 min. The solvent is removed and the product purified by Flash Chromatography to yield 2-fluoro-5-((triisopropylsilyl)ethynyl)phenol.

Step 2) 5-ethynyl-2-fluorophenol

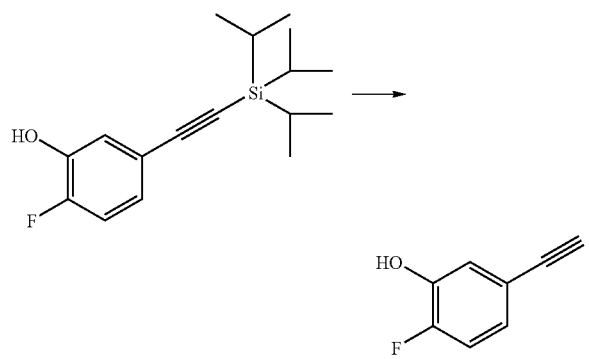

2-fluoro-5-((triisopropylsilyl)ethynyl)phenol is dissolved in THF and tetrabutyl ammoniumflouride is added. The solution is stirred overnight at RT. Et$_2$O is added and the solution is washed with H$_2$O, Brine, dried, and the solvent removed. This material is used without any further purification.

Steps 3 Through 6 are Completed in a Similar Fashion to Example 8 Using 5-Ethynyl-2-Fluorophenol in Place of 3-ethynylphenol in the First Step

Example 10

Preparation of (5R)- and (5S)-2-amino-5-[3-(but-3-en-1-yloxy)phenyl]-5-[4-(difluoromethoxy)phenyl]-3-methyl-3,5-dihydro-4H-imidazol-4-one Using the same chemistry as Example 8 the following compounds were made using optically active phenols generated from chiral separation of 2-amino-4-(4-(difluoromethoxy)phenyl)-4-(3-hydroxyphenyl)-1-methyl-1H-imidazol-5(4H)-one:

Example 10A

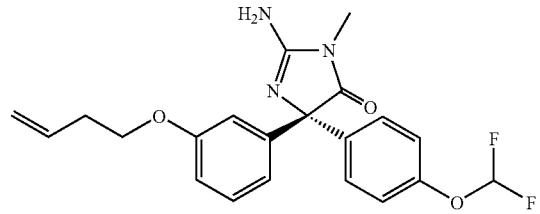

(5R)-2-amino-5-[3-(but-3-en-1-yloxy)phenyl]-5-[4-(difluoromethoxy)phenyl]-3-methyl-3,5-dihydro-4H-imidazol-4-one

Example 10B

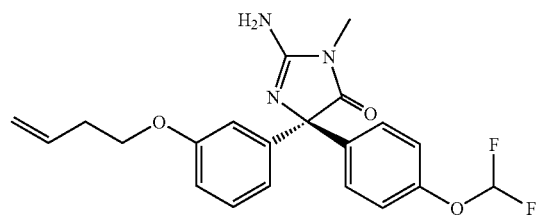

(5S)-2-amino-5-[3-(but-3-en-1-yloxy)phenyl]-5-[4-(difluoromethoxy)phenyl]-3-methyl-3,5-dihydro-4H-imidazol-4-one Using the same chemistry the following compounds are made:

Example 10C

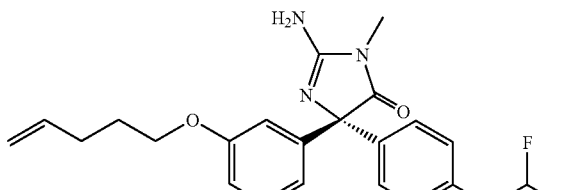

(R)-2-amino-4-(4-(difluoromethoxy)phenyl)-1-methyl-4-(3-(pent-4-enyloxy)phenyl)-1H-imidazol-5(4H)-one Example 10D

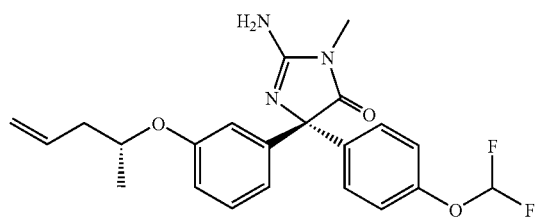

(R)-2-amino-4-(4-(difluoromethoxy)phenyl)-1-methyl-4-(3-((R)-pent-4-en-2-yloxy)phenyl)-1H-imidazol-5(4H)-one Example 10E

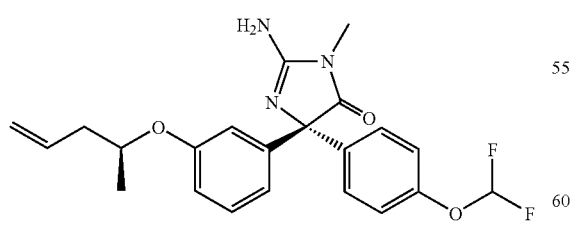

(R)-2-amino-4-(4-(difluoromethoxy)phenyl)-1-methyl-4-(3-((S)-pent-4-en-2-yloxy)phenyl)-1H-imidazol-5(4H)-one Example 10F

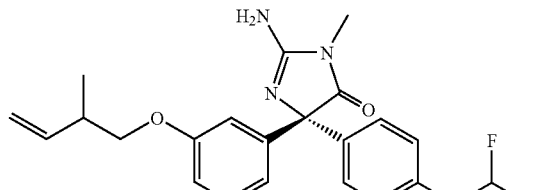

(4R)-2-amino-4-(4-(difluoromethoxy)phenyl)-1-methyl-4-(3-(2-methylbut-3-enyloxy)phenyl)-1H-imidazol-5(4H)-one Example 10G

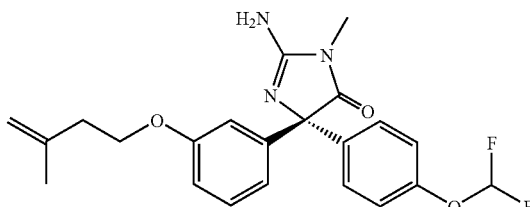

(R)-2-amino-4-(4-(difluoromethoxy)phenyl)-1-methyl-4-(3-(3-methylbut-3-enyloxy)phenyl)-1H-imidazol-5(4H)-one Example 10H

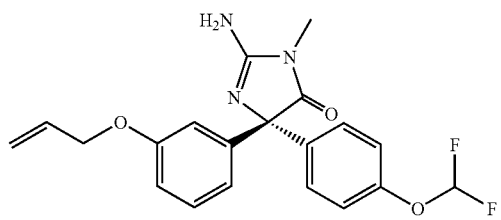

(R)-4-(3-(allyloxy)phenyl)-2-amino-4-(4-(difluoromethoxy)phenyl)-1-methyl-1H-imidazol-5(4H)-one

Example 11

Chiral separation of 5-(3-{(4R)-2-amino-4-[4-(difluoromethoxy)phenyl]-1-methyl-5-oxo-4,5-dihydro-1H-imidazol-4-yl}phenyl)pentanenitrile (A) and 5-(3-{(4S)-2-amino-4-[4-(difluoromethoxy)phenyl]-1-methyl-5-oxo-4,5-dihydro-1H-imidazol-4-yl}phenyl)pentanenitrile (B)

A
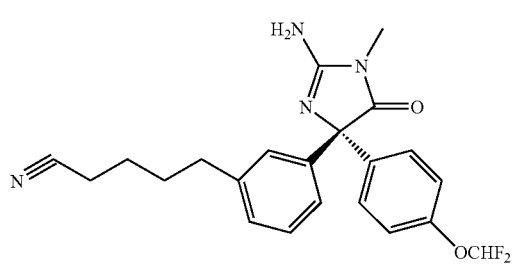

B
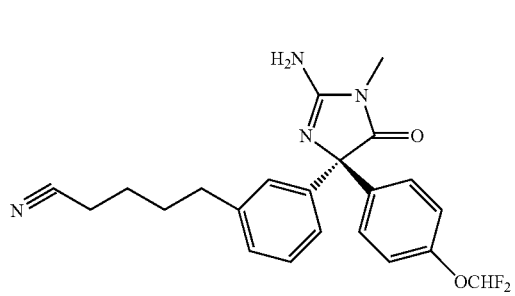

The enantiomers of 5-(3-{-2-amino-4-[4-(difluoromethoxy)phenyl]-1-methyl-5-oxo-4,5-dihydro-1H-imidazol-4-yl}phenyl)pentanenitrile (prepared as shown in Example 83) were separated to give 5-(3-{(4S)-2-amino-4-[4-(difluoromethoxy)phenyl]-1-methyl-5-oxo-4,5-dihydro-1H-imidazol-4-yl}phenyl)pentanenitrile [MS (ES+): 413 (M+H). OR=−20] and 5-(3-{(4R)-2-amino-4-[4-(difluoromethoxy)phenyl]-1-methyl-5-oxo-4,5-dihydro-1H-imidazol-4-yl}phenyl)pentanenitrile [MS (ES+): 413 (M+H). OR=+22].

Example 12

Preparation of 2-Amino-5-(4-difluoromethoxy-phenyl)-5-[3-(1-fluoro-pent-4-enyl)-phenyl]-3-methyl-3,5-dihydro-imidazol-4-one

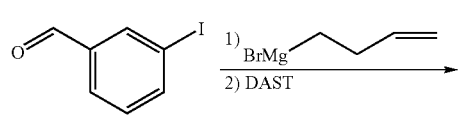

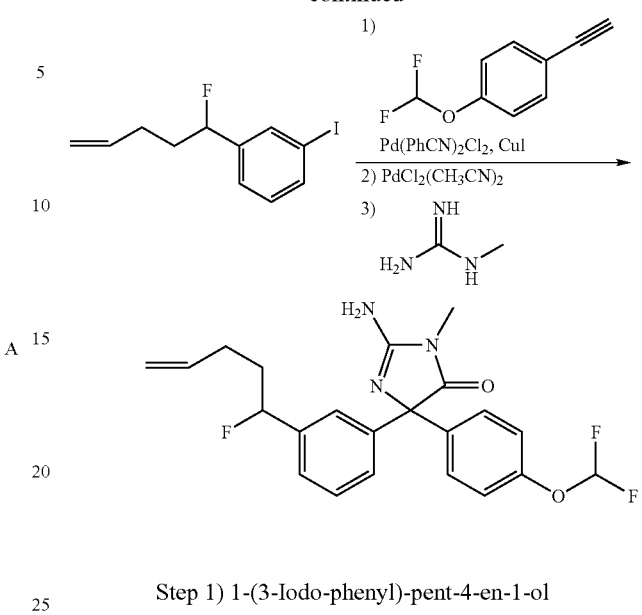

Step 1) 1-(3-Iodo-phenyl)-pent-4-en-1-ol

To a stirred solution of 3-iodo-benzaldehyde (3.0 g, 12.93 mmol) in dry THF (45 mL) at −78° C. under nitrogen was added 0.5 M 3-butenyl magnesium bromide in THF (25.86 mL, 12.93 mmol) over 20 min. The reaction was stirred for 0.5 h and allowed to warm to −30° C. over 1 h and then quenched with sat ammonium chloride (20 mL). The reaction was diluted with water (10 mL) and then extracted with ethyl acetate (2×50 mL). The extracts were dried (MgSO$_4$) and concentrated in vacuo. Purification by flash chromatography (5% to 10% ethyl acetate/petroleum ether) gave the title compound as a clear oil (3.5 g, 95%) and was used directly in the next step.

Step 2) 1-(1-Fluoro-pent-4-enyl)-3-iodo-benzene

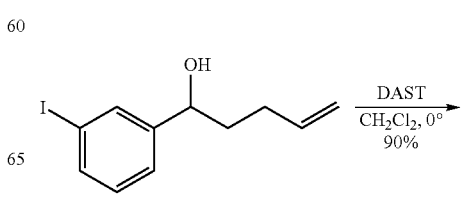

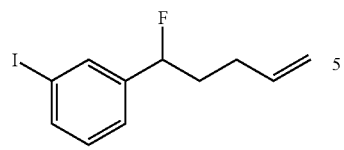

To a stirred solution of 1-(3-Iodo-phenyl)-pent-4-en-1-ol (0.51 g, 1.77 mmol), in dry methylene chloride (10 mL) at −78° C. and under a nitrogen atmosphere was added DAST (0.28 mL, 2.1 mmol). The cooling bath was removed and the mixture was warmed to room temperature for 1 h, and then quenched with sat sodium bicarbonate (4 mL). The mixture was partitioned between methylene chloride and H₂O, and the aqueous layer was extracted with methylene chloride (2×10 mL). The organic layer was washed with brine and dried over MgSO₄, filtered and concentrated in vacuo to a clear oil (0.46 g, 90%) and used directly in the next step.

Step 3) 1-{[4-(difluoromethoxy)phenyl]ethynyl}-3-(1-fluoropent-4-en-1-yl)benzene

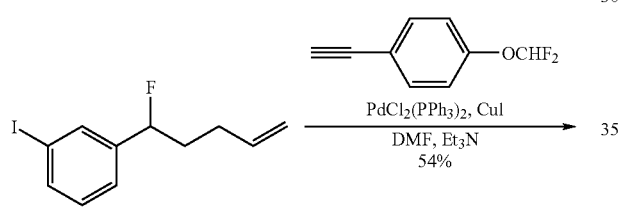

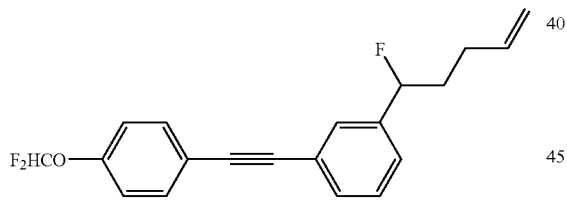

To a solution of 1-(1-Fluoro-pent-4-enyl)-3-iodo-benzene (0.4 g, 1.38 mmol) in DMF (6 ml) were added TEA (0.96 ml, 6.9 mmol) and 1-Difluoromethoxy-4-ethynyl-benzene (0.233 g, 1.378 mmol). The reaction was degassed by bubbling argon through it for 5 minute and then dichlorbis(triphenylphospine)palladium (0.048 g, 0.069 mmol), and copper iodide (0.013 g, 0.693 mmol) were added simultaneously. The reaction mixture was heated at 65° C. for 15 min. cooled and quenched with 0.1 N HCl (15 ml). The aqueous was extracted with Et₂O (3×15 ml). The combined organic extracts were washed with brine (20 ml), dried (MgSO₄), and concentrated. The crude material was purified by chromatography (2.5%-5% Ethyl acetate/Petroleum Ether) to afford the titled compound (0.246 g, 54%) as a slight orange oil, identified by NMR and mass spectral analyses; MS (EI+): 330 (M+)

Step 4) 1-(4-Difluoromethoxy-phenyl)-2-[3-(1-fluoro-pent-4-enyl)-phenyl]-ethane-1,2-dione

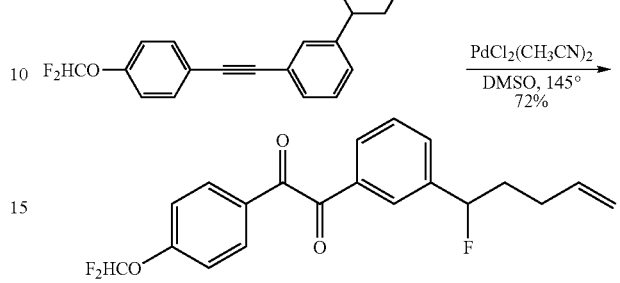

A solution of 1-{[4-(difluoromethoxy)phenyl]ethynyl}-3-(1-fluoropent-4-en-1-yl)benzene (0.240 g, 0.73 mmol) in anhydrous DMSO (3.0 mL) was added dichlorbis(acetonitrile)palladium (0.018 g, 0.073 mmol) and heated to 145° C. for 6 h. The mixture was partitioned between ethyl acetate and H₂O, and the aqueous layer was extracted with ethyl acetate (15 mL). The combined organic layers were washed with brine (1×15 mL), dried (MgSO₄), filtered and concentrated under reduced pressure. Silica gel chromatography (10-20% Ethyl acetate/petroleum ether) gave the title compound as a clear oil (0.19 g, 72%) which was used directly in the next step.

Step 5) 2-Amino-5-(4-difluoromethoxy-phenyl)-5-[3-(1-fluoro-pent-4-enyl)-phenyl]-3-methyl-3,5-dihydro-imidazol-4-one

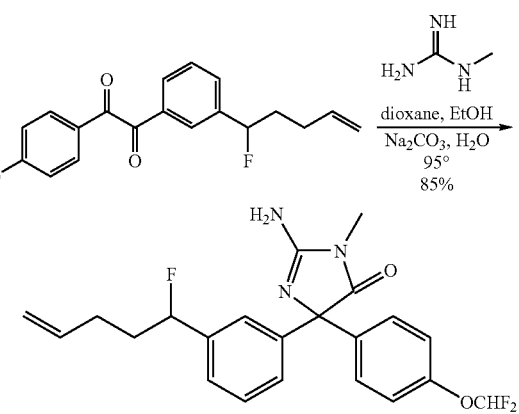

Into a mixture of 1-(4-Difluoromethoxy-phenyl)-2-[3-(1-fluoro-pent-4-enyl)-phenyl]-ethane-1,2-dione 0.18 g, 0.5 mmol), dioxane (4 mL), ethanol (6.0 mL) and water (1.0 mL) were added Na₂CO₃ (0.236 g, 2.23 mmol), and 1-methylguanidine hydrochloride (0.245 g, 2.23 mmol). The new mixture was stirred at 95° C. for 3 h. The volatiles were removed under vacuum and the residue taken up in water and extracted with ethyl acetate (3×20 mL). The combined organic layers were washed with brine, dried (MgSO₄), filtered and concentrated under reduced pressure. Silica gel chromatography (5-10% ethyl alcohol/dichloromethane) gave the title compound as a slight white foam (0.176 g, 85%), identified by NMR and mass spectral analyses; Mp: 50-55° C. MS (ES+): 418 (M+H).

Example 13

Preparation of 2-Amino-5-(4-difluoromethoxy-phenyl)-5-[4-fluoro-3-(1-fluoro-pent-4-enyl)-phenyl]-3-methyl-3,5-dihydro-imidazol-4-one

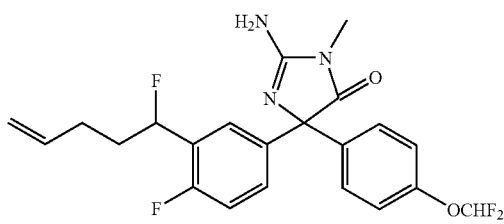

The title compound was prepared in substantially the same manner as described in Example 12, steps 1-5 starting from 2-Fluoro-5-iodo-benzaldehyde (1.0 g, 4 mmol), and identified by NMR and mass spectral analyses; Mp: 50-55° C. MS (ES+): 436 (M+H).

Example 14

Preparation of 4-{5-[2-Amino-4-(4-difluoromethoxy-phenyl)-1-methyl-5-oxo-4,5-dihydro-1H-imidazol-4-yl]-2-fluoro-phenyl}-butyronitrile Step 1) 3-(5-Bromo-2-fluoro-phenyl)-acrylic acid methyl ester

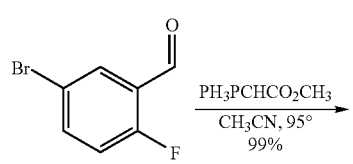

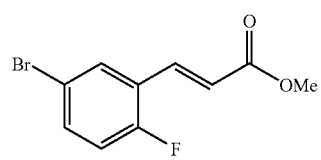

A solution of 5-Bromo-2-fluoro-benzaldehyde (1.0 g, 4.9 mmol) in anhydrous acetonitrile (20.0 mL) was added methyl (triphenylphosphoranylidene)acetate (3.3 g, 9.0 mmol) and heated to 95° C. for 12 h. The mixture was cooled, filtered and concentrated under reduced pressure. Silica gel chromatography (5% Ethyl acetate/petroleum ether) gave the title compound as a white solid (1.27 g, 99%) which was used directly in the next step.

Step 2) 3-(5-Bromo-2-fluoro-phenyl)-acrylic acid methyl ester

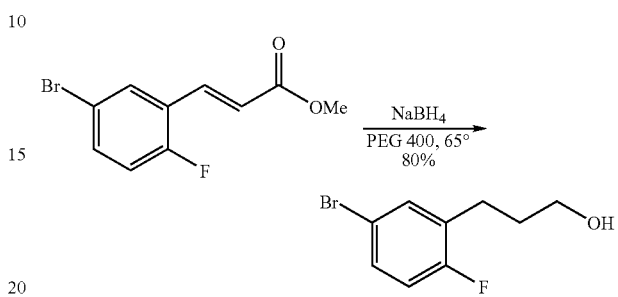

To a solution of 3-(5-Bromo-2-fluoro-phenyl)-acrylic acid methyl ester (1.2 g, 4.7 mmol) in PEG 400 (20 mL) was added sodium borohydride (0.53 g, 14 mmol) portionwise. Under stirring the solution was slowly brought to 65° C. (evolution of hydrogen) for 12 h. Diluted HCl (10%) was added to the reaction mixture dropwise, and the products were extracted (3×30 mL) with diethyl ether. The combined organic layers were washed with brine, dried (MgSO$_4$), filtered and concentrated under reduced pressure. The crude material was purified by silica gel chromatography (20-30% Ethyl acetate/Petroleum Ether) to afford the titled compound (0.872 g, 80%) as a clear oil, identified by NMR and mass spectral analyses; MS (EI+): 233 (M+).

Step 3) Toluene-4-sulfonic acid 3-(5-bromo-2-fluoro-phenyl)-propyl ester

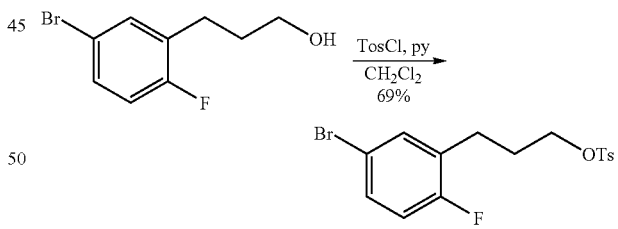

To a stirred solution of 3-(5-Bromo-2-fluoro-phenyl)-propan-1-ol (0.53 g, 2.3 mmol) in dry methylene chloride (10 mL) at 0° C. and under a nitrogen atmosphere was added pyridine (0.46 mL, 5.6 mmol) and tosyl chloride (0.47, 2.5 mmol). The cooling bath was removed and the mixture was warmed to room temperature for 12 h, and then quenched with 2 N HCl (6 mL). The mixture was partitioned between methylene chloride and H$_2$O, and the aqueous layer was extracted with methylene chloride (2×10 mL). The organic layer was washed with brine and dried over MgSO$_4$, filtered and concentrated in vacuo. The crude material was purified by silica gel chromatography (10-20% Ethyl acetate/Petroleum Ether) to afford the titled compound (0.6 g, 69%) as a clear oil, identified by NMR and mass spectral analyses; MS (ES+): 403 (M+NH$_4$+).

Step 4) 4-(5-Bromo-2-fluoro-phenyl)-butyronitrile

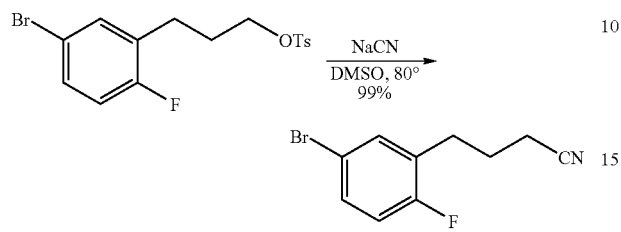

A solution of Toluene-4-sulfonic acid 3-(5-bromo-2-fluoro-phenyl)-propyl ester (0.59 g, 1.5 mmol) in anhydrous DMSO (3.0 mL) was added sodium cyanide (0.112 g, 2.3 mmol) and heated to 80° C. for 12 h. The mixture was cooled and partitioned between ethyl acetate and H$_2$O, and the aqueous layer was extracted with ethyl acetate (15 mL). The combined organic layers were washed with brine (1×15 mL), dried (MgSO$_4$), filtered and concentrated under reduced pressure. Silica gel chromatography (10-20% Ethyl acetate/petroleum ether) gave the title compound as a clear oil (0.37 g, 99%), and was used directly in the next step.

Step 5) 4-(2-Fluoro-5-trimethylsilanylethynyl-phenyl)-butyronitrile

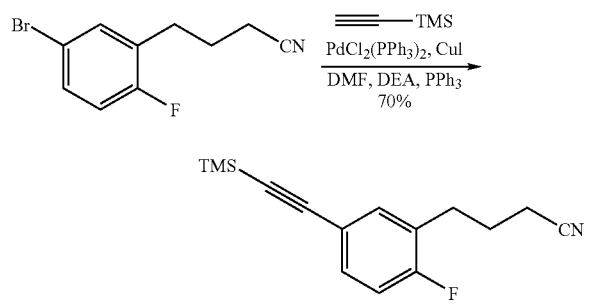

To a stirred solution of 4-(5-Bromo-2-fluoro-phenyl)-butyronitrile (0.37 g, 1.52 mmol) in diethyl amine (6 mL) and DMF (2 mL) was added triphenylphosine (0.08 g, 0.31 mmol), trimethylsilylacetylene (0.23 ml, 1.7 mmol), CuI (0.015 g, 0.076 mmol), and dichlorbis(triphenylphospine) palladium (0.054 g, 0.076 mmol). The reaction was heated at 85° C. for 12 h and then cooled to room temperature. The reaction was diluted with ethyl acetate (20 mL) and then poured into 0.1 N HCl (20 mL) and extracted with ethyl acetate (3×50 ml). The extracts were washed with water (10 mL) and brine (10 mL), dried (MgSO$_4$) and concentrated in vacuo. Purification by flash chromatography (5% to 10% ethyl acetate/petroleum ether) gave the title compound as a clear oil (0.28 g, 70%), identified by NMR and mass spectral analyses; MS (ES+): 260 (M+H).

Step 6) 4-(5-Ethynyl-2-fluoro-phenyl)-butyronitrile

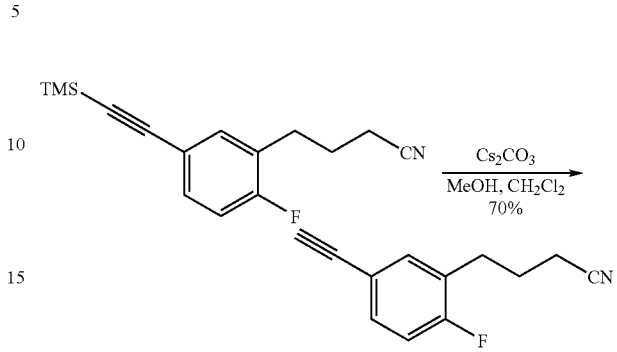

To a stirred solution of 4-(2-Fluoro-5-trimethylsilanyl-ethynyl-phenyl)-butyronitrile (0.27 g, 1.04 mmol), in dry methylene chloride (2.5 mL) and methanol (2.5 mL) was added cesium carbonate (0.41 g, 1.2 mmol) and stirred for 2 h under a nitrogen atmosphere. The mixture was diluted with diethyl ether (15 mL), and partitioned between diethyl ether and H$_2$O (10 mL), and the aqueous layer was extracted with diethyl ether (10 mL), washed with brine and dried over MgSO$_4$, filtered and concentrated in vacuo. Purification by flash chromatography (5-10% ethyl acetate/petroleum ether) gave the title compound as a brown semi solid (0.154 g, 79%), identified by NMR and mass spectral analyses. MS (EI+): 187 (M+).

Step 7) 4-[5-(4-Difluoromethoxy-phenylethynyl)-2-fluoro-phenyl]-butyronitrile

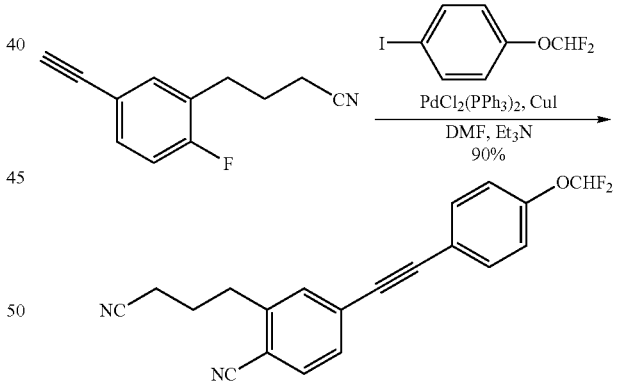

To a solution of 1-Difluoromethoxy-4-iodo-benzene (0.21 g, 0.79 mmol) in DMF (3.5 ml) were added TEA (0.55 mL, 57.4 mmol) and 4-(5-Ethynyl-2-fluoro-phenyl)-butyronitrile (0.48 g, 0.79 mmol). The reaction was degassed by bubbling argon through it for 5 min and then dichlorbis(triphenylphospine)palladium (0.0.28 g, 0.04 mmol), and copper iodide (0.008 g, 0.57 mmol) were added simultaneously. The reaction mixture was heated at 65° C. for 15 min. cooled and quenched with 0.1 N HCl (10 ml). The aqueous layer was extracted with Et$_2$O (3×10 ml). The combined organic extracts were washed with brine (25 ml), dried (MgSO$_4$), and concentrated. The crude material was purified by silica gel chromatography (10-20% Ethyl acetate/Petroleum Ether) to afford the titled compound (0.235 g, 90%) as a brown oil that solidified on standing, and was identified by NMR and mass spectral analyses. MS (EI+): 329 (M+).

Step 8) 4-{5-[2-(4-Difluoromethoxy-phenyl)-2-oxo-acetyl]-2-fluoro-phenyl}-butyronitrile

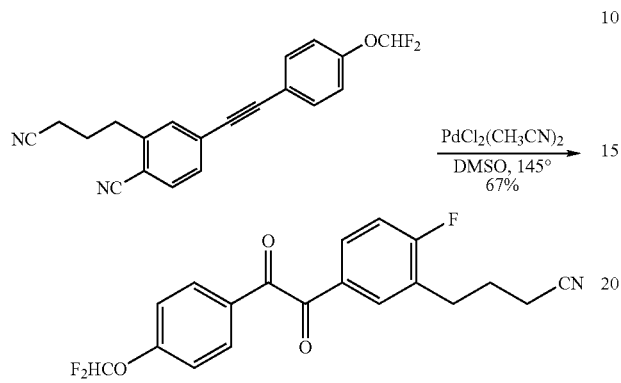

The title compound was prepared in substantially the same manner as described in Example 12, step 4 starting from 4-[5-(4-Difluoromethoxy-phenylethynyl)-2-fluoro-phenyl]-butyronitrile (0.23 g, 0.7 mmol), and was obtained as a clear waxy solid, (0.17 g, 67%), and identified by NMR and mass spectral analyses. MS (ES−): 420 (M+CH$_3$COO−).

Step 9) 4-[5-[2-Amino-4-(4-difluoromethoxy-phenyl)-1-methyl-5-oxo-4,5-dihydro-1H-imidazol-4-yl]-2-fluoro-phenyl]-butyronitrile

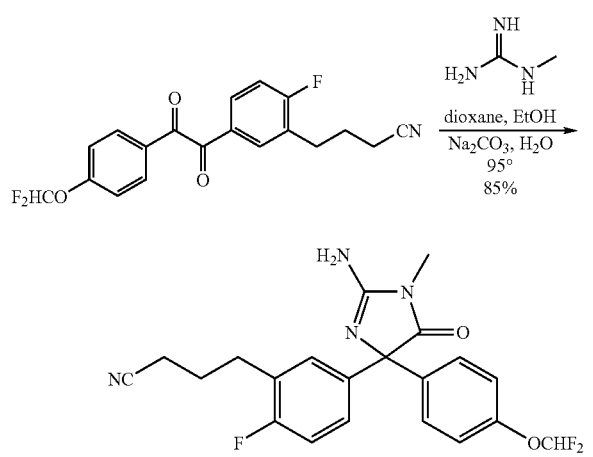

The title compound was prepared in substantially the same manner as described in Example 12, step 5 starting from 4-{5-[2-(4-Difluoromethoxy-phenyl)-2-oxo-acetyl]-2-fluoro-phenyl}-butyronitrile (0.16 g, 0.44 mmol), and was obtained as a white foam, (0.156 g, 85%), and identified by NMR and mass spectral analyses. Mp: 65-70° C. HRMS (ESI+): 417.1534 (M+H).

Example 15

Preparation of 2-Amino-5-(4-difluoromethoxy-phenyl)-5-(4-fluoro-3-methyl-phenyl)-3-methyl-3,5-dihydro-imidazol-4-one Step 1) 4-(4-Difluoromethoxy-phenylethynyl)-1-fluoro-2-methyl-benzene

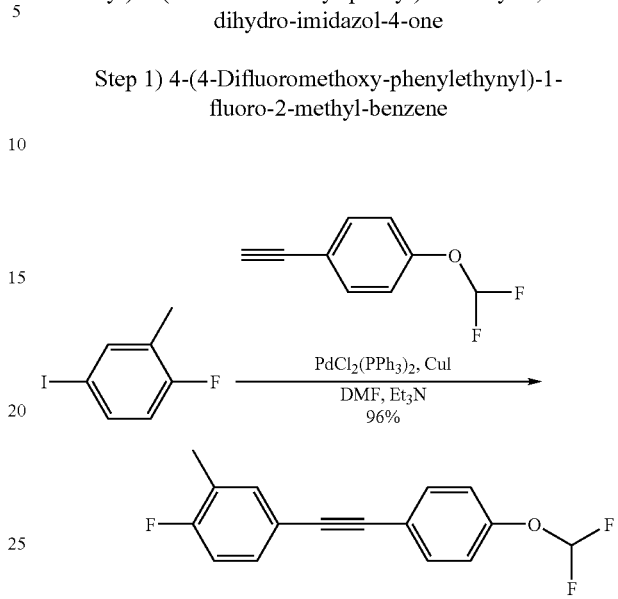

The title compound was prepared in substantially the same manner as described in Example 12, step 3 starting from 1-Fluoro-4-iodo-2-methyl-benzene (0.125 g, 0.53 mmol), and 1-Difluoromethoxy-4-ethynyl-benzene (0.09 g, 0.53 mmol), and was obtained as a yellow semi solid, (0.141 g, 96%), and identified by NMR and mass spectral analyses. MS (EI+): 276 (M+).

Step 2) 1-(4-Difluoromethoxy-phenyl)-2-(4-fluoro-3-methyl-phenyl)-ethane-1,2-dione

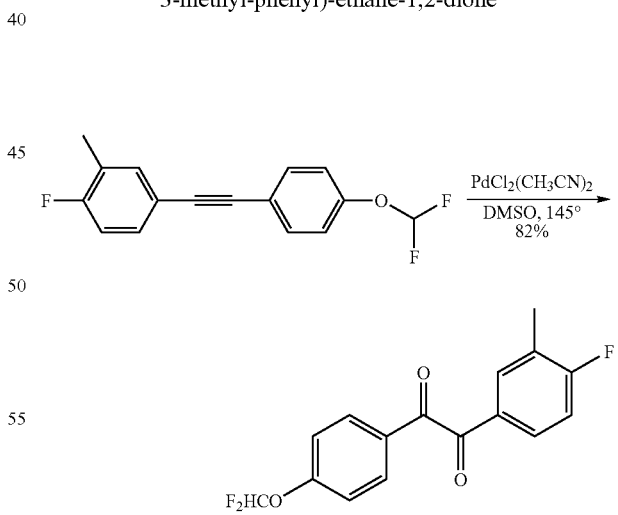

The title compound was prepared in substantially the same manner as described in Example 12, step 4 starting from 4-(4-Difluoromethoxy-phenylethynyl)-1-fluoro-2-methyl-benzene (0.137 g, 0.5 mmol), and was obtained as a yellow solid, (0.126 g, 82%), and identified by NMR and mass spectral analyses. Mp: 77-78° C. MS (EI+): 308 (M+).

Step 3) 2-Amino-5-(4-difluoromethoxy-phenyl)-5-(4-fluoro-3-methyl-phenyl)-3-methyl-3,5-dihydro-imidazol-4-one

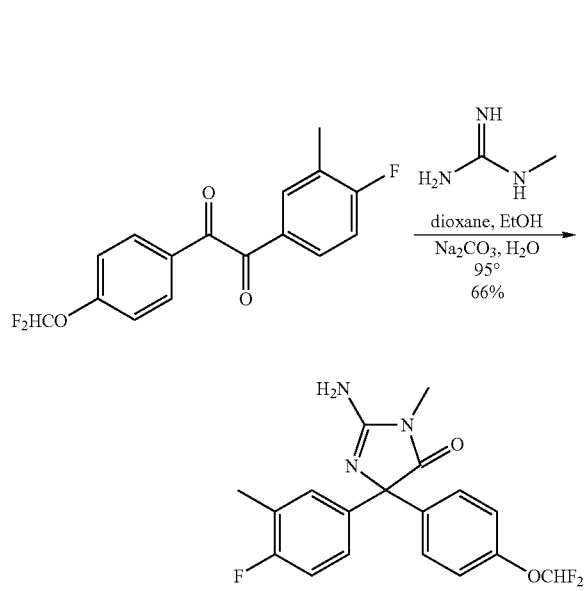

The title compound was prepared in substantially the same manner as described in Example 12, step 5 starting from 1-(4-Difluoromethoxy-3-methyl-phenyl)-2-(4-fluoro-3-methyl-phenyl)-ethane-1,2-dione (0.088 g, 0.29 mmol), and was obtained as a white foam, (0.07 g, 66%), identified by NMR and mass spectral analyses. Mp: 70° C. HRMS (ESI+): 364.1273 (M+H).

Example 16

Preparation of 5-[2-Amino-4-(4-difluoromethoxy-phenyl)-1-methyl-5-oxo-4,5-dihydro-1H-imidazol-4-yl]-2-methoxy-benzonitrile

Step 1) 2-Fluoro-5-trimethylsilanylethynyl-benzonitrile

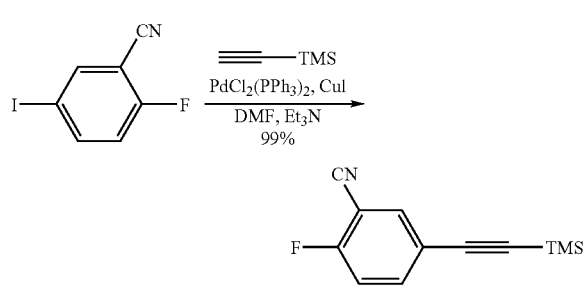

The title compound was prepared in substantially the same manner as described in Example 1, step 3 starting from 2-Fluoro-5-iodo-benzonitrile (1.0 g, 4.14 mmol), and Ethynyl-trimethyl-silane (0.487 g, 4.97 mmol), and was obtained as a waxy brown solid, (0.90 g, 99%), identified by NMR and mass spectral analyses. MS (EI+): 216 (M+).

Step 2) 5-Ethynyl-2-methoxy-benzonitrile

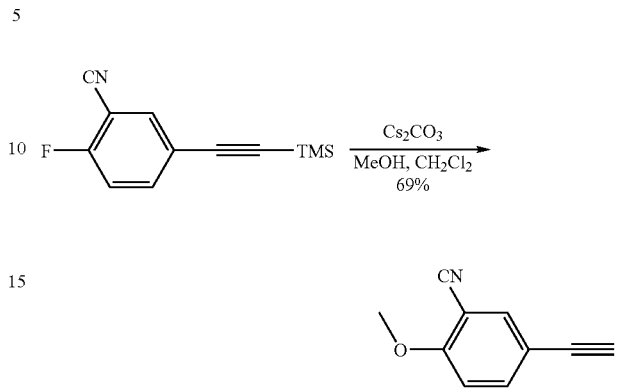

To a stirred solution of 2-Fluoro-5-trimethylsilanylethynyl-benzonitrile (0.935 g, 4.3 mmol), in dry methylene chloride (10 mL) and methanol (10 mL) was added cesium carbonate (1.7 g, 5.2 mmol) and stirred for 2 h under a nitrogen atmosphere. The mixture was diluted with diethyl ether (100 mL), and partitioned between diethyl ether and H₂O (100 mL), and the aqueous layer was extracted with diethyl ether (50 mL), washed with brine and dried over MgSO₄, filtered and concentrated in vacuo. Purification by flash chromatography (20-30% ethyl acetate/petroleum ether) gave the title compound as a tan solid (0.468 g, 69%), identified by NMR and mass spectral analyses. Mp: 100-101° C. MS (EI+): 157 (M+).

Step 3) 5-(4-Difluoromethoxy-phenylethynyl)-2-methoxy-benzonitrile

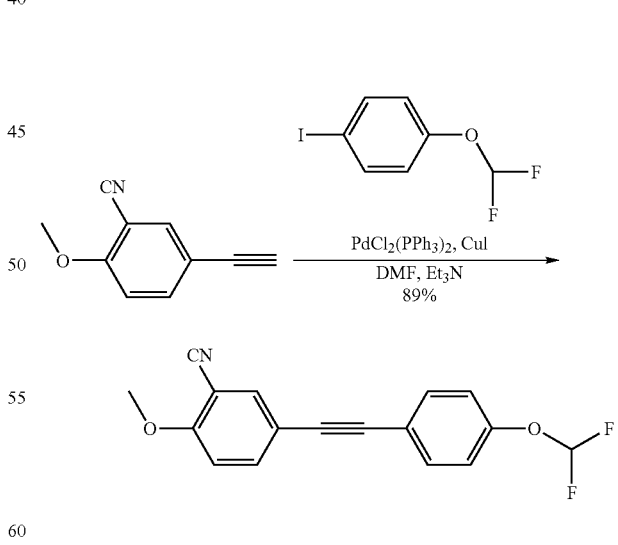

The title compound was prepared in substantially the same manner as described in Example 12, step 3 starting from 1-Difluoromethoxy-4-iodo-benzene (0.17 g, 0.64 mmol), and 5-Ethynyl-2-methoxy-benzonitrile (0.10 g, 0.64 mmol), and was obtained as a light brown solid, (0.170 g, 89%), identified by NMR and mass spectral analyses. MS (APPI+): 299 (M+)

Step 4) 5-[2-(4-Difluoromethoxy-phenyl)-2-oxo-acetyl]-2-methoxy-benzonitrile

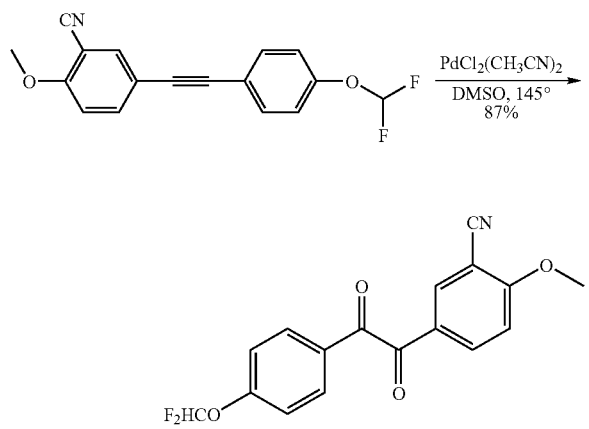

The title compound was prepared in substantially the same manner as described in Example 12, step 4 starting from 5-(4-Difluoromethoxy-phenylethynyl)-2-methoxy-benzonitrile (0.16 g, 0.53 mmol), and was obtained as a tan solid, (0.24 g, 87%), identified by NMR and mass spectral analyses. Mp: 150-155° C. MS (EI+): 331 (M+).

Step 5) 5-[2-Amino-4-(4-difluoromethoxy-phenyl)-1-methyl-5-oxo-4,5-dihydro-1H-imidazol-4-yl]-2-methoxy-benzonitrile

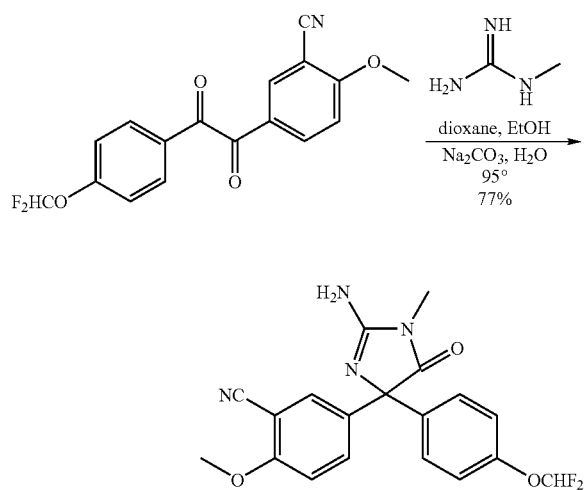

The title compound was prepared in substantially the same manner as described in Example 12, step 5 starting from 5-[2-(4-Difluoromethoxy-phenyl)-2-oxo-acetyl]-2-methoxy-benzonitrile (0.099 g, 0.30 mmol), and was obtained as a white foam, (0.089 g, 77%), identified by NMR and mass spectral analyses. Mp: 104-105° C. HRMS (ESI+): 387.1259 (M+H).

Example 17

Preparation of 2-Amino-5-(4-difluoromethoxy-phenyl)-5-(4-fluoro-3-fluoromethyl-phenyl)-3-methyl-3,5-dihydro-imidazol-4-one Step 1) (2-Fluoro-5-iodo-phenyl)-methanol

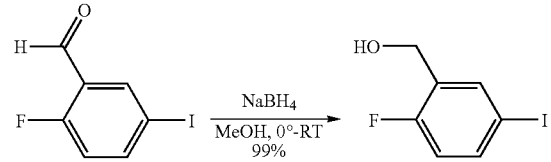

To an ice cooled solution of 2-Fluoro-5-iodo-benzaldehyde (1.0 g, 4.0 mmol) in $CH_3OH$ (10 mL) was added $NaBH_4$ (0.182 g, 4.8 mmol) in two portions over 10 min. The reaction mixture was stirred for 1 h and concentrated in vacuo. The residue was dissolved in EtOAc (50 mL) and washed sequentially with $2 \times H_2O$ (20 mL) and brine (20 mL). The organic layer was dried ($MgSO_4$), and concentrated. The crude material was purified by flash chromatography (30% Ethyl acetate/Petroleum Ether) to afford the titled compound (1.0 g, 99%) as a white solid, identified by NMR and mass spectral analyses. Mp: 42° C. MS (EI+): 252 (M+).

Step 2) 1-Fluoro-2-fluoromethyl-4-iodo-benzene

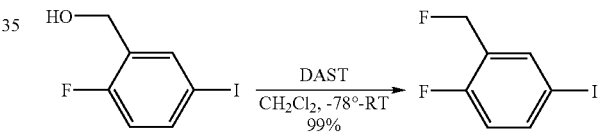

To a stirred solution of (2-Fluoro-5-iodo-phenyl)-methanol (1.0 g, 3.97 mmol) in dry methylene chloride (10 mL) at −78° C. and under a nitrogen atmosphere was added DAST (0.63 mL, 4.76 mmol). The cooling bath was removed and the mixture was warmed to room temperature for 1 h, and then quenched with sat sodium bicarbonate (4 mL). The mixture was partitioned between methylene chloride and $H_2O$, and the aqueous layer was extracted with methylene chloride (2×10 mL). The organic layer was washed with brine and dried over $MgSO_4$, filtered and concentrated in vacuo to a clear oil (0.999 g, 99%) and used directly in the next step.

Step 3) 1-(difluoromethoxy)-4-{[4-fluoro-3-(fluoromethyl)phenyl]ethynyl}-2-methylbenzene

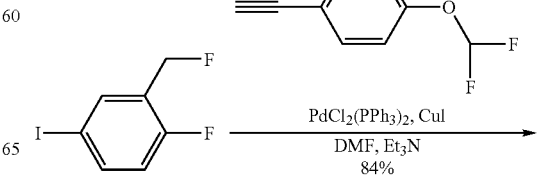

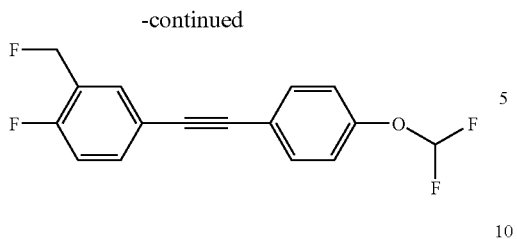

The title compound was prepared in substantially the same manner as described in Example 12, step 3 starting from 1-Fluoro-2-fluoromethyl-4-iodo-benzene (0.211 g, 0.83 mmol), and 1-Difluoromethoxy-4-ethynyl-benzene (0.14 g, 0.83 mmol), and was obtained as a yellow semi solid, (0.207 g, 84%), identified by NMR and mass spectral analyses. MS (EI+): 294 (M+).

Step 4) 1-(4-Difluoromethoxy-phenyl)-2-(4-fluoro-3-fluoromethyl-phenyl)-ethane-1,2-dione

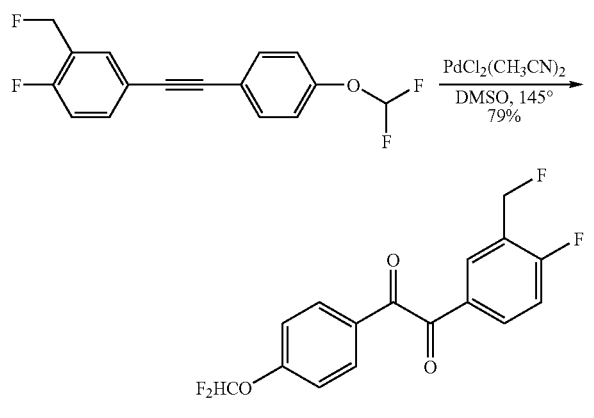

The title compound was prepared in substantially the same manner as described in Example 12, step 4 starting from 1-(difluoromethoxy)-4-{[4-fluoro-3-(fluoromethyl)phenyl]ethynyl}-2-methylbenzene (02 g, 0.68 mmol), and was obtained as a yellow solid, (0.176 g, 79%), identified by NMR and mass spectral analyses. Mp: 68-70° C. MS (EI+): 326 (M+).

Step 5) 2-Amino-5-(4-difluoromethoxy-phenyl)-5-(4-fluoro-3-fluoromethyl-phenyl)-3-methyl-3,5-dihydro-imidazol-4-one

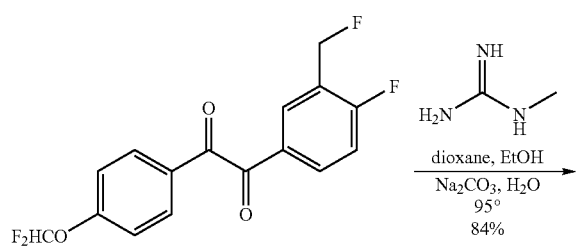

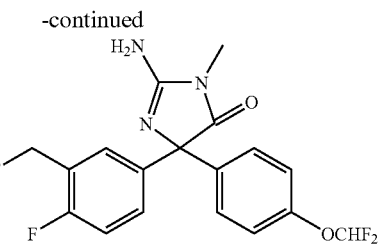

The title compound was prepared in substantially the same manner as described in Example 12, step 5 starting from 1-(4-Difluoromethoxy-phenyl)-2-(4-fluoro-3-fluoromethyl-phenyl)-ethane-1,2-dione (0.12 g, 0.37 mmol), and was obtained as a white foam, (0.12 g, 84%), identified by NMR and mass spectral analyses. Mp: 70-73° C. HRMS (ESI+): 382.1172 (M+H).

Example 18

Preparation of 2-Amino-5-(4-difluoromethoxy-phenyl)-3-methyl-5-o-tolyl-3,5-dihydro-imidazol-4-one Step 1) 1-{[4-(difluoromethoxy)phenyl]ethynyl}-2-methylbenzene

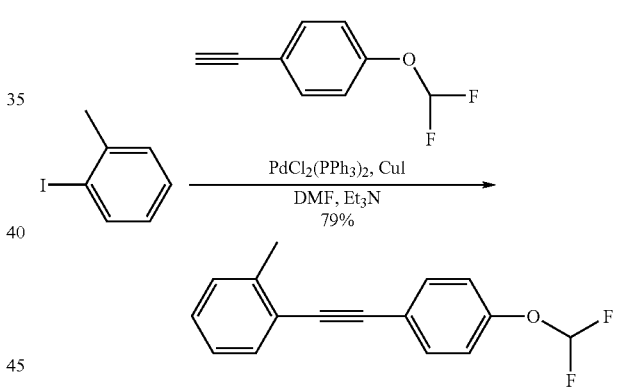

The title compound was prepared in substantially the same manner as described in Example 12, step 3 starting from 1-Iodo-2-methyl-benzene (0.15 g, 0.69 mmol), and 1-Difluoromethoxy-4-ethynyl-benzene (0.116 g, 0.69 mmol), and was obtained as a light brown oil, (0.141 g, 79%), identified by NMR and mass spectral analyses. MS (EI+): 258 (M+).

Step 2) 1-(4-Difluoromethoxy-phenyl)-2-o-tolyl-ethane-1,2-dione

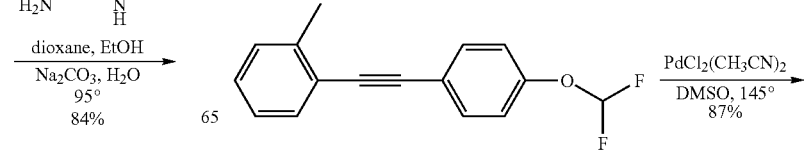

-continued

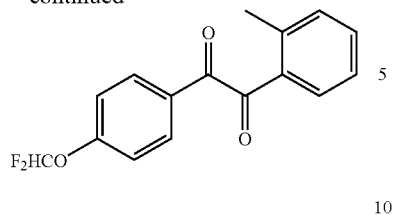

The title compound was prepared in substantially the same manner as described in Example 12, step 4 starting from 1-{[4-(difluoromethoxy)phenyl]ethynyl}-2-methylbenzene (0.85 g, 0.33 mmol), and was obtained as a yellow semi solid, (0.083 g, 87%), identified by NMR and mass spectral analyses. MS (EI+): 290 (M+).

Step 3) 2-Amino-5-(4-difluoromethoxy-phenyl)-3-methyl-5-o-tolyl-3,5-dihydro-imidazol-4-one

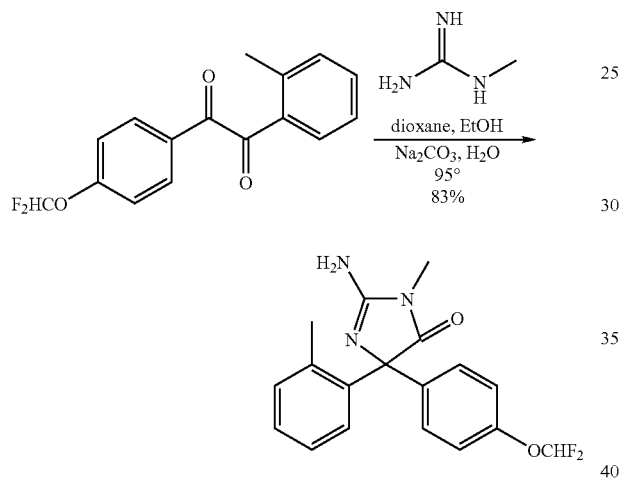

The title compound was prepared in substantially the same manner as described in Example 12, step 5 starting from 1-(4-Difluoromethoxy-phenyl)-2-o-tolyl-ethane-1,2-dione (0.083 g, 0.29 mmol), and was obtained as a white foam, (0.082 g, 83%), identified by NMR and mass spectral analyses. Mp: 85-90° C. MS (ES−): 344 (M−H)⁻.

Example 19

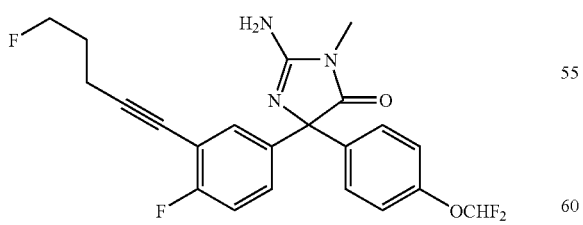

2-amino-5-[4-(difluoromethoxy)phenyl]-5-[4-fluoro-3-(5-fluoropent-1-yn-1-yl)phenyl]-3-methyl-3,5-dihydro-4H-imidazol-4-one (A) [MS (ES+): 434 (M+H)⁺]

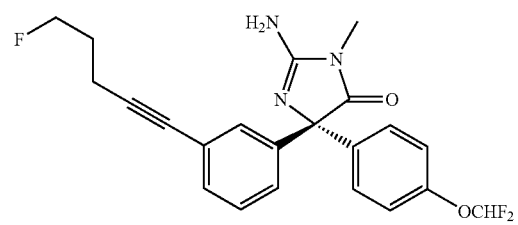

(5R)-2-amino-5-[4-(difluoromethoxy)phenyl]-5-[4-fluoro-3-(5-fluoropent-1-yn-1-yl)phenyl]-3-methyl-3,5-dihydro-4H-imidazol-4-one (B)

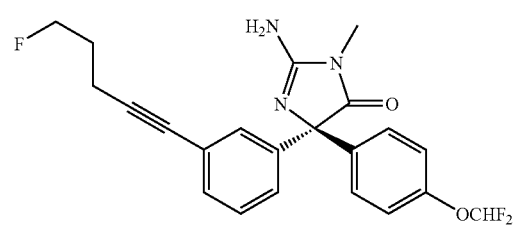

(5S)-2-amino-5-[4-(difluoromethoxy)phenyl]-5-[4-fluoro-3-(5-fluoropent-1-yn-1-yl)phenyl]-3-methyl-3,5-dihydro-4H-imidazol-4-one (C)

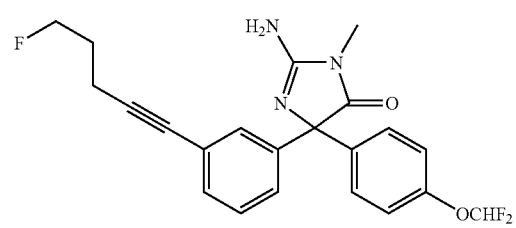

2-amino-5-[4-(difluoromethoxy)phenyl]-5-[3-(5-fluoropent-1-yn-1-yl)phenyl]-3-methyl-3,5-dihydro-4H-imidazol-4-one (D)

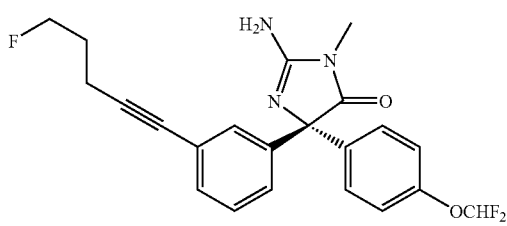

(5R)-2-amino-5-[4-(difluoromethoxy)phenyl]-5-[3-(5-fluoropent-1-yn-1-yl)phenyl]-3-methyl-3,5-dihydro-4H-imidazol-4-one (E)

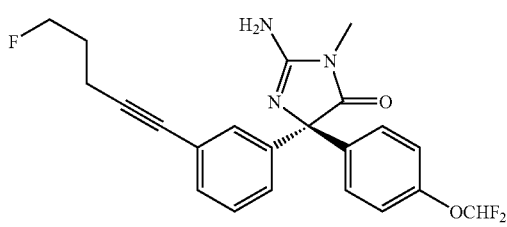

(5S)-2-amino-5-[4-(difluoromethoxy)phenyl]-5-[3-(5-fluoropent-1-yn-1-yl)phenyl]-3-methyl-3,5-dihydro-4H-imidazol-4-one (F)

Example 20

2-amino-5-[3-(5-chloropent-1-yn-1-yl)-4-fluorophenyl]-5-[4-(difluoromethoxy)phenyl]-3-methyl-3,5-dihydro-4H-imidazol-4-one (A)

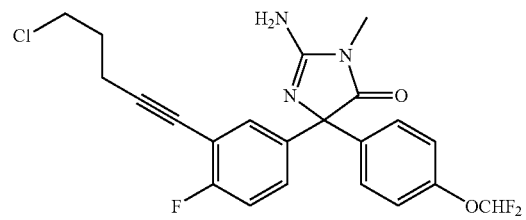

2-amino-5-[3-(5-chloropent-1-yn-1-yl)-4-fluorophenyl]-5-[4-(difluoromethoxy)phenyl]-3-methyl-3,5-dihydro-4H-imidazol-4-one [MS (ES+): 450 (M+H)+]

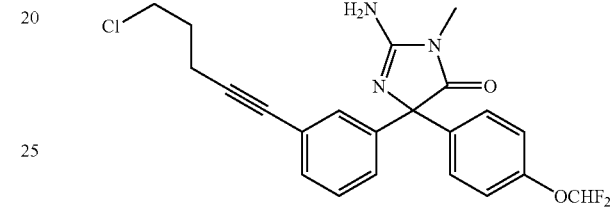

2-amino-5-[3-(5-chloropent-1-yn-1-yl)-phenyl]-5-[4-(difluoromethoxy)phenyl]-3-methyl-3,5-dihydro-4H-imidazol-4-one (B)

Examples 21-51

Preparation of 2-amino-4-(3-aminophenyl)-4-(4-(difluoromethoxy)phenyl)-1-methyl-1H-imidazol-5 (4H)-one derivatives

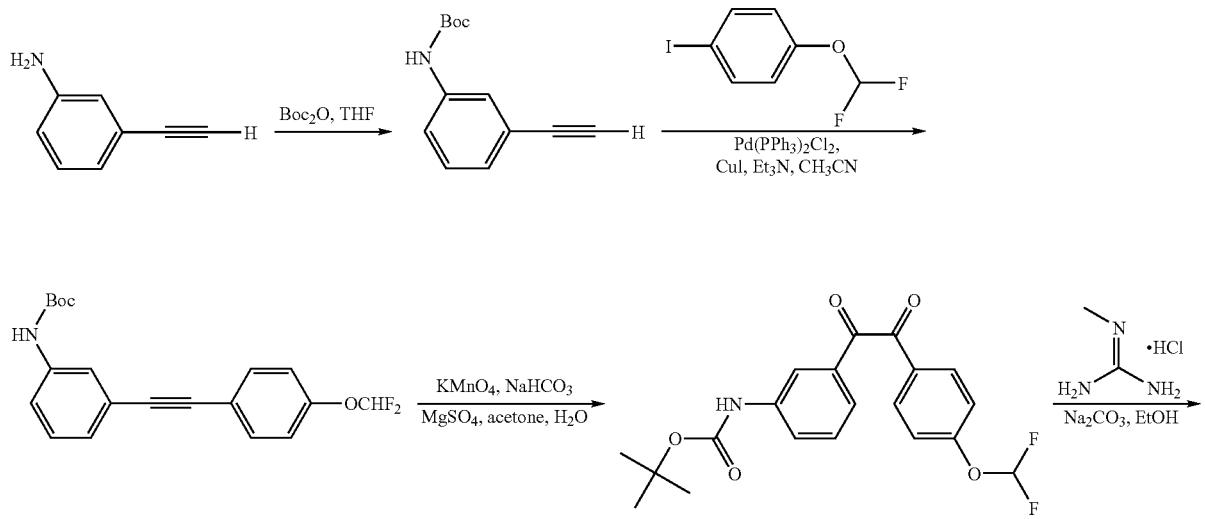

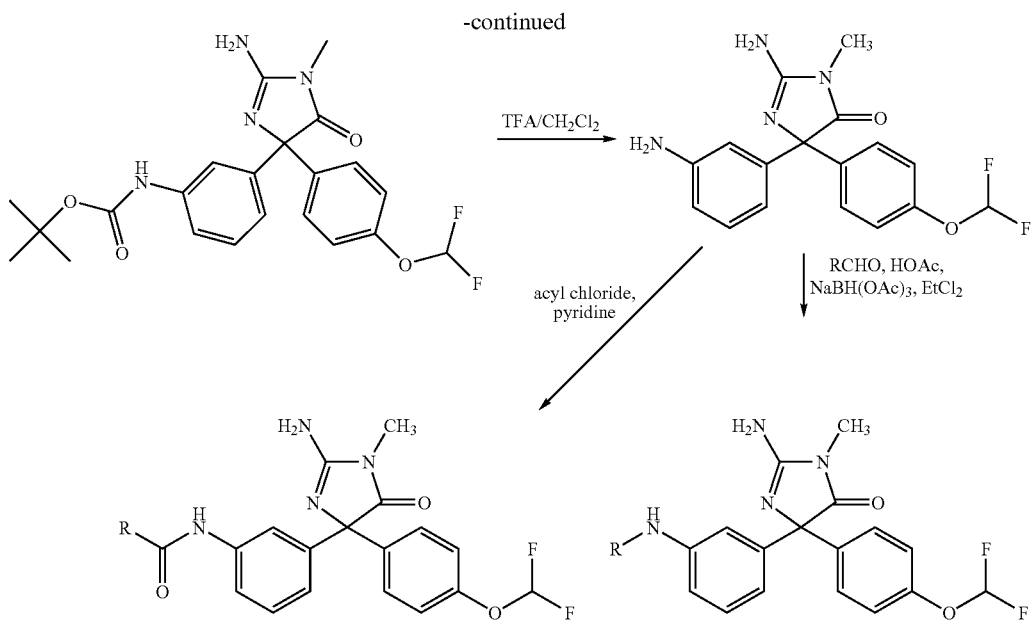

Step a) (3-Ethynyl-phenyl)-carbamic acid tert-butyl ester

A solution of 3-ethynyl-phenylamine (25.0 g, 213 mmol) and di-tert-butyldicarbonate (93.1 g, 427 mmol) in THF (427 mL) was heated at 70° C. overnight. The reaction was cooled to room temperature and then 3-dimethylamino-1-propylamine (32.1 g, 320 mmol) was added and allowed to stir at room temperature for 1 h. The reaction was concentrated and taken in diethyl ether, washed with 1N HCl, brine, sodium bicarbonate, brine and dried over sodium sulfate and concentrated in vacuo to provide the title compound (45.0 g, 97%), characterized by NMR and mass spectral analyses.

Step b) [3-(4-Difluoromethoxy-phenylethynyl)-phenyl]-carbamic acid tert-butyl ester A mixture of (3-ethynyl-phenyl)-carbamic acid tert-butyl ester (14.7 g, 67.7 mmol), 1-difluoromethoxy-4-iodo-benzene (18.2 g, 67.7 mmol), NEt$_3$ (47 mL, 338 mmol), acetonitrile (225 mL), CuI (1.29 g, 6.77 mmol), and Pd(PPh$_3$)$_2$Cl$_2$ (2.85 g, 4.05 mmol) was heated to 60° C. for 1 h. The reaction was diluted with EtOAc/Hex (1:10) and then passed through a pad of silica gel and concentrated and purified with chromatography using hexanes/ethyl acetate (10:1) as the eluting solvents gave the title compound (24.3 g, 100%), characterized by NMR and mass spectral analyses.

Step c) {3-[2-(4-Difluoromethoxy-phenyl)-2-oxo-acetyl]-phenyl}-carbamic acid tert-butyl ester A mixture of [3-(4-difluoromethoxy-phenylethynyl)-phenyl]-carbamic acid tert-butyl ester (21.6 g, 60.1 mmol), sodium bicarbonate (3.30 g, 39.0 mmol), magnesium sulfate (10.9 g, 90.2 mmol) in water (400 mL) and acetone (1200 mL) was treated with potassium permanganate (28.5 g, 180 mmol) and the resulting mixture was stirred for 1 h at room temperature. The reaction mixture was concentrated briefly and extracted with ethyl acetate. The organic layer was diluted with hexanes and then passed through a pad of silica gel and concentrated to provide the title compound (19.81 g, 84%), characterized by NMR and mass spectral analyses.

Step d) {3-[2-Amino-4-(4-difluoromethoxy-phenyl)-1-methyl-5-oxo-4,5-dihydro-1H-imidazol-4-yl]-phenyl}-carbamic acid tert-butyl ester A mixture of {3-[2-(4-difluoromethoxy-phenyl)-2-oxo-acetyl]-phenyl}-carbamic acid tert-butyl ester (19.8 g, 50.6 mmol), N-methyl guanidine HCl salt (6.65 g, 60.7 mmol), sodium carbonate (8.05 g, 75.9 mmol) in ethanol (169 mL) was heated at reflux for 3 h. The reaction mixture was diluted with methanol/methylene chloride (1:10) and passed through a pad of silica gel and concentrated and purified with chromatography using methanol/methylene chloride (1:10) gave the title compound (15.3 g, 68%), characterized by NMR and mass spectral analyses.

Step e) 2-Amino-5-(3-amino-phenyl)-5-(4-difluoromethoxy-phenyl)-3-methyl-3,5-dihydro-imidazol-4-one {3-[2-Amino-4-(4-difluoromethoxy-phenyl)-1-methyl-5-oxo-4,5-dihydro-1H-imidazol-4-yl]-phenyl}-carbamic acid tert-butyl ester (15.3 g, 34.3 mmol) was dissolved in trifluoroacetic acid/methylene chloride (1:1) (20 mL) and allowed to stir for 4.5 h. Additional trifluoroacetic acid (3.0 mL) was added and the reaction was allowed to stir for an additional hour and concentrated. To the residue was added Na$_2$CO$_3$ followed by extraction with methylene chloride. The organic layer was dried over Na$_2$SO$_4$ and concentrated in vacuo to provide the title compound (11.8 g, 99%), characterized by NMR and mass spectral analyses. MS (ES+) m/e 347 (M+H)$^+$.

Step f1) N-(3-(2-Amino-4-(4-(difluoromethoxy)phenyl)-1-methyl-5-oxo-4,5-dihydro-1H-imidazol-4-yl)phenyl)acetamide hydrochloride A mixture of 2-amino-5-(3-amino-phenyl)-5-(4-difluoromethoxy-phenyl)-3-methyl-3,5-dihydro-imidazol-4-one (88 mg, 0.25 mmol), acetyl chloride (20 mg, 0.25 mmol), $NEt_3$ (51 mg, 0.51 mmol) in THF (2.5 mL) was stirred at rt for 1 h, concentrated and purified by reverse-phase HPLC followed by treatment with hydrochloric acid to provide the title compound (42 mg, 43%), characterized by NMR and mass spectral analyses. MS (ES+) m/e 389 (M+H)+.

Using essentially this procedure and employing the desired acyl halides, the compounds shown on Table X were obtained and identified by NMR and mass spectral analyses.

Step f2) 2-Amino-4-(4-(difluoromethoxy)phenyl)-1-methyl-4-(3-(propylamino)phenyl)-1H-imidazol-5 (4H)-one hydrochloride A mixture 2-amino-5-(3-amino-phenyl)-5-(4-difluoromethoxy-phenyl)-3-methyl-3,5-dihydro-imidazol-4-one (150 mg, 0.43 mmol), propionaldehyde (25 mg, 0.43 mmol), sodium triacetoxyborohydride (184 mg, 0.87 mmol), and acetic acid (0.87 mmol) in dichloroethane (4.3 mL) was stirred at room temperature overnight. The reaction was diluted with methylene chloride and washed with sodium carbonate. The organic layer was concentrated and purified by reverse-phase HPLC followed by treatment with hydrochloric acid to provide the title compound (122 mg, 73%), characterized by NMR and mass spectral analyses. MS (ES+) m/e 389 (M+H)+.

Using essentially this procedure and employing the desired aldehydes, the compounds shown on Table X and Y were obtained and identified by NMR and mass spectral analyses.

TABLE X

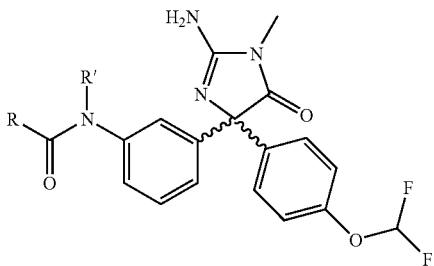

| Ex. No. | Chiral | R | R' | [M + H] | $[\alpha]_D^{25*}$ |
|---|---|---|---|---|---|
| 21 | — | $CH_2CH_3$ | H | 403 | |
| 22 | — | $CH_2CH_2CH_3$ | H | 417 | |
| 23 | — | $CH_2CH_2CH_2CH_3$ | H | 431 | |
| 24 | — | $CH_2CH_2Cl$ | H | 437 | |
| 25 | — | $CF_3$ | H | 443 | |
| 26 | — | $CH_2CH(CH_3)_2$ | H | 431 | |
| 27 | — | $CH(CH_3)_2$ | H | 417 | |
| 28 | — | cyclopropyl | H | 415 | |
| 29 | — | cyclobutyl | H | 429 | |
| 30 | — | $CH_3CH=CH$ | H | 415 | |
| 31 | — | $(CH_3)_2C=CH$ | H | 429 | |
| 32 | — | PhCH=CH | H | 477 | |
| 33 | — | Furan-2-yl | H | 441 | |
| 34 | — | $PhCH_2OCH_2$ | H | 495 | |
| 35 | — | Ph | H | 451 | |
| 36 | — | $Cl_3C$ | H | 491 | |
| 37 | — | 1-Ph-5-$CF_3$-pyrazole-4-yl | H | 585 | |
| 38 | — | 1-(4-Cl-Ph)-5-$CF_3$-pyrazole-4-yl | H | 619 | |
| 39 | — | 3-bromo-thiophen-2-yl | H | 535 | |
| 40 | — | Benzofuran-3-yl | H | 491 | |
| 41 | — | Benzofuran-5-yl | H | 491 | |
| 42 | — | Thiophene-2-yl | H | 457 | |

TABLE Y

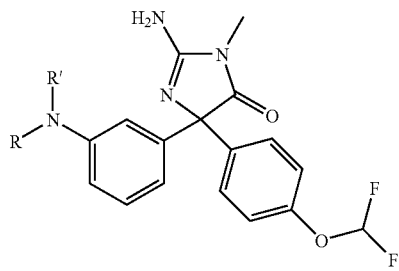

| Ex. No. | Chiral | R | R' | [M + H]+ | $[\alpha]_D^{25*}$ |
|---|---|---|---|---|---|
| 43 | — | $CH_2CH_2CH_3$ | H | 389 | |
| 44 | — | $CH_2CH_2CH_2CH_3$ | H | 403 | |
| 45 | — | $(CH_3)_2CHCH_2$ | H | 403 | |
| 46 | — | Isopropyl | H | 389 | |
| 47 | — | Cyclopentyl | H | 415 | |
| 48 | — | cyclohexyl | H | 429 | |
| 49 | — | $CH_3CH=CH$ | H | 401 | |
| 50 | — | cycobutyl | H | 401 | |
| 51 | — | Furan-2-yl-$CH_2$ | H | 427 | |

Example 52

Preparation of (5S)-2-amino-5-{3-[(4,4-difluorobut-3-en-1-yl)oxy]phenyl}-5-[4-(difluoromethoxy)phenyl]-3-methyl-3,5-dihydro-4H-imidazol-4-one A racemic mixture of 2-amino-5-{3-[(4,4-difluorobut-3-en-1-yl)oxy]phenyl}-5-[4-(difluoromethoxy)phenyl]-3-methyl-3,5-dihydro-4H-imidazol-4-one was separated by chiral HPLC using column type Chiralcel AD, 2×25 cm; the mobile phase was 14% ethanol in hexane with 0.1% diethylamine at 20 mL/min to obtain the title S-isomer as a glass, identified by NMR and mass spectral analyses [mp glass; $[\alpha]_D^{25}$=−31.0° (c=1% SOLUTION, $CHCl_3$); MS (ES) m/z 436.2].

Example 53

Preparation of (5S)-2-amino-5-{3-[(4,4-difluorobut-3-en-1-yl)oxy]-4-fluorophenyl}-5-[4-(difluoromethoxy)phenyl]-3-methyl-3,5-dihydro-4H-imidazol-4-one Using the same procedure as described for Example 80 except that 5-bromo-2-fluorophenol was used as starting material, racemic 2-amino-5-{3-[(4,4-difluorobut-3-en-1-yl) oxy]-4-fluorophenyl}-5-[4-(difluoromethoxy)phenyl]-3-methyl-3,5-dihydro-4H-imidazol-4-one was obtained and identified by NMR and mass spectral analyses.

A racemic mixture of 2-amino-5-{3-[(4,4-difluorobut-3-en-1-yl)oxy]-4-fluorophenyl}-5-[4-(difluoromethoxy)phenyl]-3-methyl-3,5-dihydro-4H-imidazol-4-one was separated by chiral HPLC using column type Chiralcel AD, 5×50 cm; the mobile phase was 15% ethanol in hexane with 0.1% diethylamine at 100 mL/min to obtain the title S-isomer as a glass, identified by NMR and mass spectral analyses [mp glass; $[\alpha]_D^{25}$=16° (c=1%, MeOH); MS (ES) m/z 454.0].

Example 54

Preparation of (5R)-2-amino-5-{3-[(4,4-difluorobut-3-en-1-yl)oxy]-4-fluorophenyl}-5-[4-(difluoromethoxy)phenyl]-3-methyl-3,5-dihydro-4H-imidazol-4-one A racemic mixture of 2-amino-5-{3-[(4,4-difluorobut-3-en-1-yl)oxy]-4-fluorophenyl}-5-[4-(difluoromethoxy)phenyl]-3-methyl-3,5-dihydro-4H-imidazol-4-one (preparation described in previous Example) was separated by chiral HPLC using column type Chiralcel AD, 5×50 cm; the mobile phase was 15% ethanol in hexane with 0.1% diethylamine at 100 mL/min to obtain the title R-isomer as a glass, identified by NMR and mass spectral analyses [mp glass; $[\alpha]_D^{25}=-14°$ (c=1%, MeOH); MS (ES) m/z 454.0].

Example 55

Preparation of methyl[3-(3-{2-amino-4-[4-(difluoromethoxy)phenyl]-1-methyl-5-oxo-4,5-dihydro-1H-imidazol-4-yl}phenyl)-1-methoxycyclobutyl]acetate-methyl[3-(3-{2-amino-4-[4-(difluoromethoxy)phenyl]-1-methyl-5-oxo-4,5-dihydro-1H-imidazol-4-yl}phenyl)cyclobutylidene]acetate (3:1)

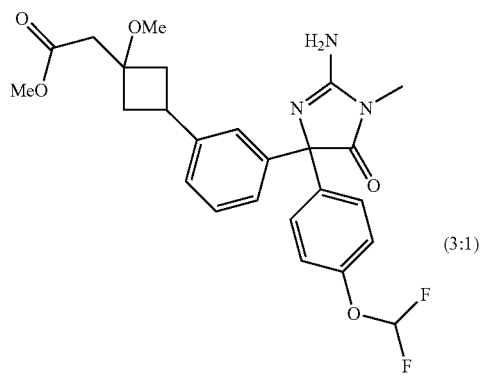

(3:1)

Step 1) [3-(3-Bromo-phenyl)-cyclobutylidene]-acetic acid methyl ester

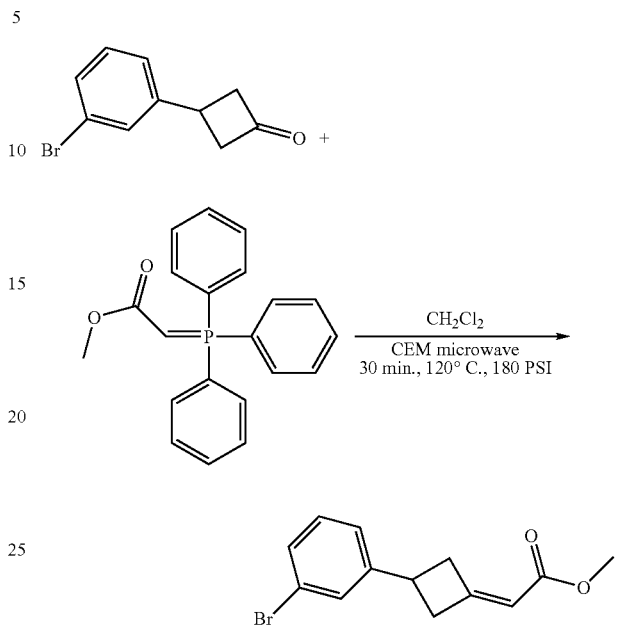

3-(3-Bromo-phenyl)-cyclobutanone (2.00 g, 8.89 mmol) and Triphenyl-phosphoranylidene acetic acid methyl ester (8.33 g, 24.9 mmol) were dissolved in dichloromethane (30 mL) inside a CEM 80 ml microwave vessel. The solution was irradiated in a CEM Discover™ microwave instrument for 30 minutes at 120° C. Pressure reached a maximum of 180 PSI. Purification by column chromatography (isocratic elution; 10% diethyl ether in hexanes) afforded 2.49 gm of a colorless oil. $^1$H NMR (400 MHz, DMSO-$d_6$) δ ppm 2.90-3.00 (m, 1H) 3.02-3.14 (m, 1H) 3.17-3.28 (m, 1H) 3.46-3.58 (m, 1H) 3.62 (s, 3H) 3.63-3.71 (m, 1H) 5.74 (q, J=3.0 Hz, 1H) 7.27-7.35 (m, 2H) 7.39-7.43 (m, 1H) 7.50 (t, J=1.9 Hz, 1H); MS (EI) m/z 280 [M+.].

Step 2) (3-{3-[2-(4-Difluoromethoxy-phenyl)-2-oxo-acetyl]-phenyl}-cyclobutyl)-acetic acid methyl ester

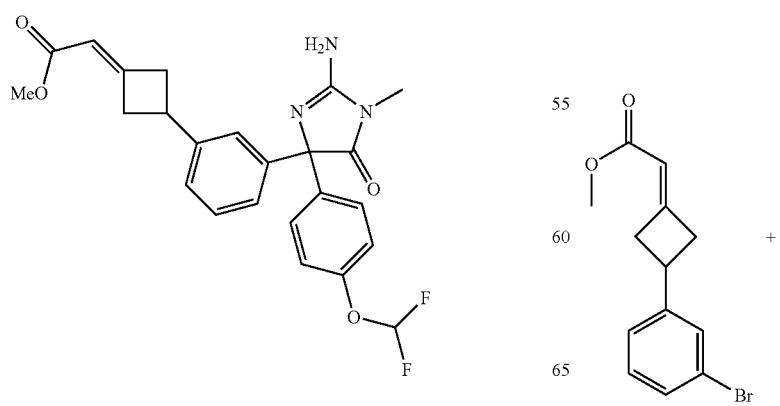

-continued

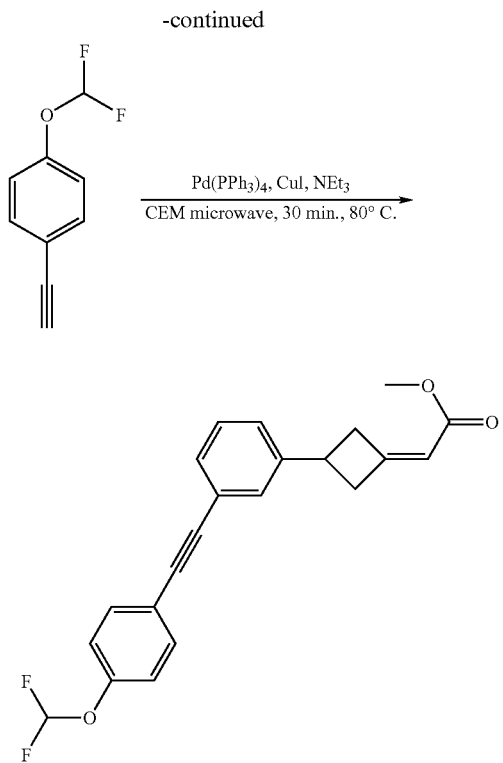

In a CEM snap top microwave vial were combined 1-Difluoromethoxy-4-ethynyl-benzene (0.99 gm 5.89 mmol), 3-(3-Bromo-phenyl)-2,2-dimethyl-cyclobutanone (1.422, 5.06 mmol), copper iodide (173 mg, 0.908 mmol), tetrakis(triphenylphosphine)palladium (292 mg, 0.253 mmol) and triethylamine (4.3 g, 42.5 mmol). The vial was quickly agitated then irradiated in a CEM Explorer™ microwave instrument for 30 minutes at 80° C. Purification by column chromatography (gradient; 0%-10% EtOAc in hexanes) afforded an amber oil 1.348 g (72%). $^1$H NMR (400 MHz, DMSO-$d_6$) δ ppm 2.94-3.03 (m, 1H) 3.06-3.15 (m, 1H) 3.20-3.30 (m, 1H) 3.49-3.59 (m, 1H) 3.62 (s, 3H) 3.63-3.72 (m, 1H) 5.76 (q, J=2.9 Hz, 1H) 7.23 (dt, J=9.1, 2.5 Hz, 2H) 7.32 (t, J=73.7 Hz, 1H) 7.34-7.44 (m, 3H) 7.47-7.50 (m, 1H) 7.62 (dt, J=9.2, 2.6 Hz, 2H); MS (ES) m/z 369.1 [M+H]$^+$ Step 3) (3-{3-[2-(4-Difluoromethoxy-phenyl)-2-oxo-acetyl]-phenyl}-cyclobutylidene)-acetic acid methyl ester

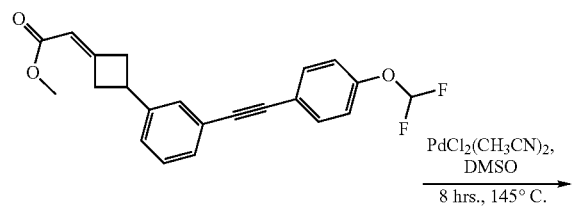

-continued

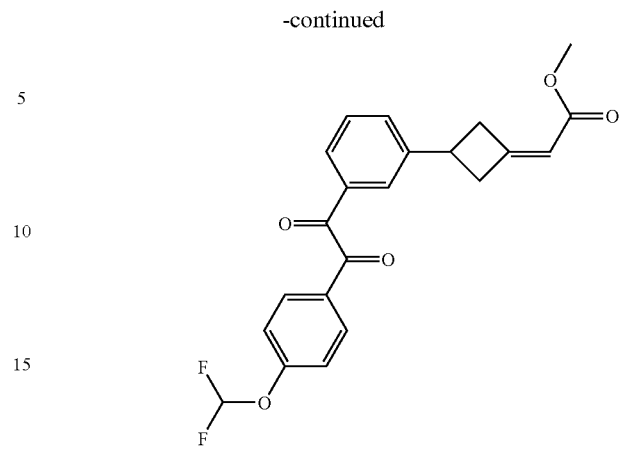

In a 250 ml round bottom flask was dissolved (3-{3-[2-(4-Difluoromethoxy-phenyl)-2-oxo-acetyl]-phenyl}-cyclobutyl)-acetic acid methyl ester (1.348 g, 3.66 mmol) in DMSO (45 mL). Bis(acetonitrile)dichloropalladium was added and the flask heated (oil bath; 145° C.) for 4 hours. More Bis(acetonitrile)dichloro-palladium (90 mg) was added and heating was continued for another 4 hours. The crude material was partitioned between water (50 mls) and dichloromethane. Dichloromethane extracts (2×50 mls) were combined and concentrated onto silica gel. Purification by column chromatography (gradient; 10-20% EtOAc in hexanes) afforded 1.17 gm of a yellow oil (80%). $^1$H NMR (400 MHz, DMSO-$d_6$) δ ppm 2.90-3.02 (m, 1H) 3.05-3.16 (m, 1H) 3.22-3.28 (m, 1H) 3.49-3.59 (m, 1H) 3.62-3.64 (m, 3H) 3.72-3.82 (m, 1H) 5.73-5.77 (m, 1H) 7.39 (dt, J=9.3, 2.5 Hz, 2H) 7.46 (t, J=73.0 Hz, 2H) 7.59 (t, J=7.8 Hz, 1H) 7.72-7.80 (m, 2H) 7.85 (t, J=1.9 Hz, 1H) 8.02 (dt, J=9.4, 2.6 Hz, 2H); MS (ES) m/z 401.1 [M+H]$^+$ Step 4) methyl[3-(3-{2-amino-4-[4-(difluoromethoxy)phenyl]-1-methyl-5-oxo-4,5-dihydro-1H-imidazol-4-yl}phenyl)-1-methoxycyclobutyl]acetate-methyl[3-(3-{2-amino-4-[4-(difluoromethoxy)phenyl]-1-methyl-5-oxo-4,5-dihydro-1H-imidazol-4-yl}phenyl)cyclobutylidene]acetate (3:1)

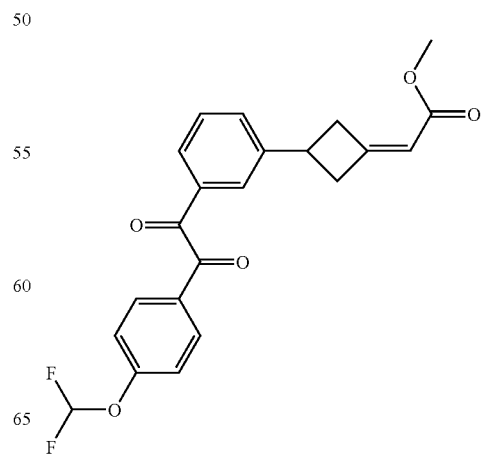

+

-continued

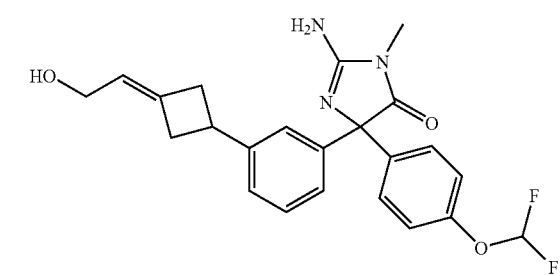

(3:1)

In a 250 ml round bottom flask was dissolved (3-{3-[2-(4-Difluoromethoxy-phenyl)-2-oxo-acetyl]-phenyl}-cyclobutylidene)-acetic acid methyl ester (0.34 g, 0.849 mmol) in ethanol (10 mL). Methylguanidine hydrochloride (0.186 g, 1.70 mmol) was added, followed by sodium carbonate (0.180 g, 1.70 mmol). The mixture was heated (oil bath; 85° C.) for 16 hours. The ethanol was removed by rotary evaporation. The residue was partitioned between water and chloroform. The chloroform layer was dried with sodium sulfate and concentrated onto silica gel. Attempted purification by column chromatography (Gradient, basic alumina; 50-70% EtOAc in hexanes) produced 0.300 g of an oily mixture was diluted with dichloromethane and absorbed onto basic alumina. Attempted purification by column chromatography (Gradient, basic alumina; 0-10% methanol in dichloromethane returned an inseparable mixture 0.164 g as a white solid (40%); m.p. 58-60° C. $^1$H NMR (400 MHz, DMSO-$d_6$), a mixture of α,β-unsaturated methyl ester and its methanol adduct (1:3) δ ppm 2.01-2.16 (m, 2H) 2.83-3.05 (m, 1H) 2.97 (s, 3H) 3.10 (s, 3H of methanol adduct cis/trans) 3.12-3.28 (m, 1H) 3.18 (s, 3H of methanol adduct cis/trans) 3.39-3.54 (m, 1H) 3.56 (s, 3H of α,β-unsaturated methyl ester) 3.60 (s, 3H of methanol adduct cis/trans) 3.61 (s, 3H of methanol adduct cis/trans) 5.66-5.74 (m, 1H of α,β-unsaturated methyl ester) 6.67 (s, 2H) 7.10 (d, J=8.8 Hz, 2H) 7.16 (t, J=74.2 Hz, 1H) 7.19-7.33 (m, 2H) 7.47 (d, J=8.6 Hz, 2H); MS (ES) m/z 454.2 (α,β-unsaturated methyl ester) [M−H]$^-$; MS (ES) m/z 486.2 (methanol adduct) [M−H]$^-$ Example 56

Preparation of 2-amino-5-[4-(difluoromethoxy)phenyl]-5-{3-[3-(2-hydroxyethylidene)cyclobutyl]phenyl}-3-methyl-3,5-dihydro-4H-imidazol-4-one Step 1) [3-(3-Bromo-phenyl)-cyclobutylidene]-acetic acid ethyl ester

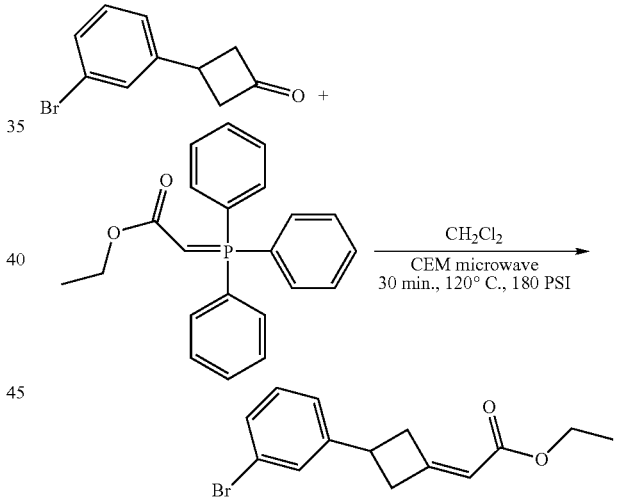

3-(3-Bromo-phenyl)-cyclobutanone (2.03 g 9.02 mmol) and Triphenyl-phosphoranylidene acetic acid ethyl ester (15.72 gms 45.12 mmol) were dissolved in dichloromethane (30 mL) inside a CEM 80 ml microwave vessel. The solution was irradiated in a CEM Discover™ microwave instrument for 30 minutes at 120° C. Pressure reached a maximum of 180 PSI. The product was purified by column chromatography (isocratic; 10% diethyl ether in hexanes) to give 2.37 gm of an oil (89%) 1H NMR (400 MHz, DMSO-$d_6$) δ ppm 1.20 (t, J=7.1 Hz, 3H) 2.89-3.00 (m, 1H) 3.03-3.11 (m, 1H) 3.16-3.27 (m, 1H) 3.46-3.57 (m, 1H) 3.63 (q, J=8.0 Hz, 1H) 4.08 (q, J=7.0 Hz, 2H) 5.71 (q, J=2.9 Hz, 1H) 7.25-7.35 (m, 2H) 7.39-7.43 (m, 1H) 7.48-7.52 (m, 1H); MS (APPI) m/z 295 [M+H].$^+$.

Step 2) {3-[3-(4-Difluoromethoxy-phenylethynyl)-phenyl]-cyclobutylidene}-acetic acid ethyl ester

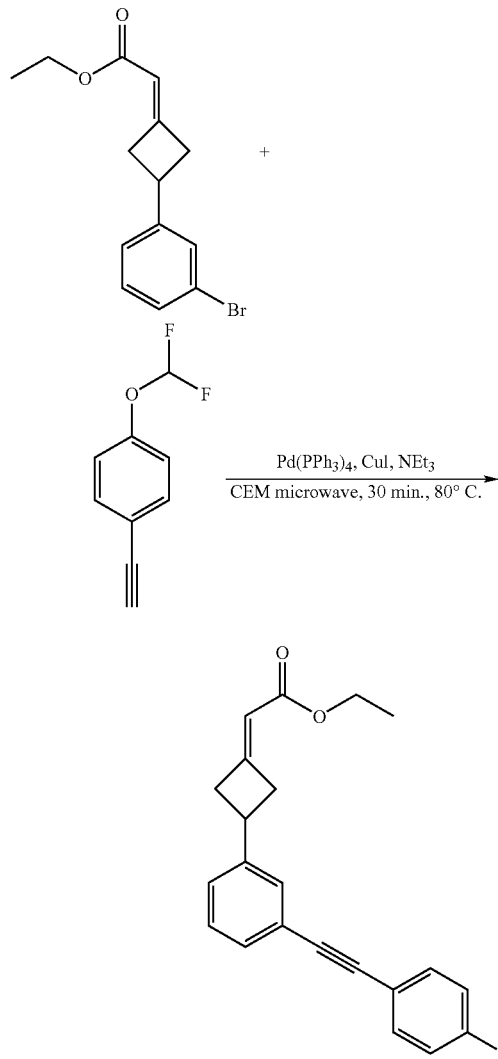

In a CEM snap top microwave vial were combined 1-Difluoromethoxy-4-ethynyl-benzene (1.48 g, 8.80 mmol), [3-(3-Bromo-phenyl)-cyclobutylidene]-acetic acid ethyl ester (2.00 g, 6.78 mmol), Copper iodide (232 mg, 0.131 mmol), Tetrakis(triphenylphosphine)palladium (470 mg, 1155.56 g/mol, 0.046 mmol), and triethylamine (20 g, 198 mmol). The capped vial was placed in a CEM Explorer microwave instrument and irradiated for 30 minutes at 80° C. The crude reaction mixture and dichloromethane washings were poured directly onto silica gel. Purification by column chromatography (isocratic; 5% EtOAc in hexanes) afforded an oil 1.42 g (55%). $^1$H NMR (400 MHz, DMSO-$d_6$) δ ppm 1.20 (t, J=7.2 Hz, 3H) 2.94-3.03 (m, 1H) 3.06-3.16 (m, 1H) 3.19-3.28 (m, 1H) 3.49-3.60 (m, 1H) 3.62-3.72 (m, 1H) 4.08 (q, J=7.2 Hz, 2H) 5.68-5.78 (m, 1H) 7.06-7.32 (m, 3H) 7.39 (dd, J=8.8, 3.7 Hz, 3H) 7.46-7.52 (m, 2H) 7.62 (d, J=8.8 Hz, 2H); MS (ES) m/z 383.1 [M+H]$^+$.

Step 3) Synthesis of (3-{3-[2-(4-Difluoromethoxy-phenyl)-2-oxo-acetyl]-phenyl}-cyclobutylidene)-acetic acid ethyl ester

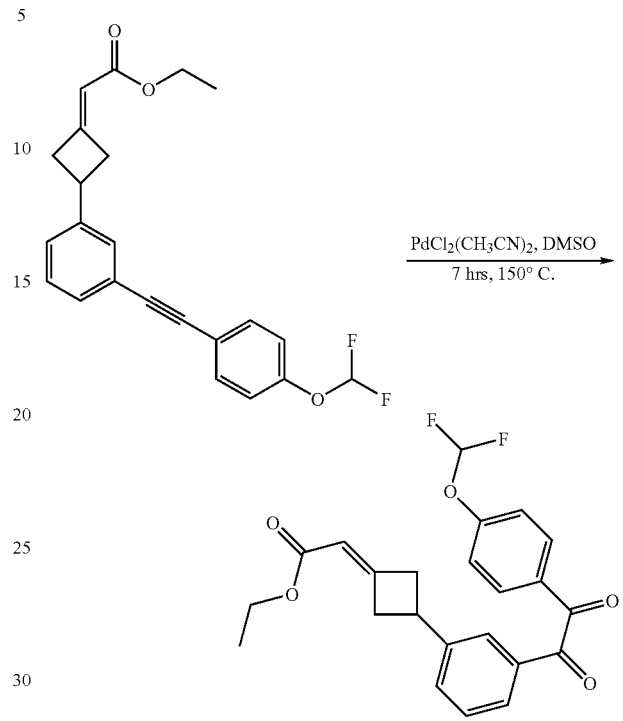

In a 250 ml round bottom flask was dissolved {3-[3-(4-Difluoromethoxy-phenylethynyl)-phenyl]-cyclobutylidene}-acetic acid ethyl ester (1.22 gm, 3.21 mmol) in DMSO (10 mL, Bis(acetonitrile)dichloro-palladium (95 mg, 0.366 mmol) was added and the reaction was heated in an oil bath (150° C.) for seven hours. The reaction was partitioned between water and dichloromethane. The aqueous layer was extracted with dichloromethane and the combined organic layers were concentrated onto silica gel. The product was purified by column chromatography (gradient; 0-100% EtOAc in hexanes) to afford 0.888 mg of a yellow oil L37285-40 (67%). mp oil; $^1$H NMR (400 MHz, DMSO-$d_6$) δ ppm 1.18 (t, J=8.2 Hz, 3H) 2.92-3.01 (m, 1H) 3.06-3.16 (m, 1H) 3.22-3.30 (m, 1H) 3.51-3.62 (m, 1H) 3.71-3.82 (m, 1H) 4.03 (q, J=7.1 Hz, 2H) 5.70-5.75 (m, 1H) 7.35-7.41 (m, 2H) 7.46 (t, J=73.0 Hz, 1H) 7.59 (t, J=7.8 Hz, 1H) 7.72-7.76 (m, 1H) 7.77-7.80 (m, 1H) 7.85 (t, J=1.7 Hz, 1H) 7.99-8.04 (m, 2H); MS (ES) m/z 413.1 [M−H]$^-$.

Step 4) (3-{3-[2-Amino-4-(4-difluoromethoxy-phenyl)-1-methyl-5-oxo-4,5-dihydro-1H-imidazol-4-yl]-phenyl}-cyclobutylidene)-acetic acid ethyl ester

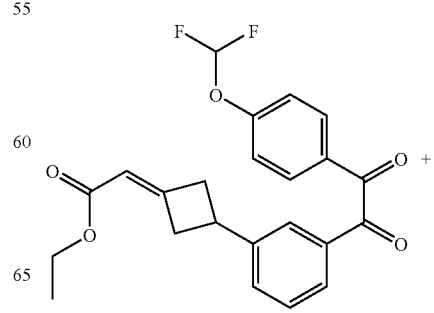

-continued

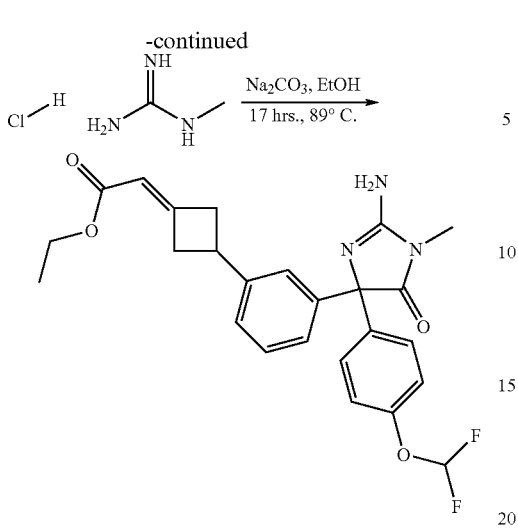

In a 250 ml round bottom flask was dissolved (3-{3-[2-(4-Difluoromethoxy-phenyl)-2-oxo-acetyl]-phenyl}-cyclobutylidene)-acetic acid ethyl ester (0.845 g, 2.04 mmol) in ethanol (50 mL). Methylguanidine hydrochloride (263 mg, 2.40 mmol) was added, followed by sodium carbonate (254 mg, 2.40 mmol). The mixture was heated (oil bath; 89° C.) for 17 hours. The crude reaction was concentrated onto silica gel. Purification by column chromatography (gradient; 50-100% ethyl acetate in hexanes) gave an oily substance. The oily product was dissolved in diethyl ether. Evaporation under high vacuum afforded 704 mg (74%) of a white foam solid. Mp 78-80° C.; $^1$H NMR (400 MHz, DMSO-d$_6$) δ ppm 1.19 (t, J=7.1 Hz, 3H) 2.78-2.89 (m, 1H) 2.97 (s, 3H) 3.02-3.07 (m, 1H) 3.16-3.26 (m, 1H) 3.45-3.53 (m, 1H) 3.55-3.66 (m, 1H) 4.07 (q, J=7.0 Hz, 2H) 5.64-5.75 (m, 1H) 6.67 (s, 2H) 7.05-7.11 (m, 2H) 7.16 (t, J=74.2 Hz, 1H) 7.17-7.21 (m, 1H) 7.23-7.33 (m, 2H) 7.37 (s, 1H) 7.43-7.51 (m, 2H); MS (ES) m/z 468.1 [M−H]$^−$.

Step 5) 2-amino-5-[4-(difluoromethoxy)phenyl]-5-{3-[3-(2-hydroxyethylidene)cyclobutyl]phenyl}-3-methyl-3,5-dihydro-4H-imidazol-4-one

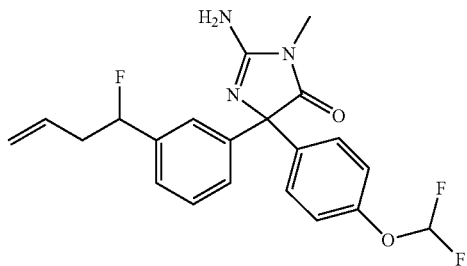

(3-{3-[2-Amino-4-(4-difluoromethoxy-phenyl)-1-methyl-5-oxo-4,5-dihydro-1H-imidazol-4-yl]-phenyl}-cyclobutylidene)-acetic acid ethyl ester (0.202 g, 0.430 mmol) was dissolved in tetrahydrofuran (THF, 2 mL) and chilled in an ice bath. To this solution was added a 1 M solution of diisobutylaluminum hydride (DIBAL) in THF (11 ml). The reaction was stirred for 1 hour at ambient temperature, and then quenched with crushed ice, followed by addition of sodium chloride and ammonium chloride salts. The crude mixture was extracted with diethyl ether and dried with magnesium sulfate to yield a yellow oil 33 mg (18%); MS (ES) m/z 426.1 [M−H]$^−$.

Example 57

Preparation of 2-amino-5-[4-(difluoromethoxy)phenyl]-5-[3-(1-fluorobut-3-en-1-yl)phenyl]-3-methyl-3,5-dihydro-4H-imidazol-4-one Step 1) 3-[3-(4-Difluoromethoxy-phenylethynyl)-phenyl]-cyclobutanol

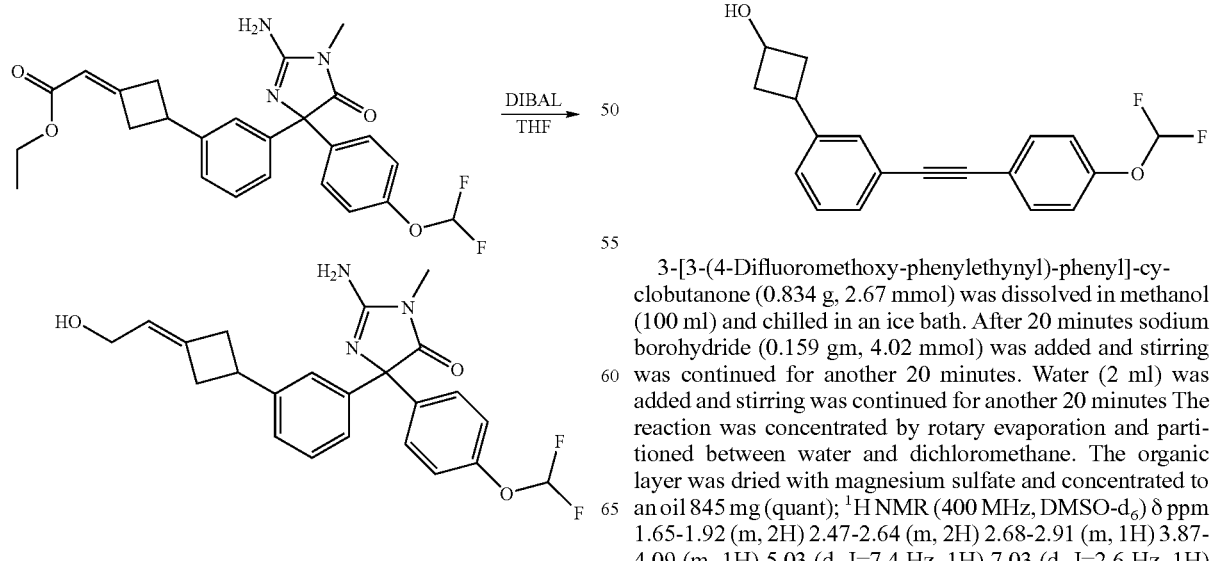

3-[3-(4-Difluoromethoxy-phenylethynyl)-phenyl]-cyclobutanone (0.834 g, 2.67 mmol) was dissolved in methanol (100 ml) and chilled in an ice bath. After 20 minutes sodium borohydride (0.159 gm, 4.02 mmol) was added and stirring was continued for another 20 minutes. Water (2 ml) was added and stirring was continued for another 20 minutes The reaction was concentrated by rotary evaporation and partitioned between water and dichloromethane. The organic layer was dried with magnesium sulfate and concentrated to an oil 845 mg (quant); $^1$H NMR (400 MHz, DMSO-d$_6$) δ ppm 1.65-1.92 (m, 2H) 2.47-2.64 (m, 2H) 2.68-2.91 (m, 1H) 3.87-4.09 (m, 1H) 5.03 (d, J=7.4 Hz, 1H) 7.03 (d, J=2.6 Hz, 1H)

7.18 (d, J=8.8 Hz, 2H) 7.21-7.25 (m, 1H) 7.27-7.32 (m, 2H) 7.38 (s, 1H) 7.58 (d, J=8.8 Hz, 2H).

Step 2) 3-(4-Difluoromethoxyphenylethynyl)-(1-fluoro-but-3-enyl)-benzene

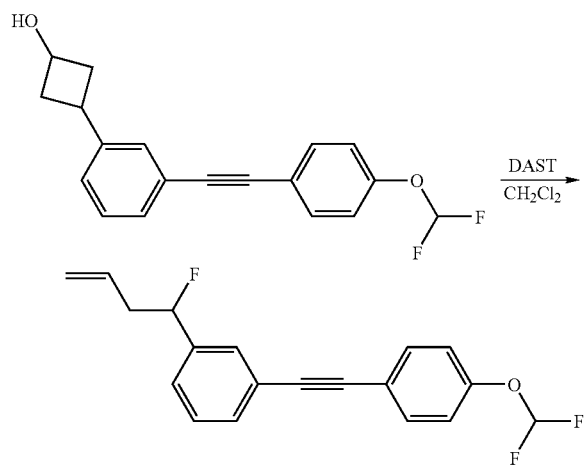

3-[3-(4-Difluoromethoxy-phenylethynyl)-phenyl]-cyclobutanol (0.820 gm, 2.61 mmol) was dissolved in dichloromethane (10 ml) and treated with (diethylamino)sulfur trifluoride (DAST, 0.500 gm, 3.20 mmol). Upon completion of reaction as determined by thin layer chromatography (TLC) the crude material was absorbed onto silica and purified by column chromatography (gradient elution; 0%-10% EtOAc in hexanes) to yield an oil 267 mg (32%); $^1$H NMR (500 MHz, DMSO-$d_6$) δ ppm 2.55-2.75 (m, 2H) 4.97-5.20 (m, 2H) 5.52-5.83 (m, 2H) 7.04-7.32 (m, 3H) 7.40-7.48 (m, 2H) 7.50-7.55 (m, 2H) 7.62 (d, J=8.8 Hz, 2H); MS (EI) m/z 316 [M$^+$].

Step 3) 1-(4-Difluoromethoxy-phenyl)-2-[3-(1-fluoro-but-3-enyl)-phenyl]-ethane-1,2-dione

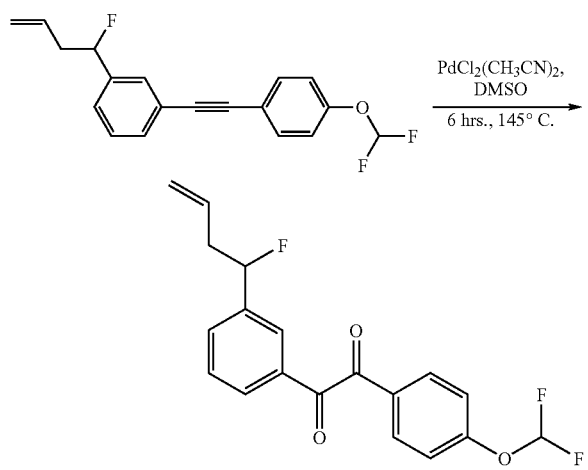

In a 250 ml round bottom flask was dissolved 3-(4-Difluoromethoxyphenylethynyl)-(1-fluoro-but-3-enyl)-benzene (0.267 g, 0.844 mmol) in DMSO (5 mL). Bis(aceto-nitrile) dichloropalladium (28 mg, 0.100 mmol) was added and the flask was heated (oil bath, 145° C.) for 14 hours. The crude material was partitioned between water (50 ml) and dichloromethane. Dichloromethane extracts (2×50 ml) were combined and concentrated onto silica gel. Purification by column chromatography (gradient; 20% to 50% EtOAc in hexanes) afforded 0.120 gm of a yellow oil (41%); $^1$H NMR (400 MHz, CHLOROFORM-d) δ ppm 2.48-2.81 (m, 2H) 5.11 (s, 1H) 5.14 (dd, J=5.5, 1.3 Hz, 1H) 5.41-5.63 (m, 1H) 5.70-5.85 (m, 1H) 6.61 (t, J=72.61 Hz, 1H) 7.22 (d, J=8.8 Hz, 1H) 7.52 (t, J=7.7 Hz, 1H) 7.64 (d, J=7.7 Hz, 1H) 7.89 (d, J=7.7 Hz, 2H) 8.01 (d, J=9.0 Hz, 2H); MS (EI) m/z 348 [M$^+$].

Step 4) 2-amino-5-[4-(difluoromethoxy)phenyl]-5-[3-(1-fluorobut-3-en-1-yl)phenyl]-3-methyl-3,5-dihydro-4H-imidazol-4-one

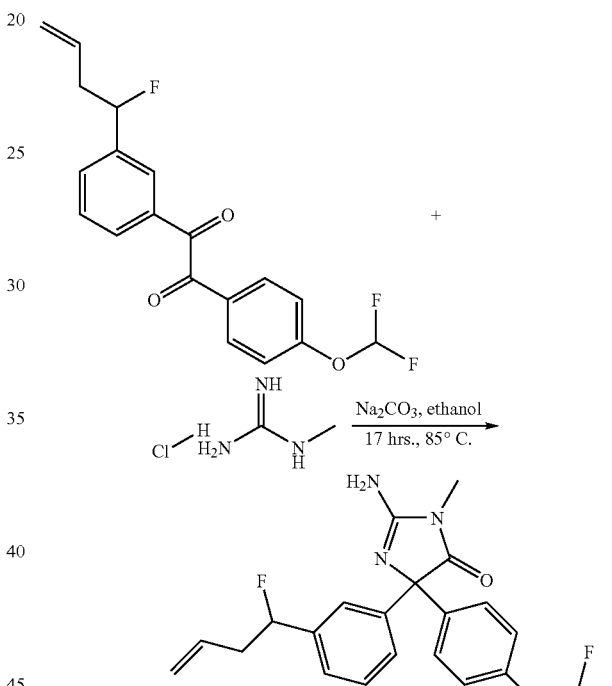

In a 100 ml round bottom flask was dissolved 1-(4-Difluoromethoxy-phenyl)-2-[3-(1-fluoro-but-3-enyl)-phenyl]-ethane-1,2-dione (0.120 g, 0.344 mmol) in ethanol (10 mL). Methylguanidine hydrochloride (0.070 g, 0.642 mmol) was added followed by sodium carbonate (0.068 g, 0.642 mmol). The mixture was heated (oil bath; 89° C.) for 17 hours cooled to room temperature and concentrated onto silica gel. Purification by column chromatography (Gradient; 90-100% EtOAc/hexanes then 0-20% MeOH/EtOAc) produced an oil that was dissolved in diethylether and precipitated with hexanes to yield 0.100 gm of a white material (72%); mp 49-51° C.; $^1$H NMR (400 MHz, DMSO-$d_6$) δ ppm 2.93 (s, 3H) 5.00-5.10 (m, 2H) 5.40-5.61 (m, 1H) 5.63-5.78 (m, 1H) 6.66 (br. s., 2H) 7.06 (d, J=8.8 Hz, 2H) 7.12 (t, J=74.18 Hz, 1H) 7.18-7.22 (m, 1H) 7.28 (t, J=7.5 Hz, 1H) 7.36-7.45 (m, 4H); MS (ES) m/z 402.1 [M−H]$^-$

Example 58

Preparation of 2-amino-5-[4-(difluoromethoxy)phenyl]-5-{3-[3-(2-fluoroethyl)cyclobutyl]phenyl}-3-methyl-3,5-dihydro-4H-imidazol-4-one

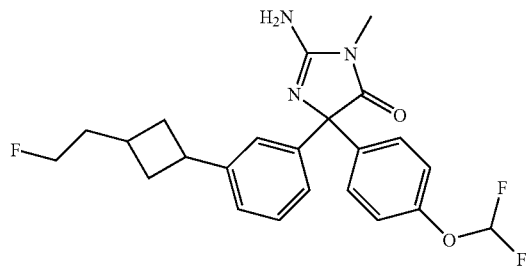

Step 1) 2-[3-(3-Bromo-phenyl)-cyclobutyl]-ethanol

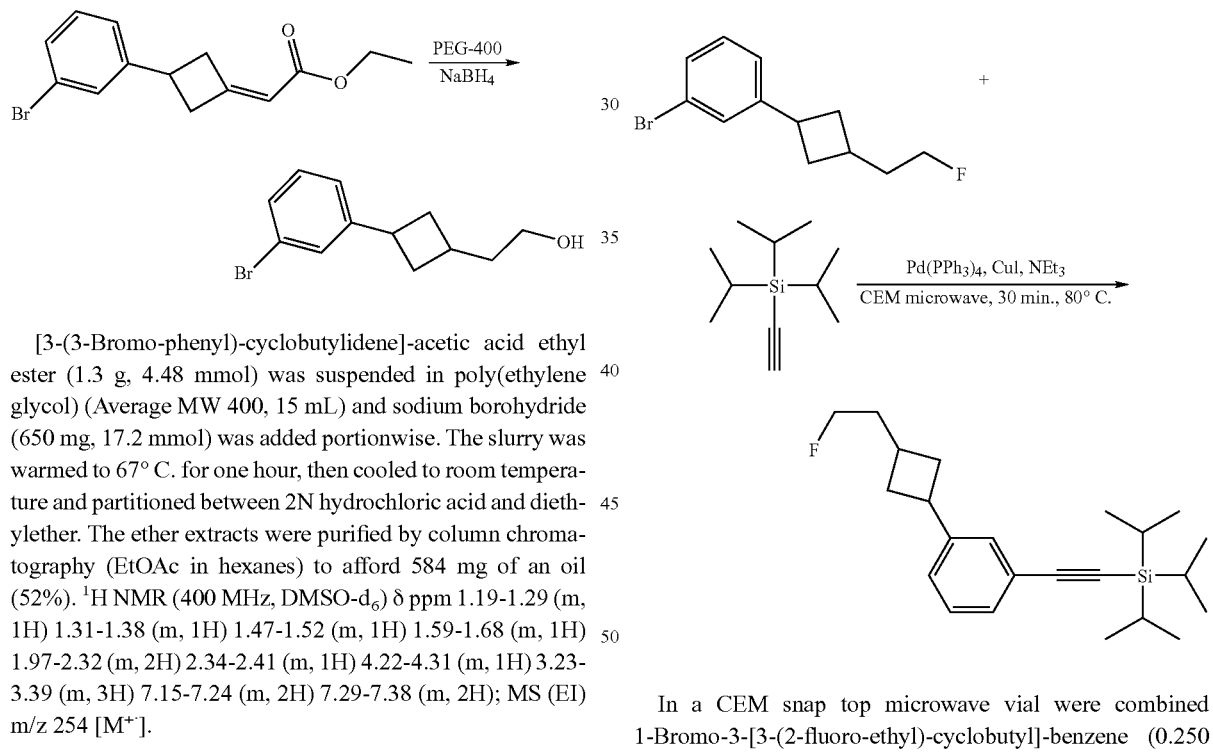

[3-(3-Bromo-phenyl)-cyclobutylidene]-acetic acid ethyl ester (1.3 g, 4.48 mmol) was suspended in poly(ethylene glycol) (Average MW 400, 15 mL) and sodium borohydride (650 mg, 17.2 mmol) was added portionwise. The slurry was warmed to 67° C. for one hour, then cooled to room temperature and partitioned between 2N hydrochloric acid and diethylether. The ether extracts were purified by column chromatography (EtOAc in hexanes) to afford 584 mg of an oil (52%). $^1$H NMR (400 MHz, DMSO-d$_6$) δ ppm 1.19-1.29 (m, 1H) 1.31-1.38 (m, 1H) 1.47-1.52 (m, 1H) 1.59-1.68 (m, 1H) 1.97-2.32 (m, 2H) 2.34-2.41 (m, 1H) 4.22-4.31 (m, 1H) 3.23-3.39 (m, 3H) 7.15-7.24 (m, 2H) 7.29-7.38 (m, 2H); MS (EI) m/z 254 [M$^+$].

Step 2) 1-Bromo-3-[3-(2-fluoro-ethyl)-cyclobutyl]-benzene

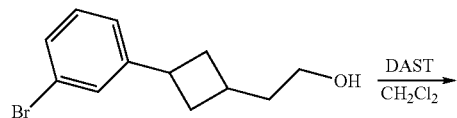

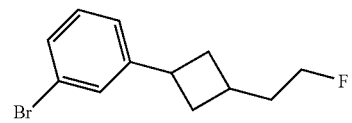

2-[3-(3-Bromo-phenyl)-cyclobutyl]-ethanol (0.600 gm, 2.35 mmol) was dissolved in dichloromethane (10 mL) and chilled to −78° C. The solution was treated with (diethylamino)sulfur trifluoride (468 mg, 2.88 mmol) and monitored by TLC. The crude reaction was poured onto silica and purified by column chromatography (10% EtOAc in hexanes) to afford 250 mg of an oil (41%). $^1$H NMR (400 MHz, DMSO-d$_6$) δ ppm 1.65-1.79 (m, 2H) 1.83-2.09 (m, 2H) 2.14-2.34 (m, 2H) 2.37-2.44 (m, 1H) 3.27-3.63 (m, 1H) 4.27-4.52 (m, 2H) 7.16-7.24 (m, 2H) 7.29-7.40 (m, 2H); MS (EI) m/z 256 [M$^+$].

Step 3) {3-[3-(2-Fluoro-ethyl)-cyclobutyl]-phenylethynyl}-triisopropyl-silane

In a CEM snap top microwave vial were combined 1-Bromo-3-[3-(2-fluoro-ethyl)-cyclobutyl]-benzene (0.250 gm 9.72 mmol), triisopropylsilylacetylene (0.22 gm, 1.21 mmol), copper iodide (7 mg, 0.178 mmol), tetrakis(triphenylphosphine)palladium (22 mg, 0.088 mmol) and triethylamine (0.600 g, 5.93 mmol). The vial was quickly agitated then irradiated in a CEM Explorer™ microwave instrument for 30 minutes at 80° C. Purification by column chromatography (hexanes) afforded an oil 349 mg. $^1$H NMR (400 MHz, DMSO-d$_6$) δ ppm 1.06 (s, 21H) 1.62-1.81 (m, 2H) 1.82-1.97 (m, 1H) 2.00-2.45 (m, 4H) NMR (400 MHz, DMSO-d$_6$) δ ppm 3.31-3.62 (m, 1H) 4.30-4.51 (m, 2H) 7.17-7.41 (m, 4H); MS (EI) m/z 256 [M$^+$].

Step 4) 1-difluoromethoxy-4-{3-[3-(2-fluoro-ethyl)-cyclobutyl]phenyl-ethynyl}benzene

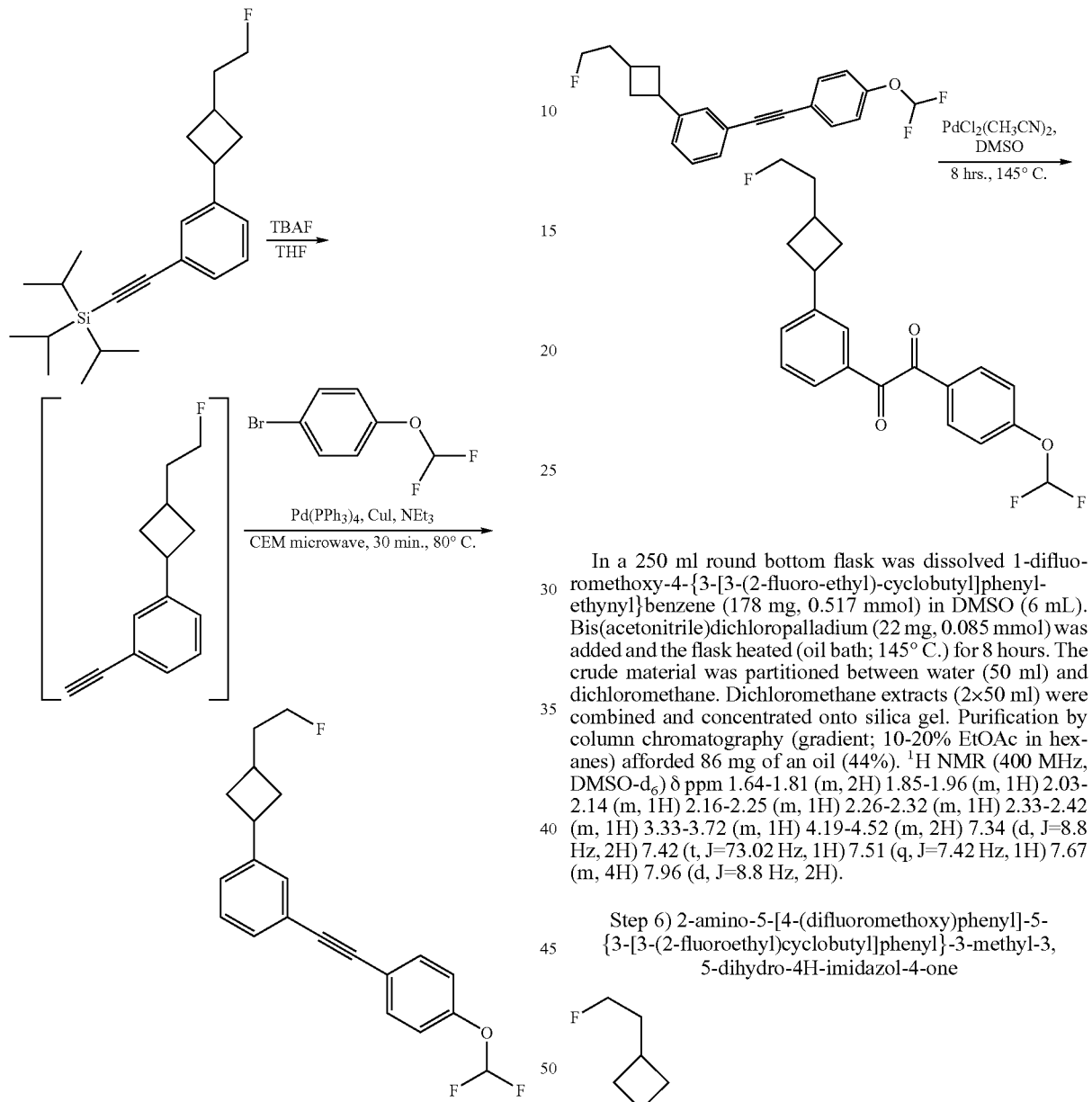

Step 5) 1-(4-Difluoromethoxy-phenyl)-2-{3-[3-(2-fluoro-ethyl)-cyclobutyl]-phenyl}-ethane-1,2-dione {3-[3-(2-Fluoro-ethyl)-cyclobutyl]-phenylethynyl}-triisopropyl-silane (349 mg, 0.973 mmol) was dissolved in THF (2 ml) and treated with a 1M solution of tetrabutylammonium fluoride (TBAF) in THF (2 ml) at room temperature. The crude product obtained from aqueous work-up was placed in a CEM snap top microwave vial and combined with 1-Bromo-4-Difluoromethoxybenzene (300 mg 1.30 mmol), copper iodide (35 mg, 0.131 mmol), tetrakis(triphenylphosphine)palladium (70 mg, 0.060 mmol) and triethylamine (4.3 g, 42.5 mmol). The vial was quickly agitated then irradiated in a CEM Explorer™ microwave instrument for 30 minutes at 80° C. Purification by column chromatography (gradient; 0%, then 5% EtOAc in hexanes) afforded an oil 178 mg (53%). $^1$H NMR (400 MHz, DMSO-d$_6$) δ ppm 1.68-1.80 (m, 2H) 1.85-2.11 (m, 2H) 2.17-2.36 (m, 2H) 2.38-2.43 (m, 1H) 3.28-3.65 (m, 1H) 4.24-4.52 (m, 2H) 7.01-7.47 (m, 5H) 7.18 (d, J=8.8 Hz, 2H) 7.58 (d, J=8.8 Hz, 2H).

In a 250 ml round bottom flask was dissolved 1-difluoromethoxy-4-{3-[3-(2-fluoro-ethyl)-cyclobutyl]phenyl-ethynyl}benzene (178 mg, 0.517 mmol) in DMSO (6 mL). Bis(acetonitrile)dichloropalladium (22 mg, 0.085 mmol) was added and the flask heated (oil bath; 145° C.) for 8 hours. The crude material was partitioned between water (50 ml) and dichloromethane. Dichloromethane extracts (2×50 ml) were combined and concentrated onto silica gel. Purification by column chromatography (gradient; 10-20% EtOAc in hexanes) afforded 86 mg of an oil (44%). $^1$H NMR (400 MHz, DMSO-d$_6$) δ ppm 1.64-1.81 (m, 2H) 1.85-1.96 (m, 1H) 2.03-2.14 (m, 1H) 2.16-2.25 (m, 1H) 2.26-2.32 (m, 1H) 2.33-2.42 (m, 1H) 3.33-3.72 (m, 1H) 4.19-4.52 (m, 2H) 7.34 (d, J=8.8 Hz, 2H) 7.42 (t, J=73.02 Hz, 1H) 7.51 (q, J=7.42 Hz, 1H) 7.67 (m, 4H) 7.96 (d, J=8.8 Hz, 2H).

Step 6) 2-amino-5-[4-(difluoromethoxy)phenyl]-5-{3-[3-(2-fluoroethyl)cyclobutyl]phenyl}-3-methyl-3,5-dihydro-4H-imidazol-4-one

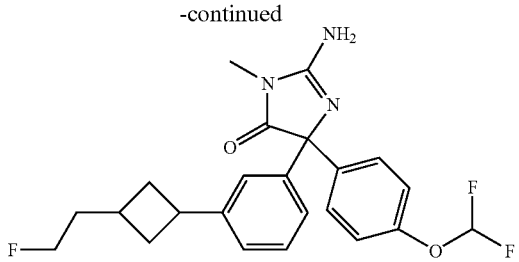

In a 100 ml round bottom flask was dissolved 1-(4-Difluoromethoxy-phenyl)-2-{3-[3-(2-fluoro-ethyl)-cyclobutyl]-phenyl}-ethane-1,2-dione (70 mg, 0.183 mmol) in ethanol (10 mL). Methylguanidine hydrochloride (41 mg, 0.374 mmol) was added, followed by sodium carbonate (40 g, 0.377 mmol). The mixture was heated (oil bath; 89° C.) for 16 hours. The mixture was concentrated onto silica gel. Purification by column chromatography (EtOAc; then 10% EtOH/EtOAc) produced an oil 68 mg (84%); $^1$H NMR (400 MHz, DMSO-$d_6$) δ ppm 1.55-1.77 (m, 3H) 1.82-1.95 (m, 1H) 1.98-2.15 (m, 1H) 2.21-2.42 (m, 2H) 3.14-3.57 (m, 1H) 4.20-4.52 (m, 2H) 6.62 (br. s., 2H) 7.05 (d, J=8.6 Hz, 2H) 7.09 (s, 1H) 7.12 (t, J=74.18 Hz, 1H) 7.15-7.28 (m, 3H) 7.41 (d, J=8.6 Hz, 2H); MS (ES) m/z 432.1 [M+H]$^+$ Example 59

Preparation of 2-amino-5-[4-(difluoromethoxy)phenyl]-5-{3-[3-(2-methoxyethyl)cyclobutyl]phenyl}-3-methyl-3,5-dihydro-4H-imidazol-4-one

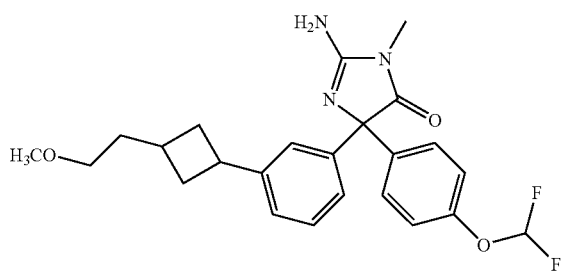

Step 1) 2-[3-(3-Bromo-phenyl)-cyclobutyl]-ethanol

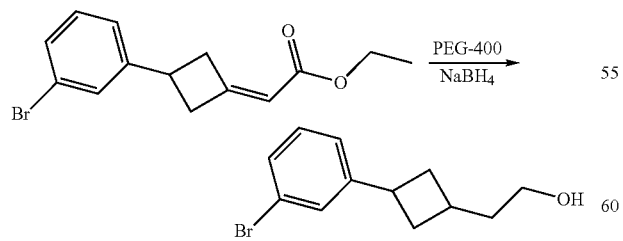

[3-(3-Bromo-phenyl)-cyclobutylidene]-acetic acid ethyl ester (1.96 gm, 6.63 mmol) was suspended in poly(ethylene glycol) (Average MW 400, 40 mL) and sodium borohydride (1.00 g, 26.4 mmol) was added portionwise. The slurry was warmed at 67° C. overnight, then cooled to room temperature and partitioned between 2N hydrochloric acid and diethyl-ether. The ether extracts were dried with sodium sulfate and purified by column chromatography (50% EtOAc/hexanes) to afford 512 mg of an oil (30%). $^1$H NMR (400 MHz, DMSO-$d_6$) δ ppm 1.19-1.29 (m, 1H) 1.31-1.38 (m, 1H) 1.47-1.52 (m, 1H) 1.59-1.68 (m, 1H) 1.97-2.32 (m, 2H) 2.34-2.41 (m, 1H) 4.22-4.31 (m, 1H) 3.23-3.39 (m, 3H) 7.15-7.24 (m, 2H) 7.29-7.38 (m, 2H); MS (EI) m/z 254 [M$^+$].

Step 2) 1-Bromo-3-[3-(2-methoxy-ethyl)-cyclobutyl]-benzene

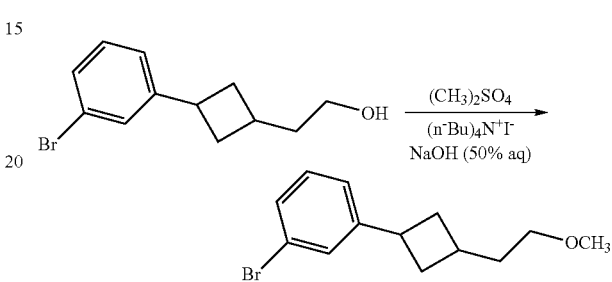

2-[3-(3-Bromo-phenyl)-cyclobutyl]-ethanol (0.500 gm, 1.96 mmol) was dissolved in diethylether (7 mL) and combined with tetrabutylammonium iodide (75 mg, 0.203 mmol), an aqueous solution of sodium hydroxide (5 gm, 50% wt/wt, 62.5 mmol) and dimethylsulfate (0.50 ml, 5.27 mmol). The mixture was stirred overnight at ambient temperature then diluted with diethyl ether and decanted. The supernatant was concentrated onto silica and purified by column chromatography (25% diethylether in hexanes) to afford 389 mg of an oil (74%). This material was used in next step without further characterization.

Step 3) {3-[3-(2-methoxy-ethyl)-cyclobutyl]-phenyl-ethynyl}-triisopropyl-silane

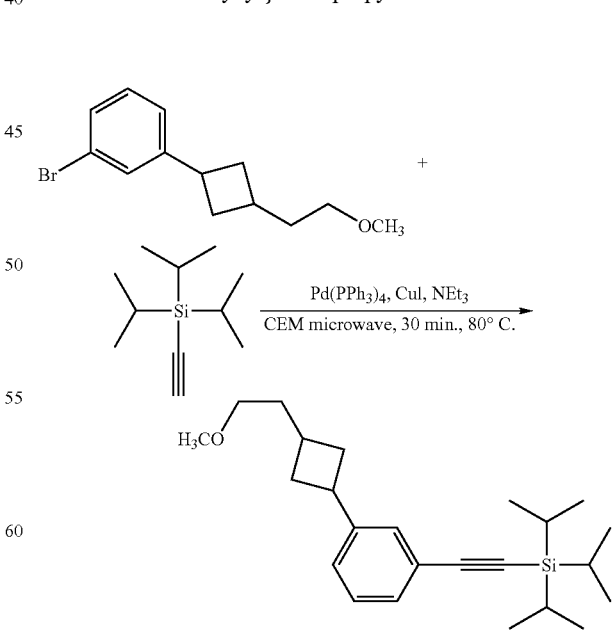

In a CEM snap top microwave vial were combined 1-Bromo-3-[3-(2-methoxy-ethyl)-cyclobutyl]-benzene (0.340 gm 1.28 mmol), triisopropylsilylacetylene (0.29 g, 1.12 mmol), copper iodide (9 mg, 0.178 mmol), tetrakis(triphenylphosphine)palladium (29 mg, 0.088 mmol) and triethylamine (1.30 g, 12.8 mmol). The vial was quickly agitated then irradiated in a CEM Explorer™ microwave instrument for 30 minutes at 80° C. Purification by column chromatography (hexanes) afforded an oil 375 mg (80%). This material was used in next step without further characterization.

Step 4) 1-difluoromethoxy-4-{3-[3-(2-methoxy-ethyl)-cyclobutyl]phenyl-ethynyl}benzene

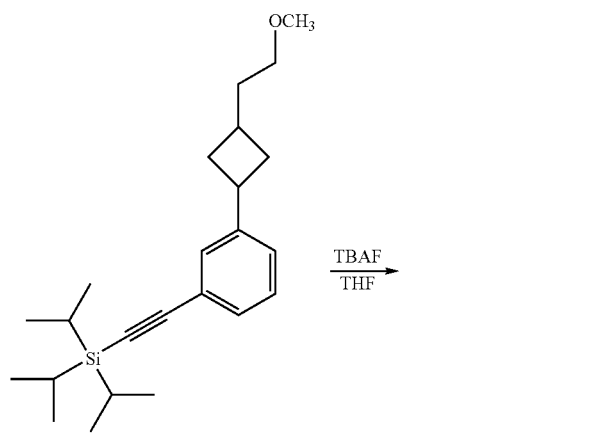

{3-[3-(2-methoxy-ethyl)-cyclobutyl]-phenylethynyl}-triisopropyl-silane (1.00 g, 2.70 mmol) was dissolved in THF (5 ml) and treated with a 1M solution of tetrabutylammonium fluoride (TBAF) in THF (5 ml) at room temperature. The crude product obtained from aqueous work-up was placed in a CEM snap top microwave vial and combined with 1-Bromo-4-Difluoromethoxybenzene (1.20 gm, 5.38 mmol), copper iodide (70 mg, 0.262 mmol), tetrakis(triphenylphosphine)palladium (140 mg, 0.120 mmol) and triethylamine (5.8 g, 98 mmol). The vial was quickly agitated then irradiated in a CEM Explorer™ microwave instrument for 30 minutes at 80° C. Purification by column chromatography (gradient; 0%-10% EtOAc in hexanes) afforded an oil 882 mg (46%). This material was used in next step without further characterization.

Step 5) 1-(4-Difluoromethoxy-phenyl)-2-{3-[3-(2-methoxy-ethyl)-cyclobutyl]-phenyl}-ethane-1,2-dione

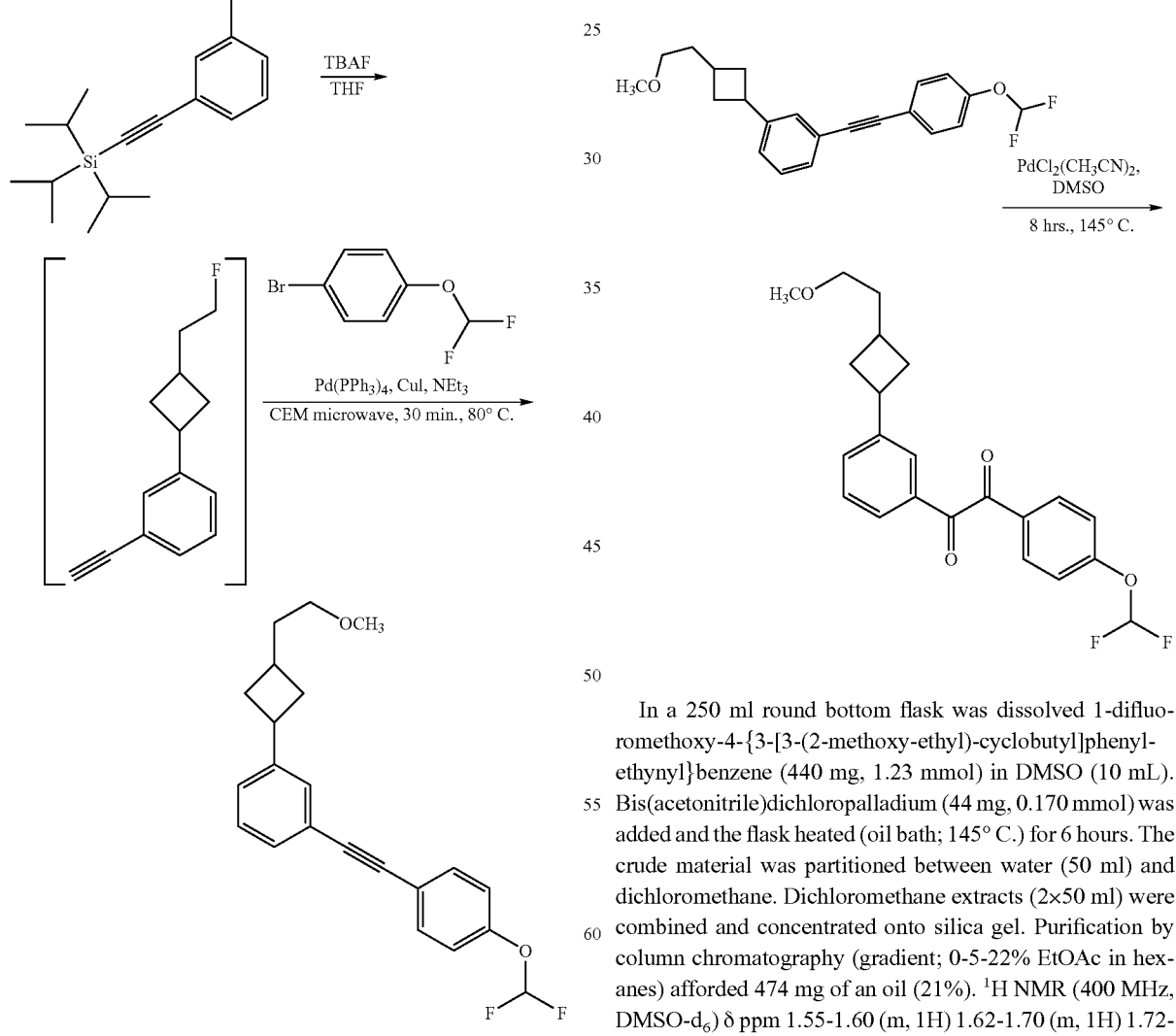

In a 250 ml round bottom flask was dissolved 1-difluoromethoxy-4-{3-[3-(2-methoxy-ethyl)-cyclobutyl]phenyl-ethynyl}benzene (440 mg, 1.23 mmol) in DMSO (10 mL). Bis(acetonitrile)dichloropalladium (44 mg, 0.170 mmol) was added and the flask heated (oil bath; 145° C.) for 6 hours. The crude material was partitioned between water (50 ml) and dichloromethane. Dichloromethane extracts (2×50 ml) were combined and concentrated onto silica gel. Purification by column chromatography (gradient; 0-5-22% EtOAc in hexanes) afforded 474 mg of an oil (21%). $^1$H NMR (400 MHz, DMSO-$d_6$) δ ppm 1.55-1.60 (m, 1H) 1.62-1.70 (m, 1H) 1.72-1.77 (m, 1H) 2.03-2.44 (m, 4H) 7.34 (d, J=8.8 Hz, 2H) 7.42 (t, J=73.02 Hz, 1H) 7.51 (q, J=7.57 Hz, 1H) 7.61-7.74 (m, 3H) 7.96 (d, J=8.8 Hz, 2H); MS (ES) m/z 387.1 [M–H]–

Step 6) 2-amino-5-[4-(difluoromethoxy)phenyl]-5-{3-[3-(2-methoxyethyl)cyclobutyl]phenyl}-3-methyl-3,5-dihydro-4H-imidazol-4-one

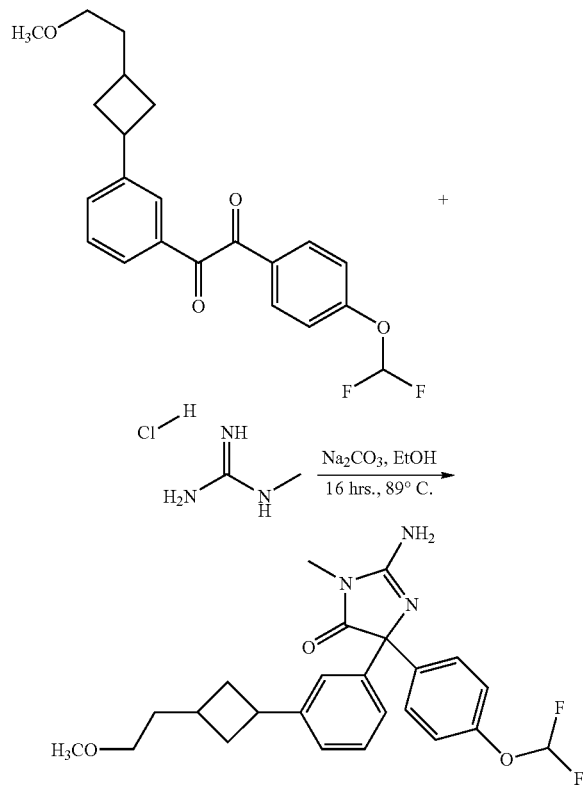

In a 100 ml round bottom flask was dissolved 1-(4-Difluoromethoxy-phenyl)-2-{3-[3-(2-methoxy-ethyl)-cyclobutyl]-phenyl}-ethane-1,2-dione (463 mg, 1.19 mmol) in ethanol (50 mL). Methylguanidine hydrochloride (265 mg, 2.42 mmol) was added, followed by sodium carbonate (260 g, 2.45 mmol). The mixture was heated (oil bath; 89° C.) for 16 hours. The mixture was concentrated onto silica gel. Purification by column chromatography (10-100% EtOAc/hexanes; then 0-10% MeOH/EtOAc) produced an oil 380 mg (72%); $^1$H NMR (400 MHz, DMSO-$d_6$) δ ppm 1.51-1.75 (m, 3H) 1.94-2.38 (m, 4H) 2.93 (s, 3H) 3.16 (s, 3H) 3.19-3.36 (m, 3H) 6.72 (br. s., 2H) 7.02-7.11 (m, 1H) 7.05 (d, J=8.8 Hz, 2H) 7.12 (t, J=74.1 Hz, 1H) 7.14-7.27 (m, 3H) 7.41 (d, J=8.8 Hz, 2H); MS (ES) m/z 444.2 [M+H]+

Example 60

Preparation of 2-amino-5-(3-anilinophenyl)-5-[4-(difluoromethoxy)phenyl]-3-methyl-3,5-dihydro-4H-imidazol-4-one

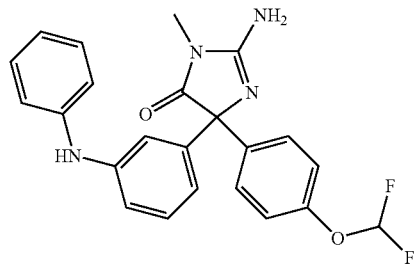

Step 1) Phenyl-{3-[(triisopropylsilanyl)-ethynyl]-phenyl}-amine

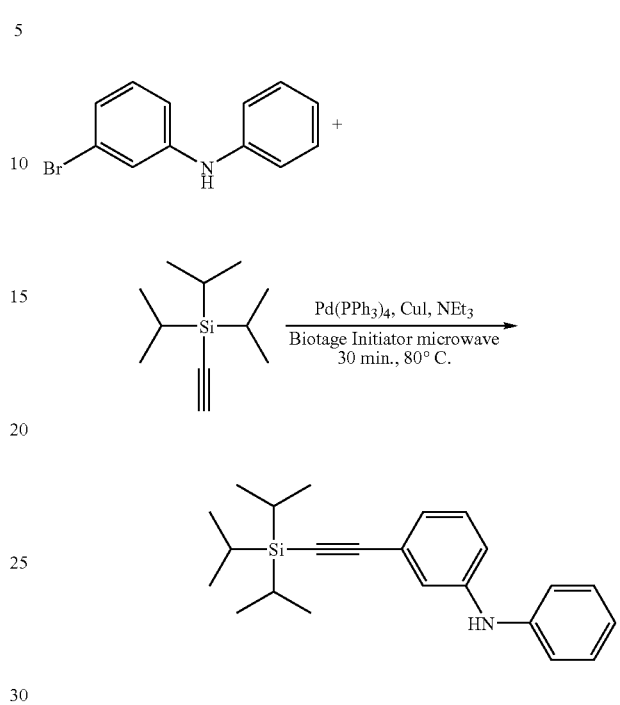

Into two Biotage microwave process vials (0.5-2.0 ml) were divided 3-Bromodiphenylamine (636 mg, 2.56 mmol), triisopropylsilylacetylene (0.46 g, 2.56 mmol), copper iodide (20 mg, 0.356 mmol), tetrakis(triphenylphosphine)palladium (60 mg, 0.176 mmol) and triethylamine (3.40 g, 3.36 mmol). The vials were quickly agitated then irradiated in a Biotage Initiator™ microwave instrument for 30 minutes at 80° C. The microwave reactions were recombined and purified by column chromatography (5% EtOAc/hexanes) to afford an oil 698 mg (78%). $^1$H NMR (400 MHz, DMSO-$d_6$) δ ppm 1.05 (s, 21H) 6.82-6.86 (m, 2H) 7.00-7.12 (m, 4H) 7.15-7.28 (m, 3H) 8.23 (s, 1H); MS (ES) m/z 350.2 [M+H]+

Step 2) 1-anilino-3-{[4-(difluoromethoxy)phenyl]ethynyl}benzene

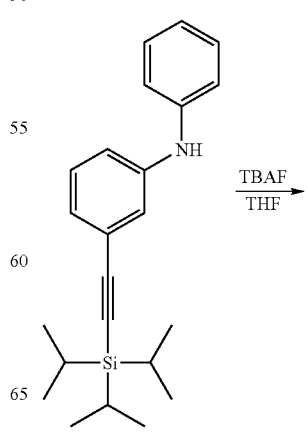

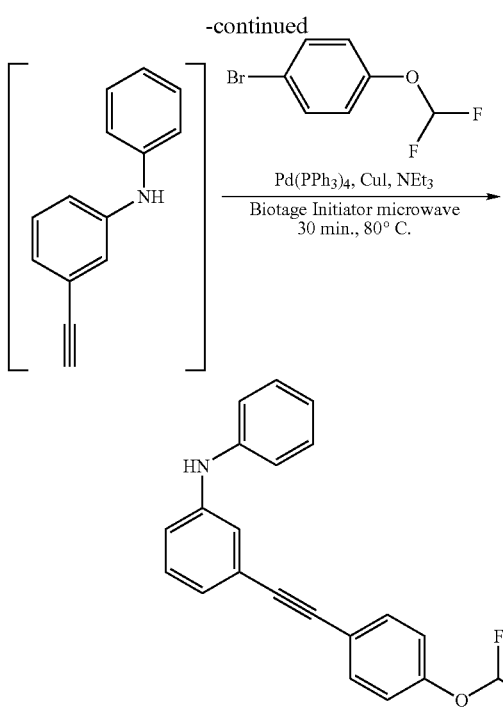

Phenyl-{3-[(triisopropylsilanyl)-ethynyl]-phenyl}-amine (441 mg, 1.26 mmol) was dissolved in THF (2 ml) and treated with a 1M solution of tetrabutylammonium fluoride (TBAF) in THF (2 ml) at room temperature. The crude product (250 mg, 1.29 mmol) obtained from aqueous work-up was introduced to a Biotage microwave process vial (0.5-2.0 ml) and combined with 1-Bromo-4-Difluoromethoxybenzene (700 mg, 3.13 mmol), copper iodide (40 mg, 0.210 mmol), tetrakis(triphenylphosphine)palladium (80 mg, 0.069 mmol) and triethylamine (2.74 g, 27 mmol). The vial was quickly crimp capped, agitated then irradiated in a Biotage Initiator™ microwave instrument for 30 minutes at 80° C. Purification by column chromatography (gradient; 0-10% EtOAc in hexanes) afforded an oil 229 mg (53%). This material was used in the subsequent oxidation without further characterization.

Step 3) 1-(4-Difluoromethoxy-phenyl)-2-(3-phenylamino-phenyl)-ethane-1,2-dione

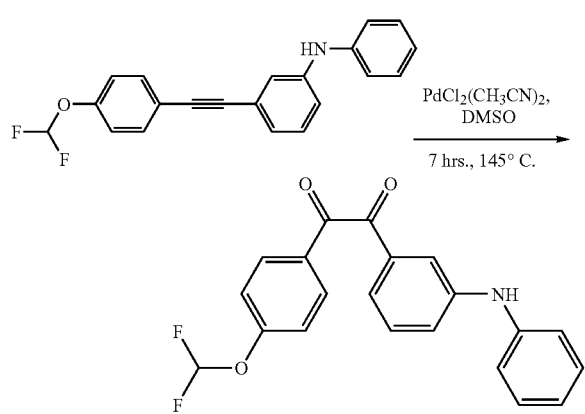

In a 50 ml round bottom flask was dissolved 1-anilino-3-{[4-(difluoromethoxy)phenyl]-ethynyl}benzene (0.229 g, 0.68 mmol) in DMSO (7 mL). Bis(acetonitrile)dichloro-palladium (22 mg, 0.084 mmol) was added and the flask heated for seven hours (oil bath 145° C.). The reaction was diluted with water (50 ml), extracted with dichloromethane (3×50 ml), dried with magnesium sulfate, and concentrated onto silica gel. Column chromatography (5-35% EtOAc in hexanes) afforded 0.250 g of oil. $^1$H NMR (400 MHz, DMSO-$d_6$) δ ppm 6.86-6.90 (m, 1H) 7.01-7.08 (m, 2H) 7.20-7.23 (m, 3H) 7.35 (q, J=4.9 Hz, 2H) 7.38-7.40 (m, 2H) 7.42 (t, J=73.0 Hz, 1H) 7.47-7.53 (m, 1H) 7.95 (q, J=4.9 Hz, 2H) 8.50 (s, 1H); MS (ES) m/z 366.1 [M−H]−

Step 4) 2-amino-5-(3-anilinophenyl)-5-[4-(difluoromethoxy)phenyl]-3-methyl-3,5-dihydro-4H-imidazol-4-one

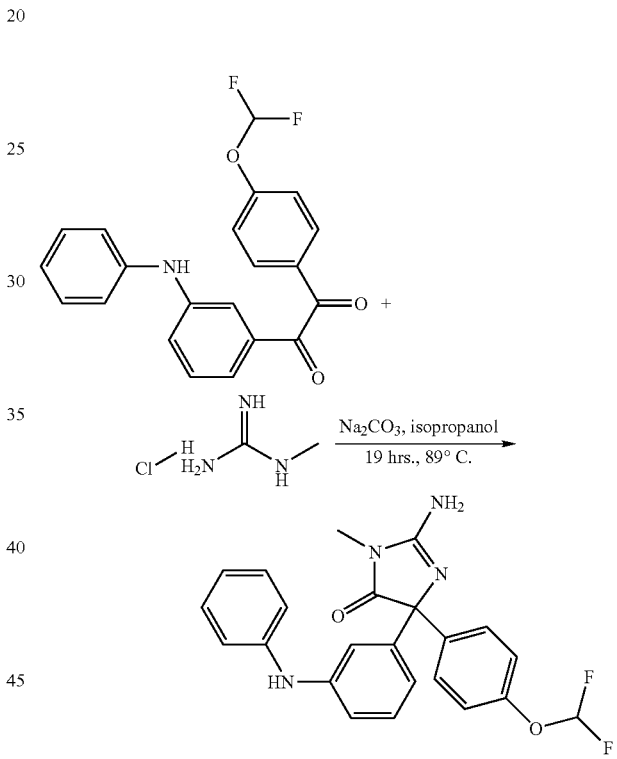

In a 100 ml round bottom flask was dissolved 1-(4-Difluoromethoxy-phenyl)-2-(3-phenylamino-phenyl)-ethane-1,2-dione (0.250 g, 0.680 mmol) in ethanol (30 mL). Methylguanidine hydrochloride (0.154 g, 1.41 mmol) was added followed by sodium carbonate (0.151 g, 105.99 g/mol, 1.42 mmol). The mixture was heated (oil bath 89° C.) for 19 hours. The crude reaction was concentrated directly onto silica and purified by column chromatography [gradient (70-100% EtOAc in hexanes)] to afford a residue 95 mg (33%). The residue was redissolved in diethylether/hexanes and concentrated, twice then placed under vacuum to give a white solid 67 mg. $^1$H NMR (400 MHz, DMSO-$d_6$) δ ppm 2.95 (s, 3H) 6.63 (br. s., 2H) 6.75 (t, J=7.2 Hz, 1H) 6.83 (d, J=7.4 Hz, 1H) 6.91 (d, J=8.4 Hz, 1H) 6.94-7.33 (m, 9H) 7.45 (d, J=8.8 Hz, 2H) 8.16 (s, 1H); MS (ES) m/z 421.1 [M−H]−

Example 61

Preparation of 2-Amino-5-(4-difluoromethoxy-phenyl)-5-[3-(isopropylamino-methyl)-phenyl]-3-methyl-3,5-dihydro-imidazol-4-one

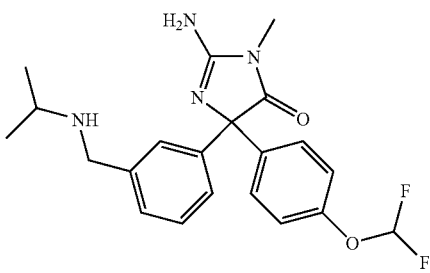

Step 1) 3-[2-Amino-4-(4-difluoromethoxy-phenyl)-1-methyl-5-oxo-4,5-dihydro-1H-imidazol-4-yl]-benzaldehyde

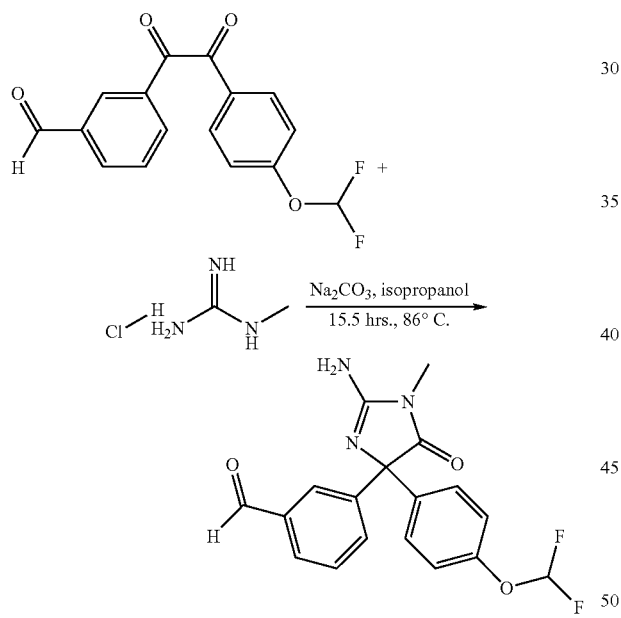

In a 50 ml round bottom flask was dissolved 3-[2-(4-Difluoromethoxy-phenyl)-2-oxo-acetyl]-benzaldehyde (96 mg, 0.320 mmol) in isopropanol (20 mL). Methylguanidine hydrochloride (0.071 g, 0.700 mmol) was added followed by sodium carbonate (0.070 g, 105.99 g/mol, 0.71 mmol). The mixture was heated (oil bath 86° C.) for 15½ hours, cooled to ambient temperature, and concentrated onto silica gel. Purification by column chromatography [step gradient (70% EtOAc in hexanes, EtOAc, then 20% MeOH/EtOAc-100%)] afforded 0.105 gm of a white solid (93%) $^1$H NMR (400 MHz, DMSO-$d_6$) δ ppm 2.96 (s, 3H) 6.76 (br. s., 2H) 7.09 (d, J=8.8 Hz, 2H) 7.15 (t, J=74.12 Hz, 1H) 7.44 (d, J=8.8 Hz, 2H) 7.52 (t, J=7.7 Hz, 1H) 7.75 (dq, J=11.0, 3.1 Hz, 2H) 7.96 (t, J=1.5 Hz, 1H) 9.93 (s, 1H).

Step 2) 2-Amino-5-(4-difluoromethoxy-phenyl)-5-[3-(isopropylamino-methyl)-phenyl]-3-methyl-3,5-dihydro-imidazol-4-one

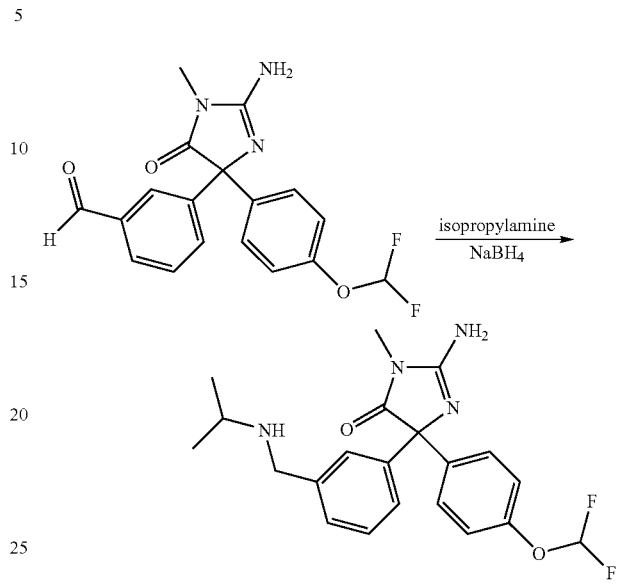

A small vial (2 ml) was charged with 3-[2-Amino-4-(4-difluoromethoxy-phenyl)-1-methyl-5-oxo-4,5-dihydro-1H-imidazol-4-yl]-benzaldehyde (27.9 mg, 77.6 □mol). To this was added half of a solution of isopropylamine (10 mg, 0.169 mmol) in methanol (1 ml). After stirring for two hours sodium borohydride (7.4 mg) was added, then after another 20 minutes 1N sodium hydroxide (1 ml) was added and the mixture extracted with diethyl ether. The ethereal layer was concentrated by rotary evaporation, diluted with methanol and re-concentrated (repeated three times). Finally the oily residue was redissolved in diethylether/hexanes and concentrated, twice then placed under vacuum to give a white foam 29 mg (93%) $^1$H NMR (400 MHz, DMSO-$d_6$) δ ppm 0.92 (d, J=6.26 Hz, 6H) 1.63-1.68 (m, 1H) 2.59-2.63 (m, 1H) 2.93 (s, 3H) 3.57 (d, J=7.2 Hz, 2H) 6.60 (br. s., 2H) 7.05 (d, J=8.8 Hz, 2H) 7.12 (t, J=74.18 Hz, 1H) 7.15-7.18 (m, 2H) 7.22 (t, J=4.2 Hz, 1H) 7.35 (s, 1H) 7.42 (d, J=8.8 Hz, 2H); MS (ES) m/z 401.2 [M−H]−

Example 62

Preparation of 2-amino-5-[4-(difluoromethoxy)phenyl]-5-{3-[(dimethylamino)-methyl]phenyl}-3-methyl-3,5-dihydro-4H-imidazol-4-one

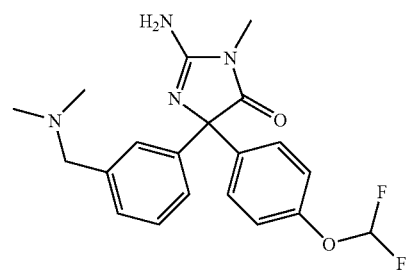

Step 1) 3-[2-Amino-4-(4-difluoromethoxy-phenyl)-1-methyl-5-oxo-4,5-dihydro-1H-imidazol-4-yl]-benzaldehyde Same as step 1 of Example 61.

Step 2) 2-amino-5-[4-(difluoromethoxy)phenyl]-5-{3-[(dimethylamino)-methyl]phenyl}-3-methyl-3,5-dihydro-4H-imidazol-4-one

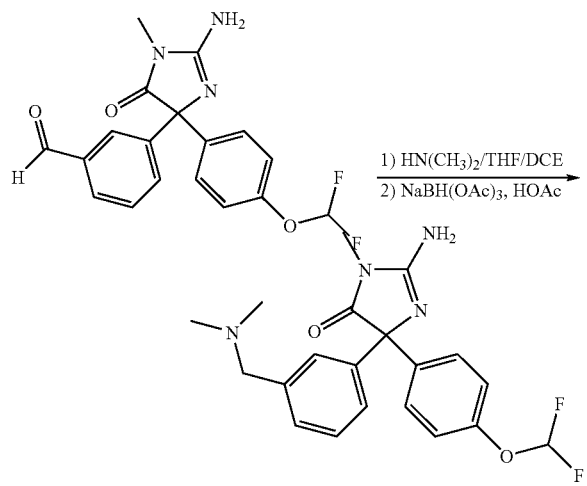

A small vial (10 ml) was charged with 3-[2-Amino-4-(4-difluoromethoxy-phenyl)-1-methyl-5-oxo-4,5-dihydro-1H-imidazol-4-yl]-benzaldehyde (69 mg, 192 µmol) and 1,2-dichloroethane (DCE, 1 ml). To this was added a 2M solution of dimethylamine in THF (1 ml). After stirring overnight at room temperature sodium triacetoxyborohydride (58 mg, 270 µmol) was added followed by 1 drop of glacial acetic acid (~12 mg), then after another 20 hours 1N sodium hydroxide (1 ml) was added and the mixture extracted with diethyl ether. The ethereal layer was concentrated by rotary evaporation, diluted with methanol and re-concentrated (repeated three times). Finally the oily residue was redissolved in diethyl-ether/hexanes and concentrated, twice then placed under vacuum to give a white foam 32 mg (43%) $^1$H NMR (400 MHz, DMSO-$d_6$) δ ppm 2.04 (s, 6H) 2.93 (s, 3H) 3.26 (s, 2H, partially obscured by solvent) 6.62 (br. s., 4H) 7.04-7.09 (m, 3H) 7.12 (t, J=74.18 Hz 1H) 7.18 (t, J=7.6 Hz, 1H) 7.27 (d, J=7.9 Hz, 1H) 7.35 (s, 1H) 7.40 (d, J=8.8 Hz, 2H); MS (APPI) m/z 389 [M+H]$^+$

Example 63

Preparation of 2-amino-5-[4-(difluoromethoxy)phenyl]-5-{3-[(ethylamino)methyl]phenyl}-3-methyl-3,5-dihydro-4H-imidazol-4-one

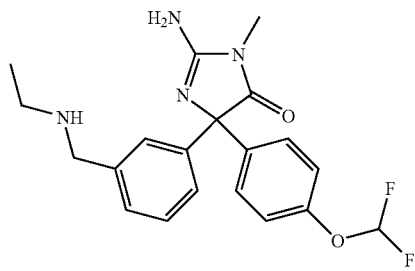

Step 1) 3-[2-Amino-4-(4-difluoromethoxy-phenyl)-1-methyl-5-oxo-4,5-dihydro-1H-imidazol-4-yl]-benzaldehyde Same as step 1 of Example 61.

Step 2) 2-amino-5-[4-(difluoromethoxy)phenyl]-5-{3-[(ethylamino)-methyl]phenyl}-3-methyl-3,5-dihydro-4H-imidazol-4-one

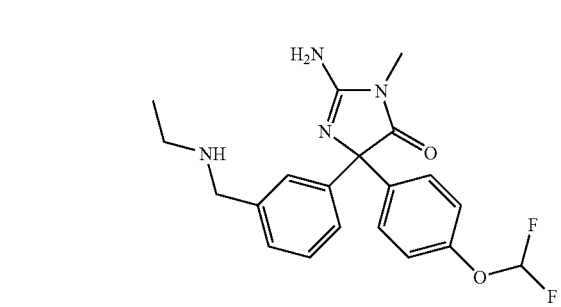

A small vial (2 ml) was charged with 3-[2-Amino-4-(4-difluoromethoxy-phenyl)-1-methyl-5-oxo-4,5-dihydro-1H-imidazol-4-yl]-benzaldehyde (68 mg, 189 µmol) and THF (0.5 ml). To this was added a 2M solution of ethylamine in THF (100 µl). After stirring overnight methanol (1 ml) and sodium borohydride (11 mg) was added, then after another hour 1N sodium hydroxide (1 ml) was added and the mixture extracted with diethyl ether. The ethereal layer was concentrated by rotary evaporation, diluted with methanol and re-concentrated (repeated three times). Finally the oily residue was redissolved in diethylether/hexanes and concentrated, twice then placed under vacuum to give a white foam 61 mg (83%). $^1$H NMR (400 MHz, DMSO-$d_6$) δ ppm 0.95 (t, J=7.1 Hz, 3H) 2.38-2.44 (m, 2H, partially obscured by solvent) 2.93 (s, 3H) 3.56 (s, 2H) 6.61 (br. s., 2H) 6.66 (br. s., 1H) 7.05 (d, J=8.8 Hz, 2H) 7.12 (t, J=74.18 Hz, 1H) 7.14-7.28 (m, 3H) 7.33-7.39 (m, 1H) 7.42 (d, J=8.8 Hz, 2H); MS (APPI) m/z 389 [M+H]$^+$

Example 64

Preparation of 2-amino-5-[4-(difluoromethoxy)phenyl]-3-methyl-5-{3-[(propylamino)-methyl]phenyl}-3,5-dihydro-4H-imidazol-4-one

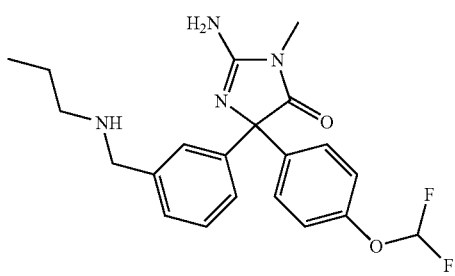

Step 1) 3-[2-Amino-4-(4-difluoromethoxy-phenyl)-1-methyl-5-oxo-4,5-dihydro-1H-imidazol-4-yl]-benzaldehyde Same as step 1 of Example 61.

Step 2) 2-amino-5-[4-(difluoromethoxy)phenyl]-3-methyl-5-{3-[(propyl-amino)methyl]phenyl}-3,5-dihydro-4H-imidazol-4-one

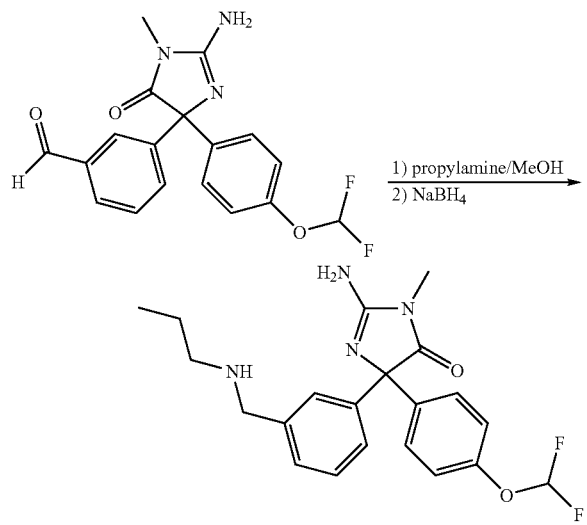

A small vial (2 ml) was charged with 3-[2-Amino-4-(4-difluoromethoxy-phenyl)-1-methyl-5-oxo-4,5-dihydro-1H-imidazol-4-yl]-benzaldehyde (32.7 mg, 91.0 µmol). To this was added one-fifth of a solution of propylamine (31 mg, 0.524 mmol) in methanol (2.50 ml). After stirring for two hours sodium borohydride (8.7 mg) was added, then after another hour 1N sodium hydroxide (1 ml) was added and the mixture extracted with diethyl ether. The ethereal layer was concentrated by rotary evaporation, diluted with methanol and re-concentrated (repeated three times). Finally the oily residue was redissolved in diethylether/hexanes and concentrated, twice then placed under vacuum to give a white foam 29 mg (78%) $^1$H NMR (400 MHz, DMSO-$d_6$) δ ppm 0.79 (t, J=7.3 Hz, 3H) 1.29-1.39 (m, 2H) 2.36 (t, J=7.1 Hz, 2H) 2.93 (s, 3H) 3.57 (s, 2H) 6.62 (br. s., 2H) 6.67 (br. s., 1H) 7.06 (d, J=8.8 Hz, 2H) 7.13 (t, J=74.12 Hz, 1H) 7.14-7.25 (m, 3H) 7.35 (s, 1H) 7.43 (d, J=8.8 Hz, 2H); MS (APPI) m/z 403 [M+H]$^+$

Example 65

Preparation of 2-amino-5-{3-[(butylamino)methyl]phenyl}-5-[4-(difluoromethoxy)phenyl]-3-methyl-3,5-dihydro-4H-imidazol-4-one

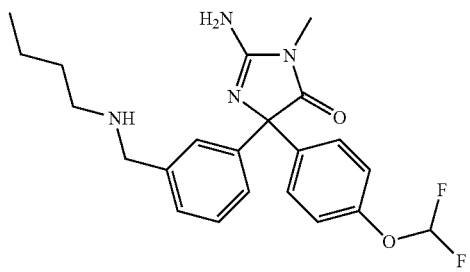

Step 1) 3-[2-Amino-4-(4-difluoromethoxy-phenyl)-1-methyl-5-oxo-4,5-dihydro-1H-imidazol-4-yl]-benzaldehyde Same as step 1 of Example 61.

Step 2) 2-amino-5-{3-[(butylamino)methyl]phenyl}-5-[4-(difluoro-methoxy)phenyl]-3-methyl-3,5-dihydro-4H-imidazol-4-one A small vial (10 ml) was charged with 3-[2-Amino-4-(4-difluoromethoxy-phenyl)-1-methyl-5-oxo-4,5-dihydro-1H-imidazol-4-yl]-benzaldehyde (90 mg, 250 µmol) and methanol (2 ml). To this was added butylamine (20 mg, 273 µmol). After stirring overnight at room temperature sodium borohydride (24 mg) was added, then after another 4 hours 1N sodium hydroxide (1 ml) was added and the mixture extracted with diethyl ether. The ethereal layer was concentrated by rotary evaporation, diluted with methanol and re-concentrated (repeated three times). Finally the oily residue was redissolved in diethylether/hexanes and concentrated, twice then placed under vacuum to give a white foam 78 mg (75%). $^1$H NMR (400 MHz, DMSO-$d_6$) δ ppm 0.76-0.83 (m, 3H) 1.21 (quin, J=7.9 Hz, 2H) 1.31 (quin, J=6.3 Hz, 2H) 2.38 (t, J=7.0 Hz, 2H) 2.93 (s, 3H) 3.56 (s, 2H) 6.61 (br. s., 4H) 6.67 (br. s., 1H) 7.04 (d, J=8.8 Hz, 2H) 7.12 (t, J=74.18 Hz, 1H) 7.13-7.27 (m, 3H) 7.37 (s, 1H) 7.42 (d, J=8.8 Hz, 2H); MS (APPI) m/z 417 [M+H]$^+$ Example 66

Preparation of 2-amino-5-[4-(difluoromethoxy)phenyl]-3-methyl-5-[3-(pyrrolidin-1-ylmethyl)phenyl]-3,5-dihydro-4H-imidazol-4-one

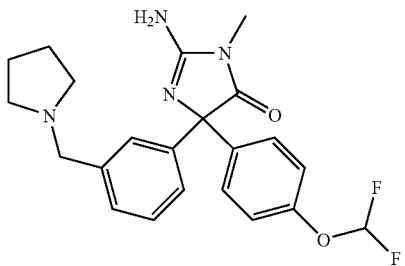

Step 1) 3-[2-Amino-4-(4-difluoromethoxy-phenyl)-1-methyl-5-oxo-4,5-dihydro-1H-imidazol-4-yl]-benzaldehyde Same as step 1 of Example 61.

Step 2) 2-amino-5-[4-(difluoromethoxy)phenyl]-3-methyl-5-[3-(pyrrolidin-1-ylmethyl)phenyl]-3,5-dihydro-4H-imidazol-4-one

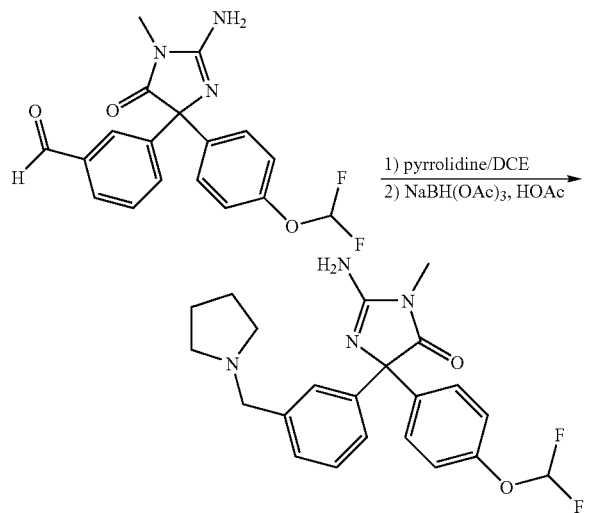

A small vial (10 ml) was charged with 3-[2-Amino-4-(4-difluoromethoxy-phenyl)-1-methyl-5-oxo-4,5-dihydro-1H-imidazol-4-yl]-benzaldehyde (69 mg, 192 μmol) and 1,2-dichloroethane (DCE, 1 ml). To this was added one-third of a solution of pyrrolidine (41 mg, 0.576 mmol) in 1,2-dichloroethane (3.00 ml). After stirring overnight at room temperature sodium triacetoxyborohydride (58 mg, 270 μmol) was added followed by 1 drop of glacial acetic acid (~12 mg), then after another 20 hours 1N sodium hydroxide (1 ml) was added and the mixture extracted with diethyl ether. The ethereal layer was concentrated by rotary evaporation, diluted with methanol and re-concentrated (repeated three times). Finally the oily residue was redissolved in diethylether/hexanes and concentrated, twice then placed under vacuum to give a white foam 66 mg (82%) $^1$H NMR (400 MHz, DMSO-$d_6$) δ ppm 1.61 (t, J=3.4 Hz, 4H) 2.32 (t, J=6.5 Hz, 4H) 2.93 (s, 3H) 3.44 (s, 2H) 6.62 (br. s., 3H) 7.05 (d, J=8.8 Hz, 2H) 7.08-7.11 (m, 1H) 7.12 (t, J=74.18 Hz, 1H) 7.17 (t, J=7.6 Hz, 1H) 7.25 (t, J=4.6 Hz, 1H) 7.34 (s, 1H) 7.40 (d, J=8.8 Hz, 2H); MS (ES) m/z 413.3 [M−H]$^-$ Example 67

Preparation of 2-amino-5,5-bis[4-(difluoromethoxy)phenyl]-3-methyl-3,5-dihydro-4H-imidazol-4-one

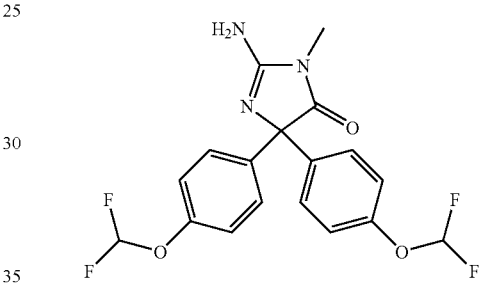

Step 1) Bis(4-difluoromethoxyphenyl)acetylene

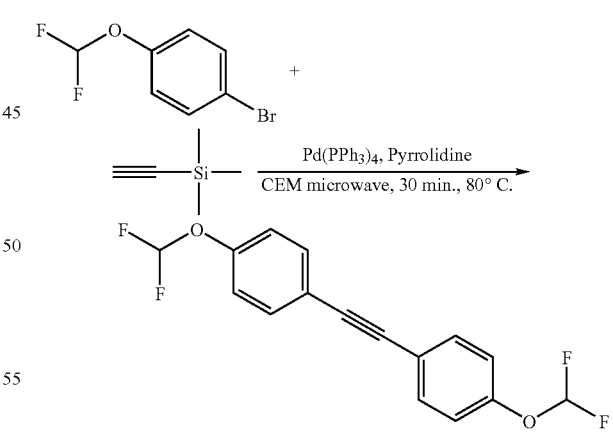

In a CEM snap top microwave vial (10 ml) were combined trimethylsilylacetylene (0.220 g, 3.29 mmol), 4-Bromo-1-difluoromethoxybenzene (1.00 g, 4.48 mmol), tetrakis(triphenyl-phosphine)palladium (36 mg, 0.0302 mmol) and pyrrolidine (1 ml, 12 mmol). The reaction vial was placed in a CEM Explorer™ microwave and irradiated for 30 minutes at 80° C. The crude reaction mixture was poured directly onto silica gel and purification by column chromatography (hexanes) yielded 0.350 g of a clear oil (50%). $^1$H NMR (400 MHz, DMSO-d$_6$) δ ppm 7.19 (q, J=4.56 Hz, 4H) 7.58 (t, J=73.65 Hz, 2H) 7.58 (q, J=4.87 Hz, 4H); MS (EI) m/z 310 [M$^+$]

Step 2)
1,2-Bis-(4-difluoromethoxyphenyl)-ethane-1,2-dione

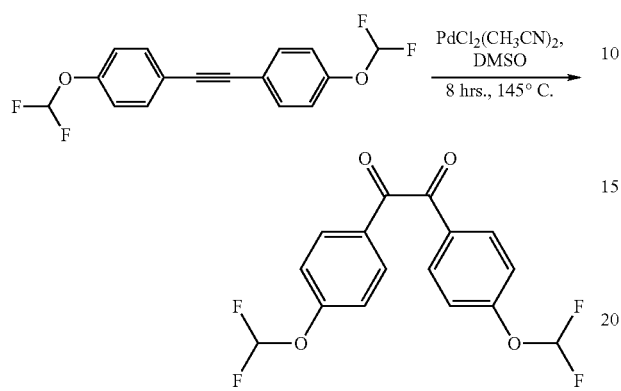

In a 50 ml round bottom flask was dissolved Bis(4-difluoromethoxyphenyl)acetylene (0.311 g, 1.00 mmol) in DMSO (10 mL). Bis(acetonitrile)dichloro-palladium (30 mg, 0.116 mmol) was added and the flask heated for 8 hours (oil bath 145° C.). The reaction was diluted with water (50 ml), extracted with dichloromethane (3×50 ml), dried with magnesium sulfate, and concentrated onto silica gel. Column chromatography (25% EtOAc in hexanes) afforded 0.219 g of a yellow solid (64%). $^1$H NMR (400 MHz, DMSO-d$_6$) δ ppm 7.34 (q, J=4.87 Hz, 4H) 7.58 (t, J=72.96 Hz, 2H) 7.97 (q, J=4.95 Hz, 4H); MS (EI) m/z 342 M$^{+\cdot}$ Step 3) 2-amino-5,5-bis[4-(difluoromethoxy)phenyl]-3-methyl-3,5-dihydro-4H-imidazol-4-one

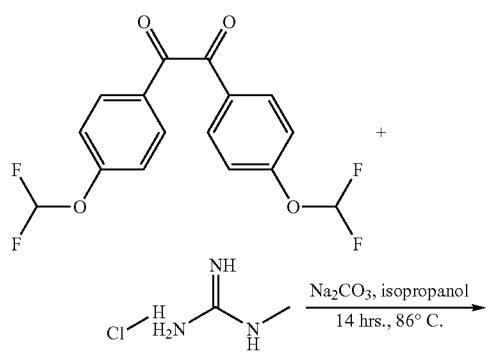

In a 100 ml round bottom flask was dissolved 1,2-bis-(4-difluoromethoxyphenyl)-ethane-1,2-dione (0.205 g, 0.600 mmol) in isopropanol (10 mL). Methylguanidine hydrochloride (0.098 g, 0.894 mmol) was added followed by sodium carbonate (0.095 g, 105.99 g/mol, 0.896 mmol). The mixture was heated (oil bath 85° C.) for 14 hours. The isopropanol was removed at the rotovap and the residue partitioned between water and chloroform. The organic layer was dried with sodium sulfate and concentrated onto silica gel. Purification by column chromatography [gradient (70-100% EtOAc in hexanes)] afforded 0.141 gm of a clear oil. The oil was redissolved in diethylether and concentrated, twice then placed under vacuum to give a white foam 141 mg (59%) $^1$H NMR (400 MHz, DMSO-d$_6$) δ ppm 2.93 (s, 3H) 6.65 (br. s., 2H) 7.06 (d, J=8.81 Hz, 4H) 7.12 (t, J=74.12 Hz, 2H) 7.42 (d, J=8.58 Hz, 4H); MS (APPI) m/z 398 [M+H]$^+$ Example 68

Preparation of 2-amino-5-[4-(difluoromethoxy)phenyl]-5-(3-{[(2-furylmethyl)-amino]methyl}phenyl)-3-methyl-3,5-dihydro-4H-imidazol-4-one

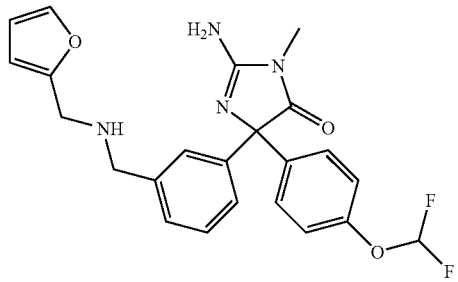

Step 1) 3-[2-Amino-4-(4-difluoromethoxy-phenyl)-1-methyl-5-oxo-4,5-dihydro-1H-imidazol-4-yl]-benzaldehyde Same as step 1 of Example 61.

Step 2) 2-amino-5-[4-(difluoromethoxy)phenyl]-5-(3-{[(2-furylmethyl)-amino]methyl}phenyl)-3-methyl-3,5-dihydro-4H-imidazol-4-one

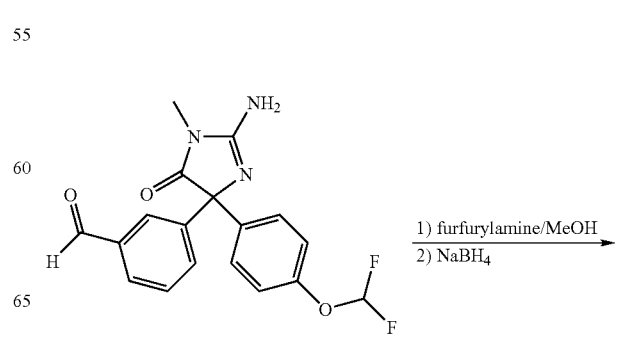

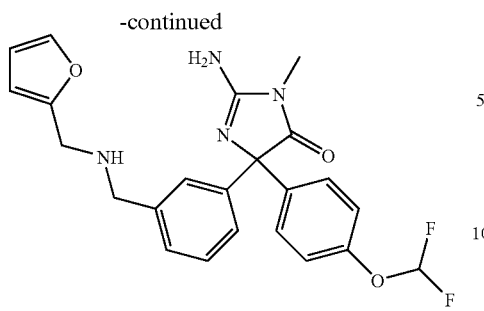

A small vial (2 ml) was charged with 3-[2-amino-4-(4-difluoromethoxy-phenyl)-1-methyl-5-oxo-4,5-dihydro-1H-imidazol-4-yl]-benzaldehyde (110 mg, 306 μmol). To this was added furfurylamine (30 mg, 308 μmol) in methanol (1 ml). After stirring overnight at room temperature sodium borohydride (29 mg) was added, then after another 90 minutes 1N sodium hydroxide (1 ml) was added and the mixture extracted with diethyl ether. The ethereal layer was concentrated by rotary evaporation, diluted with methanol and re-concentrated (repeated three times). Finally the oily residue was redissolved in diethylether/hexanes and concentrated, twice then placed under vacuum to give a white foam 96 mg (71%) $^1$H NMR (400 MHz, DMSO-$d_6$) δ ppm 2.94 (s, 3H) 3.56 (br. s., 4H) 6.15 (d, J=3.2 Hz, 1H) 6.68 (br. s., 1H) 6.34 (t, J=2.4 Hz, 1H) 6.64 (s, 2H) 7.06 (d, J=8.8 Hz, 2H) 7.13 (t, J=74.18 Hz, 1H) 7.15-7.28 (m, 3H) 7.37 (s, 1H) 7.43 (d, J=8.8 Hz 2H) 7.51 (t, J=1.4 Hz, 1H); MS (ES) m/z 439.2 [M−H]$^-$ Example 69

Preparation of 2-Amino-5-[4-(difluoromethoxy)phenyl]-5-{3-[(1R)-1-fluoropent-4-en-1-yl]phenyl}-3-methyl-3,5-dihydro-4H-imidazol-4-one

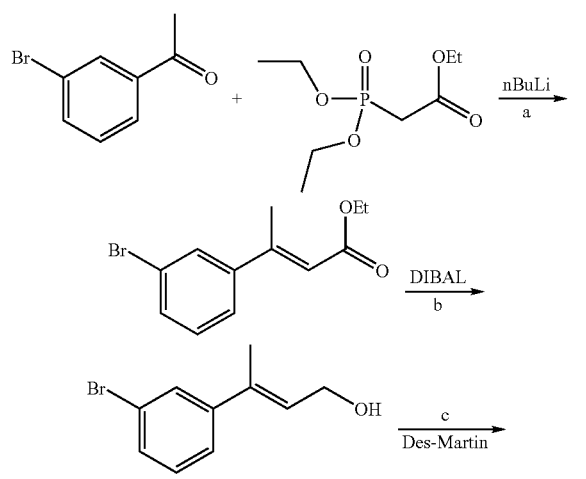

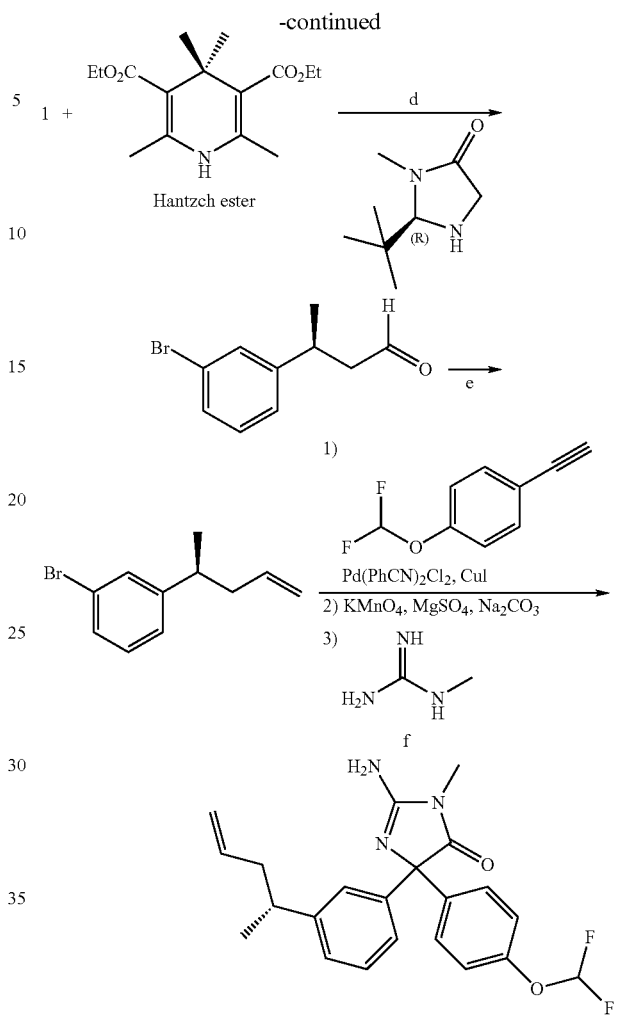

Step a) (3-bromophenyl)-but-2-enoic acid ethyl ester

To a stirred solution of triethyl phosphonoacetate (6.19 g, 27.6 mmol) in THF (70 mL) at −78 C, nBuLi in hexanes (1.6N, 18 mL, 29 mmol) was added in small portions. After the mixture was stirred at this temperature for additional 30 minutes, 3-bromoacetophenone (5 g, 25.1 mmol) was added and the reaction stirred at −78° C. for 30 min. The reaction mixture was warmed to room temperature and stirred for 18 hours. Solvent was removed under reduced pressure to afford oil. Hexanes (250 mL) was added to this crude product and stirred for 10 min. The resulting precipitate was removed and filtrate was concentrated under reduced pressure to afford crude product which was used directly in the next step (mixture of E and Z were obtained with major isomer being E).

Step b) (3-bromophenyl)-2-buten-1-ol

To a stirred solution of ester (5.4 g, 20 mmol) dissolved in hexane (650 mL) at −40 C, DIBALH (45 mL, 1.0M in hexanes) was added drop-wise and stirred until the temperature reached 5 deg C. The reaction mixture was quenched with 10% aqueous solution of Rochelle salt (50 mL) and stirred for additional 2 hrs. The salt was filtered and the organic residue washed with water, dried (MgSO$_4$), and the solvent removed under reduced pressure. The crude product was purified by flash chromatography (30% EtOAc and hexane) to afford 4 g of alcohol which is clear oil.

Step c) (3-bromophenyl)-but-2-enal

To a solution of (E)-3-(3-bromophenyl)-but-2-en-1-ol (1.03 g, 4.54 mmol) in DCM (10 mL) at 0 deg C., was added Dess-Martin periodinane (2.11 g, 5 mmol). The resulting suspension was warmed to 23° C. and stirred for approx. 30 min. until the reaction was complete by TLC. The mixture was poured into 50 mL of saturated aqueous $NaHCO_3$, containing $Na_2S_2O_3$ (1 g). This mixture was stirred vigorously until both layers became clear. The aqueous layer was extracted with DCM (2x) and the combined organic layers were dried over $MgSO_4$, filtered and concentrated under vacuum. The residue was purified by flash chromatography (10% EtOAc/hexanes) to afford the titled compound as a white solid (910 mg, 89% yield) that was a 5:1 ratio of E:Z isomers.

Step d) (S)-3-(3-bromophenyl)-butanal (Procedure for Organocatalytic Reduction of α,β-unsaturated Aldehyde. Ref: MacMillan et. al. JACS 2004, 127(1), 32)

To a solution of (3-bromophenyl)-but-2-enal (225 mg, 1 mmol) dissolved in 5 mL of toluene (0.2 M) was added the trichloroacetic acid salt of (R)-2-tert-butyl-3-methylimidazolidin-4-one (64 mg, 0.2 mmol) and Hantzsch ester (304 mg, 1.2 mmol). The resulting yellow suspension was stirred room temperature until the reaction was determined to be complete by TLC. Upon completion of the reaction, the mixture was a homogeneous solution of light yellow color. The reaction mixture was then diluted with ether and passed through a short pad of silica. The resulting solution was concentrated under vacuum and purified by flash chromatography. The ee of the reaction was not determined but according to the reference, enantiomeric ratio was determined by GLC using Bodman Chiraldex β-DM column at 90 deg C. isotherm. The reported e.e. for unsubstituted phenyl in JACS 2004, 127(1), 32 (Table 1 entry 8) 93% ee after 23 hr. stirring at −30 deg C. or 1 hr. at room temperature.

(R)-3-(3-bromophenyl)-butanal was made using the S-isomer of the catalyst using the similar organic catalytic reduction procedure described above.

Step e) (S)-4-(3-bromophenyl)-1-pentene

To a suspension of methyl triphenylphsophonium iodide (1.58 g, 3.9 mmol) in THF (15 mL) at 0 deg C., nBuLi in hexanes (2.5N, 1.5 mL, 3.87 mmol) was added in small portions over 5 min. The resulting orange mixture was stirred at this temperature for additional 45 minutes and aldehyde (0.8 g, 3.56 mmol) was added in 3.4 mL of THF dropwise. The reaction was then warmed up to room temperature and stirred for 18 hours. The reaction was quenched with sat. $NH_4Cl$, layers were separated and the aqueous layer was saturated $NH_4Cl$ was added and the layers were separated. The aqueous layer was washed with ether (2x) and the combined organic layer was concentrated under reduced pressure to afford product which was purified by flash chromatography (10% EtOAc and Hexanes) to yield clear oil.

(R)-4-(3-bromophenyl)-1-pentene was made using the same condition.

Step f) 2-amino-4-(4-(difluoromethoxy)phenyl)-1-methyl-4-(3-((R)-pent-4-en-2-yl)phenyl)-1H-imidazol-5(4H)-one Using essentially the same procedure described in Example 83, steps f, g and h, and employing (S)-4-(3-bromophenyl)-1-pentene as the starting material, the title product is obtained and identified by NMR and mass spectral analyses.

Example 70

Preparation of 2-amino-4-(3-cyclopropylphenyl)-4-(4-(difluoromethoxy)phenyl)-1-methyl-1H-imidazol-5(4H)-one

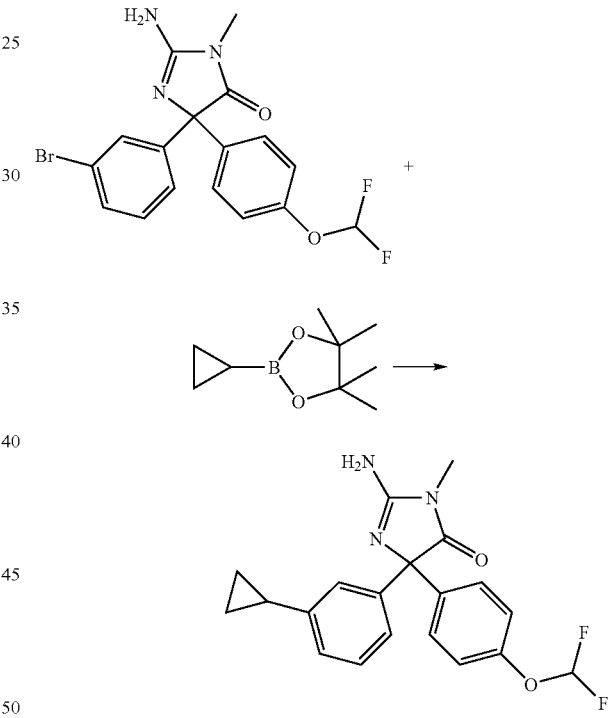

To a microwave vessel containing 2-amino-4-(3-bromophenyl)-4-(4-(difluoromethoxy)phenyl)-1-methyl-1H-imidazol-5(4H)-one (103 mg, 0.25 mmol) and cyclopropylboronic acid pinacol ester (84 mg, 0.5 mmol) in 4 ml of 1:1:3 ratio of EtOH:water:1,2-dimethoxyethane, palladium(0) teterakis and aqueous sodium carbonate (400 µL of 2N solution) were added. The reaction mixture was heated in CEM microwave at 165° C. (40 mW power) for 8 minutes. The reaction mixture was filtered, and partitioned between DCM and water. The water layer was extracted w/DCM and the combined organic layer was dried ($MgSO_4$) and concentrated under reduced pressure to afford crude product which was purified by reverse chromatography ((M+H)$^+$ 372.4).

Example 71

Preparation of (E)-2-amino-4-(4-(difluoromethoxy)phenyl)-4-(3-(4-methoxybut-2-en-2-yl)phenyl)-1-methyl-1H-imidazol-5(4H)-one

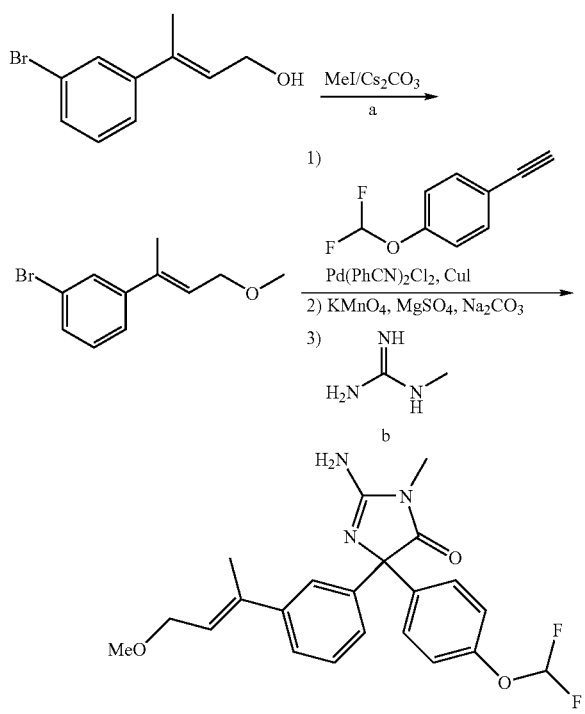

3-(3-bromophenyl)but-2-en-1-ol (described above) was alkylated using the standard condition described (Example 81 and 82) to afford either 1-bromo-3-(4-methoxybut-2-en-2-yl)benzene or (E)-1-bromo-3-(4-ethoxybut-2-en-2-yl)benzene. Then using essentially the same procedure described in Example 83, steps f, g and h, and employing either 1-bromo-3-(4-methoxybut-2-en-2-yl)benzene or (E)-1-bromo-3-(4-ethoxybut-2-en-2-yl)benzene as the starting materials, the title products are obtained and identified by NMR and mass spectral analyses ((M+H)$^+$ 416.4 for Methyl ether and (M+H)$^+$ 430.5 for ethyl ether).

Example 72

Preparation of 2-amino-5-[4-(difluoromethoxy)phenyl]-5-(3-ethylphenyl)-3-methyl-3,5-dihydro-4H-imidazol-4-one

Step 1) ((3-ethylphenyl)ethynyl)trimethylsilane

In a 100 mL round-bottomed flask was 1-bromo-3-ethylbenzene (5 g, 27.0 mmol), ethynyltrimethylsilane (4.58 ml, 32.4 mmol), and triethylamine (18.83 ml, 135 mmol) in DMF (54.0 ml) to give a yellow solution. Bistriphenylphosphine dichloropalladium (0.948 g, 1.351 mmol) and copper(I) iodide (0.515 g, 2.70 mmol) were added at 25° C. The reaction was initial an orange color that gradually darkened to black. The reaction was stirred for 2 h. The reaction was partitioned between ether (400 mL) and 2M HCl (300 mL). The organic layer was washed with 2M HCl (300 mL), water (2×300 mL) and brine (300 mL). The organic was dried over Na$_2$SO$_4$. The crude was purified by flash chromatography (100% hexanes) to give ((3-ethylphenyl)ethynyl)trimethylsilane (3.17 g, 15.66 mmol, 58.0% yield) as a orange oil. $^1$H NMR (400 MHz, DMSO-d$_6$) $\delta$7.15-7.40 (m, 4H), 2.56 (q, J=7.49 Hz, 2H), 1.13 (t, J=7.5 Hz, 3H), 0.19 (s, 9H).

Step 2) 2-amino-5-[4-(difluoromethoxy)phenyl]-5-(3-ethylphenyl)-3-methyl-3,5-dihydro-4H-imidazol-4-one In a 100 mL round-bottomed flask was placed ((3-ethylphenyl)ethynyl)trimethylsilane (3.17 g, 15.66 mmol) and MeOH (31.3 ml) was added to give a yellow solution. Potassium carbonate (21.65 g, 157 mmol) was added and reaction stirred at 25° C. for 1 h. The reaction was partitioned between water (200 mL) and hexanes (200 mL). The organic was washed with water (100 mL) and brine (100 mL). The organic was dried over Na$_2$SO$_4$. The solvent was removed providing 1-ethyl-3-ethynylbenzene (2.24 g, 17.21 mmol, 110% yield) as a dark brown oil that was used as is without further purification.

Using essentially the same procedure as Example 1 steps a-c the racemic 2-amino-5-[4-(difluoromethoxy)phenyl]-5-(3-ethylphenyl)-3-methyl-3,5-dihydro-4H-imidazol-4-one was obtained. MS m/e (M+H)$^+$ 360.0.

Example 73

Preparation of 2-Amino-5-[4-(difluoromethoxy)phenyl]-5-[3-(4-ethoxybut-1-yn-1-yl)phenyl]-3-methyl-3,5-dihydro-4H-imidazol-4-one

Step 1) 3-Bromophenylacetylene

To each of 2 one-liter flasks were charged K$_2$CO$_3$ (68 g, 493 mmol), a large magnetic stirbar and MeOH (250 mL). Stirring was begun on both reaction mixtures and once it was satisfied that they were stirring without any problems, 3-bromophenyltrimethylsilylacetylene (12.5 g, 49.3 mmol, 10.5 mL) was added to each reaction vessel and the mixtures were refluxed overnight. The reaction mixtures were filtered and the filter cakes were washed with MeOH. The combined filtrate was concentrated in vacuo, diluted with hexanes, and washed with water twice. The organic layer was concentrated to give a yellow oil. Flash chromatography (SiO$_2$, Hexanes), provided 9.1 g, 50%, of the title compound as a colorless to light yellow oil. $^1$H NMR 500 MHz (CDCl$_3$) $\delta$ 3.08 (s, 1H); 7.16 (t, 1H, J=7.89 Hz); 7.38 (dt, 1H, J=7.77 Hz, 2.44 Hz); 7.44-7.47 (m, 1H); 7.61 (t, 1H, J=1.68 Hz).

Step 2) 1-Bromo-3-((4-(difluoromethoxy)phenyl)ethynyl)benzene

To a solution of 3-bromophenylacetylene (9.1 g, 50.26 mmol), TEA (22.4 g, 221 mmol, 30.8 mL), bis(triphenylphosphine)dichloropalladium(II) (1.41 g, 2.01 mmol), and CuI (230 mg, 1.2 mmol) in DMF (60 mL) was added 4-iodo(difluoromethoxy)benzene (10.85 g, 40.21 mmol) at room temperature. The reaction mixture had gotten warm after the addition was completed. The mixture was stirred for 4 h then the mixture was portioned between EtOAc and water. The aqueous layer was separated and extracted twice with EtOAc. The combined organic layers were dried over Na$_2$SO$_4$, filtered, and concentrated over 40 g Celite. Flash chromatography (SiO$_2$, Hexanes) gave 12 g, 92%, of the title compound as a yellow oil that had crystallized into a solid after being undisturbed for 3d. $^1$H NMR 500 MHz (DMSO-d$_6$) $\delta$ 7.34 (dt, 2H, J=8.92 Hz, 4.70 Hz); 7.42 (t, 1H, 72.99 Hz); 7.54 (t, 1H, J=7.88 Hz); 7.85-7.88 (m, 1H); 7.94-7.97 (m, 1H); 8.00 (dt, 1H, J=8.93 Hz, 4.87 Hz); 8.04 (t, 1H, J=1.80 Hz).

Step 3) 1-(3-Bromophenyl)-2-(4-(difluoromethoxy)phenyl)ethane-1,2-dione

To a solution of the alkyne from the previous step (10 g, 31 mmol) in dry DMSO (125 mL) was added bis(acetonitrile)dichloropalladium(II) (803 mg, 3.1 mmol) and the mixture was heated at 145° C. overnight. The cooled reaction mixture was poured into water and extracted with EtOAc. The aqueous layer was separated and extracted with EtOAc twice. The combined organic layers were washed with water, dried over Na$_2$SO$_4$, filtered, and concentrated onto 40 g Celite. Flash chromatography (SiO$_2$, 1:9 EtOAc:Hexanes to 25:75 EtOAc:Hexanes) yielded 7.8 g, 70%, of the title compound as an orange-yellow solid. MS (+ESI): 355 m/z ([M+H]$^+$).

Step 4) 1-(4-(Difluoromethoxy)phenyl)-2-(3-(4-hydroxybut-1-ynyl)phenyl)ethane-1,2-dione Dioxane was degassed by bubbling N$_2$ through it for at least 15 minutes. To a mixture of PdCl$_2$(PhCN)$_2$ (575 mg, 1.5 mmol), CuI (571 mg, 3.0 mmol), tributylphosphine (10 wt % solution in hexanes, 197 mg, 0.974 mmol, 197 µL) in degassed dioxane (15 mL) was added diisopropyl amine (1.82 g, 18 mmol, 2.5 mL), the ketone from the previous step (5.32 g, 15 mmol), and 4-butyn-1-ol (1.31 g, 18.75 mmol, 1.42 mL). The mixture was stirred under N$_2$ overnight at room temperature. The mixture was diluted with water and extracted with EtOAc. The aqueous layer was extracted with EtOAc 2 more times. The combined organic layers were dried over Na$_2$SO$_4$, filtered, and concentrated onto 20 g Celite. Flash chromatography (SiO$_2$, 1:9 EtOAc:Hexanes to 1:1 EtOAc:Hexanes) yielded 3.45 g, 66%, of the title compound as an orange-yellow solid. MS (−ESI): m/z 403.2 ([M+CH$_3$COO]$^-$).

Step 5) 1-(4-(difluoromethoxy)phenyl)-2-(3-(4-ethoxybut-1-ynyl)phenyl)ethane-1,2-dione To a solution of the alcohol from the previous step (344 mg, 1.0 mmol) in DCM (5 mL) was added tetrabutylammonium bromide (64 mg, 0.2 mmol) followed by 2.5N NaOH (5 mL). Ethyl iodide (3.9 g, 2.0 mL, 25 mmol) was added and the mixture was vigorously stirred at room temperature for 2 d then worked up as follows. The reaction mixture was diluted with water and DCM and the organic layer was separated. The aqueous layer was extracted once with DCM and the combined organic layers were washed with water, dried over Na$_2$SO$_4$, filtered, and concentrated onto 1.5 g Celite. Flash chromatography (SiO$_2$, 1:9 EtOAc:Hexanes to 1:1 EtOAc:Hexanes) yielded 100 mg, 26%, of the title compound as a yellow oil.
MS (+APPI): m/z 373 ([M+H]$^+$).

Step 6) 2-Amino-5-[4-(difluoromethoxy)phenyl]-5-[3-(4-ethoxybut-1-yn-1-yl)phenyl]-3-methyl-3,5-dihydro-4H-imidazol-4-one To a mixture of the diketone from the previous step (100 mg, 0.268 mmol) and 1-methylguanidine HCl (44 mg, 0.402 mmol) in 200 P EtOH (600 µL) was added Na$_2$CO$_3$ (43 mg, 0.402 mmol). The reaction mixture was heated at 90° C. for 1 h then cooled to room temperature. The mixture was filtered and the solids from the reaction were washed with EtOH. The filtrate was concentrated onto 500 mg Celite. Flash chromatography (SiO$_2$, DCM to 1:9 MeOH:DCM) gave an oil that was dissolved in a minimum amount of DCM. Hexanes was added to the oil and most of the solvent was removed in vacuo without heating until a foam appeared then the rest of the solvent was removed with heating (T of the heating bath about 40° C.). There yielded 29.7 mg, 26%, of the title compound as a beige foam. MS (+ESI): m/z 428 ([M+H]$^+$).

Example 74

Preparation of 2-Amino-5-[4-(difluoromethoxy)phenyl]-3-methyl-5-(3-methylphenyl)-3,5-dihydro-4H-imidazol-4-one Step 1) 1-((4-(Difluoromethoxy)phenyl)ethynyl)-3-methylbenzene To a solution of 3-bromophenylacetylene (2.5 g, 21.5 mmol), TEA (9.57 g, 94.6 mmol, 13.2 mL), bis(triphenylphosphine)dichloropalladium(II) (603 mg, 0.86 mmol), and CuI (98 mg, 0.516 mmol) in DMF (26 mL) was added 4-iodo(difluoromethoxy)benzene (4.64 g, 17.2 mmol) at room temperature. The reaction mixture had gotten warm after the addition was completed. The mixture was stirred for 4 h then the mixture was portioned between EtOAc and water. The aqueous layer was separated and extracted twice with EtOAc. The combined organic layers were dried over Na$_2$SO$_4$, filtered, and concentrated over 20 g Celite. Flash chromatography (SiO$_2$, Hexanes) gave 2.4 g of a dark orange oil (component A) and 1.44 g of a dark red oil (component B). Flash chromatography of Component A (SiO$_2$, Hexanes) and Component B (SiO$_2$, Hexanes) separately yielded 3.2 g, 72%, of the title compound as a light peach oil. MS (+ESI): m/z 345 ([M+H]$^+$).

Step 2) 1-(4-(Difluoromethoxy)phenyl)-2-m-tolylethane-1,2-dione

To a solution of the alkyne from the previous step (3.2 g, 12.4 mmol) in dry DMSO (50 mL) was added bis(acetonitrile)dichloropalladium(II) (322 mg, 1.24 mmol) and the mixture was heated at 145° C. for 4 h. The cooled reaction mixture was poured into water and extracted with EtOAc. The aqueous layer was separated and extracted with EtOAc twice. The combined organic layers were washed with water, dried over Na$_2$SO$_4$, filtered, and concentrated onto 11 g Celite. Flash chromatography (SiO$_2$, 1:9 EtOAc:Hexanes to 25:75 EtOAc:Hexanes) yielded 3.32 g, 92%, of the title compound as an orange-red solid. MS (−ESI): m/z 289 ([M−H]$^-$).

Step 3) 2-Amino-5-[4-(difluoromethoxy)phenyl]-3-methyl-5-(3-methylphenyl)-3,5-dihydro-4H-imidazol-4-one To a mixture of the diketone from the previous step (1.45 g, 5 mmol) and 1-methylguanidine HCl (821 mg, 7.5 mmol) in 200 P EtOH (10 mL) was added Na$_2$CO$_3$ (795 mg, 7.5 mmol). The reaction mixture was heated at 90° C. for 1 h then cooled to room temperature. The reaction mixture was concentrated in vacuo to give a semisolid. This material was dissolved in DCM whereupon a yellow solution resulted and inorganic salts were left at the bottom of the flask. This solution and a DCM rinse portion of the solids left in the flask were combined and flash chromatographed (SiO$_2$, 1:9 MeOH:DCM) to yield 1.04 g, 60%, of the title compound as a beige foam. MS (+ESI): m/z 346 ([M+H]$^+$).

Example 75

Preparation of 2-amino-5-[4-(difluoromethoxy)phenyl]-5-(4-fluoro-3-prop-1-en-1-ylphenyl)-3-methyl-3,5-dihydro-4H-imidazol-4-one (A), 2-amino-5-[4-(difluoromethoxy)phenyl]-5-{4-fluoro-3-[(1Z)-prop-1-en-1-yl]phenyl}-3-methyl-3,5-dihydro-4H-imidazol-4-one (B), & 2-amino-5-[4-(difluoromethoxy)phenyl]-5-{4-fluoro-3-[(1E)-prop-1-en-1-yl]phenyl}-3-methyl-3,5-dihydro-4H-imidazol-4-one (C)

Step a) 2-amino-5-[4-(difluoromethoxy)phenyl]-5-(4-fluoro-3-prop-1-en-1-ylphenyl)-3-methyl-3,5-dihydro-4H-imidazol-4-one A mixture of 1-(3-bromo-4-fluorophenyl)-2-[4-(difluoromethoxy)phenyl]ethane-1,2-dione (1.5 g, 4.0 mmol), diethoxyethane (25 mL), and tributyl(prop-1-en-1-yl)stannane was degassed under argon for 5 minutes and treated with dichlorobis(tri-o-tolylphosphine)palladiumII) (251 mg, 0.018 mmol). The reaction mixture was stirred for 15 hour, poured into water and extracted with ethyl acetate. The extracts were combined, dried over MgSO$_4$ and concentrated in vacuo. Purification of the resultant residue by ICSO (EtOAc/hexane 1/10) gave the title product as a yellow solid (1.2 g); MS m/e (M)$^+$ 334.

Step b) 2-amino-5-[4-(difluoromethoxy)phenyl]-{4-fluoro-3-[(1Z)-prop-1-en-1-yl]phenyl}-3-methyl-3,5-dihydro-4H-imidazol-4-one & -amino-5-[4-(difluoromethoxy)phenyl]-5-{4-fluoro-3-[(1E)-prop-1-en-1-yl]phenyl}-3-methyl-3,5-dihydro-4H-imidazol-4-one Using essentially the same procedure described in Example 84, step b, produced isomeric mixture (Z- and E-isomers in about 1:1 ratio) 2-amino-5-[4-(difluoromethoxy)phenyl]-5-{4-fluoro-3-[(1E)-prop-1-en-1-yl]phenyl}-3-methyl-3,5-dihydro-4H-imidazol-4-one which was separated by HPLC (C18, 5×25 cm) using 72% MeOH in 10 mM NH$_4$OAc to yield the 2-amino-5-[4-(difluoromethoxy)phenyl]-5-{4-fluoro-3-[(1Z)-prop-1-en-1-yl]phenyl}-3-methyl-3,5-dihydro-4H-imidazol-4-one; MS m/e (M+H)$^+$ 390 and 2-amino-5-[4-(difluoromethoxy)phenyl]-5-{4-fluoro-3-[(1E)-prop-1-en-1-yl]phenyl}-3-methyl-3,5-dihydro-4H-imidazol-4-one; MS m/e (M+H)$^+$ 390 isomers as white solids.

Example 76

Preparation of (5S)-2-amino-5-[4-(difluoromethoxy)phenyl]-5-{4-fluoro-3-[(1Z)-prop-1-en-1-yl]phenyl}-3-methyl-3,5-dihydro-4H-imidazol-4-one (A) & (5R)-2-amino-5-[4-(difluoromethoxy)phenyl]-5-{4-fluoro-3-[(1Z)-prop-1-en-1-yl]phenyl}-3-methyl-3,5-dihydro-4H-imidazol-4-one (B)

A racemic mixture of 2-amino-5-[4-(difluoromethoxy)phenyl]-5-{4-fluoro-3-[(1Z)-prop-1-en-1-yl]phenyl}-3-methyl-3,5-dihydro-4H-imidazol-4-one was separated by chiral chromatography technique (Chiralcel OJ, 2×25 cm, using 5% (MeOH/EtOH-8/2) DEA in hexane/DEA as the mobile phase to produce the two enantiomers as white solids; [A] (5S)-2-amino-5-[4-(difluoromethoxy)phenyl]-5-{4-fluoro-3-[(1Z)-prop-1-en-1-yl]phenyl}-3-methyl-3,5-dihydro-4H-imidazol-4-one, MS m/e (M+H)$^+$ 390; $[\alpha]_D^{25}$=14.4 (c=1% in MeOH) and [B] (5R)-2-amino-5-[4-(difluoromethoxy)phenyl]-5-{4-fluoro-3-[(1Z)-prop-1-en-1-yl]phenyl}-3-methyl-3,5-dihydro-4H-imidazol-4-one, MS m/e (M+H)$^+$ 390; $[\alpha]_D^{25}$=−14.8 (c=1% in MeOH).

Example 77

Preparation of (5S)-2-amino-5-[4-(difluoromethoxy)phenyl]-5-{4-fluoro-3-[(1E)-prop-1-en-1-yl]phenyl}-3-methyl-3,5-dihydro-4H-imidazol-4-one (A) & (5R)-2-amino-5-[4-(difluoromethoxy)phenyl]-5-{4-fluoro-3-[(1E)-prop-1-en-1-yl]phenyl}-3-methyl-3,5-dihydro-4H-imidazol-4-one (B)

A racemic mixture of 2-amino-5-[4-(difluoromethoxy)phenyl]-5-{4-fluoro-3-[(1E)-prop-1-en-1-yl]phenyl}-3-methyl-3,5-dihydro-4H-imidazol-4-one was separated by chiral chromatography technique (Chiralcel OJ, 2×25 cm, using 5% (MeOH/EtOH-8/2) DEA in hexane/DEA as the mobile phase to produce the two enantiomers as white solids; [A] (5S)-2-amino-5-[4-(difluoromethoxy)phenyl]-5-{4-fluoro-3-[(1E)-prop-1-en-1-yl]phenyl}-3-methyl-3,5-dihydro-4H-imidazol-4-one, MS m/e (M−H)$^+$ 388; $[\alpha]_D^{25}$=17.4 (c=1% in MeOH) and [B] (5R)-2-amino-5-[4-(difluoromethoxy)phenyl]-5-{4-fluoro-3-[(1E)-prop-1-en-1-yl]phenyl}-3-methyl-3,5-dihydro-4H-imidazol-4-one, MS m/e (M−H)$^+$ 388; $[\alpha]_D^{25}$=−17.8 (c=1% in MeOH)

Example 78

Preparation of 2-amino-5-[3-(2-cyclopropyl-1-fluorovinyl)phenyl]-5-[4-(difluoromethoxy)phenyl]-3-methyl-3,5-dihydro-4H-imidazol-4-one (1:1 Z/E isomers)

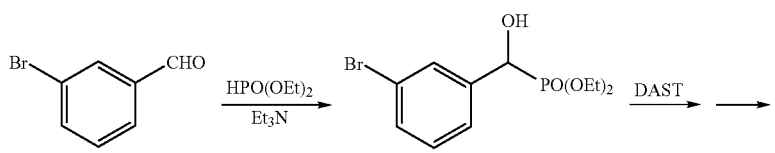

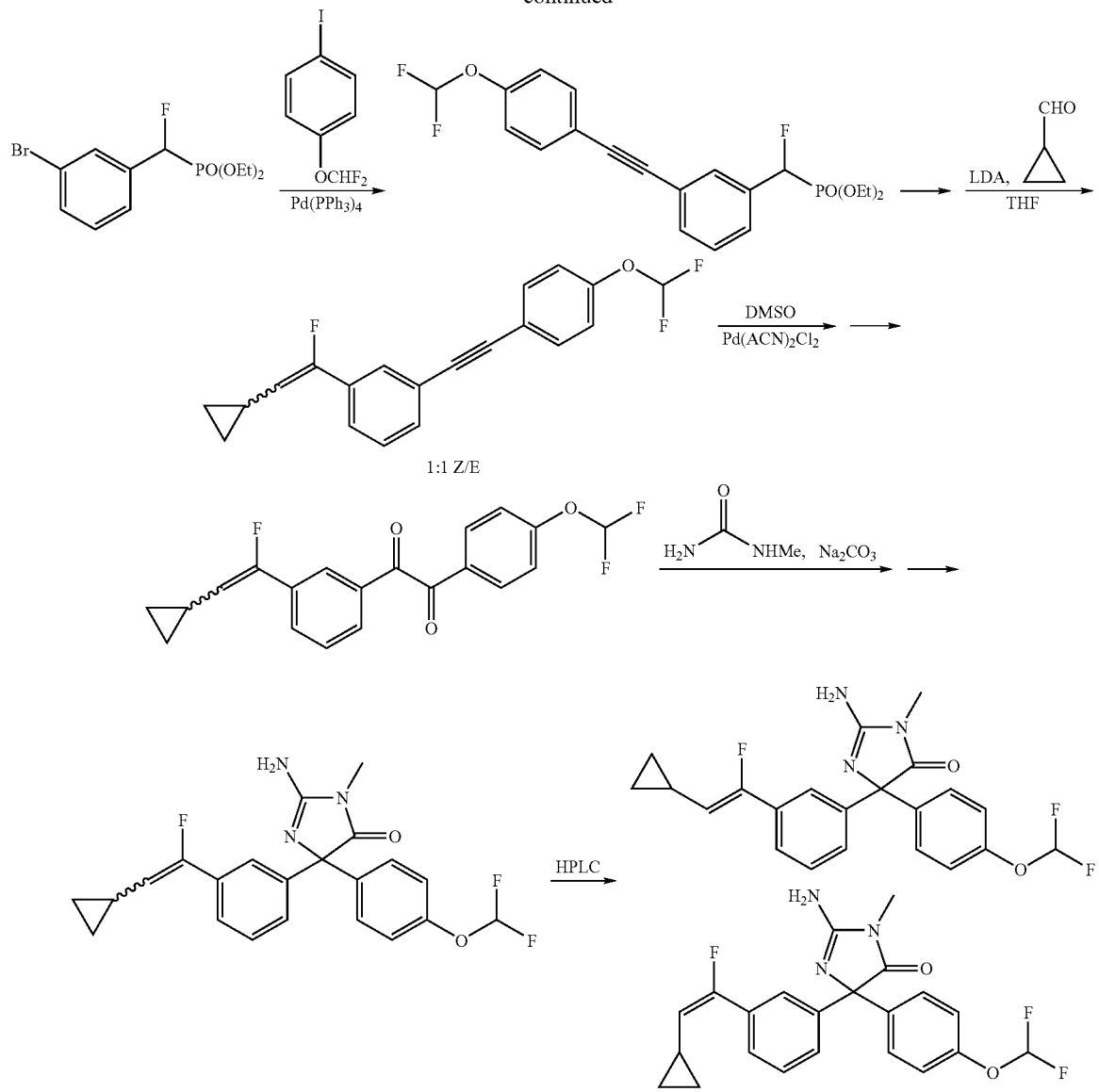

Step a)
diethyl[(3-bromophenyl)(hydroxy)methyl]phosphonite

Into a mixture of 3-bromobenzaldehyde (20 g, 108.1 mmol) and diethyl phosphonate (14.2 g, 108.1 mmol) was added triethylamine (0.44 g, 4.32 mmol) and the mixture was stirred at 40° C. for 72 hours. Purification by ISCO (hexane/EtOAc 1/1) gave diethyl[(3-bromophenyl)(hydroxy)methyl]phosphonite (32.62 g); MS m/e (M)+ 322.

Step b)
diethyl[(3-bromophenyl)(fluoro)methyl]phosphonite

Into cold mixture of diethyl[(3-bromophenyl)(hydroxy)methyl]phosphonite (30 g) and $CH_2Cl_2$ (120 mL) was added diethylaminosulfur trifluoride (16.44 g, 101.53 mmol) and the mixture was stirred for 2 hours. The mixture was then poured into water and washed with $NaHCO_3$ and brine. Purification by ISCO (hexane/EtOAc 1/1) gave diethyl[(3-bromophenyl)(fluoro)methyl]phosphonite (22.6 g); MS m/e (M+H)+ 325.

Step c) diethyl[(3-{[4-(difluoromethoxy)phenyl]ethynyl}phenyl)(fluoro) methyl]phosphonite A mixture of diethyl[(3-bromophenyl)(fluoro)methyl]phosphonite (5.5 g, 17.0 mmol), 2,6-dimethylpiperidine (10 mL), and 1-(difluoromethoxy)-4-ethynylbenzene (3.38 g, 20.4 mmol) was degassed with argon for 5 minutes. Then, tetrakis(triphenylphosphine) palladium (0) (983 mg, 0.85 mmol) was added and the mixture was stirred at 80° C. for 5 hours. The mixture was poured into water and extracted with EtOAc. The organic extracts were dried over $MgSO_4$. Evaporation and purification by ICSO (hexane/EtOAc 1/1) gave diethyl[(3-{[4-(difluoromethoxy)phenyl]ethynyl}phenyl)(fluoro)methyl]phosphonite (3.6 g) as a clear oil; MS m/e (M+H)+ 413.

Step d) 1-(2-cyclopropyl-1-fluorovinyl)-3-{[4-(difluoromethoxy)phenyl]ethynyl}benzene 1:1 Z/E isomers Into a cold solution of diethyl[(3-{[4-(difluoromethoxy)phenyl]ethynyl}phenyl)(fluoro)methyl]phosphonite (2.0 g, 4.08 mmol) and THF (20 mL) was added dropwise LDA (14.64 mL, 1.0M). The mixture was stirred for 30 minutes and then cyclopropanecarbaldehyde (410 mg, 5.8 mmol) was added and the mixture was allowed to come to room temperature and stirred for 24 hours. Then, HCl (5 mL, 2N) was added and the mixture was stirred for 30 minutes, poured into water and extracted with EtOAc. The organic extracts were dried over MgSO$_4$. Evaporation and purification by ICSO (hexane/EtOAc 20/1) gavel-(2-cyclopropyl-1-fluorovinyl)-3-{[4-(difluoromethoxy)phenyl]ethynyl}benzene 1:1 Z/E isomers as a yellow oil (0.72 g); MS m/e (M)$^+$ 328.

Step e) 1-[3-(2-cyclopropyl-1-fluorovinyl)phenyl]-2-[4-(difluoromethoxy)phenyl]ethane-1,2-dione 1:1 Z/E isomers A mixture of 1-(2-cyclopropyl-1-fluorovinyl)-3-{[4-(difluoromethoxy)phenyl]ethynyl}benzene (0.1 g, 0.3 mmol) and DMSO (1 mL) was degassed with argon for 5 minutes. Then, bis(acetonitrile)dichloropalladium (II) (7.8 mg, 0.03 mmol) was added and the mixture was stirred at 145° C. for 8 hours. Then, the mixture was poured into water and extracted with EtOAc. The organic extracts were dried over MgSO$_4$. Evaporation and purification by ICSO (hexane/EtOAc 4/1) gave 1-[3-(2-cyclopropyl-1-fluorovinyl)phenyl]-2-[4-(difluoromethoxy)phenyl]ethane-1,2-dione 1:1 Z/E isomers (78 mg); MS m/e (M)$^+$ 360.

Step f) 2-amino-5-[3-(2-cyclopropyl-1-fluorovinyl)phenyl]-5-[4-(difluoromethoxy)phenyl]-3-methyl-3,5-dihydro-4H-imidazol-4-one 1:1 Z/E isomers A mixture of 1-[3-(2-cyclopropyl-1-fluorovinyl)phenyl]-2-[4-(difluoromethoxy)phenyl]ethane-1,2-dione (400 mg, 1.1 mmol), ethanol (10 mL), 1-methylguanidine hydrochloride (0.18 g, 1.67 mmol), and Na$_2$CO$_3$ (0.18 g, 1.67 mmol) was stirred at 95° C. for 2 hours. Then, the volatiles were removed under vacuum and the residue was taken in water and extracted with EtOAc. The organic extracts were dried over MgSO$_4$. Evaporation and purification on silica gel (ISCO) using hexane/EtOAc (1/1) as the eluting solvent gave 2-amino-5-[3-(2-cyclopropyl-1-fluorovinyl)phenyl]-5-[4-(difluoromethoxy)phenyl]-3-methyl-3,5-dihydro-4H-imidazol-4-one as a white solid 1:1 Z/E isomers (0.32 g). MS m/e (M−H)$^+$ 414.

Example 79

Preparation of 2-amino-5-{3-[(Z)-2-cyclopropyl-1-fluorovinyl]phenyl}-5-[4-(difluoromethoxy)phenyl]-3-methyl-3,5-dihydro-4H-imidazol-4-one (A) & 2-amino-5-{3-[(E)-2-cyclopropyl-1-fluorovinyl]phenyl}-5-[4-(difluoromethoxy)phenyl]-3-methyl-3,5-dihydro-4H-imidazol-4-one (B)

Isomeric mixture (Z- and E-isomers 1:1 ratio) 2-amino-5-[3-(2-cyclopropyl-1-fluorovinyl)phenyl]-5-[4-(difluoromethoxy)phenyl]-3-methyl-3,5-dihydro-4H-imidazol-4-one was separated by HPLC (Primesphere C18, 5×25 cm) using 45% ACN in water/TFA gave 2-amino-5-{3-[(E)-2-cyclopropyl-1-fluorovinyl]phenyl}-5-[4-(difluoromethoxy)phenyl]-3-methyl-3,5-dihydro-4H-imidazol-4-one; MS m/e (M−H)$^+$ 414 and 2-amino-5-{3-[(Z)-2-cyclopropyl-1-fluorovinyl]phenyl}-5-[4-(difluoromethoxy)phenyl]-3-methyl-3,5-dihydro-4H-imidazol-4-one; MS m/e (M−H)$^+$ 414 as white solids.

Example 80

Preparation of 2-Amino-5-{3-[(4,4-difluorobut-3-en-1-yl)oxy]phenyl}-5-[4-(difluoromethoxy)phenyl]-3-methyl-3,5-dihydro-4H-imidazol-4-one

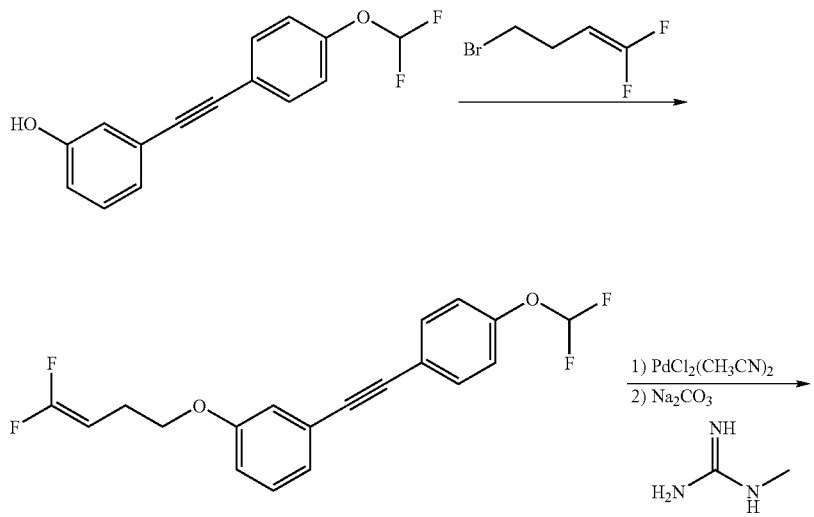

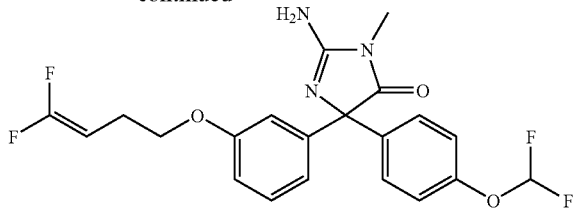

Step a) 1-(4,4-Difluorobut-3-enyloxy)-3-((4-(difluoromethoxy)phenyl)ethynyl)-benzene A mixture of 3-((4-(difluoromethoxy)phenyl)ethynyl)phenol (900 mg), potassium carbonate (636 mg), Aliquat 336 (4 drops), sodium iodide (catalytic) and 4-bromo-1,1-difluoro-1-butene (591 μL) in methyl ethyl ketone was placed in a pressure vessel, heated at 80° C. for 15 h, cooled to room temperature, diluted with dichloromethane and filtered. The filtrate was concentrated in vacuo. The resultant residue was purified by flash chromatography (silica gel, eluant: 2.5% ethyl acetate/hexane to afford 1-(4,4-difluorobut-3-enyloxy)-3-((4-(difluoromethoxy)phenyl)-ethynyl)benzene, 560 mg (46.2% yield); $^1$H NMR (chloroform-d1): δ 7.51 (d, J=8.8 Hz, 2H), 7.24 (m, 1H), 7.10 (m, 1H), 7.08 (d, J=8.8 Hz, 2H), 7.03 (m, 1H), 6.87 (m, 1H), 6.52 (t, J=73.5 Hz, 1H), 4.32 (m, 1H), 3.97 (t, J=6.4 Hz, 2H) and 2.47 (m, J=6.4 Hz, 2H); MS (ES pos) m/z 350.

Step b) 2-Amino-5-{3-[(4,4-difluorobut-3-en-1-yl)oxy]phenyl}-5-[4-(difluoro-methoxy)phenyl]-3-methyl-3,5-dihydro-4H-imidazol-4-one Using essentially the same procedure described in Example 1, steps b and c, and employing 1-(4,4-difluorobut-3-enyloxy)-3-((4-(difluoromethoxy)phenyl)ethynyl)-benzene as starting material, the title compound was obtained as a white solid, mp 127-128° C., identified by NMR and mass spectral analyses. MS (ES) m/z 436.1.

Example 81

Preparation of 2-Amino-5-[4-(difluoromethoxy)phenyl]-5-(3hydroxyphenyl)-3-methyl-3,5-dihydro-4H-imidazol-4-one

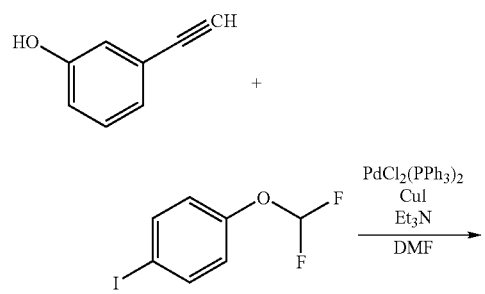

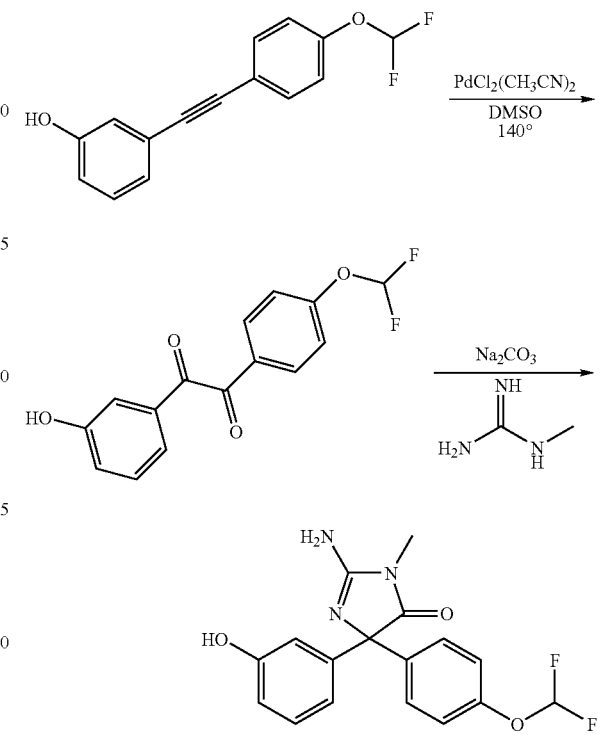

Step a) 3-((4-(Difluoromethoxy)phenyl)ethynyl)phenol

A solution of 4-(difluoromethoxy)phenyl iodide (4.70 g) in deoxygenated dimethylformamide was treated with trans-dichlorobis(triphenylphosphine) palladium(II) (244 mg) and copper(II) iodide 66 mg) followed by triethylamine (7.52 mL), stirred under a nitrogen atmosphere for 5 min., treated with 3-hydroxyphenyl acetylene (2.467 g), stirred under nitrogen atmosphere for 16 h, poured into ethyl acetate and was washed with 0.05 N HCl and water. The organic phase was dried over MgSO$_4$ and concentrated in vacuo. The residue was chromatographed, silica gel, 40% ethyl acetate/hexane as eluent, to afford 3-((4-(difluoromethoxy)phenyl)ethynyl)phenol as a tan solid, 5.40 g; $^1$H NMR (DMSO-d6): δ 9.64 (s, 1H), 7.56 (d, J=8.8 Hz, 2H), 7.27 (t, J=73.7 Hz, 1H), 7.17 (d, J=8.8 Hz, 2H), 7.16 (m, 1H), 6.94 (m, 1H), 6.86 (m, 1H), and 6.77 (m, 1H); MS (ES neg) m/z 260.

Step b) 1-(4-(Difluoromethoxy)phenyl)-2-(3-hydroxyphenyl)ethane-1,2-dione

A mixture of 3-((4-(difluoromethoxy)phenyl)ethynyl)phenol (5.0 g) and dichlorobis(acetonitrile)palladium (II) (0.50 g) and dimethylsulfoxide was heated at 140° C. for 4 h, cooled to room temperature, poured into water, stirred well for 10 min. and extracted with chloroform. The combined extracts were dried over MgSO$_4$ and evaporated to a dark oil. The oil was purified by flash chromatography (silica gel) using step gradient elution (10% ethyl acetate/hexane to 20% ethyl acetate/hexane to give 1-(4-(difluoromethoxy)phenyl)-2-(3-hydroxyphenyl)ethane-1,2-dione as a light yellow waxy solid, 2.75 g; $^1$H NMR (DMSO-d$_6$): δ 10.02 (s, 1H), 7.95 (d, J=8.9 Hz, 2H), 7.41 (t, J=73.0 Hz, 1H), 7.38 (m, 1H), 7.34 (d, J=8.9 Hz, 2H), 7.25 (m, 2H), and 7.12 (m, 1H); MS (ES neg) m/z 292.

Step c) 2-Amino-5-[4-(difluoromethoxy)phenyl]-5-(3-hydroxyphenyl)-3-methyl-3,5-dihydro-4H imidazol-4-one A mixture of 1-(4-(difluoromethoxy)phenyl)-2-(3-hydroxyphenyl)ethane-1,2-dione (2.75 g), N-methylguanidine hydrochloride (1.237 g) and sodium carbonate (2.20 g) in ethanol was heated at 85° C. for 8 h, cooled to room temperature and evaporated in vacuo. The resultant residue was partitioned between water and chloroform. The organic phase was separated, dried over Na$_2$SO$_4$ and evaporated to a light brown oil. The oil was purified by flash chromatography (silica gel) using step gradient elution (100% chloroform to 15% methanol/chloroform) to afford the title compound as a white foamy glass, 2.20 g; $^1$H NMR (DMSO-d6): δ 9.24 (bs, 1H), 7.42 (d, J=8.8 Hz, 2H), 7.12 (t, J=74.3 Hz, 1H), 7.06 (d, J=8.8 Hz, 2H), 7.02 (m, 1H), 6.80 (m, 2H), 6.57 (bs, 2H), and 6.56 (m, 1H); MS (APPI) m/z 348.

Example 82

Preparation of 2-Amino-5-[4-(difluoromethoxy)phenyl]-5-[3-(3-fluoropropox-1-yl)phenyl]-3-methyl-3,5-dihydro-4H-imidazol-4-one

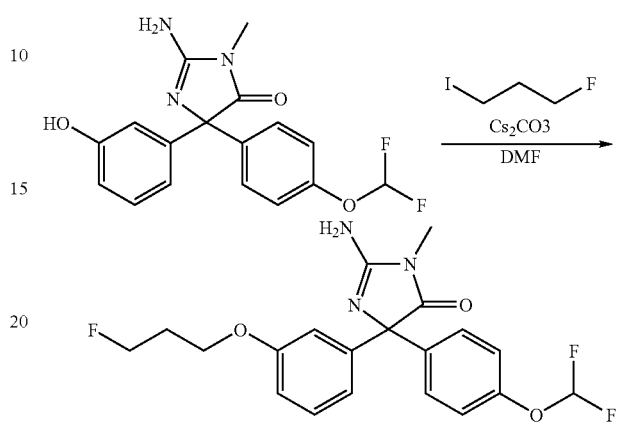

A mixture of 2-amino-5-[4-(difluoromethoxy)phenyl]-5-(3-hydroxyphenyl)-3-methyl-3,5-dihydro-4H-imidazol-4-one (197 mg), 1-iodo-3-fluoropropane (127 mg), and cesium carbonate (240 mg) in dry DMF was stirred at room temperature under nitrogen atmosphere for 16 h, diluted with chloroform, stirred for 5 min. and filtered through a glass fibre 3.1 μm syringe filter. The filtrate was evaporated, The resultant residue was purified by HPLC; CN bonded phase prep column, gradient elution (80% A/20% B to 20% A/80% B, A=hexane; B=(20% methanol/80% dichloromethane) to afford a clear oil. The oil was crystallized from warm ethyl acetate/hexane to give the title compound as white crystals, mp 161-162° C.; identified by NMR and mass spectral analyses. MS (APPI) m/z 408.

Example 83

Preparation of 5-(3-{2-Amino-4-[4-(difluoromethoxy)phenyl]-1-methyl-5-oxo-4,5-dihydro-1H-imidazol-4-yl}phenyl)pentanenitrile

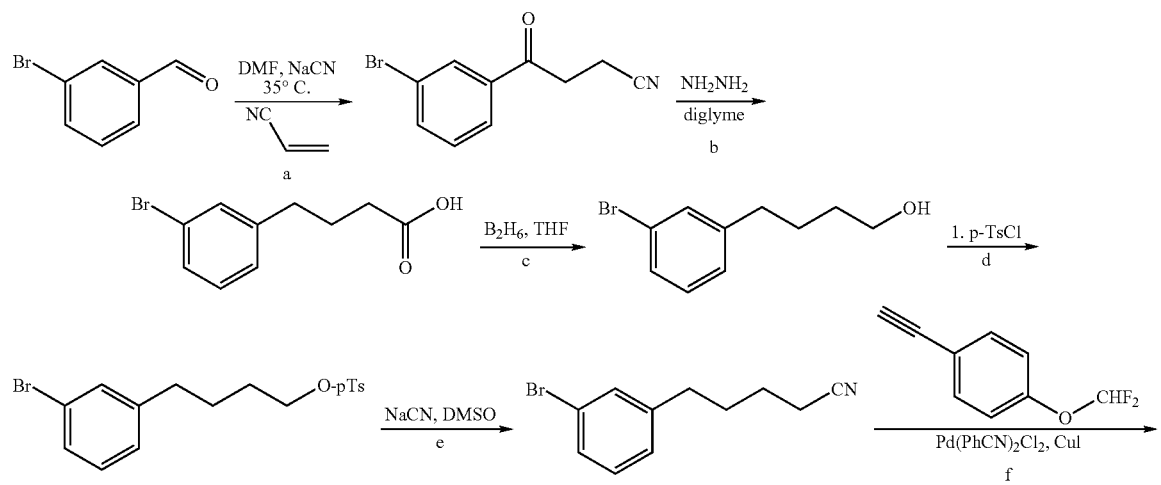

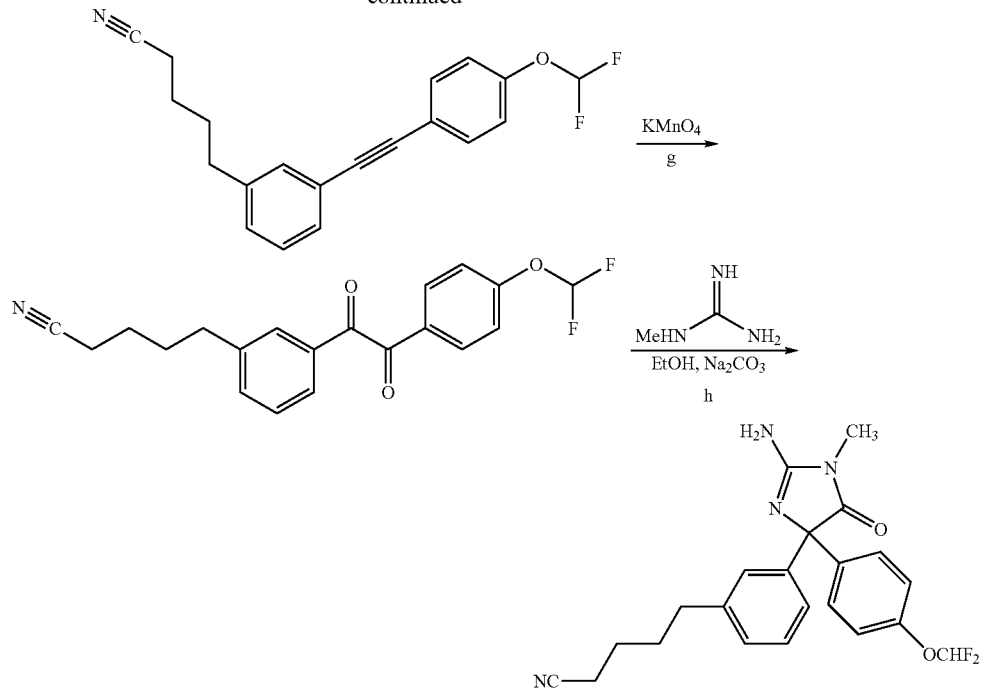

Step a) 4-(3-Bromophenyl)-4-oxo-butyronitrile

A mixture of powder sodium cyanide (1.23 g, 25 mmol) in DMF was treated slowly with a solution of 3-bromo-benzaldehyde in DMF, stirred at 35° C. for 3 hours, cooled to room temperature, poured into a cold 0.5 N HCl solution and extracted with ethyl ether. The extracts were combined, washed with saturated aqueous sodium bicarbonate, brine, dried over MgSO$_4$ and concentrated in vacuo. The resultant residue was triturated in ethyl ether and filtered. The filtercake was dried to give 4-(3-bromophenyl)-4-oxo-butyronitrile as a yellow solid (4 g, 58% yield)... m/e (M)$^+$ 237. $^1$H NMR (400 MHz, DMSO-d$_6$) δ ppm, 2.7 (t, J=6.7 Hz, 2H), 3.5 (t, J=6.7 Hz, 2H), 7.5 (t, J=7.8 Hz, 1H), 7.9 (ddd, J=7.9, 2.1, 0.9 Hz, 1H), 8.0 (ddd, J=7.8, 1.7, 0.9 Hz, 1H), 8.1 (t, J=1.7 Hz, 1H).

Step b) 4-(3-Bromophenyl)butyric acid

The title compound was prepared in substantially the same manner as described in (example 1 step c) and was obtained as light brown oil (2.85 g, 93% yield). m/e (M−H)$^−$ 241. $^1$H NMR (400 MHz, DMSO-d$_6$) δ ppm, 1.7-1.8 (m, 2H), 2.2 (t, J=7.4 Hz, 2H), 2.6 (t, J=7.9 Hz, 2H), 7.2-7.2 (m, 1H), 7.3 (t, J=7.5 Hz, 1H), 7.4-7.4 (m, 1H), 7.4-7.4, (m, 1H), 12.1 (s, 1H).

Step c) 4-(3-Bromophenyl)butan-1-ol

A cold (0° C.) solution of 4-(3-bromophenyl)butyric acid (2.85 g, 11.7 mmol) in THF was treated slowly with a solution of B$_2$H$_6$-THF (35 mL), stirred at room temperature for 18 hours, poured into ice/water, basified with 2.5 N NaOH to pH=11 and extracted with CH$_2$Cl$_2$. The extracts were combined, washed with brine, dried over MgSO$_4$ and concentrated in vacuo. Purification of the resultant residue by column chromatography using hexanes/CH$_2$Cl$_2$/MeOH (4/4.5/0.5) as the eluting solvent afforded 4-(3-bromophenyl)butan-1-ol as a colorless oil (1.9 g, 70% yield.

m/e (M)$^+$ 228; $^1$H NMR (400 MHz, DMSO-d$_6$) δ ppm, 1.3-1.4 (m, 2H) 1.5-1.6 (m, 2H), 2.55-2.59 (m, 2H), 3.3-3.38 (m, 2H), 4.3 (t, J=7.5, 1H), 7.2-7.2 (m, 1H), 7.3 (t, J=7.5 Hz, 1H), 7.4-7.4 (m, 1H), 7.4-7.4 (m, 1H).

Step d) Toluene-4-sulfonic acid 4-(3-bromo-phenyl)butyl ester

A cold (0° C.) solution of 4-(3-bromophenyl)butan-1-ol (1.08 g, 4.7 mmol) and p-toluenesulfonyl chloride (1.2 g, 6.3 mmol) in THF was treated slowly with triethyl amine (1.8 mL, 12.3 mmol), stirred at room temperature for 4 hours, poured into cold saturated aqueous NH$_4$Cl and extracted with ether. The organic extracts were combined, washed with brine, dried over MgSO$_4$ and concentrated in vacuo. Purification of the resultant residue on silica gel (ISCO) using (hexanes/EtOAC 9.5/0.5) as the eluting solvent afforded toluene-4-sulfonic acid 4-(3-bromophenyl)-butyl ester as a colorless oil (2.4 g, 76% yield). m/e (M+NH$_4$)$^+$ 400.1 $^1$H NMR (400 MHz, DMSO-d$_6$) δ ppm, 1.4-1.6 (m, 4H), 2.4 (s, 3H), 2.4-2.5 (m, 2H), 4.0 (t, J=6.0 Hz, 2H), 7.2 (t, J=7.8 Hz, 1H), 7.3-7.3 (m, 1H), 7.3-7.3 (m, J=8.0, 1.0 Hz, 1H), 7.4-7.5 (m, J=8.6 Hz, 2H), 7.7-7.8 (m, 2H).

Step e) 5-(3-Bromophenyl)pentanenitrile

A mixture of toluene-4-sulfonic acid 4-(3-bromophenyl) butyl ester (2.3 g, 6 mmol) and powdered sodium cyanide (0.65 g, 13 mmol) in DMSO was heated up to 80° C., stirred for 1.5 hours and monitored by NMR. When the reaction was complete, the reaction mixture was cooled to room temperature, diluted with H$_2$O and extracted with CH$_2$Cl$_2$. The combined organic extracts were washed with brine, dried over MgSO$_4$ and concentrated in vacuo. Purification of this residue on silica gel (ISCO) using (hexanes/EtOAC 9.5/0.5) as the eluting solvent gave 5-(3-bromo-phenyl)pentanenitrile as a colorless oil (1.12 g, 78% yield). m/e (M)$^+$ 237; $^1$H NMR (400

MHz, DMSO-d$_6$) δ ppm, 2.63-2.65 (m, 2H), 2.75-2.78 (m, 2H), 2.35-2.38 (m, 2H), 2.60-2.63 (m, 2H), 7.05-7.10 (m, 2H), 7.25-7.28 (m, 2H).

Step f) 5-[3-(4-Difluoromethoxyphenylethynyl)phenyl]pentanenitrile

Using essentially the same procedure described in Example 1, Step a, 5-[3-(4-difluoromethoxyphenylethynyl)phenyl]pentanenitrile was obtained as a light brown oil (0.54 g, 88% yield). m/e (M+H)$^+$ 326. $^1$H NMR (400 MHz, DMSO-d$_6$) δ ppm, 1.5-1.6 (m, 2H), 1.6-1.7 (m, 2H), 2.5 (t, J=7.0 Hz, 2H), 2.6 (t, J=7.5 Hz, 2H), 7.3 (dd, J=73.7 Hz, 1H), 7.2-7.3 (m, 2H), 7.3 (t, J=7.4 Hz, 1H), 7.4-7.4 (m, 1H), 7.4-7.4 (m, 1H).

Step g) 5-{3-[2-(4-Difluoromethoxyphenyl)-2-oxo-acetyl]phenyl}pentanenitrile Using essentially the same procedure described in Example 85, Step e, 5-{3-[2-(4-difluoromethoxyphenyl)-2-oxo-acetyl]phenyl}pentanenitrile was obtained as a light yellow oil (0.46 g, 77% yield). m/e (M+H)$^+$ 358; $^1$H NMR (400 MHz, CDCl$_3$) δ 1.20 ppm, 1.6-1.8 (m, 2H), 1.7-2.0 (m, 2H), 2.3-2.5 (m, J=7.0, 7.0 Hz, 2H), 2.6-2.9 (m, J=7.5, 7.5 Hz, 2H), 6.6 (t, J=72.7 Hz, 1H), 7.2-7.4 (m, 2H) 7.4-7.6, (m, 2H) 7.6-7.9, (m, 2H), 7.9-8.2 (m, 2H).

Step h) 5-(3-[2-Amino-4-[4-(difluoromethoxy)phenyl]-1-methyl-5-oxo-4,5-dihydro-1H-imidazol-4-yl]phenyl)pentanenitrile Using essentially the same procedure described in Example 1, Step c, the title product was obtained as a white solid, 0.23 g (43% yield), mp 65° C.; m/e (M+H)$^+$ 413 $^1$H NMR (400 MHz, DMSO-d$_6$) δ ppm, 1.4-1.6 (m, 4H), 2.4-2.5 (m, 2H), 2.5 (t, J=7.2 Hz, 2H), 2.9 (s, 3H), 6.6 (bs., 2H), 7.1 (t, J=74.2 Hz, 1H), 7.0-7.1 (m, 3H), 7.2 (t, J=7.8 Hz, 1H), 7.2-7.2, (m, 2H), 7.4-7.5 (m, 2H).

Example 84

Preparation of 2-amino-5-[3-(cyclopropylethynyl)-4-fluorophenyl]-5-[4-(difluoromethoxy)phenyl]-3-methyl-3,5-dihydro-4H-imidazol-4-one

Step a) 1-[3-(cyclopropylethynyl)-4-fluorophenyl]-2-[4-(difluoromethoxy)phenyl]ethane-1,2-dione A mixture of 1-(3-bromo-4-fluorophenyl)-2-[4-(difluoromethoxy)phenyl]ethane-1,2-dione (2.1 g, 5.63 mmol), 2,6-dimethylpiperidine (10 mL), and ethynylcyclopropane (0.74 g, 11.27 mmol) was degassed with argon for 5 minutes. Then, tetrakis(triphenylphosphine) palladium (0) (327 mg, 0.28 mmol) was added and the mixture was stirred at 80° C. for 5 hours. The mixture was poured into water and extracted with EtOAc. The organic extracts were dried over MgSO$_4$. Evaporation and purification by ICSO (hexane/EtOAc 5/1) gave 1-[3-(cyclopropylethynyl)-4-fluorophenyl]-2-[4-(difluoromethoxy)phenyl]ethane-1,2-dione as a yellow oil solid (1.37 g); MS m/e (M)$^+$ 358.

Step b) 2-Amino-5-[3-(cyclopropylethynyl)-4-fluorophenyl]-5-[4-(difluoromethoxy)phenyl]-3-methyl-3,5-dihydro-4H-imidazol-4-one A mixture of 1-[3-(cyclopropylethynyl)-4-fluorophenyl]-2-[4-(difluoromethoxy)phenyl]ethane-1,2-dione (1.35 g, 3.97 mmol), ethanol (30 mL), 1-methylguanidine hydrochloride (0.65 g, 5.96 mmol), and Na$_2$CO$_3$ (0.63 g, 5.96 mmol) was stirred at 95° C. for 2 hours. Then, the volatiles were removed under vacuum and the residue was taken in water and extracted with EtOAc. The organic extracts were dried over MgSO$_4$. Evaporation and purification on silica gel (ISCO) using MeOH/EtOAc (1/20) as the eluting solvent gave 2-amino-5-[3-(cyclopropylethynyl)-4-fluorophenyl]-5-[4-(difluoromethoxy)phenyl]-3-methyl-3,5-dihydro-4H-imidazol-4-one as a white solid (0.29 g). MS m/e (M+H)$^+$ 414.

Example 85

Preparation of 2-Amino-5-[4-(difluoromethoxy)phenyl]-3-methyl-5-[3-(4,4,4-trifluorobutyl)phenyl]-3,5-dihydro-4H-imidazol-4-one

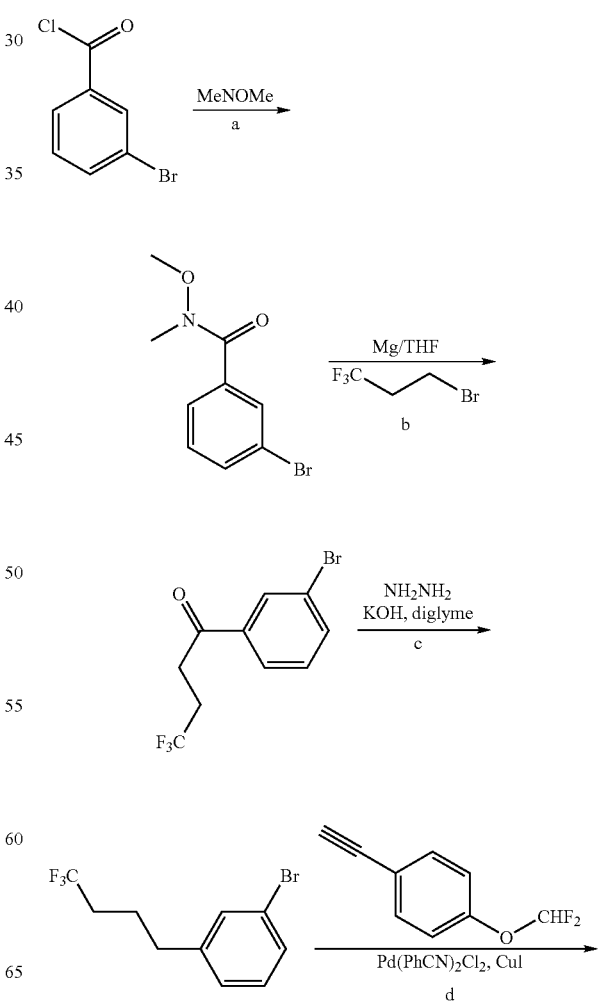

-continued

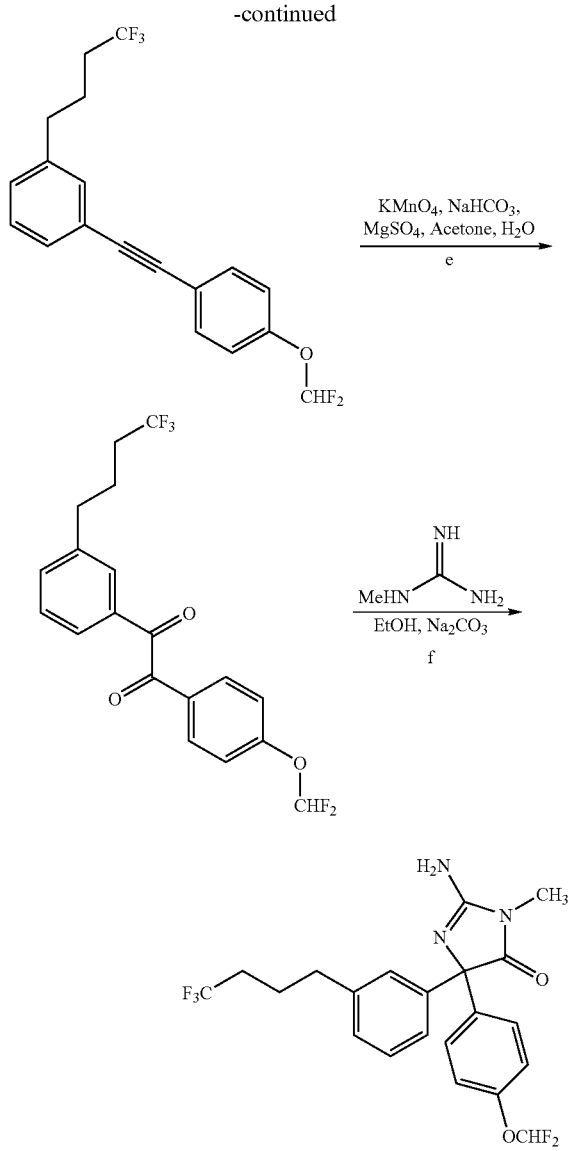

Step a) 3-Bromo-N-methoxy-N-methylbenzamide

A solution of 3-bromobenzoyl chloride (20 g, 91.1 mmol) in $CH_2Cl_2$ was added dropwise to a cold (0° C.) solution of N,O-dimethylhydroxylamine hydrochloride (33.6 g, 319 mmol), diisopropylamine (98 mL, 551 mmol) in $CH_2Cl_2$ over 1 hour. The stirring continued at room temperature for 30 minutes then concentrated under vacuo. The resultant residue was dispersed in water and extracted with ethyl ether. The organic extracts were combined, dried over $MgSO_4$ and concentrated in vacuo. This residue was purified on silica gel (ISCO) using hexanes/EtOAc (4/1) as the eluting solvent to give 3-bromo-N-methoxy-N-methylbenzamide as light yellow solid (20 g, 89% yield). m/e (M+H)$^+$ 244. $^1$H NMR (400 MHz, DMSO-d$_6$) δ ppm, 3.21 (s, 3H), 3.50 (s, 3H), 7.37-7.39, (m, 1H), 7.53-7.55 (m, 1H), 7.64-7.66 (m, 1H), 7.67-7.69 (m, 1H).

Step b) 1-(3-Bromo-phenyl)-4,4,4-trifluoro-butan-1-one

A prepared solution of trifluoromethyl ethane-magnesium bromide (made by refluxing Mg with 1-bromo, 2-trifluoromethyl ethane in THF for 2 hours; 4.6 g=25.82 mmol) in THF was added slowly to a cold (0° C.) solution of 3-bromo-N-methoxy-N-methylbenzamide (3.5 g, 14.3 mmol) in THF. The stirring continued at room temperature for 1 hour, quenched with cold saturated aqueous $NH_4Cl$, acidified with 1 N HCl and extracted with ethyl ether. The organic extracts were combined, dried over $MgSO_4$ and concentrated in vacuo. The crude product was purified on silica gel (ISCO) using hexanes/EtOAc (10/1) as the eluting solvent to give 1-(3-Bromo-phenyl)-4,4,4-trifluoro-butan-1-one as a colorless oil (3.1 g, 77% yield). m/e (M−H)-279, 1H NMR (400 MHz, DMSO-d$_6$) δ ppm, 2.5-2.6 (m, 2H), 3.3-3.4 (m, 2H), 7.5 (t, J=7.9 Hz, 1H), 7.8-7.8 (m, 1H), 7.9-8.0 (m, 1H), 8.1 (t, J=1.7 Hz, 1H).

Step c) 1-Bromo-3-(4,4,4-trifluoro-butyl)-benzene

A mixture of 1-(3-bromo-phenyl)-4,4,4-trifluoro-butan-1-one (3.1 g, 11 mmol) and diglyme was treated with hydrazine mono hydrate (5.5 g, 110.3 mmol), and stirred at 100° C. for 2 hours then treated with powder KOH (3.1 g, 55.1 mmol). The stirring continued at 150° C. for 6 hours. The mixture was cooled to room temperature, poured into a mixture of ice/water and extracted with ethyl ether. The extracts were combined, dried over $MgSO_4$ and concentrated in vacuo. The crude product was purified on silica gel (ISCO) using hexanes as the eluting solvent to give 1-Bromo-3-(4,4,4-trifluoro-butyl)-benzene as a colorless oil (2.4 g, 88% yield). m/e (M)$^+$ 266; $^1$H NMR (400 MHz, DMSO-d$_6$) δ ppm, 1.7-1.8 (m, 2H), 2.1-2.2 (m, 2H), 2.6 (t, J=7.6 Hz, 2H), 7.2-7.25 (m, 2H), 7.3-7.35 (m, 1H), 7.4 (s, 1H)

Step d) 1-Difluoromethoxy-4-[3-(4,4,4-trifluorobutyl)phenylethynyl]benzene

Using essentially the same procedure described in Example 1, Step a, 1-difluoromethoxy-4-[3-(4,4,4-trifluorobutyl)phenylethynyl]benzene was obtained as a colorless oil (0.19 g, 30% yield). m/e (M)$^+$ 354; $^1$H NMR (400 MHz, DMSO-d$_6$) δ ppm, 1.74-1.78 (m, 2H), 2.17-2.21 (m, 2H), 2.62-266 (t, J=7.65 Hz, 2H), 7.17-7.20 (d, J=8.8 Hz, 2H), 7.23-7.39 (m, 5H), 7.56-7.58 (d, J=8.8 Hz, 2H).

Step e) 1-(4-Difluoromethoxyphenyl)-2-[3-(4,4,4-trifluorobutyl)phenyl]ethane-1,2-dione A solution of 1-difluoromethoxy-4-[3-(4,4,4-trifluorobutyl)phenylethynyl]-benzene (7.62 mmol) in acetone is treated with $MgSO_4$ (1.83 g, 15.25 mmol) followed by an aqueous solution of $NaHCO_3$ (0.38 g, 4.57 mmol) in $H_2O$ and $KMnO_4$ (2.41 g, 15.24 mmol). The suspension is stirred for 20 hours, diluted with $H_2O$ and ether and filtered through a pad of solka floc. The filtrate is extracted with ether. The extracts are washed with brine, dried over $MgSO_4$ and concentrated in vacuo to give 1-(4-difluoromethoxyphenyl)-2-[3-(4,4,4-trifluorobutyl)phenyl]ethane-1,2-dione as a yellow oil. m/e (M−H)$^-$385; $^1$H NMR (400 MHz, CDCl$_3$) δ ppm, 1.8-1.9 (m, 2H), 2.0-2.1 (m, 2H), 2.7 (t, J=7.8 Hz, 2H), 6.6 (t, J=72.6 Hz, 1H), 7.2-7.2 (m, 2H), 7.4-7.5 (m, 2H), 7.7-7.8 (m, 2H), 8.0-8.0 (m, 2H),

Step f) 2-Amino-5-[4-(difluoromethoxy)phenyl]-3-methyl-5-[3-(4,4,4-trifluorobutyl)phenyl]-3,5-dihydro-4H-imidazol-4-one Using essentially the same procedure described in Example 1, Step c, the title product was obtained as a white solid, 0.11 g (55% yield), mp 70° C.; m/e (M−H)⁻ 440.1; $^1$H NMR (400 MHz, DMSO-$d_6$) δ ppm, 1.64-1.68 (dd, J=7.9 Hz, 2H), 2.16-219 (m, 2H), 2.54-2.58 (t, J=7.76 Hz, 2H), 2.93 (s, 3H), 6.61 (bs, 2H), 6.93+7.3 (s, 1H), 7.04-7.06 (d, J=8.81 Hz, 2H), 7.18-7.19 (t, J=7.6 Hz, 1H), 7.23 (m, 3H), 7.40-7.42 (d, J=8.81 Hz, 2H).

Example 86

Preparation of: 2-amino-4-(4-(difluoromethoxy)phenyl)-4-(4-fluoro-3-morpholinophenyl)-1-methyl-1H-imidazol-5(4H)-one

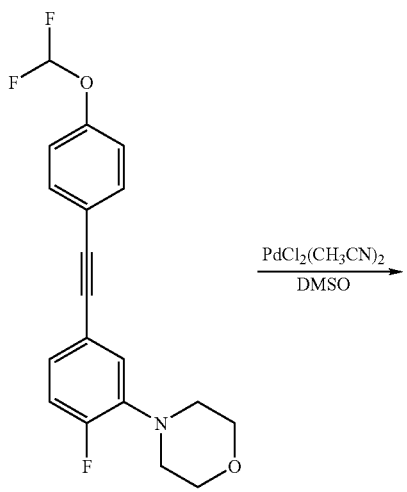

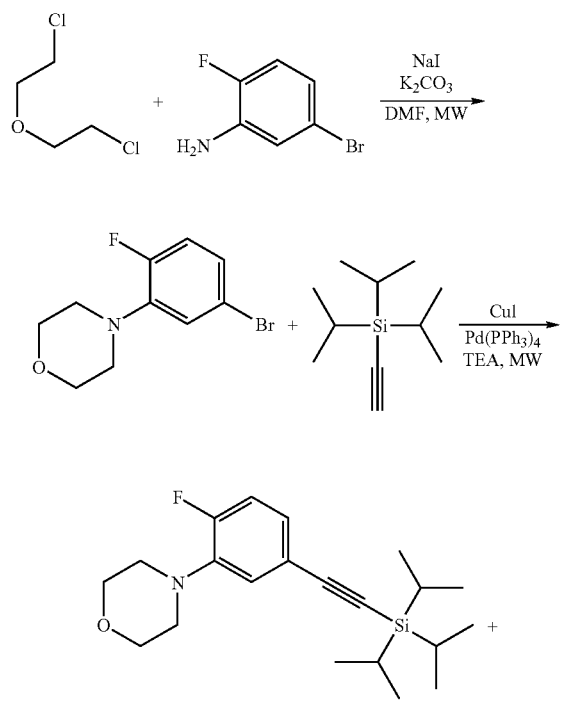

Step 1: Synthesis of 4-(5-bromo-2-fluorophenyl)morpholine

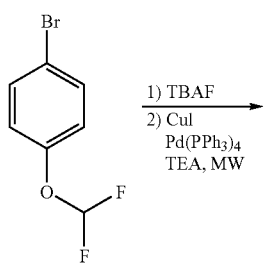

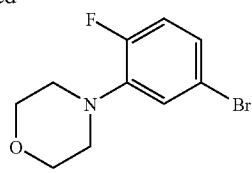

To a CEM snap top microwave vial (10 ml) equipped with a magnetic stir bar (3×10 mm) was added 5-Bromo-2-fluoroaniline (1.00 g, 5.26 mmol), sodium iodide (2.37 gm, 15.8 mmol), potassium carbonate (1.45 gm, 10.5 mmol), and 2-chloroethyl ether (1.30 gm, 9.09 mmol) in dimethylformamide (6.5 mL). The reaction was capped and irradiated in a CEM Explorer microwave at 120° C. for 4 hours then forced air-cooled. Purification by column chromatography [default gradient (ISCO); EtOAc/hexanes] afforded 397 mg (29%) an oil; $^1$H NMR (400 MHz, DMSO-$d_6$) δ ppm 3.00 (t, J=1.7 Hz, 4H) 3.69-3.73 (m, 4H) 7.10-7.15 (m, 3H); MS (EI) m/z 259.0 [M+].

Step 2: Synthesis of 4-(2-fluoro-5-((triisopropylsilyl)ethynyl)phenyl)morpholine

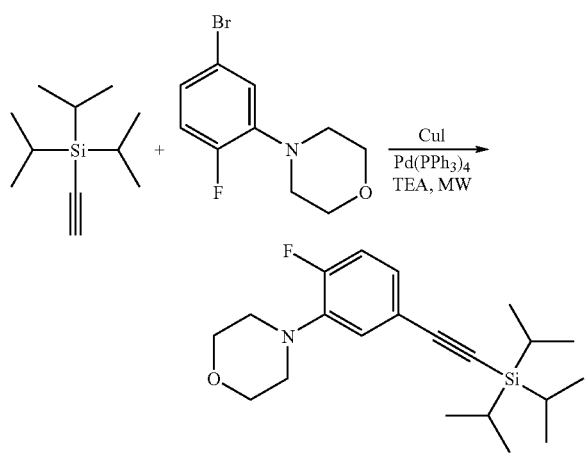

To a CEM snap top microwave vial (10 ml) equipped with a magnetic stir bar (3×10 mm) was added 4-(5-bromo-2-fluorophenyl)morpholine (390 mg, 1.50 mmol) in triethylamine (1.5 mL). Copper iodide (12 mg, 0.060 mmol), Tetrakis(triphenylphosphine) palladium (35 mg, 0.030 mmol) and triisopropylsilyl-acetylene (0.390 mg, 2.14 mmol) were added at room temperature. The reaction was capped and irradiated in a CEM Explorer microwave at 80° C. for 30 minutes then forced air-cooled. The crude material was loaded onto silica gel and chased with dichloromethane. Purification by chromatography (hexanes) afforded 540 mg of an oil (quant); $^1$H NMR (400 MHz, DMSO-$d_6$) δ ppm 1.06-1.10 (m, 21H) 3.00 (t, J=4.6 Hz, 4H) 3.71 (t, J=4.6 Hz, 4H) 7.01 (dd, J=8.5, 2.0 Hz, 1H) 7.08 (ddd, J=4.9, 2.9, 2.6 Hz, 1H) 7.11-7.18 (m, 1H); MS (ES) m/z 362.2 [M+H]+

Step 3: Synthesis of 4-(5-((4-(difluoromethoxy)phenyl)ethynyl)-2-fluorophenyl)morpholine

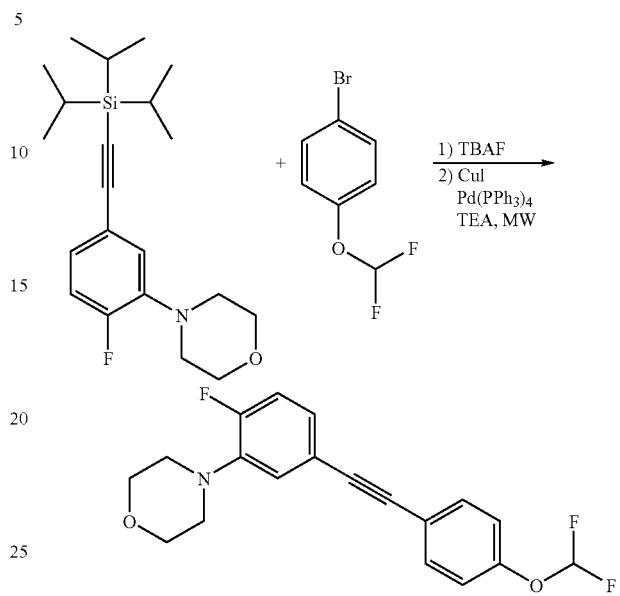

A 25 mL round bottom flask was charged with 4-(2-fluoro-5-((triisopropylsilyl)ethynyl)phenyl)morpholine (0.540 g, 1.50 mmol), diluted with tetrahydrofuran (THF, 1.5 ml) at room temperature. A 1M solution of tetrabutylammonium fluoride in THF (2.0 mL) was added. After 105 minutes reaction the mixture was partitioned between ethylacetate and water, separated, dried with sodium sulfate, and concentrated to an oil by rotary evaporation to yield 0.305 g of 4-(5-ethynyl-2-fluorophenyl)morpholine.

In a 0.5-2 ml Biotage conical microwave vial equipped with magnetic spin vane was dissolved 4-(5-ethynyl-2-fluorophenyl)morpholine (540 mg, 1.50 mmol) in triethylamine (1.5 mL). Copper iodide (54 mg, 0.283 mmol) and Tetrakis(triphenylphosphine) palladium (105 mg, 0.091 mmol) were added. Lastly 1-bromo-4-(difluoromethoxy)benzene (0.750 g, 3.36 mmol) was added, the vial was covered with a teflon septa, an aluminum cap was crimped in place, and the assembly was set on a Biotage Emrys microwave instrument to irradiate at 80° C. for 30 minutes. The crude reaction was diluted with diethylether, washed with saturated ammonium chloride, and purified via column chromatography on a Yamazen W-Prep 2XY using 25% EtOAc in hexanes. Concentration by rotary evaporation afforded 500 mg of oil (96%); $^1$H NMR (400 MHz, DMSO-$d_6$) δ ppm 3.03 (t, J=4.6 Hz, 4H) 3.73 (t, J=4.6 Hz, 4H) 7.13-7.14 (m, 1H) 7.16 (d, J=2.6 Hz, 1H) 7.17-7.19 (m, 2H) 7.22 (d, J=8.8 Hz, 2H) 7.24 (t, J=73.8 Hz, 1H) 7.60 (d, J=8.8 Hz, 2H); MS (ES) m/z 348.2 [M+H]+

Step 4: Synthesis of 1-(4-(difluoromethoxy)phenyl)-2-(4-fluoro-3-morpholinophenyl)ethane-1,2-dione

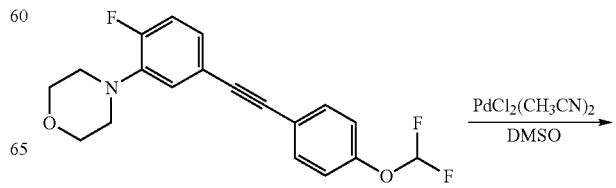

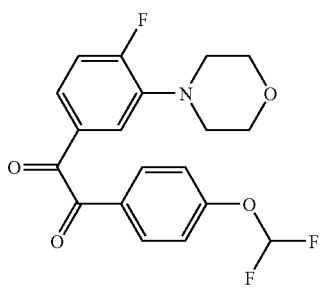

In a 50 ml round bottom flask was dissolved 4-(5-((4-(difluoromethoxy)phenyl)ethynyl)-2-fluorophenyl)morpholine (500 mg, 1.44 mmol) and Dichlorobis(acetonitrile)palladium (47 mg, 0.181 mmol) in DMSO (10 mL) was sparged with Argon for 15 minutes. The mixture was heated (oil bath 145° C.) for 1 hour. After cooling slightly the mixture was poured over silica gel. Purification by chromatography (25% ethylacetate in hexanes) afforded 200 mg of oil (37%); $^1$H NMR (400 MHz, DMSO-d$_6$) δ ppm 3.07 (t, J=4.6 Hz, 4H) 3.74 (t, J=4.6 Hz, 4H) 7.34-7.40 (m, 1H) 7.46 (t, J=72.8 Hz, 1H) 7.38 (d, J=8.8 Hz, 2H) 7.48 (td, J=4.2, 2.1 Hz, 1H) 7.59 (dd, J=8.4, 2.1 Hz, 1H) 8.00 (q, J=4.9 Hz, 2H); MS (ES) m/z 380.2 [M+H]$^+$ Step 5: Synthesis of 2-amino-4-(4-(difluoromethoxy)phenyl)-4-(4-fluoro-3-morpholinophenyl)-1-methyl-1H-imidazol-5(4H)-one

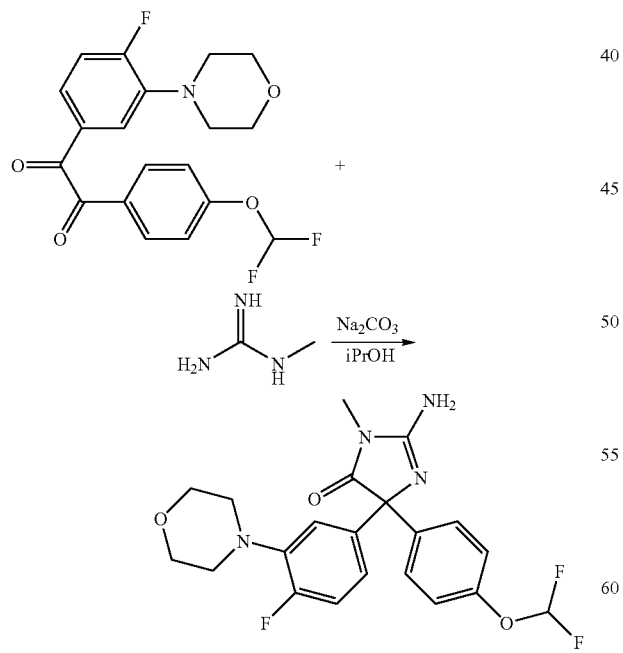

In a 50 ml round bottom flask was dissolved 1-(4-(difluoromethoxy)phenyl)-2-(4-fluoro-3-morpholinophenyl)ethane-1,2-dione (0.197 g, 0.519 mmol) in isopropanol (23 mL). Methylguanidine hydrochloride (84 mg, 0.766 mmol) was added followed by sodium carbonate (83 mg, 0.783 mmol). The mixture was heated (oil bath 86° C.) for 11 hours. The isopropanol was removed by rotary evaporation and the residue was transferred onto silica gel using ethyl acetate. Purification by column chromatography [step gradient; EtOAc, 5% MeOH/EtOAc then 10% MeOH/EtOAc] afforded an oil. The oil was re-dissolved in diethylether, diluted with hexanes and concentrated, twice to give a white foam, 123 mg (55%); $^1$H NMR (400 MHz, DMSO-d$_6$) δ ppm 2.92 (t, J=4.6 Hz, 4H) 2.96 (s, 3H) 3.70 (t, J=4.6 Hz, 4H) 6.69 (br s., 2H) 7.03-7.10 (m, 2H) 7.08 (d, J=8.8 Hz, 2H) 7.15 (t, J=74.2 Hz, 1H) 7.15-7.18 (m, 1H) 7.43 (d, J=8.8 Hz, 2H); MS (ES) m/z 435.2 [M+H]$^+$ Example 87

Preparation of: 2-amino-4-(3-(but-3-en-1-ynyl)-4-fluorophenyl)-4-(4-(difluoromethoxy)phenyl)-1-methyl-1H-imidazol-5(4H)-one

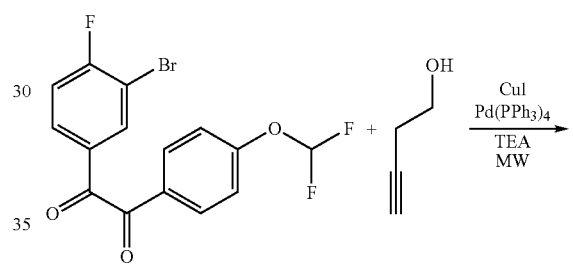

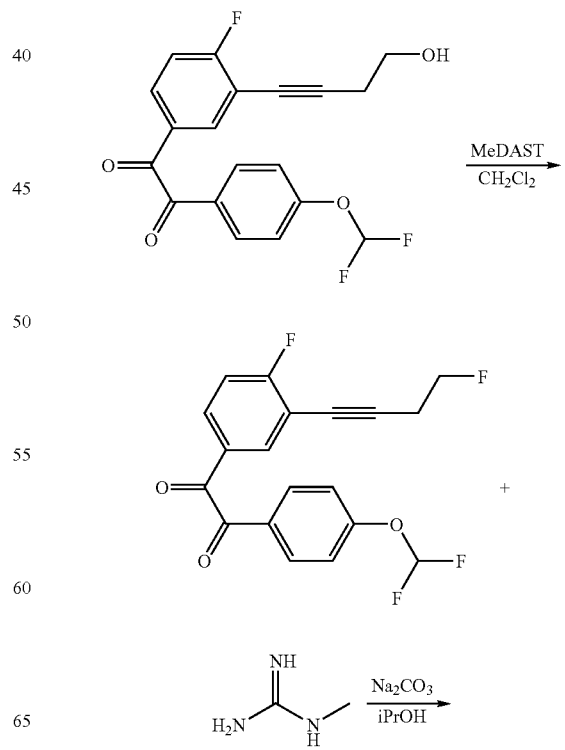

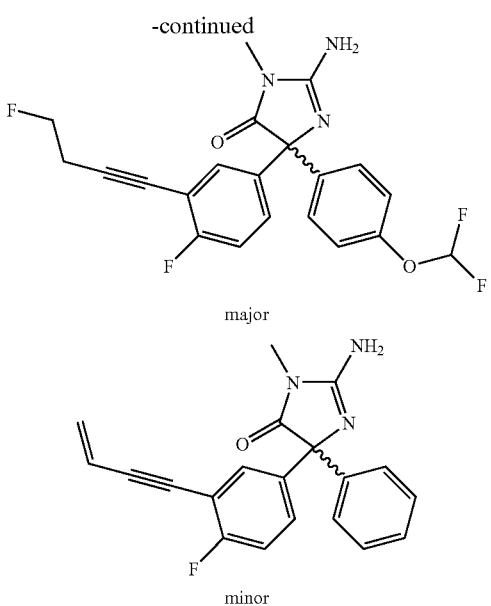

major minor

Step 1: Synthesis of 1-(4-(difluoromethoxy)phenyl)-2-(4-fluoro-3-(4-hydroxybut-1-ynyl)phenyl)ethane-1,2-dione

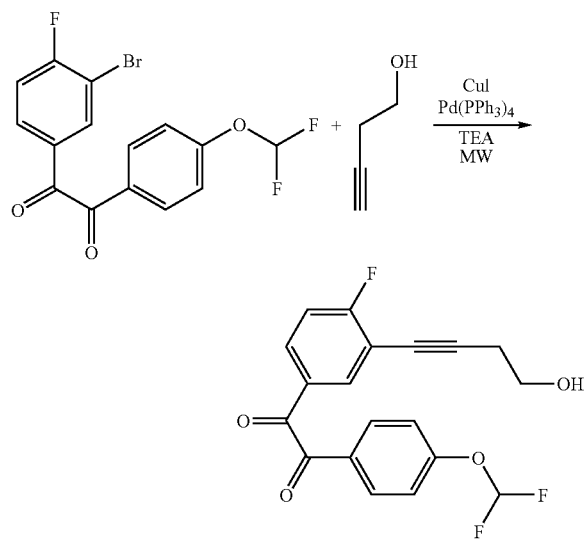

In a 0.5-2 ml Biotage conical microwave vial equipped with magnetic spin vane was dissolved 1-(3-Bromo-4-fluoro-phenyl)-2-(4-difluoromethoxy-phenyl)-ethane-1,2-dione (100 mg, 0.268 mmol) in triethylamine (1.25 mL). Copper iodide (10 mg, 0.052 mmol) and Tetrakis(triphenylphosphine) palladium (20 mg, 0.017 mmol) were added. Lastly But-3-yn-1-ol (100 mg, 1.04 mmol) was added, the vial was covered with a teflon septa, an aluminum cap was crimped in place, and the assembly was set on a Biotage Emrys microwave instrument to irradiate at 80° C. for one hour. The crude reaction was diluted with diethylether (60 mL), washed with saturated ammonium chloride (2×30 mL) and purified via column chromatography on a Yamazen W-Prep 2XY using a two-step automatic gradient elution: 100% hexanes (4 min) to 18% EtOAc (12 min), hold 4 min then to 80% EtOAc (16 min) hold 15 minutes. The resultant oil was placed under high vacuum overnight to afford 80 mgs of beige solid (82%).

SCALE-UP: Repeated above method using 10 times the reagent amounts in a 20 mL Biotage microwave vial affords 680 mgs (70%).

$^1$H NMR (400 MHz, DMSO-$d_6$) δ ppm 2.57 (t, J=6.7 Hz, 2H) 3.55 (q, J=6.7 Hz, 2H) 4.88 (t, J=5.7 Hz, 1H) 7.42 (t, J=73.02 Hz, 1H) 7.34 (q, J=4.9 Hz, 2H) 7.48 (t, J=8.9 Hz, 1H) 7.91-8.02 (m, 2H) 7.99 (d, J=9.04 Hz, 2H); MS (EI) m/z 362 [M$^+$].

Step 2: Synthesis of 1-(4-(difluoromethoxy)phenyl)-2-(4-fluoro-3-(4-fluorobut-1-ynyl)phenyl)ethane-1,2-dione

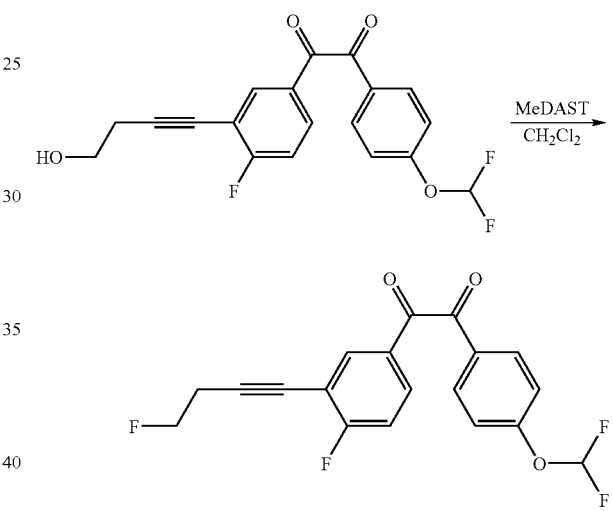

In a 100 mL round bottom dissolve 1-(4-Difluoromethoxy-phenyl)-2-[4-fluoro-3-(4-hydroxy-but-1-ynyl)-phenyl]-ethane-1,2-dione (0.670 g, 1.85 mmol) was dissolved in dichloromethane (40 mL) and chilled to −78° C. Add (Dimethylamino)sulfur trifluoride (MeDAST; 2.99 g, 22.4 mmol) was introduced via syringe injection. After 30 minutes dry-ice bath was removed. After 2 hours at ambient temperature the crude reaction was carefully poured into a 500 mL beaker containing 200 cc ice-chips and sodium bicarbonate. An attempted diethyl ether extraction with diethyl ether resulted in emulsion. Sodium chloride was added to break emulsion. Organic layer was concentrated to a residue, and loaded directly on top of an 80 gm chromatography column. Purification [YAMAZEN W-Prep 2XY using automatic gradient elution: 3% EtOAc/hexanes (hold 4 min) to 24% EtOAc (in 12 min), hold 8 minutes] afforded oil that begins to solidify as a wax 360 mg (53%).

$^1$H NMR (400 MHz, DMSO-$d_6$) δ ppm 2.87 (t, J=5.9 Hz, 1H) 2.93 (t, J=6.0 Hz, 1H) 4.55 (dt, J=41.8, 5.9 Hz, 2H) 7.34 (q, J=4.9 Hz, 2H) 7.43 (t, J=73.02 Hz, 1H) 7.50 (t, J=9.2 Hz, 1H) 7.94-8.02 (m, 4H).

Step 3: Synthesis of 2-amino-4-(3-(but-3-en-1-ynyl)-4-fluorophenyl)-4-(4-(difluoromethoxy)phenyl)-1-methyl-1H-imidazol-5(4H)-one

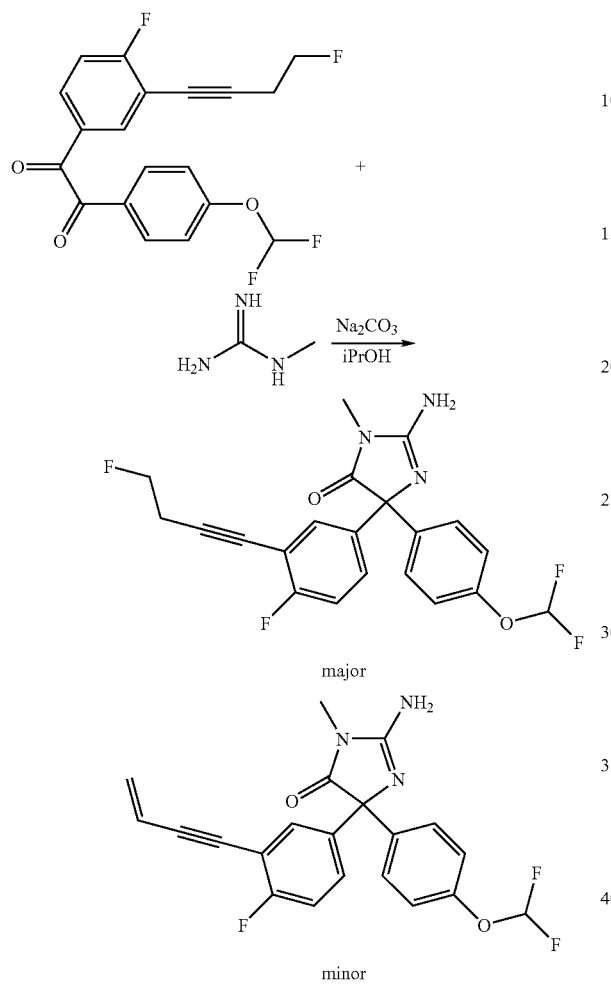

1-(4-(difluoromethoxy)phenyl)-2-(4-fluoro-3-(4-fluorobut-1-ynyl)phenyl)ethane-1,2-dione (0.220 g, 0.443 mmol) was dissolved in isopropanol (20 mL). Methylguanidine hydrochloride (138 mg, 1.26 mmol) was added followed by sodium carbonate (136 mg, 1.28 mmol). The mixture was heated (oil bath 86° C.) for 16 hours. The isopropanol was removed by rotary evaporation and the residue was transferred onto silica gel using ethyl acetate. Purification by column chromatography [100% EtOAc] afforded a mixture. The mixture of 2-amino-4-(4-(difluoromethoxy)phenyl)-4-(4-fluoro-3-(4-fluorobut-1-ynyl)phenyl)-1-methyl-1H-imidazol-5(4H)-one and 2-amino-4-(3-(but-3-en-1-ynyl)-4-fluorophenyl)-4-(4-(difluoromethoxy)phenyl)-1-methyl-1H-imidazol-5(4H)-one (360 mg) was separated by HPLC chromatography (Luna CN, 5×25 cm) eluting with 20% ethanol (0.1% diethylamine) in hexanes to provide a minor product, peak 1 (RT=7.7 min) 2-amino-4-(3-(but-3-en-1-ynyl)-4-fluorophenyl)-4-(4-(difluoromethoxy)phenyl)-1-methyl-1H-imidazol-5(4H)-one as an oil (100 mg). The oil was re-dissolved in diethylether, diluted with hexanes and concentrated, twice to give a white foam (25 mg) $^1$H NMR (400 MHz, DMSO-d$_6$) δ ppm 2.94 (s, 3H) 5.69 (dd, J=11.4, 2.1 Hz, 1H) 5.80 (dd, J=17.6, 1.9 Hz, 1H) 6.15 (dd, J=17.6, 11.1 Hz, 1H) 6.74 (br. s., 2H) 7.11 (d, J=8.6 Hz, 2H) 7.17 (t, J=74.2 Hz, 1H) 7.25 (t, J=9.2 Hz, 1H) 7.40-7.50 (m, 3H) 7.54 (dd, J=7.0, 2.3 Hz, 1H); MS (ES) m/z 400.1 [M+H]$^+$ The major product was peak 2 (RT=10.2 min) 2-amino-4-(4-(difluoromethoxy)phenyl)-4-(4-fluoro-3-(4-fluorobut-1-ynyl)phenyl)-1-methyl-1H-imidazol-5(4H)-one (260 mg), isolated as a racemic oil; MS (ES) m/z 420.1 [M+H]$^+$ Example 88

Preparation of: 2-amino-4-(4-(difluoromethoxy)phenyl)-4-(3-(furan-2-ylmethyl)phenyl)-1-methyl-1H-imidazol-5(4H)-one

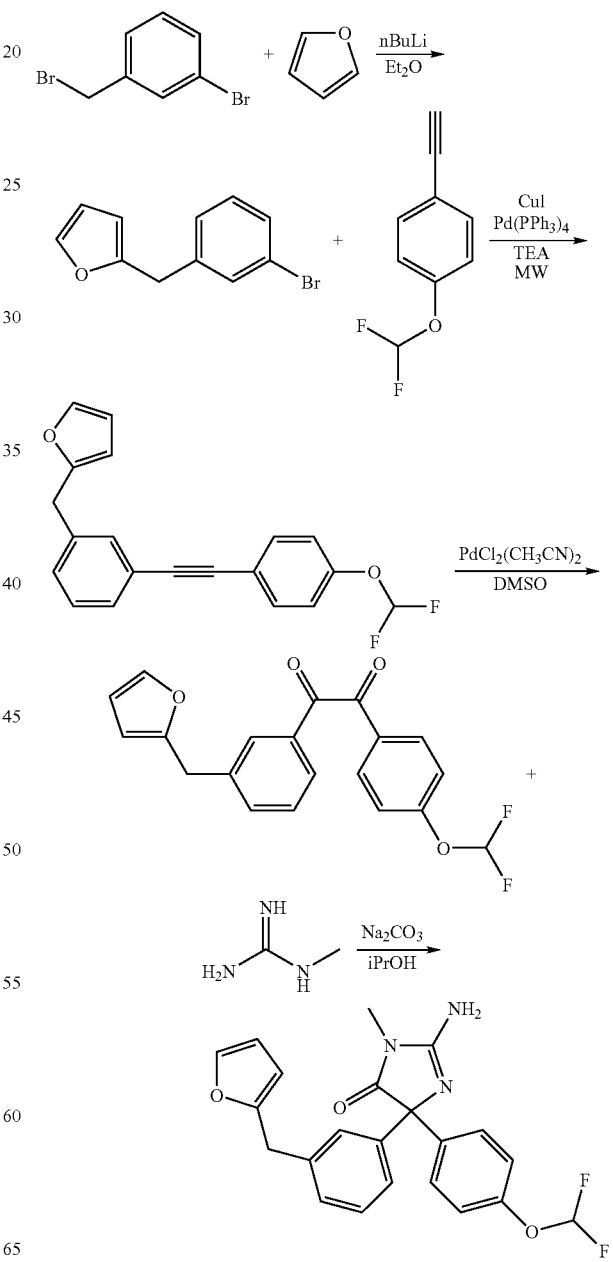

Step 1: Synthesis of 2-(3-bromobenzyl)furan

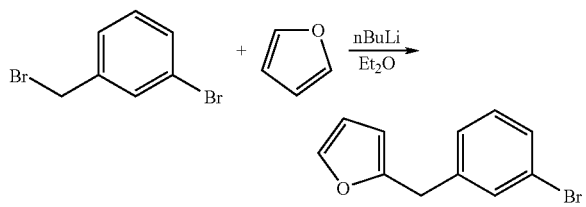

[Reference: Harold Hart in *J. Org. Chem.* 1989, 54, 5073].

Prepared in a similar manner (with the exception of 3-bromobenzyl bromide starting material). To a solution of furan (3.40 gm, 50.0 mmol) in diethylether (100 ml) at 0° C. was added 29 ml of n-BuLi (1.6 M in hexanes). The solution was allowed to warm to ambient temperature then heated to reflux for 4 hours. The solution was cooled to 0° C., and a solution of 3-bromobenzyl bromide (11.0 gm, 44.0 mmol) in diethylether (40 ml) was added dropwise. The reaction mixture was returned to reflux for 16 hours. After cooling the mixture was poured over crushed ice. The ethereal layer was dried with magnesium sulfate, concentrated and loaded onto silica gel. Purification by chromatography (hexanes) afforded 1.00 gm of an oil (8%). $^1$H NMR (400 MHz, DMSO-$d_6$) δ ppm 3.98 (s, 2H) 6.16 (dd, J=3.2, 0.9 Hz, 1H) 6.36 (dd, J=3.0, 1.9 Hz, 1H) 7.21-7.29 (m, 2H) 7.39-7.43 (m, 2H) 7.53 (dd, J=2.0, 0.8 Hz, 1H); MS (EI) m/z 236.0 [M$^+$].

Step 2: Synthesis of 2-(3-((4-(difluoromethoxy)phenyl)ethynyl)benzyl)furan

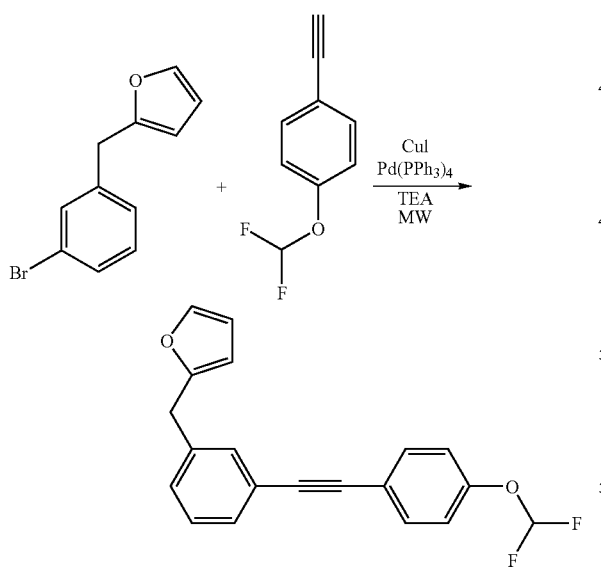

To a CEM snap top microwave vial (10 ml) equipped with a magnetic stir bar (3×10 mm) was added 2-(3-bromobenzyl)furan (385 mg, 1.62 mmol) in triethylamine (1.5 mL). Copper iodide (80 mg, 0.40 mmol), Tetrakis(triphenylphosphine)palladium (140 mg, 0.121 mmol) and 1-(difluoromethoxy)-4-ethynylbenzene (0.270 mg, 1.60 mmol) were added at room temperature. The reaction was capped and irradiated in a CEM Explorer microwave at 80° C. for 30 minutes then forced air-cooled. The crude material was loaded onto silica gel. Purification by chromatography (2% EtOAc in hexanes) afforded 0.317 gm of an oil (61%). $^1$H NMR (400 MHz, DMSO-$d_6$) δ ppm 3.99 (s, 2H) 6.16 (dd, J=3.1, 0.8 Hz, 1H) 6.37 (dd, J=3.1, 2.0 Hz, 1H) 7.21 (d, J=8.8 Hz, 2H) 7.28 (ddd, J=7.5, 1.6, 1.6 Hz, 1H) 7.31 (t, J=73.7 Hz, 1H) 7.34-7.42 (m, 3H) 7.53 (dd, J=1.9, 0.7 Hz, 1H) 7.61 (d, J=9.0 Hz, 2H); MS (EI) m/z 324.0 [M$^+$].

Step 3: Synthesis of 1-(4-(difluoromethoxy)phenyl)-2-(3-(furan-2-ylmethyl)phenyl)ethane-1,2-dione

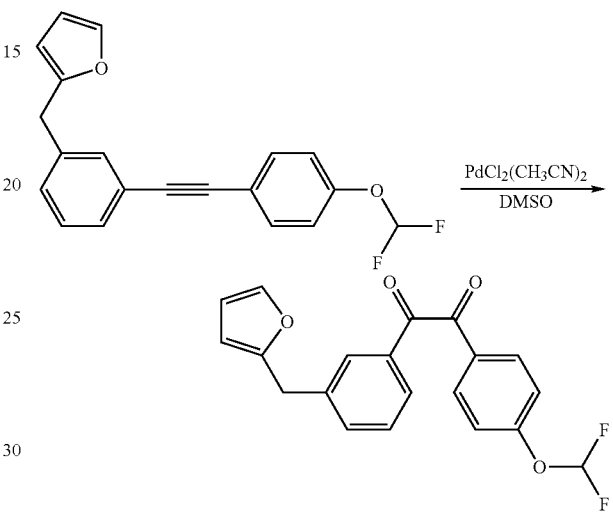

2-(3-((4-(difluoromethoxy)phenyl)ethynyl)benzyl)furan (300 mg, 0.925 mmol) and Dichlorobis(acetonitrile)palladium (41 mg, 0.158 mmol) in DMSO (10 mL) was sparged with Argon for 15 minutes. The mixture was heated (oil bath 145° C.) for 4 hours. After cooling slightly the mixture was poured over crushed ice, extracted with dichloromethane, washed with brine, dried with magnesium sulfate, concentrated and loaded onto silica gel. Purification by chromatography (5% ethylacetate in hexanes then 10% ethylacetate in hexanes) afforded 73 mg of yellow oil (22%).

$^1$H NMR (400 MHz, DMSO-$d_6$) δ ppm 4.09 (s, 2H) 6.16 (d, J=0.9 Hz, 1H) 6.36 (dd, J=3.1, 2.0 Hz, 1H) 7.37 (q, J=4.9 Hz, 2H) 7.45 (t, J=73.0, 1H) 7.52 (dd, J=1.9, 0.9 Hz, 1H) 7.56 (t, J=7.4 Hz, 1H) 7.63-7.66 (m, 1H) 7.75 (dt, J=7.6, 1.5 Hz, 1H) 7.80 (t, J=1.5 Hz, 1H) 7.99 (q, J=4.9 Hz, 2H); MS (EI) m/z 356.0 [M$^+$].

Step 4: Synthesis of 2-amino-4-(4-(difluoromethoxy)phenyl)-4-(3-(furan-2-ylmethyl)phenyl)-1-methyl-1H-imidazol-5(4H)-one

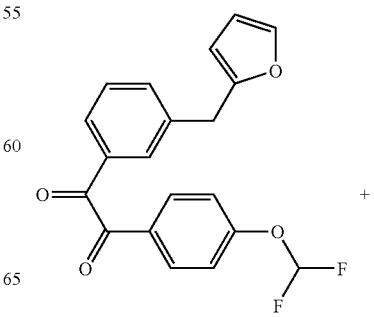

-continued

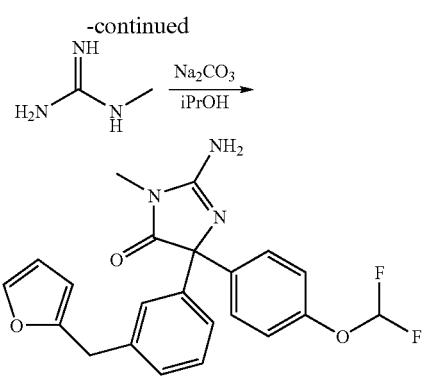

1-(4-(difluoromethoxy)phenyl)-2-(3-(furan-2-ylmethyl) phenyl)ethane-1,2-dione (70 mg, 0.196 mmol) was dissolved in isopropanol (10 mL). Methylguanidine hydrochloride (32 mg, 0.296 mmol) was added followed by sodium carbonate (31 mg, 0.292 mmol). The mixture was heated (oil bath 86° C.) for 16 hours. The isopropanol was removed by rotary evaporation and the residue was transferred onto silica gel using ethyl acetate. Purification by column chromatography [step gradient; 100% EtOAc then 10% MeOH/EtOAc] afforded oil. The oil was re-dissolved in diethylether, diluted with hexanes and concentrated, twice to give a white foam, 67 mg (83%); $^1$H NMR (400 MHz, DMSO-$d_6$) δ ppm 2.96 (s, 3H) 3.90 (s, 2H) 6.06 (dd, J=3.2, 0.7 Hz, 1H) 6.33 (dd, J=3.0, 1.9 Hz, 1H) 6.65 (br. s., 2H) 7.04-7.09 (m, 1H) 7.08 (d, J=8.6 Hz, 2H) 7.15 (t, J=73.9 Hz, 1H) 7.21 (t, J=7.6 Hz, 1H) 7.28-7.31 (m, 1H) 7.32-7.35 (m, 1H) 7.44 (d, J=8.8 Hz, 2H) 7.49 (dd, J=1.9, 0.9 Hz, 1H); MS (ES) m/z 412.2 [M+H]$^+$ Example 89

Preparation of 2-Amino-5-[4-(difluoromethoxy)phenyl]-5-[3-(3,3-difluoropropoxy)phenyl]-3-methyl-3,5-dihydro-4H-imidazol-4-one

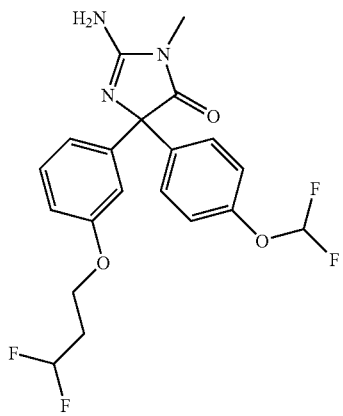

Step 1: 1-Bromo-3-(but-3-enyloxy)benzene

To a solution of 3-bromophenol (8.65 g, 50 mmol) in dry DMF (200 mL) was added $Cs_2CO_3$ (17.9 g, 55 mmol) followed by 4-bromo-1-butene (7.42 g, 5.58 mmol, 55 mmol; the alkene should be colorless for best results). The mixture was stirred overnight at 50° C., cooled to room temperature and poured into water (700 mL). EtOAc and additional water were added and the organic layer was separated. The aqueous layer was extracted with EtOAc. The combined organic layers were washed with water (3×500 mL), dried over $Na_2SO_4$, filtered, and concentrated in vacuo to give 11.24 g of a brown-red oil as crude material. This material was absorbed onto Celite (50 g). Flash chromatography ($SiO_2$, 1% EtOAc 99% Hexanes to 5:95 EtOAc:Hexanes) provided 3.68 g, 31%, of the title compound as a light yellow oil.

$^1$H NMR 500 MHz (CDCl$_3$) δ2.51 (quartet, J=6.68 Hz, 2H); 3.97 (t, J=6.67 Hz, 2H); 5.12 (m, 2H); 5.85 (m, 1H); 6.78-6.81 (m, 1H); 7.01-7.12 (m, 3H)

Step 2: 3-(3-Bromophenoxy)propanal

To a solution of 1-bromo-3-(but-3-enyloxy)benzene (3.6 g, 15.85 mmol) from the previous step in THF (335 mL) was added water (125 mL). The solution was cooled to 0° C. and $NaIO_4$ (10.17 g, 47.56 mmol) followed by $OsO_4$ (3.5 mL, 4 wt % in water). The mixture was stirred at 0° C. for 4 h then the mixture was warmed to room temperature overnight without stirring. The mixture was filtered and the solid left behind was washed with a little water. The filtrate was diluted with EtOAc and the biphasic mixture was poured into a separatory funnel. The aqueous layer was separated and extracted with EtOAc once The combined organic layers were washed with brine, dried over $Na_2SO_4$, filtered, and concentrated in vacuo to yield 4.1 g of a purple oil. The oil was absorbed onto 18 g Celite and quick flash chromatography ($SiO_2$, 1:9 EtOAc:Hexanes) provided 2.75 g, 75%, of the title compound as a brown-orange oil.

MS (EI): m/z 228 (M$^+$);

Step 3: 1-Bromo-3-(3,3-difluoropropoxy)benzene

To a cooled (−20° C.) solution of 3-(3-bromophenoxy) propanal (275 mg, 1.2 mmol) from the previous step in DCM (2.4 mL) was added (diethylamino)sulfur trifluoride (DAST; 406 mg, 330 μL, 2.52 mmol). The reaction mixture was stirred at this temperature for 1.5 h after which point a DNP stain on a tlc of the reaction showed that all the starting aldehyde had been used up. The reaction mixture was warmed to room temperature and concentrated onto 1.2 g Celite. Flash chromatography ($SiO_2$, 1% EtOAc 99% Hexanes to 5:95 EtOAc:Hexanes) provided 227 mg, 75%, of the title compound as a colorless oil.

MS (EI): m/z 250 (M$^+$);

Step 4: ((3-(3,3-difluoropropoxy)phenyl)ethynyl) trimethylsilane

A solution of 1-(3,3-difluoropropoxy)-3-ethynylbenzene (2.3 g, 9.16 mmol) from the previous step, trimethylacetylene (1.34 g, 1.94 mmol, 13.74 mmol), TEA (4.63 g, 6.38 mL, 45.8 mmol), and DMF (20.5 mL) was degassed with nitrogen for 30 min then $PdCl_2(PPh_3)_2$ (321 mg, 0.458 mmol) and CuI (174 mg, 0.916 mmol) were added. The mixture was heated at 65° C. until no more starting bromide was seen by tlc (about 6 h). The cooled reaction mixture was diluted with EtOAc and water. The aqueous layer was separated and extracted twice with EtOAc. The combined organic layers were washed with water, dried over $Na_2SO_4$, filtered, and concentrated onto 10 g Celite. Flash chromatography ($SiO_2$, 1% EtOAc 99% Hexanes to 3% EtOAc 97% Hexanes) provided 2.14 g, 87%, of the title compound as a brown oil.

MS (EI): m/z 268 (M$^+$);

Step 5: 1-(3,3-Difluoropropoxy)-3-ethynylbenzene

To a solution of ((3-(3,3-difluoropropoxy)phenyl)ethynyl)trimethylsilane (2.1 g, 7.82 mmol) from the previous step in MeOH (19.5 mL) was added $K_2CO_3$ (10.81 g, 78.2 mmol) at room temperature. The reaction mixture was stirred for 1.5 h after which it was diluted with water and EtOAc. The aqueous layer was separated and extracted with EtOAc once. The combined organic layers were dried over $Na_2SO_4$, filtered, and concentrated in vacuo to give a brown oil. The oil was absorbed onto Celite (8 g). Flash chromatography ($SiO_2$, 1% EtOAc 99% Hexanes to 3% EtOAc 97% Hexanes) provided 1.31 g, 85%, of the title compound as a yellow oil.

MS (EI): m/z 196 ($M^+$);

Step 6: 1-(Difluoromethoxy)-4-((3-(3,3-difluoropropoxy)phenyl)ethynyl)-2-methylbenzene This compound was made in a similar manner to Example 89 Step 4 using 1-(3,3-difluoropropoxy)-3-ethynylbenzene (650 mg, 3.13 mmol) from the previous step, 1-(difluoromethoxy)-4-iodo-2-methylbenzene (818 mg, 2.88 mmol), TEA (1.45 g, 2.0 mL, 14.5 mmol), $PdCl_2(PPh_3)_2$ (101 mg, 0.144 mmol), and CuI (16.4 mg, 0.0864 mmol), and DMF (4.4 mL) to provide the title compound as a yellow oil.

MS (EI): m/z 352 ($M^+$);

Step 7: 1-(4-(Difluoromethoxy)phenyl)-2-(3-(3,3-difluoropropoxy)phenyl)ethane-1,2-dione To a solution of 1-(difluoromethoxy)-4-((3-(3,3-difluoropropoxy)phenyl)ethynyl)-2-methylbenzene (675 mg, 2.0 mmol) from the previous step in DMSO (8 mL) was added $PdCl_2(ACN)_2$ (52 mg, 0.20 mmol) and the mixture was heated to 130° C. overnight. The cooled reaction mixture was poured into water and extracted with EtOAc. The aqueous layer was separated and extracted with EtOAc twice. The combined organic layers were washed with water, dried over $Na_2SO_4$, filtered, and concentrated onto 4 g Celite. Flash chromatography ($SiO_2$, 1:9 EtOAc:Hexanes to 25:75 EtOAc:Hexanes) provided 677 mg, 91%, of the title compound as an orange oil.

MS (−ESI): m/z 369 ([M−H]$^-$)

Step 8: 2-Amino-5-[4-(difluoromethoxy)phenyl]-5-[3-(3,3-difluoropropoxy)phenyl]-3-methyl-3,5-dihydro-4H-imidazol-4-one To a solution of 1-(4-(difluoromethoxy)phenyl)-2-(3-(3,3-difluoropropoxy)phenyl)ethane-1,2-dione (670 mg, 1.81 mmol) from the previous step in 200 P EtOH (5.2 mL) was added 1-methylguanidine hydrochloride (297 mg, 2.71 mmol) and $Na_2CO_3$ (288 mg, 2.71 mmol). The mixture was heated at 90° C. for 1 h and cooled to room temperature, concentrated in vacuo onto 6 g Celite to provide 433 mg of a tan foam. By $^1$H NMR this is the acetate salt of the title compound. The foam was dissolved in DCM and washed with saturated $NaHCO_3$ to release the free base. There resulted in 335 mg, 43%, of the title compound as a light yellow foam.

MS (+ESI): m/z 426.1 ([M+H]$^+$)

Example 90

Preparation of (5R)-2-Amino-5-[4-(difluoromethoxy)phenyl]-5-[3-(3,3-difluoropropoxy)phenyl]-3-methyl-3,5-dihydro-4H-imidazol-4-one

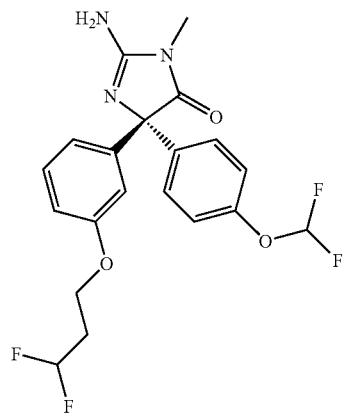

The compound from Example 89 Step 8 was separated by chiral HPLC (Chiralcel OD-H, 2×25 cm; 15% IPA in Hexanes with DEA additive) to provide the title compound as a white foam.

MS (+ESI): m/z 426.1 ([M+H]$^+$)

Example 91

Preparation of (5S)-2-Amino-5-[4-(difluoromethoxy)phenyl]-5-[3-(3,3-difluoropropoxy)phenyl]-3-methyl-3,5-dihydro-4H-imidazol-4-one

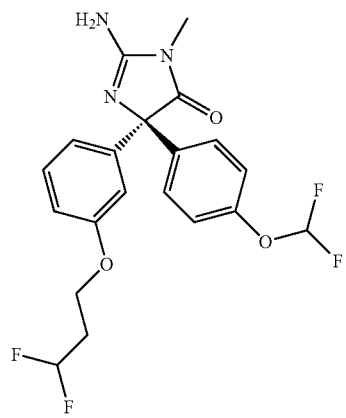

The compound from Example 89 Step 8 was separated by chiral HPLC (Chiralcel OD-H, 2×25 cm; 15% IPA in Hexanes with DEA additive) to provide the title compound as a white foam.

MS (+ESI): m/z 426.1 ([M+H]$^+$)

Example 92

Preparation of 2-Amino-5-[4-(difluoromethoxy)phenyl]-5-[3-(3,3-difluoropropoxy)-4-fluorophenyl]-3-methyl-3,5-dihydro-4H-imidazol-4-one

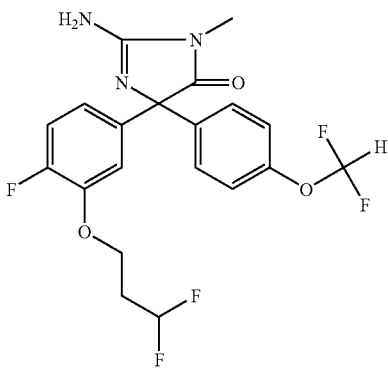

Step 1: 4-Bromo-2-(but-3-enyloxy)-1-fluorobenzene

To a solution of 5-bromo-2-fluorophenol (19.63 g, 102.8 mmol) in DMF (410 mL) was added $Cs_2CO_3$ (40.19 g, 123.36 mmol, 1.2 eq.) followed by 4-bromo-1-butene (15.26 g, 11.48 mL, 113.06 mmol, 1.1 eq.). The mixture was stirred overnight at a temperature between 50 and 60° C. Then additional amounts of $Cs_2CO_3$ and the bromoalkene (20.1 g, 0.6 eq.) and (7.53 g, 5.74 mL, 0.55 eq.) respectively were added to the reaction mixture and heating was continued overnight. The mixture was cooled to room temperature and diluted with water. The aqueous mixture was extracted with EtOAc and the aqueous layer was separated and extracted once with EtOAc. The combined organic layers were washed with water, dried over $Na_2SO_4$, filtered, and concentrated onto 50 g Celite. Flash chromatography ($SiO_2$, Hexanes to 30% EtOAc 70% Hexanes) provided 11.87 g, 47%, of the title compound as a colorless to light yellow oil.

$^1$H NMR 500 MHz (CDCl$_3$) δ 2.51 (quartet, J=6.68 Hz, 2H); 4.10 (t, J=7.19 Hz, 2H); 5.12 (ddd; J=1.13 Hz, 13.70 Hz, 27.40 Hz, 2H); 5.85 (m, 1H); 6.80 (dd, J=1.68 Hz, 7.36 Hz, 1H); 7.00-7.06 (m, 2H); 7.07-7.12 (m, 1H)

Step 2: 3-(5-Bromo-2-fluorophenoxy)propanal

To a solution of 4-bromo-3-(but-3-enyloxy)-1-fluorobenzene (11.85 g, 48.35 mmol) from the previous step in THF (1025 mL) was added water (683 mL). The solution was cooled to 0° C. and NaIO$_4$ (31.0 g, 145.0 mmol) followed by OsO$_4$ (6.1 mL, 4 wt % in water). The mixture was stirred at 0° C. for 4 h then the mixture was warmed to room temperature overnight without stirring. The mixture was filtered and the solid left behind was washed with THF. The filtrate was diluted with ice water and extracted with EtOAc. If necessary, brine was used to separate the layers. The aqueous layer was separated and extracted with EtOAc once more. The combined organic layers were dried over Na$_2$SO$_4$, filtered, and concentrated in vacuo at a temp ≦25° C. to give a green-brown oil. The oil was placed under hivac for one-half hour to give 6.39 g of crude product that by $^1$H NMR contained the desired product and EtOAc in a 60:19 mol ratio. Actual yield of the title compound is 5.74 g, 93%. This material is used as is.

$^1$H NMR 500 MHz (CDCl$_3$) δ 2.96 (td, J=1.16 Hz, 6.15 Hz, 2H); 4.32 (t, J=6.15 Hz, 2H); 6.89-6.96 (m, 1H); 7.00-7.04 (m, 1H); 7.10 (dd, J=2.32 Hz, 7.42 Hz, 1H)

Step 3: 4-Bromo-2-(3,3-difluoropropoxy)-1-fluorobenzene

To a cooled (−20° C.) solution of 3-(5-bromo-2-fluorophenoxy)propanal (5.74 g, 23.23 mmol) from the previous step in DCM (46.5 mL) was added DAST (6.39 mL, 48.8 mmol). The reaction mixture was stirred at −20° C. for 1.5 h after which it was warmed to room temperature. The mixture was concentrated directly onto 36 g Celite. Flash chromatography (SiO$_2$, 1% EtOAc 99% Hexanes to 5% Hexanes 95% EtOAc) provided 4.1 g, 65%, of the title compound as a yellow oil.

MS (EI): m/z 268 (M$^{+\cdot}$)

Step 4: ((3-(3,3-Difluoropropoxy)-4-fluorophenyl)ethynyl)trimethylsilane

This compound was made in a similar manner to Example 89 Step 4 using 4-bromo-2-(3,3-difluoropropoxy)-1-fluorobenzene (2.69 g, 10 mmol) from the previous step, trimethylsilylacetylene (1.47 g, 15 mmol, 2.1 mL), TEA (5.06 g, 50 mmol, 7.0 mL), PdCl$_2$(PPh$_3$)$_2$ (350 mg, 0.5 mmol), and CuI (190 mg, 1.0 mmol), and DMF (20 mL) to provide 2.0 g of an orange oil. By $^1$H NMR, this oil is a 6:4 mixture of the title compound and the starting bromide. This mixture is inseparable by chromatography and is carried on as is. Yield of title compound by NMR is 43%.

Step 5: 2-(3,3-Difluoropropoxy)-4-ethynyl-1-fluorobenzene

To a solution of the crude ((3-(3,3-difluoropropoxy)-4-fluorophenyl)ethynyl)trimethylsilane (2.0 g) from the previous step in MeOH (17.5 mL) was added K$_2$CO$_3$ (9.65 g, 69.8 mmol) at room temperature. The reaction mixture was stirred for 1.5 h after which the mixture was filtered. The filter cake was washed with MeOH and the combined filtrate was concentrated over 10 g Celite. Flash chromatography (SiO$_2$, % EtOAc 99% Hexanes to 5:95 EtOAc:Hexanes) provided 700 mg, 76%, of the title compound as a light yellow oil.

MS (EI): m/z 214 (M$^{+\cdot}$)

Step 6: 4-((4-(Difluoromethoxy)phenyl)ethynyl)-2-(3,3-difluoropropoxy)-1-fluorobenzene To a mixture of 2-(3,3-difluoropropoxy)-4-ethynyl-1-fluorobenzene (700 mg, 3.27 mmol) from the previous step, TEA (1.82 g, 2.5 mL, 17.99 mmol), PdCl$_2$(PPh$_3$)$_2$ (114 mg, 0.163 mmol), and CuI (19 mg, 0.098 mmol) was added 4-iodo(difluoromethoxy)benzene (707 mg, 2.61 mmol). The reaction mixture was heated at 35-40° C. for 1 h under nitrogen. The reaction mixture was cooled to room temperature then poured into water. The aqueous mixture was extracted with EtOAc three times and the combined organic layers were dried over Na$_2$SO$_4$, filtered, and concentrated onto 10 g Celite. Flash chromatography (SiO$_2$, 1% EtOAc 99% Hexanes to 5:95 EtOAc:Hexanes) provided 738 mg, 79%, of the title compound as a light yellow oil.

$^1$H NMR 500 MHz (CDCl$_3$) δ 2.29-2.42 (m, 2H); 4.19 (t, J=6.03 Hz, 2H); 6.09 (tt, J=4.71 Hz, 56.05 Hz, 1H); 6.51 (t, J=73.49 Hz, 1H); 7.00-7.10 (m, 3H); 7.47-7.50 (m, 1H)

Step 7: 1-(4-(Difluoromethoxy)phenyl)-2-(3-(3,3-difluoropropoxy)-4-fluorophenyl)ethane-1,2-dione This compound was made in a similar manner to Example 89 Step 7 using 4-((4-(difluoromethoxy)phenyl)ethynyl)-2-(3,3-difluoropropoxy)-1-fluorobenzene (735 mg, 2.06 mmol) from the previous step, PdCl$_2$(ACN)$_2$ (54 mg, 0.206 mmol), and DMSO (8.25 mL) to provide 697 mg, 87%, of the title compound as a yellow solid.

MS (+ESI): m/z 389 ([M+H]$^+$)

Step 8: 2-Amino-4-(4-(difluoromethoxy)phenyl)-4-(3-(3,3-difluoropropoxy)-4-fluorophenyl)-1-methyl-1H-imidazol-5(4H)-one This compound was made in a similar manner to Example 89 Step 8 using 1-(4-(difluoromethoxy)phenyl)-2-(3-(3,3-difluoropropoxy)-4-fluorophenyl)ethane-1,2-dione (672 mg, 1.73 mmol) from the previous step, 1-methylguanidine hydrochloride (284 mg, 2.59 mmol), Na$_2$CO$_3$ (275 mg, 2.59 mmol), and iPrOH (5.0 mL) to provide 380 mg, 50%, of the title compound as a beige foam.

MS (+ESI): m/z 441 ([M+H]$^+$)

Example 93

Preparation of (5S)-2-Amino-5-[4-(difluoromethoxy)phenyl]-5-[3-(3,3-difluoropropoxy)-4-fluorophenyl]-3-methyl-3,5-dihydro-4H-imidazol-4-one

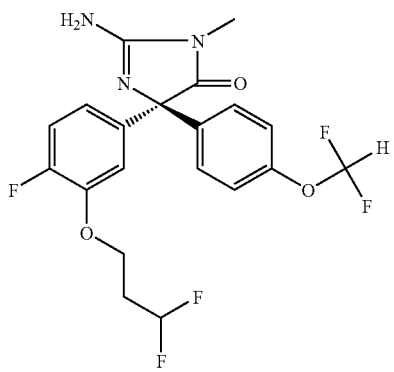

The compound from Example 92 Step 8 was separated by chiral HPLC (Chiralcel AD 5×50 cm; 15% EtOH in Hexane/DEA additive) to provide the title compound as a white foam.

MS (+ESI): m/z 441 ([M+H]$^+$)

Example 94

(5R)-2-Amino-5-[4-(difluoromethoxy)phenyl]-5-[3-(3,3-difluoropropoxy)-4-fluorophenyl]-3-methyl-3,5-dihydro-4H-imidazol-4-one

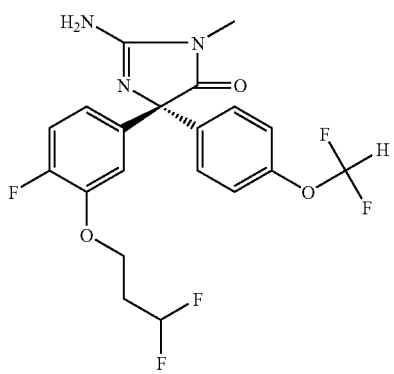

The compound from Example 92 Step 8 was separated by chiral HPLC (Chiralcel AD 5×50 cm; 15% EtOH in Hexane/DEA additive) to provide the title compound as a white foam.

MS (+ESI): m/z 441 ([M+H]$^+$)

Example 95

Preparation of 2-Amino-5-[4-(difluoromethoxy)phenyl]-3-methyl-5-(3-methylphenyl)-3,5-dihydro-4H-imidazol-4-one

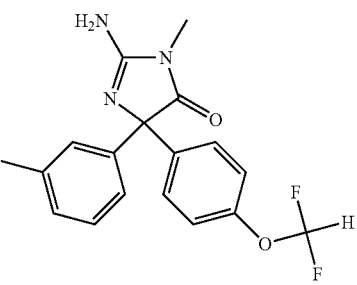

Step 1: 1-((4-(Difluoromethoxy)phenyl)ethynyl)-3-methylbenzene

To a solution of 4-iodo(difluoromethoxy)benzene (4.64 g, 17.2 mmol) in DMF (26 mL) was added TEA (9.57 g, 13.2 mL, 94.6 mmol), PdCl$_2$(PPh$_3$)$_2$ (603 mg, 0.86 mmol), CuI (98 mg, 0.516 mmol), and 3-ethynyltoluene (2.5 g, 2.78 mL, 0.90 mmol). The reaction mixture was stirred for 4 h then it was poured into water and diluted with EtOAc. The aqueous layer was separated and extracted twice more with EtOAc. The combined organic layers were dried over Na$_2$SO$_4$, filtered, and concentrated onto 20 g Celite. Flash chromatography (SiO$_2$, Hexanes) gave 1.44 g of a dark red oil and 2.44 g of a dark orange oil. Both fractions were rechromatographed, separately, to provide 3.2 g, 72%, of the title compound as a light peach oil.

$^1$H NMR 500 MHz (CDCl$_3$) δ 2.33 (s, 3H); 6.50 (t, J=73.6 Hz, 1H); 7.06 (d, J=8.81 Hz, 2H); 7.12 (d, J=6.83 Hz, 1H); 7.20 (d, J=7.53 Hz, 1H); 7.30 (d, J=7.76 Hz, 1H); 7.33 (s, 1H); 7.47-7.51 (m, 2H)

Step 2: 1-(4-(Difluoromethoxy)phenyl)-2-m-tolylethane-1,2-dione

This compound was made in a similar manner to Example 89 Step 7 using 1-((4-(difluoromethoxy)phenyl)ethynyl)-3-methylbenzene (3.2 g, 12.4 mmol) from the previous step, PdCl$_2$(ACN)$_2$ (322 mg, 1.24 mmol), and DMSO (50 mL) to provide 3.32 g, 92%, of the title compound as an orange oil. Reaction was heated at 145° C. for 4 h.

MS (−ESI): m/z 289 ([M−H]$^-$);

Step 3: 2-Amino-5-[4-(difluoromethoxy)phenyl]-3-methyl-5-(3-methylphenyl)-3,5-dihydro-4H-imidazol-4-one This compound was made in a similar manner to Example 89 Step 8 using 1-(4-(difluoromethoxy)phenyl)-2-m-tolylethane-1,2-dione (1.45 g, 5.0 mmol) from the previous step, 1-methylguanidine hydrochloride (821 mg, 7.5 mmol), Na$_2$CO$_3$ (795 mg, 7.5 mmol), and EtOH (10 mL) to provide 1.04 g, 60%, of the title compound as a beige foam.

MS (+ESI): m/z 346 ([M+H]$^+$)

Example 96

Preparation of 2-Amino-5-[4-(difluoromethoxy)phenyl]-5-[3-(4-ethoxybut-1-yn-1-yl)phenyl]-3-methyl-3,5-dihydro-4H-imidazol-4-one

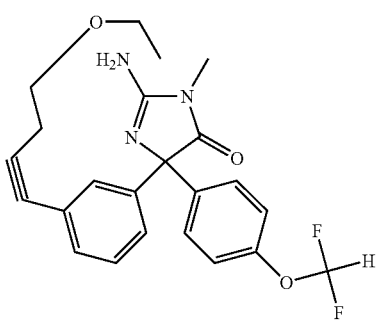

Step 1: 1-Bromo-3-ethynylbenzene

To each of two 1 L flasks was charged $K_2CO_3$ (68 g, 493.7 mmol), a large magnetic stirbar, and MeOH (250 mL). Stirring was begun and once the reaction mixtures were stirring without any problems, ((3-bromophenyl)ethynyl)trimethylsilane (12.5 g, 49.4 mmol, 10.5 mL) was added to each reaction vessel and the reaction mixtures were refluxed overnight. The cooled reaction mixtures were filtered and the filter cake was washed with MeOH. The filtrate was diluted with water and washed with Hexanes (at least 500 mL) three times. The combined organic layers were concentrated to give a yellow oil that was absorbed onto 50 g Celite. Flash chromatography ($SiO_2$, Hexanes) provided 9.1 g, 50%, of the title compound as a colorless to light yellow oil.

$^1$H NMR 500 MHz ($CDCl_3$) δ 3.08 (s, 3H); 7.16 (t, J=7.89 Hz, 1H); 7.38 (dt, J=2.44 Hz, 7.77 Hz, 1H); 7.61 (t, J=1.68 Hz, 1H)

Step 2: 1-Bromo-3-((4-(difluoromethoxy)phenyl)ethynyl)benzene

To a mixture of 1-bromo-3-ethynylbenzene (9.1 g, 50.26 mmol), TEA (22.38 g, 30.8 mL, 221.1 mmol), $PdCl_2(ACN)_2$ (1.41 g, 2.01 mmol) and DMF (60 mL) was added 4-iodo(difluoromethoxy)benzene (10.85 g, 40.21 mmol). The reaction mixture became warm after the addition was completed. The mixture was stirred for 4 h. Then it was poured into water and diluted with EtOAc. The aqueous layer was separated and extracted twice with EtOAc. The combined organic layers were dried over $Na_2SO_4$, filtered, and concentrated onto 40 g Celite. Flash chromatography ($SiO_2$, Hexanes) provided 12 g, 92%, of the title compound as a yellow oil that crystallized into a yellow solid upon standing.

$^1$H NMR 500 MHz ($CDCl_3$) δ6.51 (t, J=73.49 Hz, 1H); 7.08 (dd, J=1.27 Hz, 7.65 Hz, 2H); 7.19 (t, J=7.89 Hz, 1H); 7.40-7.46 (m, 2H); 7.47-7.51 (m, 1H); 7.64 (t, J=1.63 Hz, 1H)

Step 3: 1-(3-Bromophenyl)-2-(4-(difluoromethoxy)phenyl)ethane-1,2-dione

This compound was made in a similar manner to Example 89 Step 7 using 1-bromo-3-((4-(difluoromethoxy)phenyl)ethynyl)benzene (10.0 g, 30.95 mmol) from the previous step, $PdCl_2(ACN)_2$ (803 mg, 3.10 mmol), and DMSO (125 mL) to provide 7.8 g, 70%, of the title compound as an orange-yellow solid. The reaction was heated at 145° C. overnight.

MS (+ESI): m/z 356.9 ([M+H]$^+$)

Step 4: 1-(4-(Difluoromethoxy)phenyl)-2-(3-(4-hydroxybut-1-ynyl)phenyl)ethane-1,2-dione To a mixture of dichloropalladium(II)bis(benzonitrile) (575 mg, 1.5 mmol), CuI (571 mg, 3.0 mmol), tributylphosphine (10 wt % solution in hexanes, 197 μL, 0.974 mmol), and 5 mL degassed 1,4-dioxane was added diisopropyl amine (1.82 g, 2.5 mL, 18.0 mmol), and a solution of 1-(3-bromophenyl)-2-(4-(difluoromethoxy)phenyl)ethane-1,2-dione (5.32 g, 15.0 mmol) from the previous step in degassed 1,4-dioxane (10 mL). The reaction mixture was stirred under nitrogen at room temperature. The mixture was diluted with water and extracted with EtOAc three times. The combined organic layers were dried over $Na_2SO_4$, filtered, and concentrated onto 20 g Celite. Flash chromatography ($SiO_2$, 1:9 EtOAc:Hexanes to 1:1 EtOAc:Hexanes) provided 3.67 g, 66%, of the title compound as an orange-yellow solid.

MS (+ESI): m/z 345 ([M+H]$^+$)

Step 5: 1-(4-(Difluoromethoxy)phenyl)-2-(3-(4-methoxybut-1-ynyl)phenyl)ethane-1,2-dione To a solution of 1-(4-(difluoromethoxy)phenyl)-2-(3-(4-hydroxybut-1-ynyl)phenyl)ethane-1,2-dione (344 mg, 1.0 mmol) from the previous step in DCM (5 mL) was added tetrabutylammonium bromide (64 mg, 0.2 mmol) followed by NaOH (2.5N, 5 mL). Ethyl iodide (3.9 g, 2.0 mL, 25 mmol) was added and the mixture was stirred vigorously for 2 d then worked up as follows. The reaction mixture was diluted with water and DCM. The aqueous layer was separated and extracted once with DCM. The combined organic layers were washed with water, dried over $Na_2SO_4$, filtered, and concentrated in vacuo to give an oil. Flash chromatography ($SiO_2$, 1:9 EtOAc:Hexanes to 1:1 EtOAc:Hexanes) to provide 100 mg, 26%, of the title compound as a yellow oil.

MS (+APPI): m/z 373 ([M+H]$^+$)

Step 6: 2-Amino-5-[4-(difluoromethoxy)phenyl]-5-[3-(4-ethoxybut-1-yn-1-yl)phenyl]-3-methyl-3,5-dihydro-4H-imidazol-4-one This compound was made in a similar manner to Example 89 Step 8 using 1-(4-(difluoromethoxy)phenyl)-2-(3-(4-methoxybut-1-ynyl)phenyl)ethane-1,2-dione (100 mg, 0.268 mmol) from the previous step, 1-methylguanidine hydrochloride (44 mg, 0.402 mmol), $Na_2CO_3$ (43 mg, 0.402 mmol), and EtOH (600 μL) to provide 30 mg, 26%, of the title compound as a beige foam.

MS (+ESI): m/z 428.1 ([M+H]$^+$)

Example 97

Preparation of 2-amino-5-[4-(difluoromethoxy)phenyl]-5-[3-(3-fluoroprop-1-yn-1-yl)phenyl]-3-methyl-3,5-dihydro-4H-imidazol-4-one

Step 1—1-(4-(difluoromethoxy)phenyl)-2-(3-(3-hydroxyprop-1-ynyl)phenyl)ethane-1,2-dione A mixture of 1-(3-bromophenyl)-2-(4-(difluoromethoxy)phenyl)ethane-1,2-dione (0.500 g, 1.41 mmol), prop-2-yn-1-ol (0.395 g, 7.04 mmol), bis(triphenylphosphine)palladium(II) chloride (0.099 g, 0.14 mmol), copper(I) iodide (0.021 g, 0.11 mmol) and triethylamine (0.62 g, 6.11 mmol) in $CH_3CN$ (3 mL) was stirred at 60° C. overnight. The solvent is removed and the material is absorbed onto celite and purified by flash chromatography (silica, 25:75 ethyl acetate/hexanes) to afford 1-(4-(difluoromethoxy)phenyl)-2-(3-(3-hydroxyprop-1-ynyl)phenyl)ethane-1,2-dione (0.326 g, 70%) as an off white solid.

Step 2—1-(4-(difluoromethoxy)phenyl)-2-(3-(3-fluoroprop-1-ynyl)phenyl)ethane-1,2-dione 1-(4-(Difluoromethoxy)phenyl)-2-(3-(3-hydroxyprop-1-ynyl)phenyl)ethane-1,2-dione (0.298 g, 0.90 mmol) is dissolved in $CH_2Cl_2$ (3.0 mL) and cooled to −78° C. DAST (0.160 g, 0.99 mmol) is added and the solution is slowly warmed to RT. After 1 h at RT a saturated solution of $NaHCO_3$ is added and the mixture extracted with $CH_2Cl_2$. The $CH_2Cl_2$ is washed with $H_2O$ and brine. The solution is dried ($MgSO_4$) and the material purified by flash chromatography to yield 1-(4-(difluoromethoxy)phenyl)-2-(3-(3-fluoroprop-1-ynyl)phenyl)ethane-1,2-dione (0.232, 77%).

Step 3—2-amino-5-[4-(difluoromethoxy)phenyl]-5-[3-(3-fluoroprop-1-yn-1-yl)phenyl]-3-methyl-3,5-dihydro-4H-imidazol-4-one 1-(4-(Difluoromethoxy)phenyl)-2-(3-(3-fluoroprop-1-ynyl)phenyl)ethane-1,2-dione (0.206 g, 0.59 mmol) was dissolved in ethanol (5 mL). Methylguanidine hydrochloride (0.081 g, 0.74 mmol) was added followed by sodium carbonate (0.78 g, 0.74 mmol). The mixture was stirred at 85° C. overnight 15 hours. The solvent was removed and the material is absorbed onto celite. Purification by flash chromatography afforded (silica, 10/1 $CH_2Cl_2$/MeOH) 2-amino-5-[4-(difluoromethoxy)phenyl]-5-[3-(3-fluoroprop-1-yn-1-yl)phenyl]-3-methyl-3,5-dihydro-4H-imidazol-4-one (0.165 g, 69%).

Example 98

Preparation of 2-amino-5-[4-(difluoromethoxy)phenyl]-5-[3-(4-fluorobut-1-yn-1-yl)phenyl]-3-methyl-3,5-dihydro-4H-imidazol-4-one This material was synthesized in a fashion similar to 2-amino-5-[4-(difluoromethoxy)phenyl]-5-[3-(3-fluoroprop-1-yn-1-yl)phenyl]-3-methyl-3,5-dihydro-4H-imidazol-4-one by coupling 1-(4-(difluoromethoxy)phenyl)-2-(3-(3-hydroxyprop-1-ynyl)phenyl)ethane-1,2-dione with but-3-yn-1-ol in step 1.
MS (ES) m/z 400.2; MS (ES) m/z 460.2

Example 99

Preparation of 2-amino-5-[4-(difluoromethoxy)phenyl]-5-[4-fluoro-3-(3-fluoroprop-1-yn-1-yl)phenyl]-3-methyl-3,5-dihydro-4H-imidazol-4-one This material was synthesized in a fashion similar to 2-amino-5-[4-(difluoromethoxy)phenyl]-5-[3-(3-fluoroprop-1-yn-1-yl)phenyl]-3-methyl-3,5-dihydro-4H-imidazol-4-one by coupling 1-(3-bromo-4-fluorophenyl)-2-(4-(difluoromethoxy)phenyl)ethane-1,2-dione with prop-2-yn-1-ol in step 1.
MS (ES) m/z 404.2; MS (ES) m/z 809.4

Example 100

Preparation of (5R)-2-amino-5-[4-(difluoromethoxy)phenyl]-5-[3-(3-fluoroprop-1-yn-1-yl)phenyl]-3-methyl-3,5-dihydro-4H-imidazol-4-one The title compound is achieved through chiral separation of 2-amino-5-[4-(difluoromethoxy)phenyl]-5-[3-(3-fluoroprop-1-yn-1-yl)phenyl]-3-methyl-3,5-dihydro-4H-imidazol-4-one.
$[\alpha]_D^{25}$=+4.0° (c=1% SOLUTION, MeOH);
MS (ES) m/z 386.2; MS (ES) m/z 773.4

Example 101

Preparation of (5S)-2-amino-5-[4-(difluoromethoxy)phenyl]-5-[3-(3-fluoroprop-1-yn-1-yl)phenyl]-3-methyl-3,5-dihydro-4H-imidazol-4-one The title compound is achieved through chiral separation of 2-amino-5-[4-(difluoromethoxy)phenyl]-5-[3-(3-fluoroprop-1-yn-1-yl)phenyl]-3-methyl-3,5-dihydro-4H-imidazol-4-one.
MS (ES) m/z 386.2; MS (ES) m/z 773.4

Example 102

Preparation of 2-amino-5-[4-(difluoromethoxy)phenyl]-5-[4-fluoro-3-(4-fluorobut-1-yn-1-yl)phenyl]-3-methyl-3,5-dihydro-4H-imidazol-4-one This material was synthesized in a fashion similar to 2-amino-5-[4-(difluoromethoxy)phenyl]-5-[3-(3-fluoroprop-1-yn-1-yl)phenyl]-3-methyl-3,5-dihydro-4H-imidazol-4-one by coupling 1-(3-bromo-4-fluorophenyl)-2-(4-(difluoromethoxy)phenyl)ethane-1,2-dione with but-3-yn-1-ol in step 1.
MS (ES) m/z 418.2; MS (ES) m/z 837.4

Example 103

Preparation of (5S)-2-amino-5-[4-(difluoromethoxy)phenyl]-5-[4-fluoro-3-(4-fluorobut-1-yn-1-yl)phenyl]-3-methyl-3,5-dihydro-4H-imidazol-4-one The title compound is achieved through chiral separation of 2-amino-5-[4-(difluoromethoxy)phenyl]-5-[4-fluoro-3-(4-fluorobut-1-yn-1-yl)phenyl]-3-methyl-3,5-dihydro-4H-imidazol-4-one.
$[\alpha]_D^{25}$=+7.00° (c=1% SOLUTION, MeOH);
MS (ES) m/z 418.1; MS (ES) m/z 837.3

Example 104

Preparation of (5R)-2-amino-5-[4-(difluoromethoxy)phenyl]-5-[4-fluoro-3-(4-fluorobut-1-yn-1-yl)phenyl]-3-methyl-3,5-dihydro-4H-imidazol-4-one The title compound is achieved through chiral separation of 2-amino-5-[4-(difluoromethoxy)phenyl]-5-[4-fluoro-3-(4-fluorobut-1-yn-1-yl)phenyl]-3-methyl-3,5-dihydro-4H-imidazol-4-one.

$[\alpha]_D^{25}=-12.0°$ (c=1% SOLUTION, MeOH);
MS (ES) m/z 418.1; MS (ES) m/z 837.3

Example 105

Preparation of (5S)-2-amino-5-[4-(difluoromethoxy)phenyl]-5-[3-(4-fluorobut-1-yn-1-yl)phenyl]-3-methyl-3,5-dihydro-4H-imidazol-4-one The title compound is achieved through chiral separation of 2-amino-5-[4-(difluoromethoxy)phenyl]-5-[3-(4-fluorobut-1-yn-1-yl)phenyl]-3-methyl-3,5-dihydro-4H-imidazol-4-one.

MS (ES) m/z 400.1; MS (ES) m/z 801.2

Example 106

Preparation of (5R)-2-amino-5-[4-(difluoromethoxy)phenyl]-5-[3-(4-fluorobut-1-yn-1-yl)phenyl]-3-methyl-3,5-dihydro-4H-imidazol-4-one The title compound is achieved through chiral separation of 2-amino-5-[4-(difluoromethoxy)phenyl]-5-[3-(4-fluorobut-1-yn-1-yl)phenyl]-3-methyl-3,5-dihydro-4H-imidazol-4-one.

MS (ES) m/z 402.1; MS (ES) m/z 803.1

Example 107

(5R)-2-amino-5-[4-(difluoromethoxy)phenyl]-5-[4-fluoro-3-(3-fluoroprop-1-yn-1-yl)phenyl]-3-methyl-3,5-dihydro-4H-imidazol-4-one The title compound is achieved through chiral separation of 2-amino-5-[4-(difluoromethoxy)phenyl]-5-[4-fluoro-3-(3-fluoroprop-1-yn-1-yl)phenyl]-3-methyl-3,5-dihydro-4H-imidazol-4-one.

MS (ES) m/z 404.1; MS (ES) m/z 809.2

Example 108

(5S)-2-amino-5-[4-(difluoromethoxy)phenyl]-5-[4-fluoro-3-(3-fluoroprop-1-yn-1-yl)phenyl]-3-methyl-3,5-dihydro-4H-imidazol-4-one The title compound is achieved through chiral separation of 2-amino-5-[4-(difluoromethoxy)phenyl]-5-[4-fluoro-3-(3-fluoroprop-1-yn-1-yl)phenyl]-3-methyl-3,5-dihydro-4H-imidazol-4-one.

MS (ES) m/z 406.1; MS (ES) m/z 447.2.

Examples 109-141

Examples 109-141 are prepared according to synthetic methodology provided in Examples 1-108. Many of the compounds were screened for biological activity according to the Biological Example. Activities are shown wherein: A=≦0.01 μM-0.10 μM; B=0.11 μM-1.00 μM; and C=>1.00 μM.

| Example No. | COMPOUND | NAME | BACE1 IC$_{50}$ (μM) |
|---|---|---|---|
| 109 | | 2-amino-5-[4-(difluoromethoxy)phenyl]-5-{3-[(1E)-3-ethoxy-1-methylprop-1-en-1-yl]phenyl}-3-methyl-3,5-dihydro-4H-imidazol-4-one | B |
| 110 | | 2-amino-5-[4-(difluoromethoxy)phenyl]-3-methyl-5-{3-[(1S)-1-methylbut-3-en-1-yl]phenyl}-3,5-dihydro-4H-imidazol-4-one | B |

-continued

| Example No. | COMPOUND | NAME | BACE1 IC$_{50}$ (μM) |
|---|---|---|---|
| 111 | | 2-amino-5-[4-(difluoromethoxy)phenyl]-5-[3-(3-methoxy-1-methylpropyl)phenyl]-3-methyl-3,5-dihydro-4H-imidazol-4-one | C |
| 112 | | 2-amino-5-[4-(difluoromethoxy)phenyl]-5-[3-(3-ethoxy-1-methylpropyl)phenyl]-3-methyl-3,5-dihydro-4H-imidazol-4-one | C |
| 113 | | 2-amino-5-[4-(difluoromethoxy)phenyl]-3-methyl-5-(2-methyl-1-benzofuran-5-yl)-3,5-dihydro-4H-imidazol-4-one | C |
| 114 | | 2-amino-5-[4-(difluoromethoxy)phenyl]-3-methyl-5-(2-methyl-1-benzofuran-5-yl)-3,5-dihydro-4H-imidazol-4-one | B |
| 115 | | 2-amino-5-(3-aminophenyl)-5-[4-(difluoromethoxy)phenyl]-3-methyl-3,5-dihydro-4H-imidazol-4-one | C |

-continued

| Example No. | COMPOUND | NAME | BACE1 IC$_{50}$ (μM) |
|---|---|---|---|
| 116 | | N-(3-{2-amino-4-[4-(difluoromethoxy)phenyl]-1-methyl-5-oxo-4,5-dihydro-1H-imidazol-4-yl}phenyl)acetamide | B |
| 117 | | N-(3-{2-amino-4-[4-(difluoromethoxy)phenyl]-1-methyl-5-oxo-4,5-dihydro-1H-imidazol-4-yl}phenyl)-2,3-dihydro-1-benzofuran-5-carboxamide | A |
| 118 | | (5S)-2-amino-5-[4-(difluoromethoxy)phenyl]-3-methyl-5-[3-(3-methylbut-1-yn-1-yl)phenyl]-3,5-dihydro-4H-imidazol-4-one | C |
| 119 | | (5S)-2-amino-5-[3-(cyclopropylethynyl)-4-fluorophenyl]-5-[4-(difluoromethoxy)phenyl]-3-methyl-3,5-dihydro-4H-imidazol-4-one | C |
| 120 | | 2-amino-5-[4-(difluoromethoxy)phenyl]-5-[3-(3-hydroxypent-4-yn-1-yl)phenyl]-3methyl-3,5-dihydro-4H-imidazol-4-one | — |

-continued

| Example No. | COMPOUND | NAME | BACE1 IC$_{50}$ (μM) |
|---|---|---|---|
| 121 | | 2-amino-5-[4-(difluoromethoxy)phenyl]-5-(3-hex-5-en-1-ylphenyl)-3-methyl-3,5dihydro-4H-imidazol-4-one | A |
| 122 | | 2-amino-5-[4-(difluoromethoxy)phenyl]-5-{3-[(1E)-4-fluoro-1-methylbut-1-en-1-yl]phenyl}-3-methyl-3,5-dihydro-4H-imidazol-4-one | — |
| 123 | | 2-amino-5-[4-(difluoromethoxy)phenyl]-5-{3-[(1E)-3,3-difluoroprop-1-en-1-yl]phenyl}-3-methyl-3,5-dihydro-4H-imidazol-4-one | — |
| 124 | | 2-amino-5-[4-(difluoromethoxy)phenyl]-5-{3-[(1E)-3-fluoroprop-1-en-1-yl]phenyl}3-methyl-3,5-dihydro-4H-imidazol-4-one | — |
| 125 | | 2-amino-5-[4-(difluoromethoxy)phenyl]-5-(3-hex-5-en-1-ylphenyl)-3-methyl-3,5-dihydro-4H-imidazol-4-one | A |

-continued

| Example No. | COMPOUND | NAME | BACE1 IC$_{50}$ (μM) |
|---|---|---|---|
| 126 | | 2-amino-5-[4-(difluoromethoxy)phenyl]-5-(3-hexylphenyl)-3-methyl-3,5-dihydro-4Himidazol-4-one | B |
| 127 | | (5R)-2-amino-5-[3-(cyclopropylmethoxy)phenyl]-5-[4-(difluoromethoxy)phenyl]-3methyl-3,5-dihydro-4H-imidazol-4-one | A |
| 128 | | (5S)-2-amino-5-[3-(cyclopropylmethoxy)phenyl]-5-[4-(difluoromethoxy)phenyl]-3methyl-3,5-dihydro-4H-imidazol-4-one | C |
| 129 | | (R,E)-2-amino-4-(4-(difluoromethoxy)phenyl)-4-(3-(6-methoxyhex-1-enyl)phenyl)-1-methyl-1H-imidazol-5(4H)-one | A |
| 130 | | (5S)-2-amino-5-[3-(2,2-difluoroethoxy)phenyl]-5-[4-(difluoromethoxy)phenyl]-3-methyl-3,5-dihydro-4H-imidazol-4-one | C |

-continued

| Example No. | COMPOUND | NAME | BACE1 IC$_{50}$ (μM) |
|---|---|---|---|
| 131 | | (5R)-2-amino-5-[3-(2,2-difluoroethoxy)phenyl]-5-[4-(difluoromethoxy)phenyl]-3-methyl-3,5-dihydro-4H-imidazol-4-one | A |
| 132 | | (5S)-2-amino-5-[4-(difluoromethoxy)phenyl]-5-{3-[(1E)-4-methoxybut-1-en-1-yl]phenyl}-3-methyl-3,5-dihydro-4H-imidazol-4-one | C |
| 133 | | (5R)-2-amino-5-[4-(difluoromethoxy)phenyl]-5-{3-[(1E)-4-methoxybut-1-en-1-yl]phenyl}-3-methyl-3,5-dihydro-4H-imidazol-4-one | A |
| 134 | | (S,E)-4-(4-(difluoromethoxy)phenyl)-4-(3-(3-methoxyprop-1-enyl)phenyl)-1-methyl-1H-imidazol-5(4H)-one | C |
| 135 | | (5R)-2-amino-5-[4-(difluoromethoxy)phenyl]-5-{3-[(1E)-3-methoxyprop-1-en-1-yl]phenyl}-3-methyl-3,5-dihydro-4H-imidazol-4-one | A |

-continued

| Example No. | COMPOUND | NAME | BACE1 IC$_{50}$ (μM) |
|---|---|---|---|
| 136 | | 2-amino-5-[4-(difluoromethoxy)phenyl]-5-(4-fluoro-3-isopropoxyphenyl)-3-methyl-3,5-dihydro-4H-imidazol-4-one | B |
| 137 | | 2-amino-5-[4-(difluoromethoxy)phenyl]-5-[4-fluoro-3-(2-fluoroethoxy)phenyl]-3methyl-3,5-dihydro-4H-imidazol-4-one | B |
| 138 | | 2-amino-5-[4-(difluoromethoxy)phenyl]-5-[4-fluoro-3-(3-methylbut-1-yn-1-yl)phenyl]-3-methyl-3,5-dihydro-4H-imidazol-4-one | A |
| 139 | | (5R)-2-amino-5-[4-(difluoromethoxy)phenyl]-5-{3-[(1E)-5-methoxypent-1-en-1-yl]phenyl}-3-methyl-3,5-dihydro-4H-imidazol-4-one | A |
| 140 | | (5R)-2-amino-5-[4-(difluoromethoxy)phenyl]-5-{4-fluoro-3-[(1E)-4-fluorobut-1-en1-yl]phenyl}-3-methyl-3,5-dihydro-4H-imidazol-4-one | C |

-continued

| Example No. | COMPOUND | NAME | BACE1 IC$_{50}$ (μM) |
|---|---|---|---|
| 141 | | (5S)-2-amino-5-[4-(difluoromethoxy)phenyl]-5-{4-fluoro-3-[(1E)-4-fluorobut-1-en-1-yl]phenyl}-3-methyl-3,5-dihydro-4H-imidazol-4-one | A |

Biological Example

Evaluation of BACE1 Binding Affinity of Test Compounds

Fluorescent Kinetic Assays

Final Assay Conditions: 10 nM human BACE1 (or 10 nM Murine BACE1, 1.5 nM human BACE2), 25 μM substrate (WABC-6, MW 1549.6, from AnaSpec), Buffer: 50 mM Na-Acetate, pH 4.5, 0.05% CHAPS, 25% PBS, room temperature. Na-Acetate was from Aldrich, Cat.#24, 124-5, CHAPS was from Research Organics, Cat. #1304C 1×, PBS was from Mediatech (Cellgro), Cat# 21-031-CV, peptide substrate AbzSEVNLDAEFRDpa (SEQ ID NO:1) was from AnaSpec, Peptide Name: WABC-6

Determination of stock substrate (AbzSEVNLDAE-FRDpa) (SEQ ID NO:1) concentration: ~25 mM stock solution is made in DMSO using the peptide weight and MW, and diluted to ~25 μM (1:1000) in 1×PBS. Concentration is determined by absorbance at 354 nm using an extinction coefficient ε of 18172 M$^{-1}$ cm$^{-1}$, the concentration of stock substrate is corrected, and the substrate stock stored in small aliquots in −80° C.

[Substrate Stock]=ABS$^{354\,nm}$*10$^6$/18172 (in mM)

The extinction coefficient ε$^{354\,nm}$ was adapted from TACE peptide substrate, which had the same quencher-fluorophore pair.

Determination of Stock Enzyme Concentration: the stock concentration of each enzyme is determined by absorbance at 280 nm using an ε of 64150 M$^{-1}$ cm$^{-1}$ for hBACE1 and MuBACE1, 62870 M$^{-1}$ cm$^{-1}$ for hBACE2 in 6 M Guanidinium Hydrochloride (from Research Organics, Cat. # 5134G-2), pH ~6. The extinction coefficient ε$^{280\,nm}$ for each enzyme was calculated based on known amino acid composition and published extinction coefficients for Trp (5.69 M$^{-1}$ cm$^{-1}$) and Tyr (1.28 M$^{-1}$ cm$^{-1}$) residues (*Anal. Biochem.* 182, 319-326).

Dilution and mixing steps: total reaction volume: 100 μL

2× inhibitor dilutions in buffer A (66.7 mM Na-Acetate, pH 4.5, 0.0667% CHAPS) were prepared, 4× enzyme dilution in buffer A (66.7 mM Na-Acetate, pH 4.5, 0.0667% CHAPS) were prepared, 100 μM substrate dilution in 1×PBS was prepared, and 50 μL 2× Inhibitor, 25 μL 100 μM substrate are added to each well of 96-well plate (from DYNEX Technologies, VWR #: 11311-046), immediately followed by 25 μL 4× enzyme (added to the inhibitor and substrate mix), and the fluorescence readings are initiated.

Fluorescence Readings: Readings at λ$_{ex}$ 320 nm and λ$_{em}$ 420 nm are taken every 40 sec for 30 min at room temperature and the linear slope for substrate cleavage rate ($v_i$) determined.

Calculation of % Inhibition:

% Inhibition=100*(1−$v_i$/$v_0$)

$v_i$: substrate cleavage rate in the presence of inhibitor $v_0$: substrate cleavage rate in the absence of inhibitor IC$_{50}$ Determination:

% Inhibition=((B*IC$_{50}^n$)+(100*I$_0^n$))/(IC$_{50}^n$+I$_0^n$)

(Model # 39 from LSW Tool Bar in Excel where B is the % inhibition from the enzyme control, which should be close to 0.) % Inhibition is plotted vs. Inhibitor Concentration (I$_0$) and the data fit to the above equation to obtain IC$_{50}$ value and Hill number (n) for each compound. Testing at least 10 different inhibitor concentrations is preferred.

Results are shown in the Activity Table.

ACTIVITY TABLE

| Example No. | BACE1 IC$_{50}$ μM |
|---|---|
| 1A | B |
| 1B | C |
| 2 | A |
| 3A | A |
| 3B | C |
| 4 | A |
| 5A | B |
| 5B | A |
| 6 | B |
| 7A | C |
| 7B | A |
| 8 | A |
| 9 | A |
| 10A | A |
| 10B | B |
| 10C | A |
| 10D | A |
| 10E | B |
| 10F | A |
| 10G | A |
| 10H | A |

-continued

ACTIVITY TABLE

| Example No. | BACE1 IC$_{50}$ μM |
|---|---|
| 11A | A |
| 11B | C |
| 12 | A |
| 13 | B |
| 14 | A |
| 15 | B |
| 16 | C |
| 17 | B |
| 18 | C |
| 19B | A |
| 19C | B |
| 19D | A |
| 19E | A |
| 19F | C |
| 20A | A |
| 20B | A |
| 21 | B |
| 22 | B |
| 23 | B |
| 24 | B |
| 25 | A |
| 26 | A |
| 27 | B |
| 28 | B |
| 29 | B |
| 30 | B |
| 31 | C |
| 32 | B |
| 33 | A |
| 34 | B |
| 35 | B |
| 36 | A |
| 37 | — |
| 38 | — |
| 39 | A |
| 40 | A |
| 41 | — |
| 42 | B |
| 43 | A |
| 44 | A |
| 45 | A |
| 46 | B |
| 47 | A |
| 48 | B |
| 49 | B |
| 50 | B |
| 51 | A |
| 52 | C |
| 53 | C |
| 54 | A |
| 55 | B |
| 56 | C |
| 57 | B |
| 58 | B |
| 59 | B |
| 60 | B |
| 61 | B |
| 62 | C |
| 63 | B |
| 64 | B |
| 65 | B |
| 66 | C |
| 67 | C |
| 68 | B |
| 69 | B |
| 70 | C |

-continued

ACTIVITY TABLE

| Example No. | BACE1 IC$_{50}$ μM |
|---|---|
| 71 | B |
| 72 | A |
| 73 | A |
| 74 | B |
| 75A | B |
| 75B | B |
| 75C | C |
| 76A | C |
| 76B | C |
| 77A | C |
| 77B | A |
| 78 | B |
| 79A | A |
| 79B | B |
| 80 | A |
| 81 | B |
| 82 | A |
| 83 | A |
| 84 | A |
| 85 | A |
| 86 | B |
| 87 | A |
| 88 | B |
| 89 | A |
| 90 | A |
| 91 | C |
| 92 | A |
| 93 | B |
| 94 | A |
| 95 | B |
| 96 | A |
| 97 | A |
| 98 | A |
| 99 | A |
| 100 | A |
| 101 | C |
| 102 | A |
| 103 | C |
| 104 | A |
| 105 | C |
| 106 | A |
| 107 | A |
| 108 | C |

For Activity Table

A = ≦0.01 μM-0.10 μM

B = 0.11 μM-1.00 μM

C = >1.00 μM

What is claimed is:

1. A compound of formula I

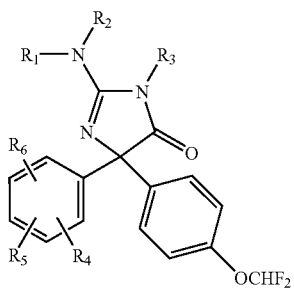

(I)

wherein, $R_1$ and $R_2$ are each independently H or an alkyl, cycloalkyl, cycloheteroalkyl, aryl or heteroaryl group each optionally substituted or $R_1$ and $R_2$ may be taken together with the atom to which they are attached form an optionally substituted 5- to 7-membered ring optionally containing an additional heteroatom selected from O, N or S;

$R_3$ is H or an alkyl, cycloalkyl, cycloheteroalkyl, aryl or heteroaryl group each optionally substituted $R_4$, $R_5$ and $R_6$ are each independently H, halogen, $NO_2$, CN, $COR_7$, $NR_{10}CO_2R_{11}$, $NR_{15}COR_{16}$, $OR_{14}$, $NR_{12}R_{13}$, $SO_nR_{17}$ or an alkyl, haloalkyl, alkenyl, haloalkenyl, alkynyl, cycloalkyl or cycloheteroalkyl group each optionally substituted or when attached to adjacent carbon atoms $R_4$ and $R_5$ may be taken together with the atoms to which they are attached to form an optionally substituted 5- to 7-membered ring optionally containing one or two heteroatoms selected from O, N or S;

n is 0, 1 or 2;

$R_7$ and $R_{17}$ are each independently H, $NR_8R_9$ or an alkyl, haloalkyl, alkoxyalkyl, alkenyl, alkynyl, cycloalkyl or aryl group each optionally substituted;

$R_8$ and $R_9$ are each independently H or an alkyl, alkenyl, alkynyl or cycloalkyl group each optionally substituted or $R_8$ and $R_9$ may be taken together with the atom to which they are attached to form an optionally substituted 5- to 7-membered ring optionally containing an additional heteroatom selected from O, N or S;

$R_{11}$, $R_{14}$ and $R_{16}$ are each independently H or an alkyl, haloalkyl, alkoxyalkyl, alkenyl, alkynyl, cycloalkyl, heteroaryl or an aryl group each optionally substituted;

$R_{10}$ and $R_{15}$ are each independently H or an optionally substituted alkyl group; and $R_{12}$ and $R_{13}$ are each independently H or an alkyl, alkenyl, aryl or cycloalkyl group each optionally substituted or $R_{12}$ and $R_{13}$ may be taken together with the atom to which they are attached to form an optionally substituted 5- to 7-membered ring optionally containing an additional heteroatom selected from O, N or S;

or a tautomer thereof, a stereoisomer thereof or a pharmaceutically acceptable salt thereof;

provided that the compound is not selected from the group consisting of:

2-amino-5-[4-(difluoromethoxy)phenyl]-3-methyl-5-phenyl-3,5-dihydro-4H-imidazol-4-one;

(5S)-2-Amino-5-[4-(difluoromethoxy)phenyl]-3-methyl-5-phenyl-3,5-dihydro-4H-imidazol-4-one;

(5R)-2-Amino-5-[4-(difluoromethoxy)-phenyl]-3-methyl-5-phenyl-3,5-dihydro-4H-imidazol-4-one (5R)-2-amino-5-(3-bromophenyl)-5-[4-(difluoromethoxy)phenyl]-3-methyl-3,5-dihydro-4H-imidazol-4-one;

2-amino-5-(3-bromophenyl)-5-[4-(difluoromethoxy)phenyl]-3-methyl-3,5-dihydro-4H-imidazol-4-one;

(5R)-2-Amino-5-(3-bromo-4-fluorophenyl)-5-[4-(difluoromethoxy)phenyl]-3-methyl-3,5-dihydro-4H-imidazol-4-one;

2-Amino-5-(3-bromo-4-fluorophenyl)-5-[4-(difluoromethoxy)phenyl]-3-methyl-3,5-dihydro-4H-imidazol-4-one;

2-Amino-5-[4-(difluoromethoxy)phenyl]-3-methyl-5-(3-propylphenyl)-3,5-dihydro-4H-imidazol-4-one;

(5R)-2-Amino-5-[4-(difluoromethoxy)phenyl]-3-methyl-5-(3-propylphenyl)-3,5-dihydro-4H-imidazol-4-one;

(5S)-2-Amino-5-[4-(difluoromethoxy)phenyl]-3-methyl-5-(3-propylphenyl)-3,5-dihydro-4H-imidazol-4-one;

(5R)-2-amino-5-(3-butylphenyl)-5-[4-(difluoromethoxy)phenyl]-3-methyl-3,5-dihydro-4H-imidazol-4-one;

(5S)-2-amino-5-(3-butylphenyl)-5-[4-(difluoromethoxy)phenyl]-3-methyl-3,5-dihydro-4H-imidazol-4-one;

2-amino-5-(3-butylphenyl)-5-[4-(difluoromethoxy)phenyl]-3-methyl-3,5-dihydro-4H-imidazol-4-one;

2-Amino-5-[4-(difluoromethoxy)phenyl]-3-methyl-5-(3-pentylphenyl)-3,5-dihydro-4H-imidazol-4-one;

2-Amino-5-[4-(difluoromethoxy)phenyl]-3-methyl-5-[3-(2-methylbutyl)phenyl]-3,5-dihydro-4H-imidazol-4-one;

2-Amino-5-(3-but-3-en-1-ylphenyl)-5-[4-(difluoromethoxy)phenyl]-3-methyl-3,5-dihydro-4H-imidazol-4-one;

2-Amino-5-[3-(cyclopropylmethyl)phenyl]-5-[4-(difluoromethoxy)phenyl]-3-methyl-3,5-dihydro-4H-imidazol-4-one 3-(3-{2-Amino-4-[4-(difluoromethoxy)phenyl]-1-methyl-5-oxo-4,5-dihydro-1H-imidazol-4-yl}phenyl)propanenitrile:

(5R)-2-Amino-5-[4-(difluoromethoxy)phenyl]-3-methyl-5-(3-pent-4-en-1-ylphenyl)-3,5-dihydro-4H-imidazol-4-one;

(5S)-2-Amino-5-[4-(difluoromethoxy)phenyl]-3-methyl-5-(3-pent-4-en-1-ylphenyl)-3,5-dihydro-4H-imidazol-4-one;

2-Amino-5-[4-(difluoromethoxy)phenyl]-3-methyl-5-(3-pent-4-en-1-ylphenyl)-3,5-dihydro-4H-imidazol-4-one;

N-(3-{(4R)-2-Amino-4-[4-(difluoromethoxy)phenyl]-1-methyl-5-oxo-4,5-dihydro-1H-imidazol-4-yl}phenyl)-2-methoxyacetamide;

N-(3-{(4S)-2-Amino-4-[4-(difluoromethoxy)phenyl]-1-methyl-5-oxo-4,5-dihydro-1H-imidazol-4-yl}phenyl)-2-methoxyacetamide;

N-(3-{2-Amino-4-[4-(difluoromethoxy)phenyl]-1-methyl-5-oxo-4,5-dihydro-1H-imidazol-4-yl}phenyl)-2-methoxyacetamide;

2-Amino-5-[4-(difluoromethoxy)phenyl]-3-methyl-5-[3-(4,414-trifluorobutyl)phenyl]-3,5-dihydro-4H-imidazol-4-one;

5-(3-{2-Amino-4-[4-(difluoromethoxy)phenyl]-1-methyl-5-oxo-4,5-dihydro-1H-imidazol-4-yl}phenyl)pentanenitrile;

4-(3-{2-amino-4-[4-(difluoromethoxy)phenyl]-1-methyl-5-oxo-4,5-dihydro-1H-imidazol-4-yl}phenyl)butanenitrile;

2-Amino-5-[3-(1,4-difluorobutyl)phenyl]-5-[4-(difluoromethoxy)-phenyl]-3-methyl-3,5-dihydro-4H-imidazol-4-one;

2-Amino-5-[4-(difluoromethoxy)phenyl]-5-[3-(3-fluorobut-3-en-1-yl)phenyl]-3-methyl-3,5-dihydro-4H-imidazol-4-one 2-Amino-5-[3-(4,4-difluorobut-3-en-1-yl)phenyl]-5-[4-(difluoromethoxy)phenyl]-3-methyl-3,5-dihydro-4H-imidazol-4-one 2-Amino-5-[3-(4,4-difluorobutyl)phenyl]-5-[4-(difluoromethoxy)-phenyl]-3-methyl-3,5-dihydro-4H-imidazol-4-one;

2-Amino-5-[4-(difluoromethoxy)phenyl]-5-[3-(4-hydroxybut-1-yn-1-yl)phenyl]-3-methyl-3,5-dihydro-4H-imidazol-4-one;

2-Amino-5-[4-(difluoromethoxy)phenyl]-5-[3-(4-hydroxybutyl)-phenyl]-3-methyl-3,5-dihydro-4H-imidazol-4-one 2-Amino-5-[4-(difluoromethoxy)phenyl]-5-[3-(3-methoxyprop-1-yn-1-yl)-phenyl]-3-methyl-3,5-dihydro-4H-imidazol-4-one;

2-Amino-5-[4-(difluoromethoxy)phenyl]-5-{3-[(1Z)-3-methoxyprop-1-en-1-yl]phenyl}-3-methyl-3,5-dihydro-4H-imidazol-4-one;

2-Amino-5-[4-(difluoromethoxy)phenyl]-5-[3-(3-methoxypropyl)phenyl]-3-methyl-3,5-dihydro-4H-imidazol-4-one 2-Amino-5-[4-(difluoromethoxy)phenyl]-5-[3-(5-fluoropentyl)-phenyl]-3-methyl-3,5-dihydro-4H-imidazol-4-one 2-Amino-5-[4-(difluoromethoxy)phenyl]-5-[3-(4-fluorobutyl)-phenyl]-3-methyl-3,5-dihydro-4H-imidazol-4-one;

2-Amino-5-[4-(difluoromethoxy)phenyl]-5-[3-(6-fluorohexyl)-phenyl]-3-methyl-3,5-dihydro-4H-imidazol-4-one;

2-Amino-5-[4-(difluoromethoxy)phenyl]-5-[3-(6-fluorohexyl)-phenyl]-3-methyl-3,5-dihydro-4H-imidazol-4-one;

3-{2-Amino-4-[4-(difluoromethoxy)phenyl]-1-methyl-5-oxo-4,5-dihydro-1H-imidazol-4-yl}-N-propylbenzamide;

2-Amino-5-[4-(difluoromethoxy)phenyl]-5-{3-[(2-fluoroethoxy)-methyl]phenyl}-3-methyl-3,5-dihydro-4H-imidazol-4-one;

2-amino-5-[4-(difluoromethoxy)phenyl]-3-methyl-5-{3-[(2,2,2-trifluoroethoxy)methyl]phenyl}-3,5-dihydro-4H-imidazol-4-one;

2-amino-5-[4-(difluoromethoxy)phenyl]-3-methyl-5-{3-[(2,2,3,3-tetrafluoropropoxy)methyl]phenyl}-3,5-dihydro-4H-imidazol-4-one;

2-Amino-5-[4-(difluoromethoxy)phenyl]-5-{3-[(1E)-6-methoxy-hex-1-en-1-yl]-phenyl}-3-methyl-3,5-dihydro-4H-imidazol-4-one;

2-Amino-5-[4-(difluoromethoxy)phenyl]-5-{3-[(1E)-5-hydroxy-pent-1-en-1-yl]-phenyl}-3-methyl-3,5-dihydro-4H-imidazol-4-one;

2-Amino-5-[4-(difluoromethoxy)phenyl]-5-{3-[2-(methoxymethyl)-cyclopropyl]phenyl}-3-methyl-3,5-dihydro-4H-imidazol-4-one;

2-Amino-5-[4-(difluoromethoxy)phenyl]-5-{3-[2-(2-methoxyethyl)-cyclopropyl]phenyl}-3-methyl-3,5-dihydro-4H-imidazol-4-one;

5-(3-Acetylphenyl)-2-amino-5-[4-(difluoromethoxy)phenyl]-3-methyl-3,5-dihydro-4H-imidazol-4-one;

2-Amino-5-[4-(difluoromethoxy)phenyl]-5-[3-(3-hydroxyhex-4-yn-1-yl)phenyl]-3-methyl-3,5-dihydro-4H-imidazol-4-one 2-Amino-5-[4-(difluoromethoxy)phenyl]-5-[3-(3-fluoroprop-1-yn-1-yl)phenyl]-3-methyl-3,5-dihydro-4H-imidazol-4-one 2-Amino-5-[4-(difluoromethoxy)phenyl]-5-(3hydroxyphenyl)-3-methyl-3,5-dihydro-4H-imidazol-4-one;

2-Amino-5-[4-(difluoromethoxy)phenyl]-5-[3-(3-fluoropropox-1-yl)phenyl]-3-methyl-3,5-dihydro-4H-imidazol-4-one;
2-Amino-5-[4-(difluoromethoxy)phenyl]-5-(4-fluoro-3-hydroxy-phenyl)-3-methyl-3,5-dihydro-4H-imidazol-4-one;
(5R)-2-Amino-5-[4-(difluoromethoxy)phenyl]-5-[4-fluoro-3-(3-fluoropropox-1-yl)phenyl]-3-methyl-3,5-dihydro-4H-imidazol-4-one;
(5S)-2-Amino-5-[4-(difluoromethoxy)phenyl]-5-[4-fluoro-3-(3-fluoropropox-1-yl)phenyl]-3-methyl-3,5-dihydro-4H-imidazol-4-one;
(5R)-2-Amino-5-[3-(2,2-difluoroethoxy)-4-fluorophenyl]-5-[4-(difluoromethoxy)phenyl]-3-methyl-3,5-dihydro-4H-imidazol-4-one;
(5S)-2-Amino-5-[3-(2,2-difluoroethoxy)-4-fluorophenyl]-5-[4-(difluoromethoxy)phenyl]-3-methyl-3,5-dihydro-4H-imidazol-4-one;
2-Amino-5-{3-[(4,4-difluorobut-3-en-1-yl)oxy]phenyl}-5-[4-(difluoromethoxy)phenyl]-3-methyl-3,5-dihydro-4H-imidazol-4-one
2-Amino-5-{3-[(4,4-difluorobut-3-en-1-yl)oxy]-4-fluorophenyl}-5-[4-(difluoromethoxy)phenyl]-3-methyl-3,5-dihydro-4H-imidazol-4-one
2-Amino-5-[4-(difluoromethoxy)phenyl]-5-(4-fluoro-3-pent-4-en-1-yl)-3-methyl-3,5-dihydro-4H-imidazol-4-one
2-Amino-5-(3-but-3-en-1-yl-4-fluorophenyl)-5-[4-(difluoromethoxy)phenyl]-3-methyl-3,5-dihydro-4H-imidazol-4-one;
2-Amino-5-[4-(difluoromethoxy)phenyl]-5-[3-(1-hydroxybut-2-yn-1-yl)phenyl]-3-methyl-3,5-dihydro-4H-imidazol-4-one;
2-Amino-5-[4-(difluoromethoxy)phenyl]-5-[3-(1,4-dihydroxybut-2-yn-1-yl)phenyl]-3-methyl-3,5-dihydro-4H-imidazol-4-one;
2-Amino-5-[4-(difluoromethoxy)phenyl]-5-[3-(2,2-dimethyl-3-oxocyclobutyl)phenyl]-3-methyl-3,5-dihydro-4H-imidazol-4-one;
2-Amino-5-[4-(difluoromethoxy)phenyl]-3-methyl-5-[3-(3-oxocyclobutyl)phenyl]-3,5-dihydro-4H-imidazol-4-one
2-Amino-5-[4-(difluoromethoxy)phenyl]-5-[3-(3-hydroxy-cyclobutyl)phenyl]-3-methyl-3,5-dihydro-4H-imidazol-4-one
ethyl[3-(3-{2-Amino-4-[4-(difluoromethoxy)phenyl]-1-methyl-5-oxo-4,5-dihydro-1H-imidazol-4-yl}phenyl)cyclobutylidene]acetate;
methyl [3-(3-{2-Amino-4-[4-(difluoromethoxy)phenyl]-1-methyl-5-oxo-4,5-dihydro-1H-imidazol-4-yl}phenyl)cyclobutylidene]acetate;
methyl [3-(3-{2-Amino-4-[4-(difluoromethoxy)phenyl]-1-methyl-5-oxo-4,5-dihydro-1H-imidazol-4-yl}phenyl)cyclobutyl]acetate;
2-Amino-5-[3-(difluoromethoxy)phenyl]-5-[4-(difluoromethoxy)phenyl]-3-methyl-3,5-dihydro-4H-imidazol-4-one
(5S)-2-Amino-5-[3-(difluoromethoxy)phenyl]-5-[4-(difluoromethoxy)phenyl]-3-methyl-3,5-dihydro-4H-imidazol-4-one
(5R)-2-Amino-5-[3-(difluoromethoxy)phenyl]-5-[4-(difluoromethoxy)phenyl]-3-methyl-3,5-dihydro-4H-imidazol-4-one
2-Amino-5-[4-(difluoromethoxy)phenyl]-5-{3-[(1R)-1-fluoropent-4-en-1-yl]phenyl}-3-methyl-3,5-dihydro-4H-imidazol-4-one;
2-Amino-5-[4-(difluoromethoxy)phenyl]-5-{3-[(1R)-1-fluorobut-3-en-1-yl]phenyl}-3-methyl-3,5-dihydro-4H-imidazol-4-one;
N-(3-{2-Amino-4-[4-(difluoromethoxy)phenyl]-1-methyl-5-oxo-4,5-dihydro-1H-imidazol-4-yl}phenyl)ethanesulfonamide;
2-Amino-5-[4-(difluoromethoxy)phenyl]-5-[3-(5-hydroxypent-1-yn-1-yl)phenyl]-3-methyl-3,5-dihydro-4H-imidazol-4-one;
2-Amino-5-{3-[(E)-2-cyclopropylvinyl]phenyl}-5-[4-(difluoromethoxy)phenyl]-3-methyl-3,5-dihydro-4H-imidazol-4-one;

and provided that the compound is not as shown in any one of the following tables (A-H):

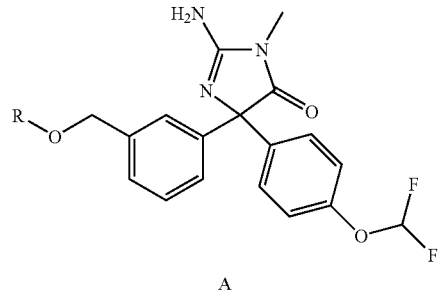

A

| R |
|---|
| $CH_2CH_2CF_3$ |
| $CH_3$ |
| $CH_2CH_2CH_2CH_3$ |
| $CH_2$-cyclopropyl |
| $CH_2CH_3$ |
| $CH_2CH_2CH_3$ |
| $CH(CH_2F)CH_2F$ |

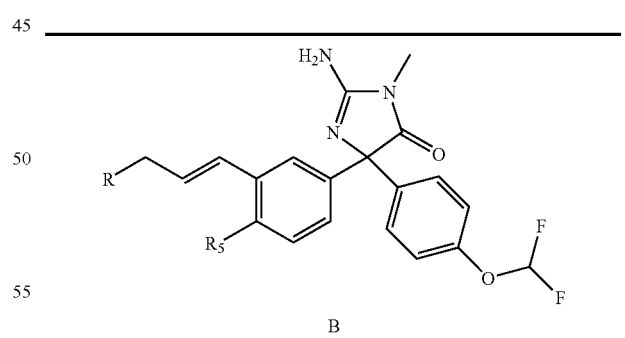

B

| R | R5 |
|---|---|
| $CH_2CH_2OCH_3$ | H |
| $OCH_3$ | H |
| $CH_2OCH_3$ | H |
| $CH_2OH$ | H |
| $CH_2F$ | H |
| $CH_2CH_2F$ | H |
| $CH_2F$ | F |
| $CHF_2$ | H |

| 187 | 188 |
|---|---|
| 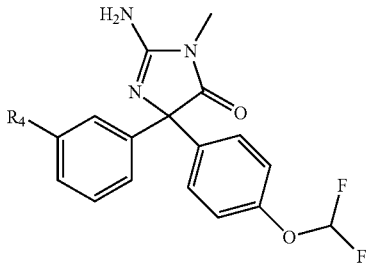<br>C | 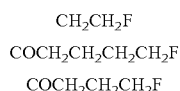<br>E |
| R4 | R |
| CH₂CH₂F<br>COCH₂CH₂CH₂F<br>COCH₂CH₂CH₂F | 3,4-difluorophenyl<br>3-methoxyphenyl<br>3-chlorophenyl<br>n-propyl<br>3-cyanophenyl<br>3-(trifluoromethoxy)phenyl<br>3-pyridyl<br>4-cyanophenyl<br>2-thienyl<br>benzyl<br>3,5-difluorophenyl |
| 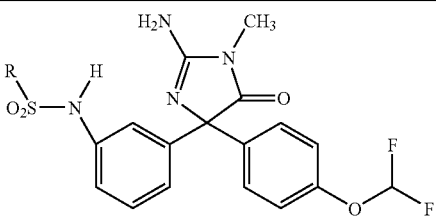<br>D | 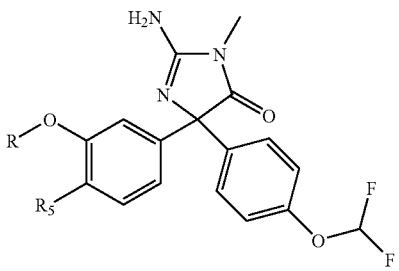<br>F |

| R | R⁵ |
|---|---|
| CH₂-cyclopropyl | H |
| CH₂CH₂CH₂CF₃ | H |
| CH₂CHF₂ | H |
| CH₂CH₂CH₂CH₂F | H |
| CH₂CH₂CH₂OC₆H₅ | H |
| CH₂CH₂CH₂CN | H |
| CH₂CH₂CHF₂ | F |
| H₂C—C≡C—CH₃ | F |
| CH₂CH₂CH₂CH₂F | F |
| CH₂CHF₂ | F |
| CH₂CH₂CH═CH₂ | H |
| CH₂CH₂CH═CH₂ | F |
| CH₂CH₂CH₂CH═CH₂ | H |
| (R)-CH₂CH(CH₃)CH₂CH═CH₂ | H |
| (S)-CH₂CH(CH₃)CH₂CH═CH₂ | H |
| CH₂═CHCH₂CH(CH₃)CH₂ | H |
| CH₃C(═CH₂)CH₂CH₂ | H |
| CH₂═CHCH₂ | H |

| Chiral | R | R' |
|---|---|---|
| — | CH₂OCH₃ | H |
| — | CH₂OCH₃ | CH₃ |
| 4-R | CH₂OCH₃ | H |
| 4-S | CH₂OCH₃ | H |

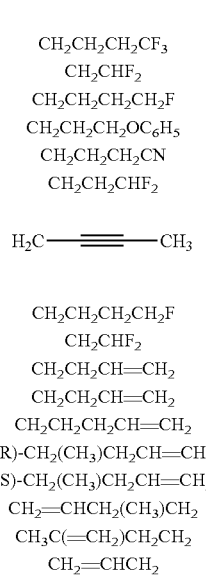
G

| Chiral | R | R5 |
|---|---|---|
| — | CH₂CH₂CH₂F | H |
| — | CH₂CH₂CH₂Cl | H |
| — | CH₂CH₂CH₃ | H |
| — | CH₂CH₂OH | H |
| — | CH₂CH₂CH₂CH₂OH | H |

-continued

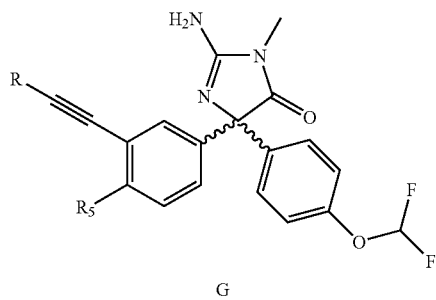

G

| Chiral | R | R5 |
|---|---|---|
| — | CH₂CH₂CH₂CH₂F | H |
| — | CH₂CH₂Cl | H |
| 5-R | CH₂CH₃ | H |
| 5-S | CH₂CH₃ | H |
| 5-S | CH₂CH₂CH₂OH | H |
| 5-R | CH₂CH₂CH₂CH₂OH | H |
| 5-S | CH₂CH₂CH₂CH₂OH | H |
| 5-R | CH₂CH₂OH | H |
| 5-S | CH₂CH₂OH | H |
| 5-S | CH₂CH₂CH₂F | H |
| 5-R | CH₂CH₂CH₂F | H |
| 5-S | CH₂CH₂CH₂OH | F |
| 5-R | CH₂CH₂CH₂OH | F |
| 5-S | CH₂CH₂CH₂F | F |
| 5-R | CH₂CH₂CH₂F | F |
| — | CH₂CH₂OCH₃ | H |
| — | CH₂OCH₃ | H |
| 5-S | CH₂CH₂OCH₃ | H |
| 5-R | CH₂CH₂OCH₃ | H |
| — | CH₂CH₂F | H |
| — | CH₂CH(CH₃)₂ | H |
| — | CH(OH)CH₂CH₃ | H |
| — | CH₂CH(OH)CH₃ | H |
| — | CH(CH₃)₂ | H |
| — | CH₂CH₃ | H |
| — | CH₂CH₂CH₂CH₃ | H |
| — | cyclopropyl | H |
| — | cyclohexyl | H |
| — | cyclopentylmethyl | H |
| — | cyclohexylmethyl | H |
| 5-S | CH₂OCH₃ | H |
| 5-R | CH₂OCH₃ | H |
| — | CH₂OCH₃ | F |
| — | CH₂CH₂OCH₃ | F |
| — | CH₂OH | H |
| — | (S)-CH(OH)CH₃ | H |
| — | (R)-CH(OH)CH₃ | H |
| — | CH(OH)CH(CH₃)₂ | H |
| — | 1-hydroxycyclopentyl | H |
| — | 1-hydroxycyclohexyl | H |
| — | C(OH)(CH₃)₂ | H |
| — | C(OH)(CH₃)CH₂CH₃ | H |
| — | H | H |
| — | (S)-CH(OH)C₆H₅ | H |
| 5-S | CH₂CH₂OCH₃ | H |
| 5-R | CH₂CH₂OCH₃ | H |
| 5-S | CH₂OCH₃ | H |
| 5-R | CH₂OCH₃ | H |
| — | CH₃ | F |
| — | CH₃ | H |
| 5-R | (S)-CH(OH)CH₃ | H |
| 5-S | (S)-CH(OH)CH₃ | H |
| 5-R | CH₃ | H |
| 5-S | CH₃ | H |
| 5-R | CH₂CH₂CH₂OH | H | or

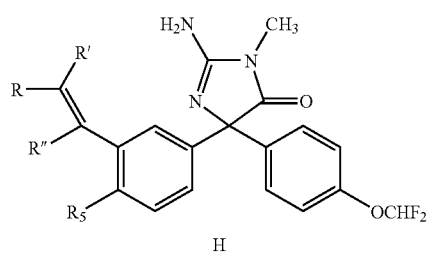

H

| R | R' | R'' | R5 |
|---|---|---|---|
| CH₃ | H | H | H |
| CH₃ | H | H | F |
| H | H | H | H |
| CH₃ | CH₃ | H | F |
| H | H | CH₃ | H |
| CH₂CH₂CH₃ | H | H | H |
| CH₂CH₂CH₂CH₂CH₃ | H | H | H |
| CH₂CH₂CH₂Cl | H | H | H |
| C₆H₅ | H | H | H |
| 2,4-difluorophenyl | H | H | H |
| CH₂CH₂CH₂CH₂CH₃ | H | H | H |
| H | H | C₆H₅ | H |
| CH₂CH₂CH₂CH₃ | H | H | H. |

2. The compound of claim 1, having the structure of formula II

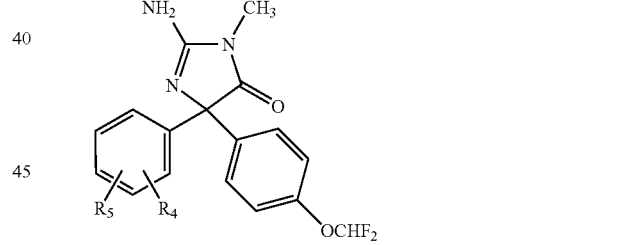

(II)

wherein, only one of $R_4$ and $R_5$ can be hydrogen.

3. The compound of claim 2, having the structure of formula IIA

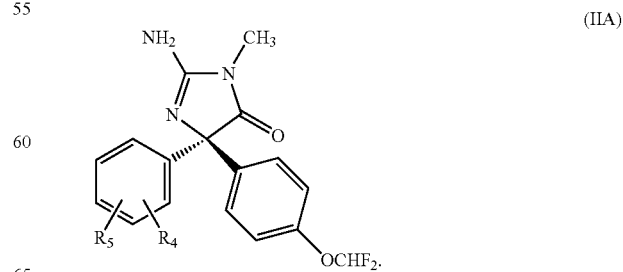

(IIA)

4. The compound of claim 2, having the structure of formula IIB

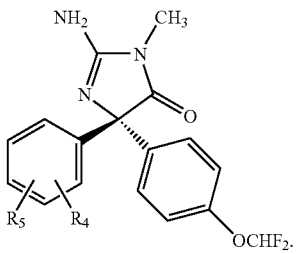

(IIB)

5. The compound of claim 1, having the structure of formula III

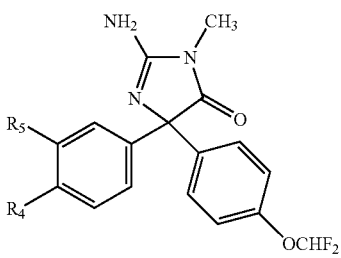

(III)

wherein, only one of $R_4$ and $R_5$ can be hydrogen.

6. The compound of claim 5, having the structure of formula IIIA

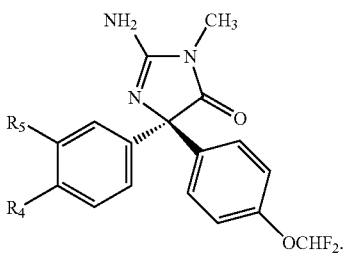

(IIIA)

7. The compound of claim 5, having the structure of formula IIIB

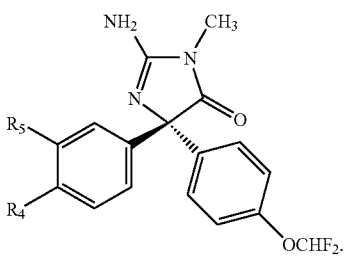

(IIIB)

8. The compound of claim 1, wherein:
$R_4$ is H or fluorine and $R_5$ is $OR_{18}$ where $R_{18}$ is an alkyl, haloalkyl, alkenyl or haloalkenyl group each optionally substituted; or
$R_4$ is H and $R_5$ is $OR_{18}$ where $R_{18}$ is an alkyl group substituted with a cycloalkyl group; or
$R_4$ is H and $R_5$ is $OR_{18}$ where $R_{18}$ is an alkyl group substituted with a cyclopropyl group; or
$R_4$ is H and $R_5$ is $OR_{18}$ where $R_{18}$ is an optionally substituted alkenyl group; or
$R_4$ is H and $R_5$ is $OR_{18}$ where $R_{18}$ is an optionally substituted haloalkyl group; or
$R_4$ is fluorine and $R_5$ is $OR_{18}$ where $R_{18}$ is an optionally substituted haloalkyl group; or
$R_4$ is H and $R_5$ is $OR_{18}$ where $R_{18}$ is an optionally substituted haloalkenyl group; or
$R_4$ is H and $R_5$ is $NHR_{19}$ where $R_{19}$ is H or an alkyl, cycloalkyl, alkenyl or aryl group each optionally substituted; or
$R_4$ is H and $R_5$ is $NHR_{19}$ where $R_{19}$ is an alkyl group substituted with a heteroaryl group; or
$R_4$ is H and $R_5$ is $NHCOR_{20}$ where $R_{20}$ is an alkyl, haloalkyl, cycloalkyl, alkoxyalkyl, alkenyl, aryl or heteroaryl group each optionally substituted; or
$R_4$ is H and $R_5$ is $NHCOR_{20}$ where $R_{20}$ is an optionally substituted alkyl group; or
$R_4$ is H and $R_5$ is $NHCOR_{20}$ where $R_{20}$ is an optionally substituted haloalkyl group; or
$R_4$ is H and $R_5$ is $NHCOR_{20}$ where $R_{20}$ is an optionally substituted cycloalkyl group; or
$R_4$ is H and $R_5$ is $NHCOR_{20}$ where $R_{20}$ is an optionally substituted heteroaryl group; or
$R_4$ is H and $R_5$ is $NHCOR_{20}$ where $R_{20}$ is an optionally substituted heteroaryl group containing one O heteroatom; or
$R_4$ is H and $R_5$ is $NHCOR_{20}$ where $R_{20}$ is an optionally substituted heteroaryl group containing one S heteroatom; or
$R_4$ is H and $R_5$ is $NHCOR_{20}$ where $R_{20}$ is a heteroaryl group fused to an aryl group; or
$R_4$ is H and $R_5$ is $CH_2NR_{21}R_{22}$ where $R_{21}$ and $R_{22}$ are independently H or an optionally substituted alkyl group or $R_{21}$ and $R_{22}$ may be taken together with the N atom to which they are attached to form an optionally substituted 5-membered ring; or
$R_4$ is H or fluorine and $R_5$ is an alkenyl or haloalkenyl group each optionally substituted; or
$R_4$ is fluorine and $R_5$ is an optionally substituted alkenyl group; or
$R_4$ is H and $R_5$ is an optionally substituted haloalkenyl group; or
$R_4$ is H and $R_5$ is a haloalkenyl group substituted with a cycloalkyl group; or
$R_4$ is H and $R_5$ is a haloalkenyl group substituted with a cyclopropyl group; or
$R_4$ is H and $R_5$ is a haloalkenyl group substituted with a cyclopropyl group where the haloalkenyl group contains one fluorine atom; or
$R_4$ is H and $R_5$ is an optionally substituted group of formula IV

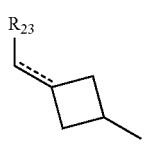

(IV)

where the dashed line denotes an optional double bond and $R_{23}$ is a haloalkyl or alkoxyalkyl group each optionally substituted or $CO_2R_{24}$ where $R_{24}$ is an alkyl group; or $R_4$ is H and $R_5$ is an optionally substituted group of formula IVA

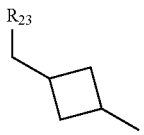

(IVA)

where $R_{23}$ is a haloalkyl group; or $R_4$ is H and $R_5$ is an optionally substituted group of formula V

(V)

where the double bond can be in a cis or trans configuration; or $R_4$ and $R_5$ are attached to adjacent carbon atoms and are taken together with the atoms to which they are attached to form an optionally substituted 5- to 7-membered ring containing one O heteroatom; or $R_4$ and $R_5$ are attached to adjacent carbon atoms and are taken together with the atoms to which they are attached to form an optionally substituted 5-membered ring containing one 0 heteroatom; or $R_4$ is H and $R_5$ is an optionally substituted cycloalkyl group; or $R_4$ is $OR_{25}$ where $R_{25}$ is an optionally substituted haloalkyl group and $R_5$ is H;

$R_4$ is H or fluorine and $R_5$ is an alkyl, haloalkyl, alkoxyalkyl, alkenyl, haloalkenyl or alkynyl group each optionally substituted; or $R_4$ is H or fluorine and $R_5$ is an optionally substituted group of formula VI

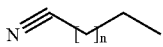

(VI)

where n is an integer of 1-4; or $R_4$ is H or fluorine and $R_5$ is a group of formula VII

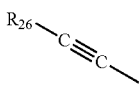

(VII)

where $R_{26}$ is an optionally substituted cycloalkyl group; or $R_4$ is H or fluorine and $R_5$ is a group of formula VII

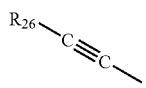

(VII)

where $R_{26}$ is an optionally substituted cyclopropyl group; or $R_4$ is H or fluorine and $R_5$ is a group of formula VIII

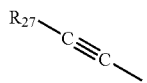

(VIII)

where $R_{27}$ is an alkyl, haloalkyl or alkoxyalkyl group each optionally substituted; or $R_4$ is H or fluorine and $R_5$ is a group of formula VIII

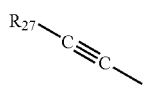

(VIII)

where $R_{27}$ is an optionally substituted alkyl group; or $R_4$ is H or fluorine and $R_5$ is a group of formula VIII

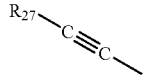

(VIII)

where $R_{27}$ is an optionally substituted haloalkyl group; or $R_4$ is H or fluorine and $R_5$ is a group of formula VIII

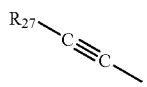

(VIII)

where $R_{27}$ is an optionally substituted alkoxyalkyl group; or $R_4$ is an optionally substituted alkoxyalkyl group and $R_5$ is CN.

9. A compound of formula IXA, IXB or a mixture thereof

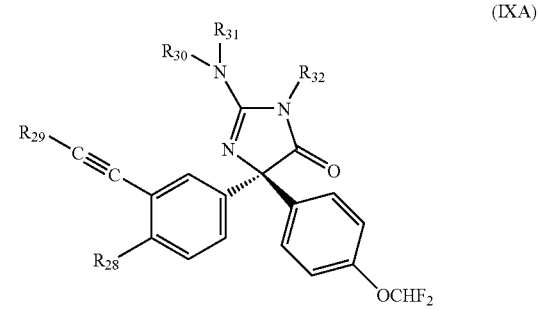

(IXA)

-continued

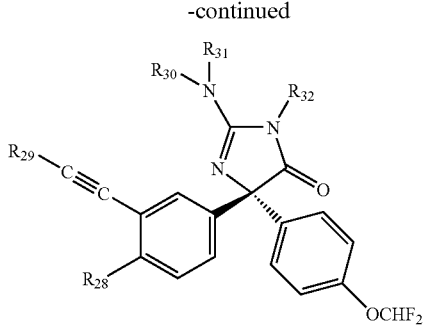

(IXB)

wherein
R$_{28}$ is H or halogen;
R$_{29}$ is an alkyl, haloalkyl, alkoxyalkyl or cycloalkyl group each optionally substituted;
R$_{30}$ and R$_{31}$ are each independently H or an alkyl, cycloalkyl, cycloheteroalkyl, aryl or heteroaryl group each optionally substituted or R$_{30}$ and R$_{31}$ may be taken together with the atom to which they are attached form an optionally substituted 5- to 7-membered ring optionally containing an additional heteroatom selected from O, N or S; and
R$_{32}$ is H or an alkyl, cycloalkyl, cycloheteroalkyl, aryl or heteroaryl group each optionally substituted.

10. The compound of claim 9, wherein R$_{28}$ is halogen and R$_{29}$ is an optionally substituted cycloalkyl group.
11. The compound of claim 9, wherein R$_{28}$ is fluorine.
12. The compound of claim 10, wherein the cycloalkyl group is a monocyclic moiety of 3-5 carbon atoms.
13. The compound of claim 9, wherein R$_{30}$, R$_{31}$ and R$_{32}$ are each independently H or an alkyl group.
14. The compound of claim 13, wherein R$_{30}$ and R$_{31}$ are both H and R$_{32}$ is an alkyl group.
15. The compound of claim 9, wherein R$_{28}$ is H and R$_{29}$ is an optionally substituted cycloalkyl group.
16. The compound of claim 1, wherein R$_1$ and R$_2$ are H.
17. The compound of claim 1, wherein R$_3$ is C$_1$-C$_4$alkyl.
18. The compound of claim 1, wherein R$_4$, R$_5$ and R$_6$ are each independently H, halogen, COR$_7$, OR$_{14}$, or an alkyl, haloalkyl, alkoxy, haloalkoxy, alkynyl or cycloalkyl group each optionally substituted.
19. The compound of claim 1, wherein R$_3$ is methyl.
20. The compound of claim 1, wherein R$_5$ and R$_6$ are each independently H or halogen.
21. The compound of claim 1, wherein R$_1$ and R$_2$ are H and R$_3$ is methyl.
22. The compound of claim 1, wherein R$_4$ is H, COR$_7$, OR$_{14}$ or an alkyl, haloalkyl, alkoxy, haloalkoxy, alkynyl or cycloalkyl group each optionally substituted; and R$_4$ is at the 3-position of the phenyl ring.
23. The compound of claim 1, selected from the group consisting of:
(E)-2-amino-5-[3-(2-cyclopropyl-1-fluorovinyl)phenyl]-5-[4-(difluoromethoxy)phenyl]-3-methyl-3,5-dihydro-4H-imidazol-4-one;
(Z)-2-amino-5-[3-(2-cyclopropyl-1-fluorovinyl)phenyl]-5-[4-(difluoromethoxy)phenyl]-3-methyl-3,5-dihydro-4H-imidazol-4-one;
2-amino-5-[4-(difluoromethoxy)phenyl]-5-(4-fluoro-3-prop-1-en-1-ylphenyl)-3-methyl-3,5-dihydro-4H-imidazol-4-one;
2-amino-5-[4-(difluoromethoxy)phenyl]-5-(3-ethylphenyl)-3-methyl-3,5-dihydro-4H-imidazol-4-one;

(E)-2-amino-4-(4-(difluoromethoxy)phenyl)-4-(3-(4-methoxybut-2-en-2-yl)phenyl)-1-methyl-1H-imidazol-5(4H)-one;
2-amino-4-(3-cyclopropylphenyl)-4-(4-(difluoromethoxy)phenyl)-1-methyl-1H-imidazol-5(4H)-one;
2-amino-5-[4-(difluoromethoxy)phenyl]-5-(3-{[(2-furylmethyl)-amino]methyl}phenyl)-3-methyl-3,5-dihydro-4H-imidazol-4-one;
2-amino-5-[4-(difluoromethoxy)phenyl]-3-methyl-5-{3-[(propylamino)-methyl]phenyl}-3,5-dihydro-4H-imidazol-4-one;
2-amino-5-[4-(difluoromethoxy)phenyl]-5-{3-[(ethylamino)methyl]phenyl}-3-methyl-3,5-dihydro-4H-imidazol-4-one;
2-amino-5-[4-(difluoromethoxy)phenyl]-5-{3-[(dimethylamino)-methyl]phenyl}-3-methyl-3,5-dihydro-4H-imidazol-4-one;
2-Amino-5-(4-difluoromethoxy-phenyl)-5-[3-(isopropylamino-methyl)-phenyl]-3-methyl-3,5-dihydro-imidazol-4-one;
methyl [3-(3-{2-amino-4-[4-(difluoromethoxy)phenyl]-1-methyl-5-oxo-4,5-dihydro-1H-imidazol-4-yl}phenyl)-1-methoxycyclobutyl]acetate;
methyl [3-(3-{2-amino-4-[4-(difluoromethoxy)phenyl]-1-methyl-5-oxo-4,5-dihydro-1H-imidazol-4-yl}phenyl)cyclobutylidene]acetate;
2-amino-5-[3-(5-chloropent-1-yn-1-yl)-4-fluorophenyl]-5-[4-(difluoromethoxy)phenyl]-3-methyl-3,5-dihydro-4H-imidazol-4-one;
2-amino-5-[4-(difluoromethoxy)phenyl]-5-[4-fluoro-3-(5-fluoropent-1-yn-1-yl)phenyl]-3-methyl-3,5-dihydro-4H-imidazol-4-one;
2-Amino-5-(4-difluoromethoxy-phenyl)-3-methyl-5-o-tolyl-3,5-dihydro-imidazol-4-one
2-Amino-5-(4-difluoromethoxy-phenyl)-5-(4-fluoro-3-fluoromethyl-phenyl)-3-methyl-3,5-dihydro-imidazol-4-one
5-[2-Amino-4-(4-difluoromethoxy-phenyl)-1-methyl-5-oxo-4,5-dihydro-1H-imidazol-4-yl]-2-methoxy-benzonitrile;
4-{5-[2-Amino-4-(4-difluoromethoxy-phenyl)-1-methyl-5-oxo-4,5-dihydro-1H-imidazol-4-yl]-2-fluoro-phenyl}-butyronitrile;
2-Amino-5-(4-difluoromethoxy-phenyl)-5-[4-fluoro-3-(1-fluoro-pent-4-enyl)-phenyl]-3-methyl-3,5-dihydro-imidazol-4-one
2-Amino-5-(4-difluoromethoxy-phenyl)-5-[3-(1-fluoro-pent-4-enyl)-phenyl]-3-methyl-3,5-dihydro-imidazol-4-one
5-(3-{(4S)-2-amino-4-[4-(difluoromethoxy)phenyl]-1-methyl-5-oxo-4,5-dihydro-1H-imidazol-4-yl}phenyl)pentanenitrile;
5-(3-{(4R)-2-amino-4-[4-(difluoromethoxy)phenyl]-1-methyl-5-oxo-4,5-dihydro-1H-imidazol-4-yl}phenyl)pentanenitrile;
(R)-2-amino-4-(4-(difluoromethoxy)phenyl)-1-methyl-4-(3-(pent-4-enyloxy)phenyl)-1H-imidazol-5(4H)-one;
(R)-2-amino-4-(4-(difluoromethoxy)phenyl)-1-methyl-4-(3-((R)-pent-4-en-2-yloxy)phenyl)-1H-imidazol-5(4H)-one;
(R)-2-amino-4-(4-(difluoromethoxy)phenyl)-1-methyl-4-(3-((S)-pent-4-en-2-yloxy)phenyl)-1H-imidazol-5(4H)-one;
(4R)-2-amino-4-(4-(difluoromethoxy)phenyl)-1-methyl-4-(3-(2-methylbut-3-enyloxy)phenyl)-1H-imidazol-5(4H)-one;

(R)-2-amino-4-(4-(difluoromethoxy)phenyl)-1-methyl-4-(3-(3-methylbut-3-enyloxy)phenyl)-1H-imidazol-5(4H)-one;
(R)-4-(3-(allyloxy)phenyl)-2-amino-4-(4-(difluoromethoxy)phenyl)-1-methyl-1H-imidazol-5(4H)-one;
2-amino-5-[3-(but-3-en-1-yloxy)phenyl]-5-[4-(difluoromethoxy)phenyl]-3-methyl-3,5-dihydro-4H-imidazol-4-one;
(5S)-2-Amino-5-[4-(difluoromethoxy)phenyl]-5-(4-fluoro-3-prop-1-yn-1-ylphenyl)-3-methyl-3,5-dihydro-4H-imidazol-4-one;
(5R)-2-Amino-5-[4-(difluoromethoxy)phenyl]-5-(4-fluoro-3-prop-1-yn-1-ylphenyl)-3-methyl-3,5-dihydro-4H-imidazol-4-one
2-amino-5-[4-(difluoromethoxy)phenyl]-3-methyl-5-(3-prop-1-yn-1-ylphenyl)-3,5-dihydro-4H-imidazol-4-one
(5S)-2-Amino-5-[3-(cyclopropylethynyl)phenyl]-5-[4-(difluoromethoxy)phenyl]-3-methyl-3,5-dihydro-4H-imidazol-4-one
(5R)-2-Amino-5-[3-(cyclopropylethynyl)phenyl]-5-[4-(difluoromethoxy)phenyl]-3-methyl-3,5-dihydro-4H-imidazol-4-one
(5R)-2-Amino-5-[3-(cyclopropylethynyl)-4-fluorophenyl]-5-[4-(difluoromethoxy)phenyl]-3-methyl-3,5-dihydro-4H-imidazol-4-one;
(5S)-2-Amino-5-[3-(cyclopropylethynyl)-4-fluorophenyl]-5-[4-(difluoromethoxy)phenyl]-3-methyl-3,5-dihydro-4H-imidazol-4-one;
methyl[3-(3-{2-amino-4-[4(difluoromethoxy)phenyl]-1-methyl-5-oxo-4,5-dihydro-1H-imidazol-4-yl}phenyl)cyclobutylidene]acetate;
ethyl [3-(3-{2-amino-4-[4-(difluoromethoxy)phenyl]-1-methyl-5-oxo-4,5-dihydro-1H-imidazol-4-yl}phenyl)cyclobutylidene]acetate;
methyl [3-(3-{2-amino-4-[4-(difluoromethoxy)phenyl]-1-methyl-5-oxo-4,5-dihydro-1H-imidazol-4-yl}phenyl)cyclobutylidene]acetate;
methyl [3-(3-{2-amino-4-[4-(difluoromethoxy)phenyl]-1-methyl-5-oxo-4,5-dihydro1H-imidazol-4-yl}phenyl)-1-methoxycyclobutyl]acetate;
2-amino-5-[4-(difluoromethoxy)phenyl]-5-{3-[3-(2-hydroxyethylidene)cyclobutyl]phenyl}-3-methyl-3,5-dihydro-4H-imidazol-4-one;
2-amino-5-[4-(difluoromethoxy)phenyl]-5-[3-(1-fluorobut-3-en-1-yl)phenyl]-3-methyl-3,5-dihydro-4H-imidazol-4-one;
2-amino-5-[4-(difluoromethoxy)phenyl]-5-{3-[3-(2-fluoroethyl)cyclobutyl]phenyl}-3-methyl-3,5-dihydro-4H-imidazol-4-one
2-amino-5-[4-(difluoromethoxy)phenyl]-5-{3-[3-(2-methoxyethyl)cyclobutyl]phenyl}-3-methyl-3,5-dihydro-4H-imidazol-4-one;
2-amino-5-(3-anilinophenyl)-5-[4-(difluoromethoxy)phenyl]-3-methyl-3,5-dihydro-4H-imidazol-4-one;
2-amino-5-[4-(difluoromethoxy)phenyl]-5-{3-[(isopropylamino)methyl]phenyl}-3-methyl-3,5-dihydro-4H-imidazol-4-one;
2-amino-5-[4-(difluoromethoxy)phenyl]-5-{3-[(dimethylamino)methyl]phenyl}-3-methyl-3,5-dihydro-4H-imidazol-4-one;
2-amino-5-[4-(difluoromethoxy)phenyl]-3-methyl-5-{3-[(ethylamino)methyl]phenyl}-3,5-dihydro-4H-imidazol-4-one;
2-amino-5-[4-(difluoromethoxy)phenyl]-3-methyl-5-{3-[(propylamino)methyl]phenyl}-3,5-dihydro-4H-imidazol-4-one;
2-amino-5-{3-[(butylamino)methyl]phenyl}-5-[4-(difluoromethoxy)phenyl]3-methyl-3,5-dihydro-4H-imidazol-4-one;
2-amino-5-[4-(difluoromethoxy)phenyl]-3-methyl-5-[3-(pyrrolidin-1-ylmethyl)phenyl]-3,5-dihydro-4H-imidazol-4-one;
2-amino-5,5-bis[4-(difluoromethoxy)phenyl]-3-methyl-3,5-dihydro-4H-imidazol-4-one
2-amino-5-[4-(difluoromethoxy)phenyl]-5-(3-{[(2-furylmethyl)amino]methyl}phenyl)-3-methyl 3,5-dihydro-4H-imidazol-4-one;
2-amino-5-(3-cyclopropylphenyl)-5-[4-(difluoromethoxy)phenyl]-3-methyl-3,5-dihydro-4H-imidazol-4-one
2-amino-5-[4-(difluoromethoxy)phenyl]-5-{3-[(1E)-3-methoxy-1-methylprop-1-en-1-yl]phenyl}-3-methyl-3,5-dihydro-4H-imidazol-4-one;
2-amino-5-[4-(difluoromethoxy)phenyl]-5-{3-[(1E)-3-ethoxy-1-methylprop-1-en-1-yl]phenyl}-3-methyl-3,5-dihydro-4H-imidazol-4-one;
2-amino-5-[4-(difluoromethoxy)phenyl]-3-methyl-5-{3-[(1S)-1-methylbut-3-en-1-yl]phenyl}-3,5-dihydro-4H-imidazol-4-one
2-amino-5-[4-(difluoromethoxy)phenyl]-5-[3-(3-methoxy-1-methylpropyl)phenyl]-3-methyl-3,5-dihydro-4H-imidazol-4-one
2-amino-5-[4-(difluoromethoxy)phenyl]-5-[3-(3-ethoxy-1-methylpropyl)phenyl]-3-methyl-3,5-dihydro-4H-imidazol-4-one
2-amino-5-[4-(difluoromethoxy)phenyl]-3-methyl-5-{3-[(1R)-1-methylbut-3-en-1-yl]phenyl}-3,5-dihydro-4H-imidazol-4-one;
2-amino-5-[4-(difluoromethoxy)phenyl]-3-methyl-5-(2-methyl-1-benzofuran-5-yl)-3,5-dihydro-4H-imidazol-4-one;
2-amino-5-[4-(difluoromethoxy)phenyl]-3-methyl-5-(2-methyl-1-benzofuran-5-yl)-3,5-dihydro-4H-imidazol-4-one;
2-amino-5-(3-aminophenyl)-5-[4-(difluoromethoxy)phenyl]-3-methyl-3,5-dihydro-4H-imidazol-4-one
N-(3-{2-amino-4-[4-(difluoromethoxy)phenyl]-1-methyl-5-oxo-4,5-dihydro-1H-imidazol-4-yl}phenyl)acetamide;
N-(3-{2-amino-4-[4-(difluoromethoxy)phenyl]-1-methyl-5-oxo-4,5-dihydro-1H-imidazol-4-yl}phenyl)propanamide;
N-(3-{2-amino-4-[4-(difluoromethoxy)phenyl]-1-methyl-5-oxo-4,5-dihydro-1H-imidazol-4-yl}phenyl)butanamide;
N-(3-{2-amino-4-[4-(difluoromethoxy)phenyl]-1-methyl-5-oxo-4,5-dihydro-1H-imidazol-4-yl}phenyl)pentanamide;
N-(3-{2-amino-4-[4-(difluoromethoxy)phenyl]-1-methyl-5-oxo-4,5-dihydro-1H-imidazol-4-yl}phenyl)-3-chloropropanamide;
N-(3-{2-amino-4-[4-(difluoromethoxy)phenyl]-1-methyl-5-oxo-4,5-dihydro-1H-imidazol-4-yl}phenyl)-2,2,2-trifluoroacetamide;
N-(3-{2-amino-4-[4-(difluoromethoxy)phenyl]-1-methyl-5-oxo-4,5-dihydro-1H-imidazol-4-yl}phenyl)-3-methylbutanamide;
N-(3-{2-amino-4-[4-(difluoromethoxy)phenyl]-1-methyl-5-oxo-4,5-dihydro-1H-imidazol-4-yl}phenyl)-2-methylpropanamide;
N-(3-{2-amino-4-[4-(difluoromethoxy)phenyl]-1-methyl-5-oxo-4,5-dihydro-1H-imidazol-4-yl}phenyl)cyclopropanecarboxamide N-(3-{2-amino-4-[4-(difluoromethoxy)phenyl]-1-methyl-5-oxo-4,5-dihydro-1H-imidazol-4-yl}phenyl)cyclobutanecarboxamide;

(2E)-N-(3-{2-amino-4-[4-(difluoromethoxy)phenyl]-1-methyl-5-oxo-4,5-dihydro-1H-imidazol-4-yl}phenyl)but-2-enamide;

N-(3-(2-amino-4-(4-(difluoromethoxy)phenyl)-1-methyl-5-oxo-4,5-dihydro-1H-imidazol-4-yl)phenyl)-3-methylbut-2-enamide;

(2E)-N-(3-{2-amino-4-[4-(difluoromethoxy)phenyl]-1-methyl-5-oxo-4,5-dihydro-1H-imidazol-4-yl}phenyl)-3-phenylacrylamide;

N-(3-{2-amino-4-[4-(difluoromethoxy)phenyl]-1-methyl-5-oxo-4,5-dihydro-1H-imidazol-4-yl}phenyl)-2-furamide;

N-(3-{2-amino-4-[4-(difluoromethoxy)phenyl]-1-methyl-5-oxo-4,5-dihydro-1H-imidazol-4-yl}phenyl)-2-(benzyloxy)acetamide 2-amino-5-[4-(difluoromethoxy)phenyl]-3-methyl-5-[3-(propylamino)phenyl]-3,5-dihydro-4H-imidazol-4-one;

2-amino-5-[3-(butylamino)phenyl]-5-[4-(difluoromethoxy)phenyl]-3-methyl-3,5-dihydro-4H-imidazol-4-one;

2-amino-5-[4-(difluoromethoxy)phenyl]-5-[3-(isobutylamino)phenyl]-3-methyl-3,5-dihydro-4H-imidazol-4-one;

2-amino-5-[4-(difluoromethoxy)phenyl]-5-[3-(isopropylamino)phenyl]-3-methyl-3,5-dihydro-4H-imidazol-4-one 2-amino-5-[3-(cyclopentylamino)phenyl]-5-[4-(difluoromethoxy)phenyl]-3-methyl-3,5-dihydro-4H-imidazol-4-one 2-amino-5-[3-(cyclohexylamino)phenyl]-5-[4-(difluoromethoxy)phenyl]-3-methyl-3, 5-dihydro-4H-imidazol-4-one 2-amino-5-{3-[(2E)-but-2-en-1-ylamino]phenyl}-5-[4-(difluoromethoxy)phenyl]-3-methyl-3,5-dihydro-4H-imidazol-4-one;

2-amino-5-[3-(cyclobutylamino)phenyl]-5-[4-(difluoromethoxy)phenyl]-3-methyl-3,5-dihydro-4H-imidazol-4-one;

2-amino-5-[4-(difluoromethoxy)phenyl]-5-{3-[(2-furylmethyl)amino]phenyl}-3-methyl-3,5-dihydro-4H-imidazol-4-one;

N-(3-{2-amino-4-[4-(difluoromethoxy)phenyl]-1-methyl-5-oxo-4,5-dihydro-1H-imidazol-4-yl}phenyl)benzamide;

N-(3-{2-amino-4-[4-(difluoromethoxy)phenyl]-1-methyl-5-oxo-4,5-dihydro-1H-imidazol-4-yl}phenyl)-2,2,2-trichloroacetamide;

N-(3-{2-amino-4-[4-(difluoromethoxy)phenyl]-1-methyl-5-oxo-4,5-dihydro-1H-imidazol-4-yl}phenyl)-1-phenyl-5-(trifluoromethyl)-1H-pyrazole-4-carboxamide;

N-(3-{2-amino-4-[4-(difluoromethoxy)phenyl]-1-methyl-5-oxo-4,5-dihydro-1H-imidazol-4-yl}phenyl)-1-(4-chlorophenyl)-5-(trifluoromethyl)-1H-pyrazole-4-carboxamide;

N-(3-{2-amino-4-[4-(difluoromethoxy)phenyl]-1-methyl-5-oxo-4,5-dihydro-1H-imidazol-4-yl}phenyl)-3-bromothiophene-2-carboxamide;

N-(3-{2-amino-4-[4-(difluoromethoxy)phenyl]-1-methyl-5-oxo-4,5-dihydro-1H-imidazol-4-yl}phenyl)-1-benzofuran-3-carboxamide;

N-(3-{2-amino-4-[4-(difluoromethoxy)phenyl]-1-methyl-5-oxo-4,5-dihydro-1H-imidazol-4-yl}phenyl)-2,3-dihydro-1-benzofuran-5-carboxamide;

N-(3-{2-amino-4-[4-(difluoromethoxy)phenyl]-1-methyl-5-oxo-4,5-dihydro-1H-imidazol-4-yl}phenyl)thiophene-2-carboxamide (5S)-2-amino-5-[4-(difluoromethoxy)phenyl]-3-methyl-5-[3-(3-methylbut-1-yn-1-yl)phenyl]-3,5-dihydro-4H-imidazol-4-one;

2-amino-5-[3-(cyclopropylethynyl)phenyl]-5-[4-(difluoromethoxy)phenyl]-3-methyl-3,5-dihydro-4H-imidazol-4-one;

(5S)-2-amino-5-[3-(cyclopropylethynyl)phenyl]-5-[4-(difluoromethoxy)phenyl]-3-methyl-3,5-dihydro-4H-imidazol-4-one;

(5R)-2-amino-5-[3-(cyclopropylethynyl)phenyl]-5-[4-(difluoromethoxy)phenyl]-3-methyl-3,5-dihydro-4H-imidazol-4-one;

2-amino-5-[3-(cyclopropylethynyl)-4-fluorophenyl]-5-[4-(difluoromethoxy)phenyl]-3-methyl-3,5-dihydro-4H-imidazol-4-one;

(5R)-2-amino-5-[3-(cyclopropylethynyl)-4-fluorophenyl]-5-[4-(difluoromethoxy)phenyl]-3-methyl-3,5-dihydro-4H-imidazol-4-one;

(5S)-2-amino-5-[3-(cyclopropylethynyl)-4-fluorophenyl]-5-[4-(difluoromethoxy)phenyl]-3-methyl-3,5-dihydro-4H-imidazol-4-one;

(5S)-2-amino-5-[3-(cyclopropylethynyl)-4-fluorophenyl]-5-[4-(difluoromethoxy)phenyl]-3-methyl-3,5-dihydro-4H-imidazol-4-one;

2-amino-5-[4-(difluoromethoxy)phenyl]-5-{4-fluoro-3-[(1E)-prop-1-en-1-yl]phenyl}-3-methyl-3,5-dihydro-4H-imidazol-4-one 2-amino-5-[4-(difluoromethoxy)phenyl]-5-(4-fluoro-3-prop-1-yn-1-ylphenyl)-3-methyl-3,5-dihydro-4H-imidazol-4-one (5R)-2-amino-5-[4-(difluoromethoxy)phenyl]-5-(4-fluoro-3-prop-1-yn-1-ylphenyl)-3-methyl-3,5-dihydro-4H-imidazol-4-one;

(5S)-2-amino-5-[4-(difluoromethoxy)phenyl]-5-(4-fluoro-3-prop-1-yn-1-ylphenyl)-3-methyl-3,5-dihydro-4H-imidazol-4-one;

(5R)-2-amino-5-[4-(difluoromethoxy)phenyl]-5-{4-fluoro-3-[(1E)-prop-1-en-1-yl]phenyl}-3-methyl-3,5-dihydro-4H-imidazol-4-one;

(5S)-2-amino-5-[4-(difluoromethoxy)phenyl]-5-{4-fluoro-3-[(1E)-prop-1-en-1-yl]phenyl}-3-methyl-3,5-dihydro-4H-imidazol-4-one;

(5S)-2-amino-5-[4-(difluoromethoxy)phenyl]-5-{4-fluoro-3-[(1Z)-prop-1-en-1-yl]phenyl}-3-methyl-3,5-dihydro-4H-imidazol-4-one;

2-amino-5-[4-(difluoromethoxy)phenyl]-5-{4-fluoro-3-[prop-1-en-1-yl]phenyl}-3-methyl-3,5-dihydro-4H-imidazol-4-one;

2-amino-5-[4-(difluoromethoxy)phenyl]-5-{4-fluoro-3-[(1Z)-prop-1-en-1-yl]phenyl}-3-methyl-3,5-dihydro-4H-imidazol-4-one;

2-amino-5-[4-(difluoromethoxy)phenyl]-5-{4-fluoro-3-[(1E)-prop-1-en-1-yl]phenyl}-3-methyl-3,5-dihydro-4H-imidazol-4-one (5R)-2-amino-5-[4-(difluoromethoxy)phenyl]-5-{4-fluoro-3-[(1Z)-prop-1-en-1-yl]phenyl}-3-methyl-3,5-dihydro-4H-imidazol-4-one;

2-amino-5-{3-[(Z)-2-cyclopropyl-1-fluorovinyl]phenyl}-5-[4-(difluoromethoxy)phenyl]-3-methyl-3,5-dihydro-4H-imidazol-4-one;

2-amino-5-{3-[(E)-2-cyclopropyl-1-fluorovinyl]phenyl}-5-[4-(difluoromethoxy)phenyl]-3-methyl-3,5-dihydro-4H-imidazol-4-one;

5-(3-{(4S)-2-amino-4-[4-(difluoromethoxy)phenyl]-1-methyl-5-oxo-4,5-dihydro-1H-imidazol-4-yl}phenyl)pentanenitrile;

5-(3-{(4R)-2-amino-4-[4-(difluoromethoxy)phenyl]-1-methyl-5-oxo-4,5-dihydro-1H-imidazol-4-yl}phenyl)pentanenitrile;

2-amino-5-[4-(difluoromethoxy)phenyl]-5-[3-(1-fluoropent-4-en-1-yl)phenyl]-3-methyl-3,5-dihydro-4H-imidazol-4-one 2-amino-5-[4-(difluoromethoxy)phenyl]-5-[4-fluoro-3-(1-fluoropent-4-en-1-yl)phenyl]-3-methyl-3,5-dihydro-4H-imidazol-4-one;

4-(5-{2-amino-4-[4-(difluoromethoxy)phenyl]-1-methyl-5-oxo-4,5-dihydro-1H-imidazol-4-yl}-2-fluorophenyl)butanenitrile 2-amino-5-[4-(difluoromethoxy)phenyl]-5-(4-fluoro-3-methylphenyl)-3-methyl-3,5-dihydro-4H-imidazol-4-one;

5-{2-amino-4-[4-(difluoromethoxy)phenyl]-1-methyl-5-oxo-4,5-dihydro-1H-imidazol-4-yl}-2-methoxybenzonitrile;

2-amino-5-[4-(difluoromethoxy)phenyl]-5-[4-fluoro-3-(fluoromethyl)phenyl]3-methyl-3,5-dihydro-4H-imidazol-4-one;

2-amino-5-[4-(difluoromethoxy)phenyl]-3-methyl-5-(2-methylphenyl)-3,5-dihydro-4H-imidazol-4-one;

2-amino-5-[4-(difluoromethoxy)phenyl]-5-[4-fluoro-3-(5-fluoropent-1-yn-1-yl)phenyl]-3-methyl-3,5-dihydro-4H-imidazol-4-one;

2-amino-5-[3-(5-chloropent-1-yn-1-yl)-4-fluorophenyl]-5-[4-(difluoromethoxy)phenyl]-3-methyl-3,5-dihydro-4H-imidazol-4-one;

2-amino-5-[4-(difluoromethoxy)phenyl]-3-methyl-5-(3-methylphenyl)-3,5-dihydro-4H-imidazol-4-one;

2-amino-5-[4-(difluoromethoxy)phenyl]-5-[3-(4-ethoxybut-1-yn-1-yl)phenyl]-3-methyl-3,5-dihydro-4H-imidazol-4-one 2-amino-5-[4-(difluoromethoxy)phenyl]-5-[3-(3-hydroxypent-4-yn-1-yl)phenyl]-3-methyl-3,5-dihydro-4H-imidazol-4-one;

2-amino-5-[4-(difluoromethoxy)phenyl]-5-(3-hex-5-en-1-ylphenyl)-3-methyl-3,5-dihydro-4H-imidazol-4-one 2-amino-5-[4-(difluoromethoxy)phenyl]-5-{3-[(1E)-4-fluoro-1-methylbut-1-en-1-yl]phenyl}-3-methyl-3,5-dihydro-4H-imidazol-4-one;

2-amino-5-[4-(difluoromethoxy)phenyl]-5-{3-[(1E)-3,3-difluoroprop-1-en-1-yl]phenyl}-3-methyl-3,5-dihydro-4H-imidazol-4-one;

2-amino-5-[4-(difluoromethoxy)phenyl]-5-{3-[(1E)-3-fluoroprop-1-en-1-yl]phenyl}-3-methyl-3,5-dihydro-4H-imidazol-4-one;

2-amino-5-[4-(difluoromethoxy)phenyl]-5-(3-hex-5-en-1-ylphenyl)-3-methyl-3,5-dihydro-4H-imidazol-4-one;

2-amino-5-[4-(difluoromethoxy)phenyl]-5-(3-hexylphenyl)-3-methyl-3,5-dihydro-4H-imidazol-4-one 2-amino-5-[4-(difluoromethoxy)phenyl]-5-(3-ethylphenyl)-3-methyl-3,5-dihydro-4H-imidazol-4-one;

(5S)-2-amino-5-{3-[(4,4-difluorobut-3-en-1-yl)oxy]phenyl}-5-[4-(difluoromethoxy)phenyl]-3-methyl-3,5-dihydro-4H-imidazol-4-one;

(5S)-2-amino-5-{3-[(4,4-difluorobut-3-en-1-yl)oxy]-4-fluorophenyl}—5-[4-(difluoromethoxy)phenyl]-3-methyl-3,5-dihydro-4H-imidazol-4-one (5R)-2-amino-5-{3-[(4,4-difluorobut-3-en-1-yl)oxy]-4-fluorophenyl}-5-[4-(difluoromethoxy)phenyl]-3-methyl-3,5-dihydro-4H-imidazol-4-one (5R)-2-amino-5-[3-(cyclopropylmethoxy)phenyl]-5-[4-(difluoromethoxy)phenyl]-3-methyl-3,5-dihydro-4H-imidazol-4-one (5S)-2-amino-5-[3-(cyclopropylmethoxy)phenyl]-5-[4-(difluoromethoxy)phenyl]-3-methyl-3,5-dihydro-4H-imidazol-4-one;

(R,E)-2-amino-4-(4-(difluoromethoxy)phenyl)-4-(3-(6-methoxyhex-1-enyl)phenyl)-1-methyl-1H-imidazol-5(4H)-one;

(5S)-2-amino-5-[3-(2,2-difluoroethoxy)phenyl]-5-[4-(difluoromethoxy)phenyl]-3-methyl-3,5-dihydro-4H-imidazol-4-one;

(5R)-2-amino-5-[3-(212-difluoroethoxy)phenyl]-5-[4-(difluoromethoxy)phenyl]-3-methyl-3,5-dihydro-4H-imidazol-4-one;

(5S)-2-amino-5-[4-(difluoromethoxy)phenyl]-5-{3-[(1E)-4-methoxybut-1-en-1-yl]phenyl}-3-methyl-3,5-dihydro-4H-imidazol-4-one;

(5R)-2-amino-5-[4-(difluoromethoxy)phenyl]-5-{3-[(1E)-4-methoxybut-1-en-1-yl]phenyl}-3-methyl-3,5-dihydro-4H-imidazol-4-one;

(5S)-2-amino-5-[4-(difluoromethoxy)phenyl]-5-{3-[(1E)-3-methoxyprop-1-en-1-yl]phenyl}-3-methyl-3,5-dihydro-4H-imidazol-4-one;

(5R)-2-amino-5-[4-(difluoromethoxy)phenyl]-5-{3-[(1E)-3-methoxyprop-1-en-1-yl]phenyl}-3-methyl-3,5-dihydro-4H-imidazol-4-one;

(5R)-2-amino-5-[4-(difluoromethoxy)phenyl]-3-methyl-5-[3-(pent-4-en-1-yloxy)phenyl]-3,5-dihydro-4H-imidazol-4-one (5R)-2-amino-5-[4-(difluoromethoxy)phenyl]-3-methyl-5-(3-{[(1S)-1-methylbut-3-en-1-yl]oxy}phenyl)-3,5-dihydro-4H-imidazol-4-one (5R)-2-amino-5-[4-(difluoromethoxy)phenyl]-3-methyl-5-(3-{[(1R)-1-methylbut-3-en-1-yl]oxy}phenyl)-3,5-dihydro-4H-imidazol-4-one (5R)-2-amino-5-[4-(difluoromethoxy)phenyl]-3-methyl-5-{3-[(2-methylbut-3-en-1-yl)oxy]phenyl}-3,5-dihydro-4H-imidazol-4-one;

(5R)-2-amino-5-[4-(difluoromethoxy)phenyl]-3-methyl-5-{3-[(3-methylbut-3-en-1-yl)oxy]phenyl}-3,5-dihydro-4H-imidazol-4-one;

(5R)-5-[3-(allyloxy)phenyl]-2-amino-5-[4-(difluoromethoxy)phenyl]-3-methyl-3,5-dihydro-4H-imidazol-4-one;

2-amino-5-[4-(difluoromethoxy)phenyl]-5-(4-fluoro-3-isopropoxyphenyl)-3-methyl-3,5-dihydro-4H-imidazol-4-one;

2-amino-5-[4-(difluoromethoxy)phenyl]-5-[4-fluoro-3-(2-fluoroethoxy)phenyl]-3-methyl-3,5-dihydro-4H-imidazol-4-one;

2-amino-5-[4-(difluoromethoxy)phenyl]-5-[4-fluoro-3-(3-methylbut-1-yn-1-yl)phenyl]-3-methyl-3,5-dihydro-4H-imidazol-4-one;

(5R)-2-amino-5-[4-(difluoromethoxy)phenyl]-5-{3-[(1E)-5-methoxypent-1-en-1-yl]phenyl}-3-methyl-3,5-dihydro-4H-imidazol-4-one;

(5R)-2-amino-5-[4-(difluoromethoxy)phenyl]-5-{4-fluoro-3-[(1E)-4-fluorobut-1-en-1-yl]phenyl}-3-methyl-3,5-dihydro-4H-imidazol-4-one; and (5S)-2-amino-5-[4-(difluoromethoxy)phenyl]-5-{4-fluoro-3-[(1E)-4-fluorobut-1-en-1-yl]phenyl}-3-methyl-3,5-dihydro-4H-imidazol-4-one; or a tautomer thereof; or a pharmaceutically acceptable salt thereof.

24. The compound of claim 1, selected from the group consisting of: 2-amino-5-[4-(difluoromethoxy)phenyl]-5-(4-fluoro-3-morpholin-4-ylphenyl)-3-methyl-3,5-dihydro-4H-imidazol-4-one;

2-amino-5-(3-but-3-en-1-yn-1-yl-4-fluorophenyl)-5-[4-(difluoromethoxy)phenyl]-3-methyl-3,5-dihydro-4H-imidazol-4-one;

2-amino-5-[4-(difluoromethoxy)phenyl]-5-[3-(2-furylmethyl)phenyl]-3-methyl-3,5-dihydro-4H-imidazol-4-one;

2-amino-5-[4-(difluoromethoxy)phenyl]-5-[3-(3,3-difluoropropoxy)phenyl]-3-methyl-3,5-dihydro-4H-imidazol-4-one;

(5R)-2-amino-5-[4-(difluoromethoxy)phenyl]-5-[3-(3,3-difluoropropoxy)phenyl]-3-methyl-3,5-dihydro-4H-imidazol-4-one;

(5S)-2-amino-5-[4-(difluoromethoxy)phenyl]-5-[3-(3,3-difluoropropoxy)phenyl]-3-methyl-3,5-dihydro-4H-imidazol-4-one;

2-amino-5-[4-(difluoromethoxy)phenyl]-5-[3-(3,3-difluoropropoxy)-4-fluorophenyl]-3-methyl-3,5-dihydro-4H-imidazol-4-one;

(5S)-2-amino-5-[4-(difluoromethoxy)phenyl]-5-[3-(3,3-difluoropropoxy)-4-fluorophenyl]-3-methyl-3,5-dihydro-4H-imidazol-4-one;

(5R)-2-amino-5-[4-(difluoromethoxy)phenyl]-5-[3-(3,3-difluoropropoxy)-4-fluorophenyl]-3-methyl-3,5-dihydro-4H-imidazol-4-one;

2-amino-5-[4-(difluoromethoxy)phenyl]-3-methyl-5-(3-methylphenyl)-3,5-dihydro-4H-imidazol-4-one 2-amino-5-[4-(difluoromethoxy)phenyl]-5-[3-(4-ethoxybut-1-yn-1-yl)phenyl]-3-methyl-3,5-dihydro-4H-imidazol-4-one;

2-amino-5-[4-(difluoromethoxy)phenyl]-5-[3-(3-fluoroprop-1-yn-1-yl)phenyl]-3-methyl-3,5-dihydro-4H-imidazol-4-one;

2-amino-5-[4-(difluoromethoxy)phenyl]-5-[3-(4-fluorobut-1-yn-1-yl)phenyl]-3-methyl-3,5-dihydro-4H-imidazol-4-one;

2-amino-5-[4-(difluoromethoxy)phenyl]-5-[4-fluoro-3-(3-fluoroprop-1-yn-1-yl)phenyl]-3-methyl-3,5-dihydro-4H-imidazol-4-one;

(5R)-2-amino-5-[4-(difluoromethoxy)phenyl]-5-[3-(3-fluoroprop-1-yn-1-yl)phenyl]-3-methyl-3,5-dihydro-4H-imidazol-4-one;

(5S)-2-amino-5-[4-(difluoromethoxy)phenyl]-5-[3-(3-fluoroprop-1-yn-1-yl)phenyl]-3-methyl-3,5-dihydro-4H-imidazol-4-one;

2-amino-5-[4-(difluoromethoxy)phenyl]-5-[4-fluoro-3-(4-fluorobut-1-yn-1-yl)phenyl]-3-methyl-3,5-dihydro-4H-imidazol-4-one;

(5S)-2-amino-5-[4-(difluoromethoxy)phenyl]-5-[4-fluoro-3-(4-fluorobut-1-yn-1-yl)phenyl]-3-methyl-3,5-dihydro-4H-imidazol-4-one;

(5R)-2-amino-5-[4-(difluoromethoxy)phenyl]-5-[4-fluoro-3-(4-fluorobut-1-yn-1-yl)phenyl]-3-methyl-3,5-dihydro-4H-imidazol-4-one;

(5S)-2-amino-5-[4-(difluoromethoxy)phenyl]-5-[3-(4-fluorobut-1-yn-1-yl)phenyl]-3-methyl-3,5-dihydro-4H-imidazol-4-one;

(5R)-2-amino-5-[4-(difluoromethoxy)phenyl]-5-[3-(4-fluorobut-1-yn-1-yl)phenyl]-3-methyl-3,5-dihydro-4H-imidazol-4-one;

(5R)-2-amino-5-[4-(difluoromethoxy)phenyl]-5-[4-fluoro-3-(3-fluoroprop-1-yn-1-yl)phenyl]-3-methyl-3,5-dihydro-4H-imidazol-4-one; and (5S)-2-amino-5-[4-(difluoromethoxy)phenyl]-5-[4-fluoro-3-(3-fluoroprop-1-yn-1-yl)phenyl]-3-methyl-3,5-dihydro-4H-imidazol-4-one; or a tautomer thereof; or a pharmaceutically acceptable salt thereof.

25. The compound of claim 1, wherein the compound is as shown in one of the following tables (X or Y):

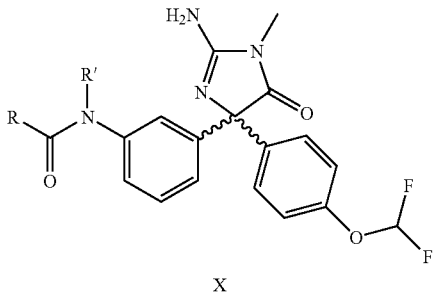

X

| Chiral | R | R' |
|---|---|---|
| — | $CH_2CH_3$ | H |
| — | $CH_2CH_2CH_3$ | H |
| — | $CH_2CH_2CH_2CH_3$ | H |
| — | $CH_2CH_2Cl$ | H |
| — | $CF_3$ | H |
| — | $CH_2CH(CH_3)_2$ | H |
| — | $CH_2CH_2CH_2CH_3$ | H |
| — | $CH(CH_3)_2$ | H |
| — | cyclopropyl | H |
| — | cyclobutyl | H |
| — | $CH_3CH\!=\!CH$ | H |
| — | $(CH_3)_2C\!=\!CH$ | H |
| — | $PhCH\!=\!CH$ | H |
| — | Furan-2-yl | H |
| — | $PhCH_2OCH_2$ | H |
| — | Ph | H |
| — | $Cl_3C$ | H |
| — | 1-Ph-5-$CF_3$- | H |
| — | pyrazole-4-yl | H |
| — | 1-(4-Cl-Ph)-5-$CF_3$- | H |
| — | pyrazole-4-yl | H |
| — | 3-bromo-thiophen-2-yl | H |
| — | Benzofuran-3-yl | H |
| — | Benzofuran-5-yl | H |
| — | Thiophene-2-yl | H |

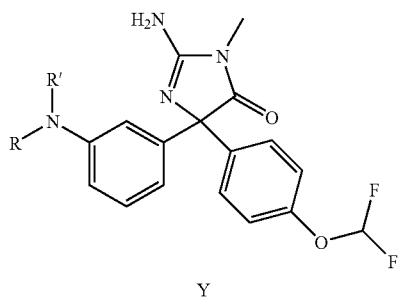

| Chiral | R | R' |
|---|---|---|
| — | CH₂CH₂CH₃ | H |
| — | CH₂CH₂CH₂CH₃ | H |
| — | (CH₃)₂CHCH₂ | H |
| — | Isopropyl | H |
| — | Cyclopentyl | H |
| — | cyclohexyl | H |
| — | CH₃CH=CH | H |
| — | cycobutyl | H |
| — | Furan-2-yl-CH₂ | H | or
a tautomer thereof; or
a pharmaceutically acceptable salt thereof.

26. The compound of claim 1, selected from the group consisting of:

a tautomer thereof; or
a pharmaceutically acceptable salt thereof.

27. A pharmaceutical composition which comprises a pharmaceutically acceptable carrier and an effective amount of a compound according to claim 1.

* * * * *

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: o-aminobenzoyl
<220> FEATURE:
<221> NAME/KEY: MOD_RES
<222> LOCATION: (10)..(10)
<223> OTHER INFORMATION: 3-(2,4-dinitrophenyl)-L-2,3-diaminopropionic
      amide

<400> SEQUENCE: 1

Ser Glu Val Asn Leu Asp Ala Glu Phe Arg
1               5                   10
```